US011220517B2

(12) United States Patent
Angibaud et al.

(10) Patent No.: US 11,220,517 B2
(45) Date of Patent: Jan. 11, 2022

(54) SPIRO BICYCLIC INHIBITORS OF MENIN-MLL INTERACTION

(71) Applicant: Janssen Pharmaceutica NV, Beerse (BE)

(72) Inventors: Patrick Rene Angibaud, Saint Pierre d'Autils (FR); Vineet Pande, Vosselaar (BE); Barbara Herkert, Flonheim (DE); Daniel Jason Krosky, Blue Bell, PA (US); Olivier Alexis Georges Querolle, Saint Vigor (FR); Aaron Nathaniel Patrick, Doylestown, PA (US); Isabelle Noelle Constance Pilatte, Louviers (FR)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/331,606

(22) PCT Filed: Sep. 13, 2017

(86) PCT No.: PCT/EP2017/073004
§ 371 (c)(1),
(2) Date: Mar. 8, 2019

(87) PCT Pub. No.: WO2018/050686
PCT Pub. Date: Mar. 22, 2018

(65) Prior Publication Data
US 2019/0211036 A1 Jul. 11, 2019

Related U.S. Application Data

(60) Provisional application No. 62/394,295, filed on Sep. 14, 2016.

(30) Foreign Application Priority Data

Oct. 5, 2016 (EP) ..................................... 16192431

(51) Int. Cl.
C07D 519/00 (2006.01)
A61P 35/02 (2006.01)
A61P 35/00 (2006.01)

(52) U.S. Cl.
CPC ............ C07D 519/00 (2013.01); A61P 35/00 (2018.01); A61P 35/02 (2018.01)

(58) Field of Classification Search
CPC ................................................... C07D 519/00
See application file for complete search history.

(56) References Cited

U.S. PATENT DOCUMENTS

| 2004/0043959 A1 | 3/2004 | Bloom et al. |
| 2006/0074102 A1 | 4/2006 | Cusack et al. |
| 2010/0331348 A1 | 12/2010 | Selles et al. |
| 2013/0310333 A1 | 11/2013 | Chesworth et al. |
| 2013/0310334 A1 | 11/2013 | Chesworth et al. |
| 2014/0221345 A1 | 8/2014 | Duncan et al. |
| 2014/0228343 A1 | 8/2014 | Duncan et al. |
| 2014/0275070 A1 | 9/2014 | Grembecka et al. |
| 2014/0329794 A1 | 11/2014 | Duncan et al. |
| 2016/0244475 A1 | 8/2016 | Tatlock et al. |
| 2017/0198006 A1 | 7/2017 | Duncan et al. |
| 2017/0355711 A1 | 12/2017 | Tabar et al. |
| 2018/0105531 A1 | 4/2018 | Grembecka et al. |
| 2018/0243328 A1 | 8/2018 | Wu et al. |
| 2019/0010167 A1* | 1/2019 | Claremon ............... A61P 43/00 |

FOREIGN PATENT DOCUMENTS

| CN | 101048412 A | 10/2007 |
| CN | 101107253 A | 1/2008 |
| CN | 102149718 A | 8/2011 |
| CN | 103664991 A | 3/2014 |
| CN | 105188705 A | 12/2015 |
| CN | 105732636 A | 7/2016 |
| EP | WO 2017-207387 | * 12/2017 |

(Continued)

OTHER PUBLICATIONS

Provisional application for Claremon US 2019/0010167—Jan. 8, 2017 (filed Dec. 22, 2015).*
Borkin, D., et al., "Pharmacologic Inhibition of the Menin-MLL Interaction Blocks Progression of MLL Leukemia in Vivo", Cancer Cell, 2015, pp. 589-602, vol. 27.
Borkin, D., et al., "Property Focused Structure-Based Optimization of Small Molecule Inhibitors of the Protein-Protein Interaction between Menin and Mixed Lineage Leukemia (MLL)", J. Med. Chem., 2016, pp. 892-913, vol. 59.
Cermakova, K., et al., "Validation and Structural Characterization of the LEDGF/p75-MLL Interface as a New Target for the Treatment of MLL—Dependent Leukemia", Cancer Research, 2014, pp. 5139-5151, vol. 15.

(Continued)

*Primary Examiner* — Valerie Rodriguez-Garcia
(74) *Attorney, Agent, or Firm* — BakerHostetler

(57) ABSTRACT

The present invention relates to compounds of formula (I):

wherein the variables have the meaning defined in the Specification. The compounds according to the present invention are useful for therapy and/or prophylaxis in a mammal, and in particular to spiro bicyclic compounds, pharmaceutical composition comprising such compounds, and their use as menin/MLL protein/protein interaction inhibitors, useful for treating diseases such as cancer, myelodysplastic syndrome (MDS) and diabetes.

12 Claims, No Drawings

Specification includes a Sequence Listing.

(56) References Cited

FOREIGN PATENT DOCUMENTS

| EP | WO 2018/024602 | * | 2/2018 |
|---|---|---|---|
| JP | 2007-537296 A | | 12/2007 |
| JP | 2010-532777 A | | 10/2010 |
| JP | 2011-026305 A | | 2/2011 |
| JP | 2013-503906 A | | 2/2013 |
| JP | 2016-512514 A | | 4/2016 |
| JP | 2018-538330 A | | 12/2018 |
| JP | 2019-532100 A | | 11/2019 |
| WO | 96/40686 A1 | | 12/1996 |
| WO | 03/70739 | | 8/2003 |
| WO | 03/74083 | | 9/2003 |
| WO | 2004/056800 A1 | | 7/2004 |
| WO | 2010/041366 A1 | | 4/2010 |
| WO | 2011/029054 A1 | | 3/2011 |
| WO | WO 2011/029054 A1 | | 3/2011 |
| WO | 2012/075500 A2 | | 6/2012 |
| WO | 2012/082436 A2 | | 6/2012 |
| WO | 2013/018404 A1 | | 2/2013 |
| WO | 2014/035140 A2 | | 3/2014 |
| WO | 2014/100695 A1 | | 6/2014 |
| WO | 2014/164543 A1 | | 10/2014 |
| WO | WO 2014/164543 A1 | | 10/2014 |
| WO | 2015/191701 A1 | | 12/2015 |
| WO | WO 2015/191701 A1 | | 12/2015 |
| WO | 2016/040330 A1 | | 3/2016 |
| WO | WO 2016/040330 A1 | | 3/2016 |
| WO | 2016/081732 A1 | | 5/2016 |
| WO | WO 2016/081732 A1 | | 5/2016 |
| WO | 2016/195776 A1 | | 12/2016 |
| WO | 2016/197027 A1 | | 12/2016 |
| WO | WO 2016/197027 A1 | | 12/2016 |
| WO | 2017/112768 A1 | | 6/2017 |
| WO | WO 2017/112768 A1 | | 6/2017 |
| WO | 2017/161002 A1 | | 9/2017 |
| WO | 2017/161028 A1 | | 9/2017 |
| WO | WO 2017/161002 A1 | | 9/2017 |
| WO | WO 2017/161028 A1 | | 9/2017 |
| WO | 2017/192543 A1 | | 11/2017 |
| WO | WO 2017/192543 A1 | | 11/2017 |
| WO | 2017/207387 A1 | | 12/2017 |
| WO | 2017/214367 A1 | | 12/2017 |
| WO | WO 2017/207387 A1 | | 12/2017 |
| WO | WO 2017/214367 A1 | | 12/2017 |
| WO | 2018/024602 A1 | | 2/2018 |
| WO | WO 2018/024602 A1 | | 2/2018 |
| WO | 2018/047598 A1 | | 3/2018 |
| WO | 2018/050684 A1 | | 3/2018 |
| WO | 2018/050686 A1 | | 3/2018 |
| WO | 2018/053267 A1 | | 3/2018 |
| WO | WO 2018/050684 A1 | | 3/2018 |
| WO | WO 2018/050686 A1 | | 3/2018 |
| WO | WO 2018/053267 A1 | | 3/2018 |
| WO | WO 2018/109088 A1 | | 6/2018 |
| WO | 2018/175746 A1 | | 9/2018 |
| WO | WO 2018/175746 A1 | | 9/2018 |

OTHER PUBLICATIONS

Charron, C.L., et al., "Recent developments in radiolabeled peptides for PET imaging of cancer", Tetrahedron Letters, 2016, pp. 4119-4127, vol. 57.

Chen, Ya-Xiong, et al., "The tumor suppressor menin regulates hematopoiesis and myeloid transformation by influencing Hox gene expression", PNAS, 2006, pp. 1018-1023, vol. 103, No. 4.

Cierpicki, T., et al., "Challenges and opportunities in targeting the menin-MLL interaction", Future Med. Chem, 2014, pp. 447-462, vol. 6, No. 4.

Grembecka, J., et al., "Menin-MLL inhibitors reverse oncogenic activity of MLL fusion proteins in leukemia", Nature Chemical Biology, 2012, pp. 277-284, vol. 8.

Greene, T.W., et al., "Greene's Protective Groups in Organic Synthesis", 4$^{th}$ ed., (2007), Wiley-Interscience, Hoboken, New Jersey.

He, S., et al., "High-Affinity Small-Molecule Inhibitors of the Menin-Mixed Lineage Leukemia (MLL) Interaction Closely Mimic a Natural Protein-Protein Interaction", J. Med. Chem., 2014, pp. 1543-1556, vol. 57.

Li, B.E., et al., "Distinct pathways regulated by menin and by MLL1 in hematopoietic stem cells and developing B cells", Blood, 2013, pp. 2039-2046, vol. 122, No. 12.

Malik, R., et al., "Targeting the MLL complex in castration-resistant prostate cancer", Nature Medicine, 2015, pp. 34-352, vol. 21, No. 4.

Marschalek, R., "Mechanisms of leukemogenesis by MLL fusion proteins", British Journal of Haematology, 2010, pp. 141-154, vol. 152, vol. 2.

Meyer, C., et al., "The MLL recombinome of acute leukemias in 2013", Leukemia, 2013, pp. 2165-2176, vol. 27.

Mishra, B.P., et al., "The Histone Methyltransferase Activity of MLL1 is Dispensable for Hematopoiesis and Leukemogenesis", Cell Reports, 2014, pp. 1239-1247, vol. 7.

Pantel, A.R., et al., "Molecular imaging to guide systematic career therapy: Illustrative examples of PET imaging cancer biomarkers", Cancer Letters, 2017, pp. 25-31, vol. 387.

Gennaro, A.R., Remington's 18$^{th}$ ed., Mack Publishing Company, (1990) see especially Part 8: Pharmaceutical preparations and their Manufacture, pp. 1435-1712.

Ren, J., et al., "Design and synthesis of benzylpiperidine inhibitors targeting the menin-MLL1 interface", Bioorganic & Medicinal Chemistry Letters, 2016, pp. 4472-4476, vol. 26.

Thiel, A.T., et al., "Menin as a hub controlling mixed lineage leukemia", Bioessays, 2012, pp. 771-880, vol. 34.

Tomizawa, D., et al., "Repetitive Cycles of High-Dose Cytarabine Are Effective for Childhood Acute Myeloid Leukemia: Long-Term Outcome of the Children With AML Treated on Two Conservative Trials of Tokyo Children's Cancer Study Group", Pediatr Blood Cancer, 2007, pp. 127-132, vol. 49, No. 2.

Yokoyama, A., et al., "The Menin Tumor Suppressor Protein Is an Essential Oncogenic Cofactor for MLL-Associated Leukemogenesis", Cell, 2005, pp. 207-218, vol. 123.

Yokoyama, A., et al., "Menin Critically Links MLL Proteins with LEDGF on Cancer-Associated Target Genes", Cancer Cell, 2008, pp. 36-46, vol. 14.

International Search Report PCT/EP2017/073004 dated Nov. 28, 2017.

Written Opinion PCT/EP2017/073004 dated Nov. 28, 2017.

European Search Report EP17150502 completed Mar. 7, 2017.

European Search Report EP18201390 completed Nov. 14, 2018.

International Search Report PCT/EP2017/073001 dated Nov. 6, 2017.

International Search Report PCT/CN2017/117536 dated Jul. 31, 2018.

Borkin et al., "Pharmacologic Inhibition of the Menin-MLL Interaction Blocks Progression of MLL Leukemia in Vivo.", Cancer Cell, Apr. 13, 2015, pp. 589-602, vol. 27.

Borkin et al., "Property Focused Structure-Based Optimization of Small Molecule Inhibitors of the Protein-Protein Interaction between Menin and Mixed Lineage Leukemia (MLL).", J. Med. Chem., 2016, pp. 892-913, vol. 59.

Cermakova et al., "Validation and Structural Characterization of the LEDGF/p75—MLL Interface as a New Target for theTreatment of MLL-Dependent Leukemia", Cancer Res., Sep. 15, 2014, pp. 5139-5151, vol. 74(18).

Charron et al., "Recent developments in radiolabelled peptides for PET imaging of cancer.", Tetrahedron Letters, 2016, pp. 4119-4127, vol. 57.

Chen et al., "The tumor suppressor menin regulates hematopoiesis and myeloid transformation by influencing Hox gene expression.", PNAS, Jan. 24, 2006, pp. 1018-1023, vol. 103(4).

Cierpicki, T. and Grembecka, J., "Challenges and opportunities in targeting the menin-MLL interaction.", Future Med. Chem., 2014, pp. 447-462, vol. 6(4).

Grembecka et al., "Menin-MLL Inhibitors Reverse Oncogenic Activity of MLL Fusion Proteins in Leukemia", Nat. Chem. Bio, published on-line on Jan. 29, 2012, DOI: 10.1038/nchembi0.773; Mar. 2012, pp. 277-284, vol. 8.

(56) References Cited

OTHER PUBLICATIONS

He et al., "High-Affinity Small-Molecule Inhibitors of the Menin-Mixed Lineage Leukemia (MLL) Interaction Closely Mimic a Natural Protein-Protein Interaction.", J. Med. Chem., 2014, 1543-1556, vol. 57.
International Search Report PCT/EP2017/082826, dated Feb. 14, 2018.
Li et al., "Distinct pathways regulated by menin and by MLL1 in hematopoietic stem cells and developing B cells.", Blood, Sep. 19, 2013, pp. 2039-2046, vol. 122(12).
Malik et al., "Targeting the MLL complex in castration resistant prostate cancer.", Nat. Med., Apr. 2015, DD. 344-352, vol. 21(4).
Marschalek, R., "Mechanisms of leukemogenesis by MLL fusion proteins.", British J. of Haematology, 2010, pp. 141-154, vol. 152.
Meyer et al., "The MLL recombinome of acute leukemias in 2013.", Leukemia, 2013, pp. 2165-2176, vol. 27.
Mishra et al., "The Histone Methyltransferase Activity of MLL1 Is Dispensable for Hematopoiesis and Leukemogenesis.", Cell Rep., May 22, 2014, pp. 1239-1247, vol. 7(4).
Pantel et al., "Molecular imaging to guide systemic cancer therapy: Illustrative examples of PET imaging cancer biomarkers.", Cancer Letters, 2017, pp. 25-31, vol. 387.
Ren et al., "Design and synthesis of benzylpiperidine inhibitors targeting the menin-MLL1 interface.", Bioorganic & Medicinal Chemistry Letters, 2016, pp. 4472-4476, vol. 26.
Shah, S.K., et al., "Synthesis and evaluation of CCR5 antagonists containing modified 4-piperidinyl-2-phenyl-1-(phenylsulfonylamino)-butane", Bioorganic & Medicinal Chemistry Letters, 2005, pp. 977-982, vol. 15.
Thiel et al., "Menin as a Hub Controlling Mixed Lineage Leukemia.", Bioessays, Sep. 2012, pp. 771-780, vol. 34(9).
Tomizawa et al., "Repetitive Cycles of High-Dose Cytarabine Are Effective for Childhood Acute Myeloid Leukemia: Long-Term Outcome of the Children With AML Treated on Two Consecutive Trials of Tokyo Children's Cancer Study Group.", Pediatr. Blood Cancer, 2007, pp. 127-132, vol. 49.
Written Opinion PCT/EP2017/082826, dated Feb. 14, 2018.
Yokoyama et al., "The Menin Tumor Suppressor Protein Is an Essential Oncogenic Cofactor for MLL-Associated Leukemogenesis.", Cell, Oct. 21, 2005, pp. 207-218, vol. 123.
Yokoyama, A. and Cleary, M., "Menin Critically Links MLL Proteins with LEDGF on Cancer-Associated Target Genes.", Cancer Cell, Jul. 2008, pp. 36-46, vol. 14.
Acute Leukemia, Merck Manual (Online Edition) 6 pages, pp. 1-6 (2013).
Gura, "Systems for identifying new drugs are often faulty.", Science, vol. 278, Nov. 1997, 1041-1042.
International Application No. PCT/EP2017/073001, Written Opinion of the International Searching Authority, dated Nov. 6, 2017.
International Application No. PCT/EP2017/073004, Written Opinion of the International Searching Authority, dated Mar. 8, 2019, 4 pages.
Johnson et al., "Relationships between drug activity in NCI preclinical in vitro and vivo models and early clinical trials.", 2001, Br J Cancer 84(10): 1424-31.
Pearce et al., "Failure modes in anticancer drug discovery and development.", Cancer Drug Design and Discovery Edited by Stephen Neidle, Chapter 18, pp. 424-435 (2008).
Simone, Introduction, Omenn, Cancer Prevention, Part XIV, Oncology, Cecil Textbook of Medecine, 20th Edition, vol. 1, pp. 1004-1010.

\* cited by examiner

SEQUENCE LISTING

<160> NUMBER OF SEQ ID NOS: 1

<210> SEQ ID NO 1
<211> LENGTH: 616
<212> TYPE: PRT
<213> ORGANISM: Artificial Sequence
<220> FEATURE:
<223> OTHER INFORMATION: MENIN protein sequence with His tag

<400> SEQUENCE: 1

Met Gly Leu Lys Ala Ala Gln Lys Thr Leu Phe Pro Leu Arg Ser Ile

```
1               5                   10                  15
Asp Asp Val Val Arg Leu Phe Ala Ala Glu Leu Gly Arg Glu Glu Pro
                20                  25                  30
Asp Leu Val Leu Leu Ser Leu Val Leu Gly Phe Val Glu His Phe Leu
                35                  40                  45
Ala Val Asn Arg Val Ile Pro Thr Asn Val Pro Glu Leu Thr Phe Gln
 50                  55                  60
Pro Ser Pro Ala Pro Asp Pro Pro Gly Gly Leu Thr Tyr Phe Pro Val
 65                  70                  75                  80
Ala Asp Leu Ser Ile Ile Ala Ala Leu Tyr Ala Arg Phe Thr Ala Gln
                85                  90                  95
Ile Arg Gly Ala Val Asp Leu Ser Leu Tyr Pro Arg Glu Gly Gly Val
                100                 105                 110
Ser Ser Arg Glu Leu Val Lys Lys Val Ser Asp Val Ile Trp Asn Ser
                115                 120                 125
Leu Ser Arg Ser Tyr Phe Lys Asp Arg Ala His Ile Gln Ser Leu Phe
                130                 135                 140
Ser Phe Ile Thr Gly Thr Lys Leu Asp Ser Ser Gly Val Ala Phe Ala
145                 150                 155                 160
Val Val Gly Ala Cys Gln Ala Leu Gly Leu Arg Asp Val His Leu Ala
                165                 170                 175
Leu Ser Glu Asp His Ala Trp Val Val Phe Gly Pro Asn Gly Glu Gln
                180                 185                 190
Thr Ala Glu Val Thr Trp His Gly Lys Gly Asn Glu Asp Arg Arg Gly
                195                 200                 205
Gln Thr Val Asn Ala Gly Val Ala Glu Arg Ser Trp Leu Tyr Leu Lys
                210                 215                 220
Gly Ser Tyr Met Arg Cys Asp Arg Lys Met Glu Val Ala Phe Met Val
225                 230                 235                 240
Cys Ala Ile Asn Pro Ser Ile Asp Leu His Thr Asp Ser Leu Glu Leu
                245                 250                 255
Leu Gln Leu Gln Gln Lys Leu Leu Trp Leu Leu Tyr Asp Leu Gly His
                260                 265                 270
Leu Glu Arg Tyr Pro Met Ala Leu Gly Asn Leu Ala Asp Leu Glu Glu
                275                 280                 285
Leu Glu Pro Thr Pro Gly Arg Pro Asp Pro Leu Thr Leu Tyr His Lys
                290                 295                 300
Gly Ile Ala Ser Ala Lys Thr Tyr Tyr Arg Asp Glu His Ile Tyr Pro
305                 310                 315                 320
Tyr Met Tyr Leu Ala Gly Tyr His Cys Arg Asn Arg Asn Val Arg Glu
                325                 330                 335
Ala Leu Gln Ala Trp Ala Asp Thr Ala Thr Val Ile Gln Asp Tyr Asn
                340                 345                 350
Tyr Cys Arg Glu Asp Glu Glu Ile Tyr Lys Glu Phe Phe Glu Val Ala
                355                 360                 365
Asn Asp Val Ile Pro Asn Leu Leu Lys Glu Ala Ala Ser Leu Leu Glu
                370                 375                 380
Ala Gly Glu Glu Arg Pro Gly Glu Gln Ser Gln Gly Thr Gln Ser Gln
385                 390                 395                 400
Gly Ser Ala Leu Gln Asp Pro Glu Cys Phe Ala His Leu Leu Arg Phe
                405                 410                 415
Tyr Asp Gly Ile Cys Lys Trp Glu Glu Gly Ser Pro Thr Pro Val Leu
                420                 425                 430
```

| | | | | | | | | | | | |
|---|---|---|---|---|---|---|---|---|---|---|---|
|His|Val|Gly|Trp|Ala|Thr|Phe|Leu|Val|Gln|Ser|Leu|Gly|Arg|Phe|Glu|
| | |435| | |440| | | |445| | |
|Gly|Gln|Val|Arg|Gln|Lys|Val|Arg|Ile|Val|Ser|Arg|Glu|Ala|Glu|Ala|
| |450| | | |455| | | |460| | | |
|Ala|Glu|Ala|Glu|Glu|Pro|Trp|Gly|Glu|Ala|Arg|Glu|Gly|Arg|Arg|
|465| | | |470| | | |475| | | |480|
|Arg|Gly|Pro|Arg|Arg|Glu|Ser|Lys|Pro|Glu|Glu|Pro|Pro|Pro|Lys|
| | | |485| | | |490| | | |495| |
|Lys|Pro|Ala|Leu|Asp|Lys|Gly|Leu|Gly|Thr|Gly|Gln|Gly|Ala|Val|Ser|
| | |500| | | |505| | | |510| | |
|Gly|Pro|Pro|Arg|Lys|Pro|Pro|Gly|Thr|Val|Ala|Gly|Thr|Ala|Arg|Gly|
| | |515| | | |520| | | |525| | |
|Pro|Glu|Gly|Gly|Ser|Thr|Ala|Gln|Val|Pro|Ala|Pro|Ala|Ala|Ser|Pro|
| |530| | | |535| | | |540| | | |
|Pro|Pro|Glu|Gly|Pro|Val|Leu|Thr|Phe|Gln|Ser|Glu|Lys|Met|Lys|Gly|
|545| | | |550| | | |555| | | |560|
|Met|Lys|Glu|Leu|Leu|Val|Ala|Thr|Lys|Ile|Asn|Ser|Ser|Ala|Ile|Lys|
| | | |565| | | |570| | | |575| |
|Leu|Gln|Leu|Thr|Ala|Gln|Ser|Gln|Val|Gln|Met|Lys|Lys|Gln|Lys|Val|
| | |580| | | |585| | | |590| | |
|Ser|Thr|Pro|Ser|Asp|Tyr|Thr|Leu|Ser|Phe|Leu|Lys|Arg|Gln|Arg|Lys|
| | |595| | | |600| | | |605| | |
|Gly|Leu|His|His|His|His|His|His|
| |610| | | |615| | |

SPIRO BICYCLIC INHIBITORS OF MENIN-MLL INTERACTION

CROSS-REFERENCE TO RELATED APPLICATIONS

This application is a U.S. national stage of PCT Application No. PCT/EP2017/073004, filed Sep. 13, 2017, which claims the benefit of priority of U.S. Patent Application No. 62/394,295, filed Sep. 14, 2016, and European Patent Application No. 16192431.1, filed Oct. 5, 2016, all of which are incorporated by reference herein, in their entireties and for all purposes.

FIELD OF THE INVENTION

The present invention relates to pharmaceutical agents useful for therapy and/or prophylaxis in a mammal, and in particular to spiro bicyclic compounds, pharmaceutical composition comprising such compounds, and their use as menin/MLL protein/protein interaction inhibitors, useful for treating diseases such as cancer, myelodysplastic syndrome (MDS) and diabetes.

BACKGROUND OF THE INVENTION

Chromosomal rearrangements affecting the mixed lineage leukemia gene (MLL; MLL1; KMT2A) result in aggressive acute leukemias across all age groups and still represent mostly incurable diseases emphasizing the urgent need for novel therapeutic approaches. Acute leukemias harboring these chromosomal translocations of MLL represent as lymphoid, myeloid or biphenotypic disease and constitute 5 to 10% of acute leukemias in adults and approximately 70% in infants (Marschalek, Br J Haematol 2011. 152(2), 141-54; Tomizawa et al., Pediatr Blood Cancer 2007. 49(2), 127-32).

MLL is a histone methyltransferase that methylates histone H3 on lysine 4 (H3K4) and functions in multiprotein complexes. Use of inducible loss-of-function alleles of Mll1 demonstrated that Mll1 plays an essential role in sustaining hematopoietic stem cells (HSCs) and developing B cells although its histone methyltransferase activity is dispensable for hematopoiesis (Mishra et al., Cell Rep 2011. 7(4), 1239-47).

Fusion of MLL with more than 60 different partners has been reported to date and has been associated with leukemia formation/progression (Meyer et al., Leukemia 2013. 27, 2165-2176). Interestingly, the SET (Su(var)3-9, enhancer of zeste, and trithorax) domain of MLL is not retained in chimeric proteins but is replaced by the fusion partner (Thiel et al., Bioessays 2012. 34, 771-80). Recruitment of chromatin modifying enzymes like DotlL and/or the pTEFb complex by the fusion partner leads to enhanced transcription and transcriptional elongation of MLL target genes including HOXA genes (e.g. HOXA9) and the HOX cofactor MEIS1 as the most prominent ones. Aberrant expression of these genes in turn blocks hematopoietic differentiation and enhances proliferation.

Menin which is encoded by the Multiple Endocrine Neoplasia type 1 (MEN1) gene is expressed ubiquitously and is predominantly localized in the nucleus. It has been shown to interact with numerous proteins and is, therefore, involved in a variety of cellular processes. The best understood function of menin is its role as an oncogenic cofactor of MLL fusion proteins. Menin interacts with two motifs within the N-terminal fragment of MLL that is retained in all fusion proteins, MBM1 (menin-binding motif 1) and MBM2 (Thiel et al., Bioessays 2012. 34, 771-80). Menin/MLL interaction leads to the formation of a new interaction surface for lens epithelium-derived growth factor (LEDGF). Although MLL directly binds to LEDGF, menin is obligatory for the stable interaction between MLL and LEDGF and the gene specific chromatin recruitment of the MLL complex via the PWWP domain of LEDGF (Cermakova et al., Cancer Res 2014. 15, 5139-51; Yokoyama & Cleary, Cancer Cell 2008. 8, 36-46). Furthermore, numerous genetic studies have shown that menin is strictly required for oncogenic transformation by MLL fusion proteins suggesting the menin/MLL interaction as an attractive therapeutic target. For example, conditional deletion of Men1 prevents leukomogenesis in bone marrow progenitor cells ectopically expressing MLL fusions (Chen et al., Proc Natl Acad Sci 2006. 103, 1018-23). Similarly, genetic disruption of menin/MLL fusion interaction by loss-of-function mutations abrogates the oncogenic properties of the MLL fusion proteins, blocks the development of leukemia in vivo and releases the differentiation block of MLL-transformed leukemic blasts. These studies also showed that menin is required for the maintenance of HOX gene expression by MLL fusion proteins (Yokoyama et al., Cell 2005. 123, 207-18). In addition, small molecule inhibitors of menin/MLL interaction have been developed suggesting druggability of this protein/protein interaction and have also demonstrated efficacy in preclinical models of AML (Borkin et al., Cancer Cell 2015. 27, 589-602; Cierpicki and Grembecka, Future Med Chem 2014. 6, 447-462). Together with the observation that menin is not a requisite cofactor of MLL1 during normal hematopoiesis (Li et al., Blood 2013. 122, 2039-2046), these data validate the disruption of menin/MLL interaction as a promising new therapeutic approach for the treatment of MLL rearranged leukemia and other cancers with an active HOX/MEIS1 gene signature. For example, an internal partial tandem duplication (PTD) within the 5' region of the MLL gene represents another major aberration that is found predominantly in de novo and secondary AML as well as myeloid dysplasia syndromes. Although the molecular mechanism and the biological function of MLL-PTD is not well understood, new therapeutic targeting strategies affecting the menin/MLL interaction might also prove effective in the treatment of MLL-PTD-related leukemias. Furthermore, castration-resistant prostate cancer has been shown to be dependent on the menin/MLL interaction (Malik et al., Nat Med 2015. 21, 344-52).

Several references describe inhibitors targeting the menin-MLL interaction: WO2011029054, J Med Chem 2016, 59, 892-913 describes the preparation of thienopyrimidine and benzodiazepine derivatives; WO2014164543 describes thienopyrimidine and thienopyridine derivatives; Nature Chemical Biology March 2012, 8, 277-284 and Ren, J.; et al. Bioorg Med Chem Lett (2016), http://dx.doi.org/10.1016/j.bmcl.2016.07.074 describe thienopyrimidine derivatives; J Med Chem 2014, 57, 1543-1556 describes hydroxy- and aminomethylpiperidine derivatives; and Future Med Chem 2014, 6, 447-462 reviews small molecule and peptidomimetic compounds. WO2017112768 describes inhibitors of the menin-MLL interaction.

DESCRIPTION OF THE INVENTION

The present invention concerns novel compounds of Formula (I):

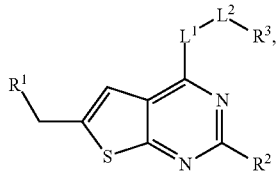

(I)

and the tautomers and the stereoisomeric forms thereof, wherein
$R^1$ is selected from the group consisting of $CH_3$, $CH_2F$, $CHF_2$, and $CF_3$;
$R^2$ is selected from the group consisting of hydrogen and $CH_3$;
$L^1$ represents a 7- to 10-membered saturated spiroheterobicyclic system containing one or two N-atoms provided that it is N-linked to the thienopyrimidinyl heterocycle; and
-$L^2$-$R^3$ is selected from (a), (b), (c), (d), (e), (f) or (g), wherein
(a) $L^2$ is selected from the group consisting of >$SO_2$, >$CR^{4a}R^{4b}$, and —$CHR^{4a}CHR^5$—; wherein
  (i) when $L^2$ is linked to a carbon atom of $L^1$, then $R^{4a}$ and $R^5$ are each independently selected from the group consisting of hydrogen; —$OR^6$; —$NR^{7a}R^{7b}$; —C(=O)$NR^{7a}R^{7b}$; $C_{1-4}$alkyl optionally substituted with a substituent selected from the group consisting of fluoro, —CN, —$OR^8$, and —$NR^{9a}R^{9b}$; and C-linked 4- to 7-membered non-aromatic heterocyclyl containing at least one nitrogen, oxygen or sulfur atom;
  (ii) when $L^2$ is linked to a nitrogen atom of $L^1$, then $R^{4a}$ is selected from the group consisting of hydrogen; —C(=O)$NR^{7a}R^{7b}$; $C_{1-4}$alkyl optionally substituted with a substituent selected from the group consisting of fluoro, —CN, —$OR^8$, and —$NR^{9a}R^{9b}$; and C-linked 4- to 7-membered non-aromatic heterocyclyl containing at least one nitrogen, oxygen or sulfur atom;
  $R^5$ is selected from the group consisting of hydrogen; —$OR^6$; —$NR^{7a}R^{7b}$; —C(=O)$NR^{7a}$Rb; $C_{1-4}$alkyl optionally substituted with a substituent selected from the group consisting of fluoro, —CN, —$OR^8$, and —$NR^{9a}R^{9b}$; and C-linked 4- to 7-membered non-aromatic heterocyclyl containing at least one nitrogen, oxygen or sulfur atom;
  $R^{4b}$ is selected from the group consisting of hydrogen and methyl; or $R^{4a}$ and $R^{4b}$ together with the carbon atom to which they are attached form a $C_{3-5}$cycloalkyl or a C-linked 4- to 6-membered heterocyclyl containing an oxygen atom; wherein
  $R^6$, $R^{7a}$, $R^{7b}$, $R^8$, $R^{9a}$ and $R^{9b}$ are each independently selected from the group consisting of hydrogen; $C_{1-4}$alkyl optionally substituted with a substituent selected from the group consisting of fluoro, —CN, and —C(=O)$NR^{10a}R^{10b}$; and $C_{2-4}$alkyl substituted with a substituent selected from the group consisting of —$OR^{11}$ and —$NR^{10a}R^{10b}$; wherein
  $R^{10a}$, $R^{10b}$ and $R^{11}$ are each independently selected from the group consisting of hydrogen; $C_{1-4}$alkyl; and C-linked 4- to 7-membered non-aromatic heterocyclyl containing at least one nitrogen, oxygen or sulfur atom; and
  $R^3$ is selected from the group consisting of Ar, $Het^1$, $Het^2$, and a 7- to 10-membered saturated spirocarbobicyclic system; or
(b) $L^2$ is selected from the group consisting of >$CR^{4c}R^{4d}$ and —$CHR^{4c}CHR^{5a}$—, wherein $R^{4c}$, $R^{4d}$, and $R^{5a}$ are each independently selected from the group consisting of hydrogen and $C_{1-4}$alkyl; and
  $R^3$ is selected from the group consisting of

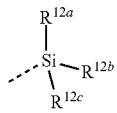

and

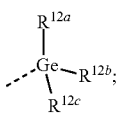

wherein $R^{12a}$, $R^{12b}$, and $R^{12c}$ are each independently selected from the group consisting of $C_{1-6}$alkyl optionally substituted with a —OH or a —$NH_2$ substituent; and —$OC_{1-6}$alkyl; or
(c) -$L^2$-$R^3$ is $C_{1-6}$alkyl optionally substituted with one, two or three fluoro substituents; or
(d) $L^2$ is O and $R^3$ is selected from the group consisting of $C_{3-6}$alkyl optionally substituted with one, two or three fluoro substituents; Ar; $Het^1$; $Het^2$; a 7- to 10-membered saturated spirocarbobicyclic system; —$CH_2$—Ar; —$CH_2$-Het; —$CH_2$-$Het^2$; and —$CH_2$-(a 7- to 10-membered saturated spirocarbobicyclic system); when $L^2$ is linked to a carbon atom of $L^1$; or
(e) -$L^2$-$R^3$ is —O—$CHR^5$—$R^3$ when $L^2$ is linked to a carbon atom of $L^1$, wherein
  $R^5$ is selected from the group consisting of —C(=O)$NR^{13a}R^{13b}$; $C_{1-4}$alkyl optionally substituted with a substituent selected from the group consisting of fluoro, —$OR^{14}$, and —$NR^{15a}R^{15b}$; and C-linked 4- to 7-membered non-aromatic heterocyclyl containing at least one nitrogen, oxygen or sulfur atom; wherein
  $R^{13a}$, $R^{13b}$, $R^{14}$, $R^{15a}$ and $R^{15b}$ are each independently selected from the group consisting of hydrogen; $C_{1-4}$alkyl optionally substituted with a substituent selected from the group consisting of fluoro and —C(=O)$NR^{16a}R^{16b}$; and $C_{2-4}$alkyl substituted with a substituent selected from the group consisting of —$OR^{17}$ and —$NR^{16a}R^{16b}$; wherein
  $R^{16a}$, $R^{16b}$ and $R^{17}$ are each independently selected from the group consisting of hydrogen; $C_{1-4}$alkyl; and C-linked 4- to 7-membered non-aromatic heterocyclyl containing at least one nitrogen, oxygen or sulfur atom; and
  $R^3$ is selected from the group consisting of hydrogen; $C_{1-4}$alkyl optionally substituted with one, two, or three fluoro substituents; —CN; Ar, $Het^1$; $Het^2$; and a 7- to 10-membered saturated spirocarbobicyclic system; or
(f) -$L^2$-$R^3$ is

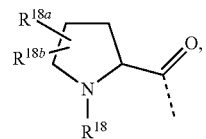

wherein
R$^{18}$ is selected from the group consisting of hydrogen; C$_{1-4}$alkyl optionally substituted with a fluoro or a —CN substituent; and C$_{2-4}$alkyl substituted with a substituent selected from the group consisting of —OR$^{19}$ and —NR$^{20a}$R$^{20b}$; wherein R$^{19}$, R$^{20a}$ and R$^{20b}$ are each independently selected from the group consisting of hydrogen; C$_{1-4}$alkyl optionally substituted with a substituent selected from the group consisting of fluoro, —CN, and —C(=O)NR$^{21a}$R$^{21b}$; C$_{2-4}$alkyl substituted with a substituent selected from the group consisting of —OR$^{22}$ and —NR$^{21a}$R$^{21b}$; and C-linked 4- to 7-membered non-aromatic heterocyclyl containing at least one nitrogen, oxygen or sulfur atom; wherein R$^{21a}$, R$^{21b}$ and R$^{22}$ are each independently selected from the group consisting of hydrogen and C$_{1-4}$alkyl; and R$^{18a}$ is selected from the group consisting of hydrogen, fluoro and C$_{1-4}$alkyl;

R$^{18b}$ is selected from the group consisting of fluoro, —OC$_{1-4}$alkyl, and C$_{1-4}$alkyl optionally substituted with 1, 2 or 3 fluoro substituents; or R$^{18a}$ and R$^{18b}$ are bound to the same carbon atom and together form a C$_{3-5}$cycloalkyl or a C-linked 4- to 6-membered heterocyclyl containing an oxygen atom; or (g) -L$^2$-R$^3$ is

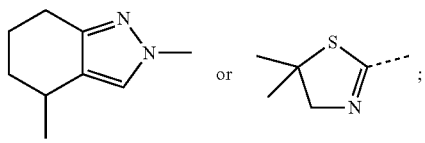

and wherein
Ar is phenyl or naphthyl, each of which may be optionally substituted with one, two, or three substituents each independently selected from the group consisting of halo, —CN, —OR$^{24}$, —NR$^{25a}$R$^{25b}$, and C$_{1-4}$alkyl optionally substituted with a substituent selected from the group consisting of fluoro, —CN, —OR$^{26}$, —NR$^{27a}$R$^{27b}$, and —C(=O)NR$^{27a}$R$^{27b}$;

Het$^1$ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, thiadiazolyl, and isoxazolyl; or a bicyclic heteroaryl selected from the group consisting of imidazothiazolyl, imidazoimidazolyl, benzofuranyl, benzothiophenyl, benzimidazolyl, benzoxazolyl, isobenzoxazolyl, benzisoxazolyl, benzothiazolyl, benzisothiazolyl, isobenzofuranyl, indolyl, isoindolyl, indolizinyl, indolinyl, isoindolinyl, indazolyl, pyrazolopyridinyl, pyrazolopyrimidinyl, imidazopyridinyl, imidazopyrazinyl, imidazopyridazinyl; each of which may be optionally substituted with one, two, or three substituents each independently selected from the group consisting of halo, —CN, —OR$^{24}$, —NR$^{25a}$R$^{25b}$, and C$_{1-4}$alkyl optionally substituted with a substituent selected from the group consisting of fluoro, —CN, —OR$^{26}$, —NR$^{27a}$R$^{27b}$, and —C(=O)NR$^{27a}$R$^{27b}$; and Het$^2$ is a non-aromatic heterocyclyl optionally substituted with one, two, or three substituents each independently selected from the group consisting of halo, —CN, —OR$^{24}$, —NR$^{25a}$R$^{25b}$, and C$_{1-4}$alkyl optionally substituted with a substituent selected from the group consisting of fluoro, —CN, —OR$^{26}$, —NR$^{27a}$R$^{27b}$, and —C(=O)NR$^{27a}$R$^{27b}$;

wherein
R$^{24}$, R$^{25a}$, R$^{25b}$, R$^{26}$, R$^{27a}$, and R$^{27b}$ are each independently selected from the group consisting of hydrogen; C$_{1-4}$alkyl optionally substituted with a substituent selected from the group consisting of fluoro and —C(=O)NR$^{28a}$R$^{28b}$; and C$_{2-4}$alkyl substituted with a substituent selected from the group consisting of —OR$^{29}$ and —NR$^{28a}$R$^{28b}$; wherein R$^{28a}$, R$^{28b}$ and R$^{29}$ are each independently selected from the group consisting of hydrogen; C$_{1-4}$alkyl; and C-linked 4- to 7-membered non-aromatic heterocyclyl containing at least one nitrogen, oxygen or sulfur atom;

and the pharmaceutically acceptable salts and the solvates thereof;

provided that the following compounds, and pharmaceutically acceptable addition salts, and solvates thereof are excluded:

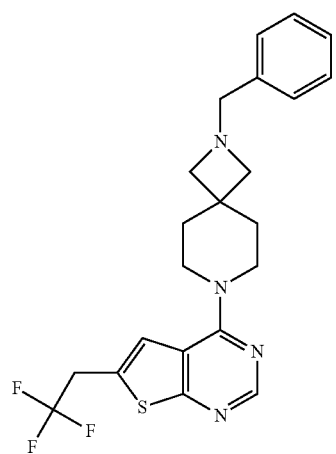 [SMILES: FC(F)(F)Cc1cc2c(N3CCC4(CC3)CN(Cc3ccccc3)C4)ncnc2s1]

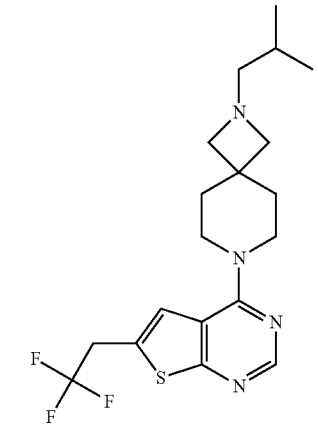 [SMILES: CC(C)CN1CC2(CCN(c3ncnc4sc(CC(F)(F)F)cc34)CC2)C1]

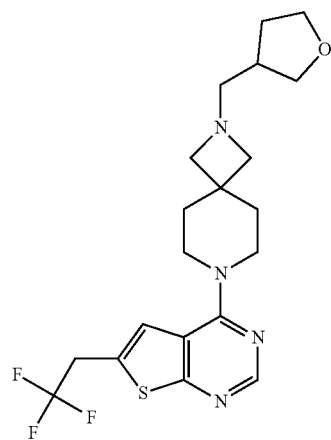 [SMILES: FC(F)(F)Cc1cc2c(N3CCC4(CC3)CN(CC3CCOC3)C4)ncnc2s1]
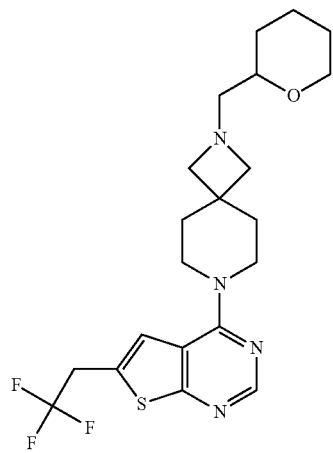
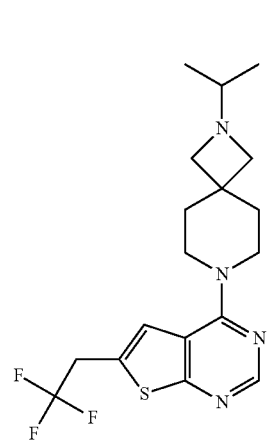 [SMILES: CC(C)N1CC2(CCN(c3ncnc4sc(CC(F)(F)F)cc34)CC2)C1]
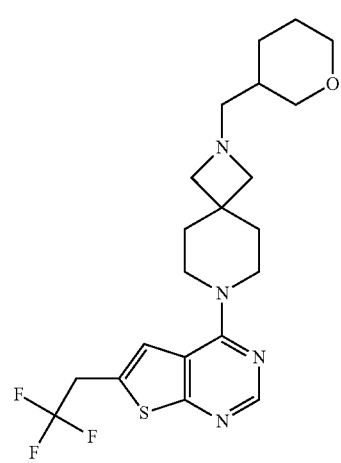
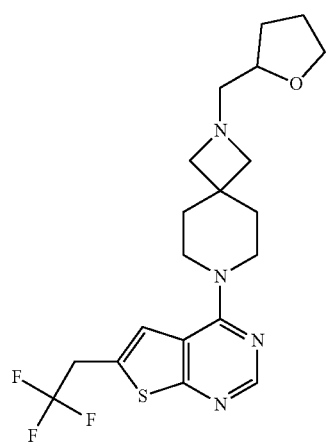 [SMILES: FC(F)(F)Cc1cc2c(N3CCC4(CC3)CN(CC3CCCO3)C4)ncnc2s1]
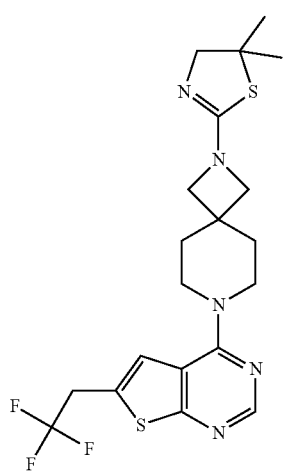 [SMILES: CC1(C)CN=C(N2CC3(CCN(c4ncnc5sc(CC(F)(F)F)cc45)CC3)C2)S1]

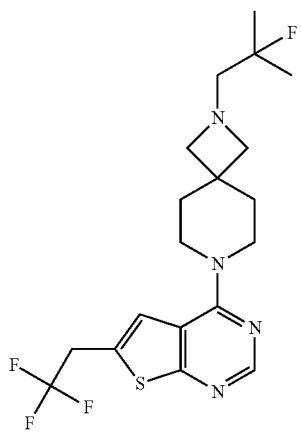 [SMILES: CC(C)(F)CN1CC2(CCN(c3ncnc4sc(CC(F)(F)F)cc34)CC2)C1]
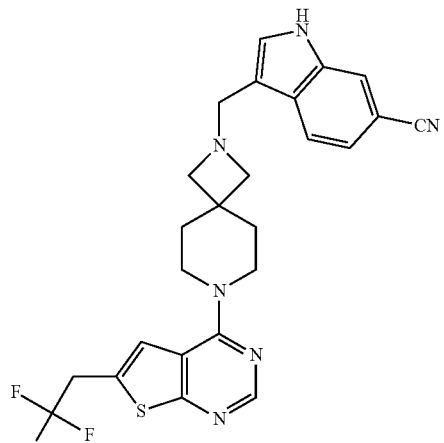

| 11 -continued | 12 -continued |
|---|---|
| 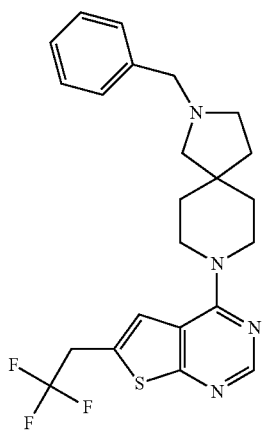 [SMILES: FC(F)(F)Cc1cc2c(N3CCC4(CCN(Cc5ccccc5)C4)CC3)ncnc2s1] | 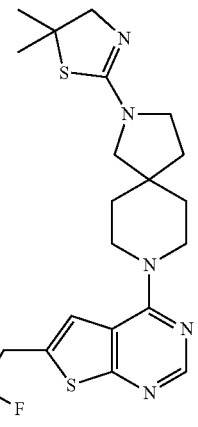 |
| 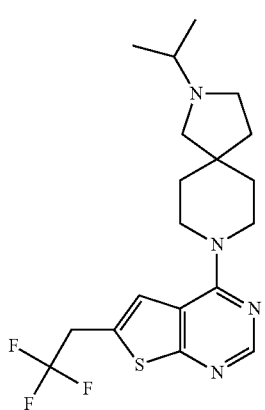 [SMILES: CC(C)N1CCC2(CCN(c3ncnc4sc(CC(F)(F)F)cc34)CC2)C1] | 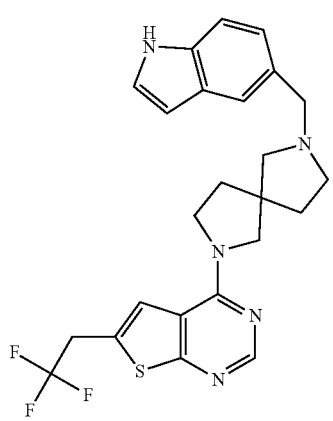 |
| 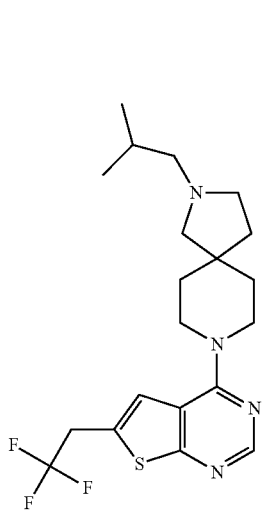 [SMILES: CC(C)CN1CCC2(CCN(c3ncnc4sc(CC(F)(F)F)cc34)CC2)C1]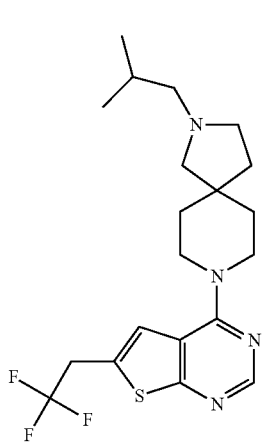 | 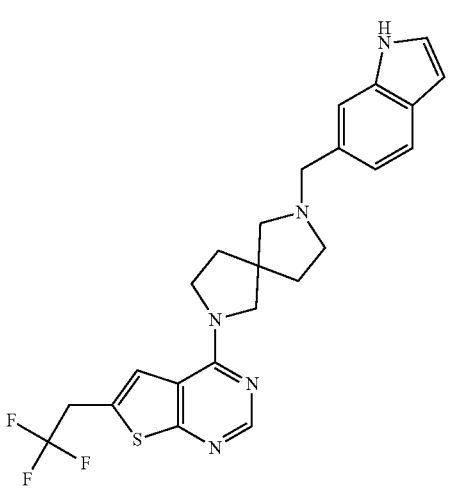 [SMILES: FC(F)(F)Cc1cc2c(N3CCC4(CCN(Cc5ccc6cc[nH]c6c5)C4)C3)ncnc2s1] |

-continued
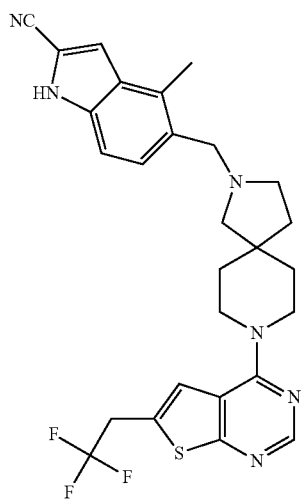 [SMILES: Cc1c(CN2CCC3(CCN(c4ncnc5sc(CC(F)(F)F)cc45)CC3)C2)ccc2[nH]c(C#N)cc12]
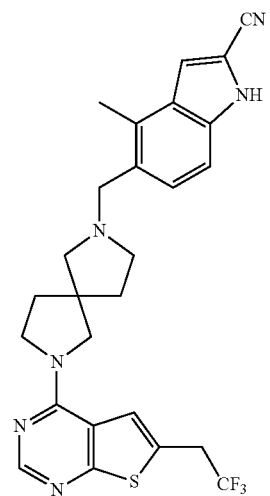 [SMILES: Cc1c(CN2CCC3(CCN(c4ncnc5sc(CC(F)(F)F)cc45)C3)C2)ccc2[nH]c(C#N)cc12]
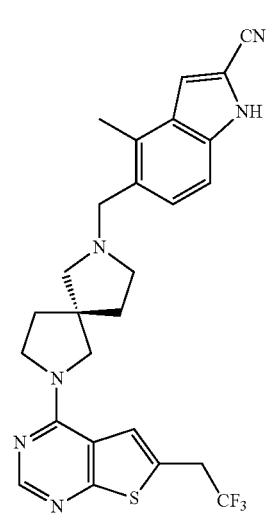 [SMILES: Cc1c(CN2CC[C@@]3(CCN(c4ncnc5sc(CC(F)(F)F)cc45)C3)C2)ccc2[nH]c(C#N)cc12]
-continued
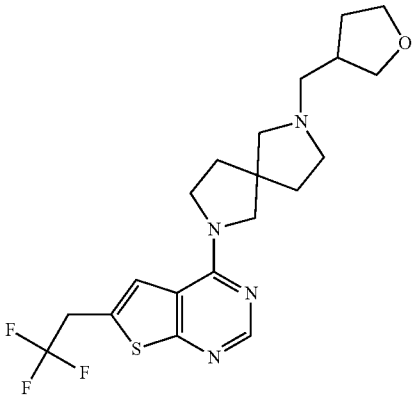 [SMILES: FC(F)(F)Cc1cc2c(N3CCC4(CCN(CC5CCOC5)C4)C3)ncnc2s1]
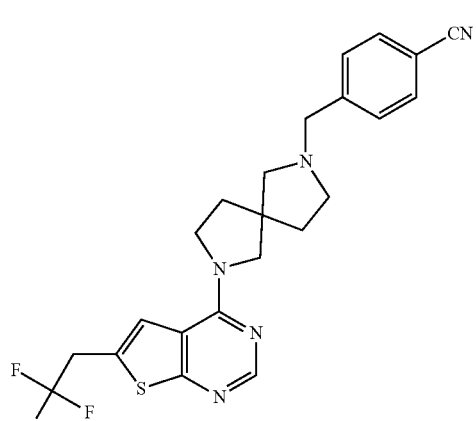
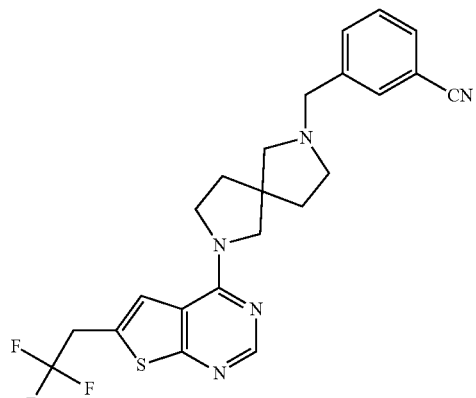

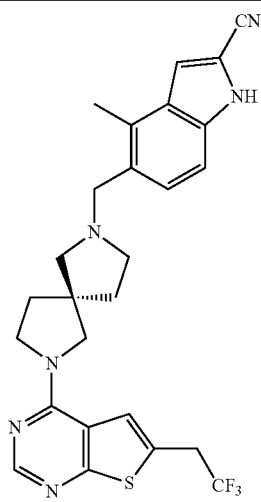
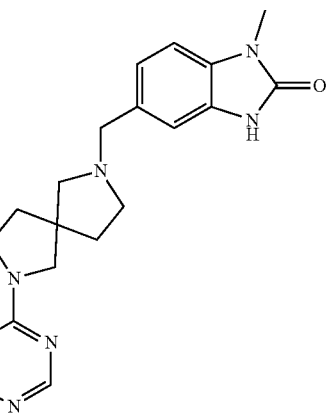
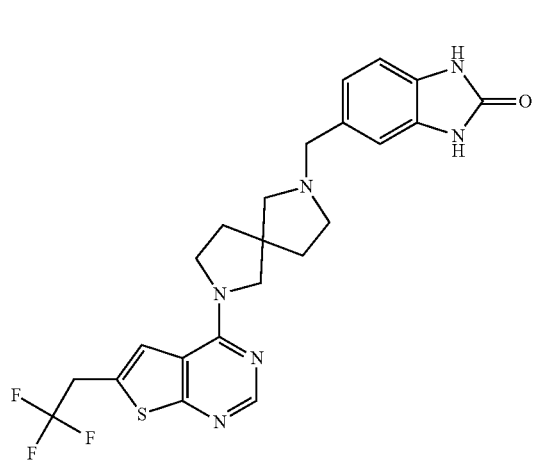 [SMILES: O=c1[nH]c2ccc(CN3CCC4(CCN(c5ncnc6sc(CC(F)(F)F)cc56)C4)C3)cc2[nH]1]
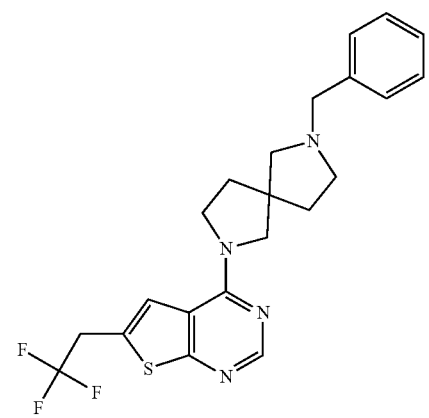
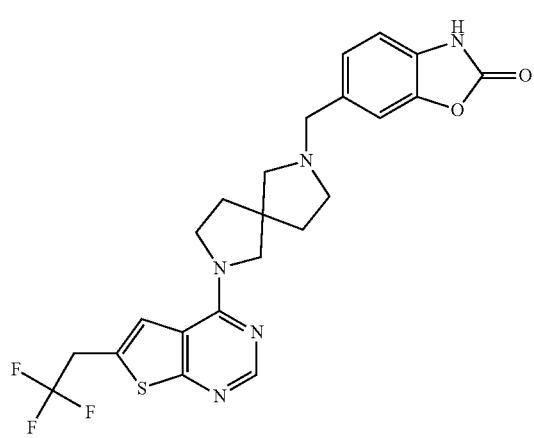 [SMILES: O=c1[nH]c2ccc(CN3CCC4(CCN(c5ncnc6sc(CC(F)(F)F)cc56)C4)C3)cc2o1]
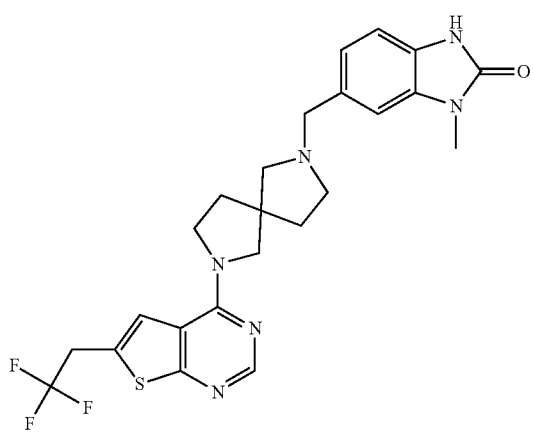 [SMILES: Cn1c(=O)[nH]c2ccc(CN3CCC4(CCN(c5ncnc6sc(CC(F)(F)F)cc56)C4)C3)cc21]

17
-continued
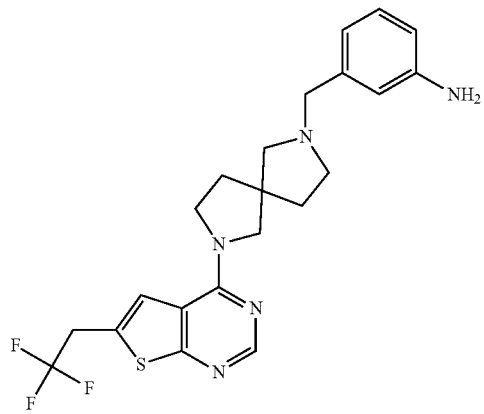 [SMILES: Nc1cccc(CN2CCC3(CCN(c4ncnc5sc(CC(F)(F)F)cc45)C3)C2)c1]
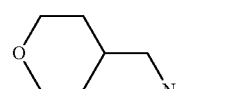
18
-continued
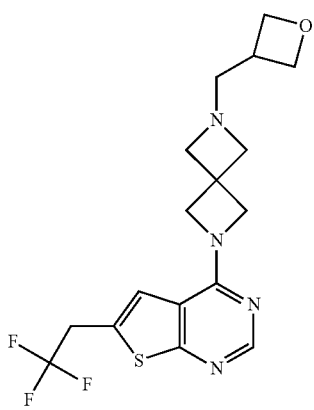 [SMILES: FC(F)(F)Cc1cc2c(N3CC4(CN(CC5COC5)C4)C3)ncnc2s1]
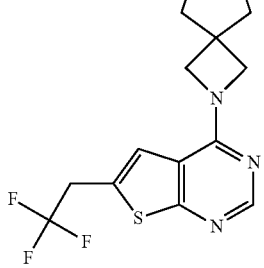
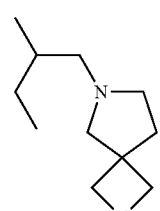
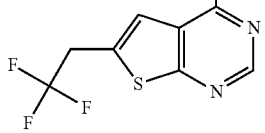
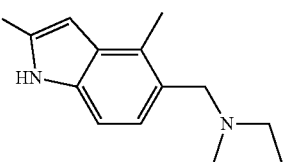
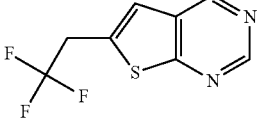

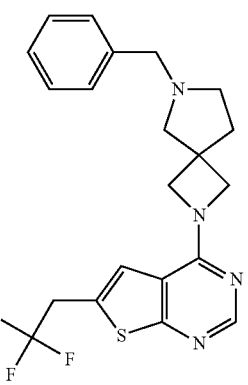
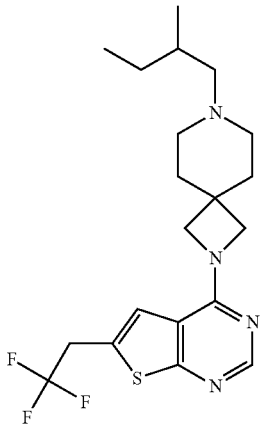 [SMILES: CCC(C)CN1CCC2(CC1)CN(c1ncnc3sc(CC(F)(F)F)cc13)C2]
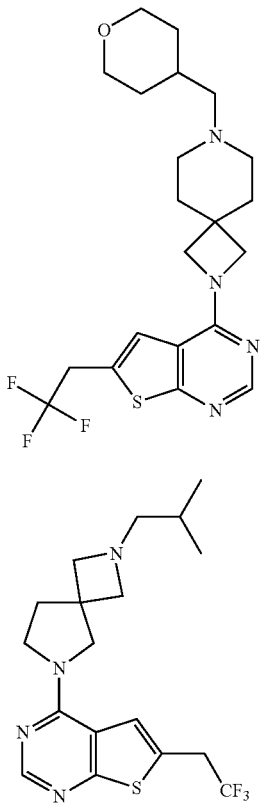

-continued
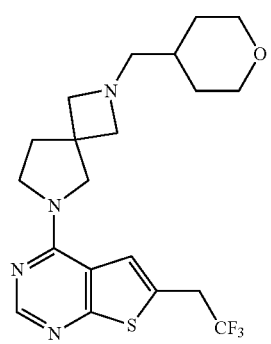 [SMILES: FC(F)(F)Cc1cc2c(N3CCC4(CN(CC5CCOCC5)C4)C3)ncnc2s1]
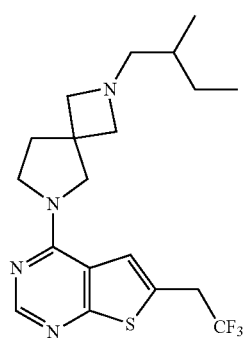 [SMILES: CCC(C)CN1CC2(CCN(c3ncnc4sc(CC(F)(F)F)cc34)C2)C1]
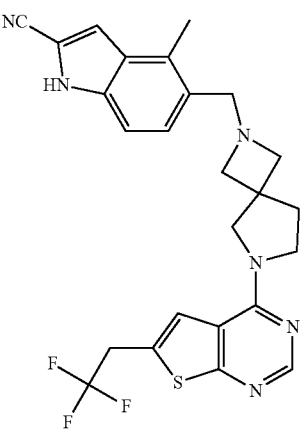 [SMILES: Cc1c(CN2CC3(CCN(c4ncnc5sc(CC(F)(F)F)cc45)C3)C2)ccc2[nH]c(C#N)cc12]
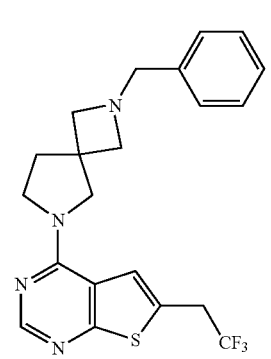 [SMILES: FC(F)(F)Cc1cc2c(N3CCC4(CN(Cc5ccccc5)C4)C3)ncnc2s1]
-continued
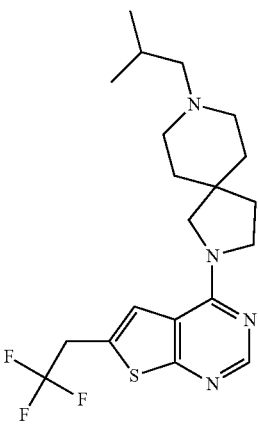 [SMILES: CC(C)CN1CCC2(CC1)CCN(c1ncnc3sc(CC(F)(F)F)cc13)C2]
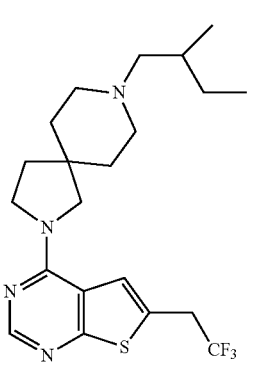 [SMILES: CCC(C)CN1CCC2(CC1)CCN(c1ncnc3sc(CC(F)(F)F)cc13)C2]
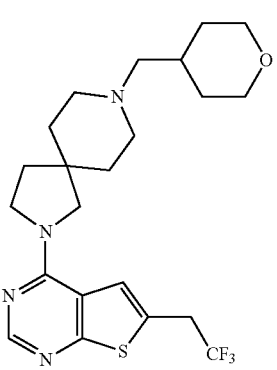 [SMILES: FC(F)(F)Cc1cc2c(N3CCC4(CCN(CC5CCOCC5)CC4)C3)ncnc2s1]
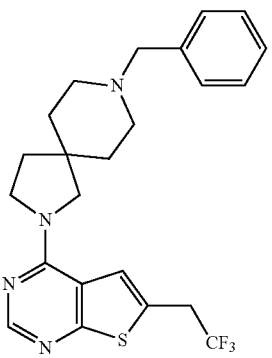 [SMILES: FC(F)(F)Cc1cc2c(N3CCC4(CCN(Cc5ccccc5)CC4)C3)ncnc2s1]

-continued

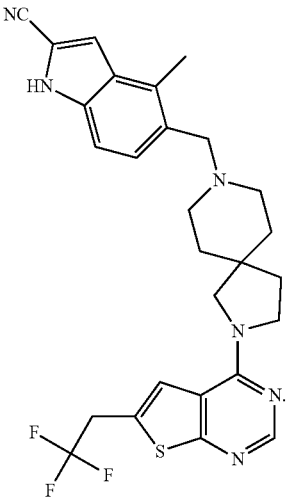 [SMILES: Cc1c(CN2CCC3(CC2)CCN(c2ncnc4sc(CC(F)(F)F)cc24)C3)ccc2[nH]c(C#N)cc12]

It is to be understood that the above proviso applies to all embodiments of the present invention described hereinafter.

The present invention also relates to a pharmaceutical composition comprising a therapeutically effective amount of a compound of Formula (I), a pharmaceutically acceptable salt, or a solvate thereof, and a pharmaceutically acceptable carrier or excipient.

Additionally, the invention relates to a compound of Formula (I), a pharmaceutically acceptable salt, or a solvate thereof, for use as a medicament, and to a compound of Formula (I), a pharmaceutically acceptable salt, or a solvate thereof, for use in the treatment or in the prevention of cancer, myelodysplastic syndrome (MDS) and diabetes.

In a particular embodiment, the invention relates to a compound of Formula (I), a pharmaceutically acceptable salt, or a solvate thereof, for use in the treatment or in the prevention of cancer.

In a specific embodiment said cancer is selected from leukemias, myeloma or a solid tumor cancer (e.g. prostate cancer, lung cancer, breast cancer, pancreatic cancer, colon cancer, liver cancer, melanoma and glioblastoma, etc.). In some embodiments, the leukemias include acute leukemias, chronic leukemias, myeloid leukemias, myelogeneous leukemias, lymphoblastic leukemias, lymphocytic leukemias, Acute myelogeneous leukemias (AML), Chronic myelogenous leukemias (CML), Acute lymphoblastic leukemias (ALL), Chronic lymphocytic leukemias (CLL), T cell prolymphocytic leukemias (T-PLL), Large granular lymphocytic leukemia, Hairy cell leukemia (HCL), MLL-rearranged leukemias, MLL-PTD leukemias, MLL amplified leukemias, MLL-positive leukemias, leukemias exhibiting HOX/MEIS1 gene expression signatures etc.

The invention also relates to the use of a compound of Formula (I), a pharmaceutically acceptable salt, or a solvate thereof, in combination with an additional pharmaceutical agent for use in the treatment or prevention of cancer, myelodysplastic syndrome (MDS) and diabetes.

Furthermore, the invention relates to a process for preparing a pharmaceutical composition according to the invention, characterized in that a pharmaceutically acceptable carrier is intimately mixed with a therapeutically effective amount of a compound of Formula (I), a pharmaceutically acceptable salt, or a solvate thereof.

The invention also relates to a product comprising a compound of Formula (I), a pharmaceutically acceptable salt, or a solvate thereof, and an additional pharmaceutical agent, as a combined preparation for simultaneous, separate or sequential use in the treatment or prevention of cancer, myelodysplastic syndrome (MDS) and diabetes.

Additionally, the invention relates to a method of treating or preventing a cell proliferative disease in a warm-blooded animal which comprises administering to the said animal an effective amount of a compound of Formula (I), a pharmaceutically acceptable salt, or a solvate thereof, as defined herein, or a pharmaceutical composition or combination as defined herein.

DETAILED DESCRIPTION OF THE INVENTION

The term 'halo' or 'halogen' as used herein represents fluoro, chloro, bromo and iodo.

The prefix '$C_{x-y}$' (where x and y are integers) as used herein refers to the number of carbon atoms in a given group. Thus, a $C_{1-6}$alkyl group contains from 1 to 6 carbon atoms, a $C_{3-6}$cycloalkyl group contains from 3 to 6 carbon atoms, and so on.

The term '$C_{1-4}$alkyl' as used herein as a group or part of a group represents a straight or branched chain saturated hydrocarbon radical having from 1 to 4 carbon atoms, such as methyl, ethyl, n-propyl, isopropyl, n-butyl, s-butyl, t-butyl and the like.

The term '$C_{2-4}$alkyl' as used herein as a group or part of a group represents a straight or branched chain saturated hydrocarbon radical having from 2 to 4 carbon atoms, such as ethyl, n-propyl, isopropyl, n-butyl, s-butyl, t-butyl and the like.

The term '$C_{1-6}$alkyl' as used herein as a group or part of a group represents a straight or branched chain saturated hydrocarbon radical having from 1 to 6 carbon atoms such as the groups defined for $C_{1-4}$alkyl and n-pentyl, n-hexyl, 2-methylbutyl and the like.

The term '$C_{3-6}$alkyl' as used herein as a group or part of a group represents a straight or branched chain saturated hydrocarbon radical having from 3 to 6 carbon atoms such as n-propyl, isopropyl, n-butyl, s-butyl, t-butyl, n-pentyl, n-hexyl, 2-methylbutyl and the like.

The term '$C_{3-5}$cycloalkyl' as used herein as a group or part of a group defines a saturated, cyclic hydrocarbon radical having from 3 to 5 carbon atoms, such as cyclopropyl, cyclobutyl and cyclopentyl.

The term 'spirobicyclic' as used herein as group or part of a group represents cyclic systems wherein two cycles are joined at a single atom. Examples of these systems are 7- to 10-membered saturated spiroheterobicyclic systems containing one or two N-atoms, wherein one of the nitrogen atoms is always linked to the thienopyrimidinyl heterocycle in the compounds of Formula (I) as defined herein. Such spirocyclic systems include, but are not limited to systems resulting from the combination of e.g. piperidine, pyrrolidine, azetidine, and cyclobutane rings. Examples of such systems include, but are not limited to (a), (b), (c), (d), (e), (f) and (g) below and the like

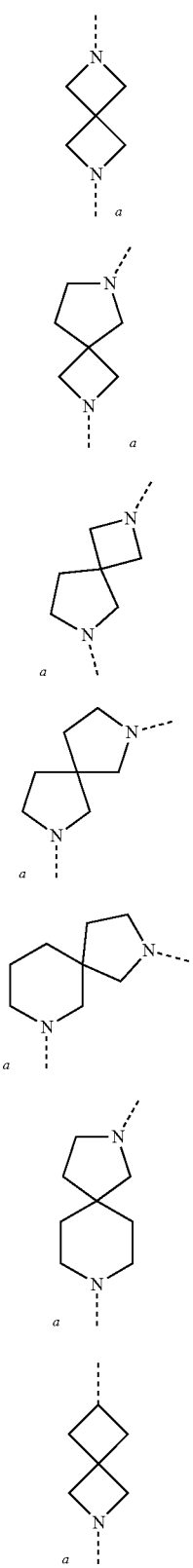

wherein a represents the position of linkage to the thienopyrimidinyl heterocycle. The skilled person will understand that in these particular examples, the options for -L²-R³ defined herein when L² is linked to a nitrogen atom of L¹, apply to examples (a)-(f); while the options for -L²-R³ defined herein when L² is linked to a carbon atom of L¹, apply to example (g).

Examples of 7- to 10-membered saturated spirocarbobicyclic systems include, but are not limited to

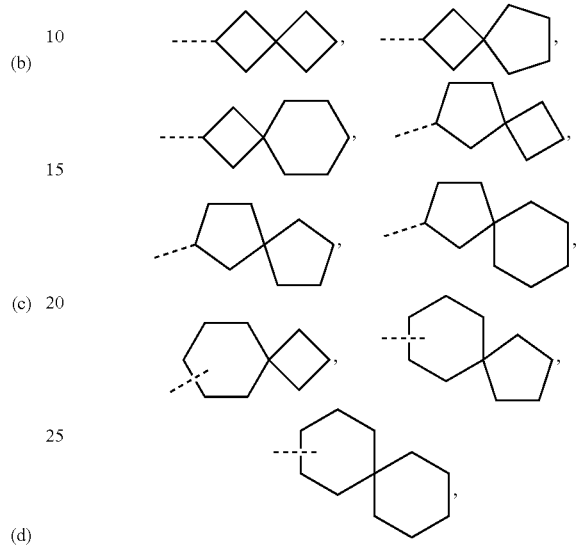

and the like.

In general, whenever the term 'substituted' is used in the present invention, it is meant, unless otherwise indicated or clear from the context, to indicate that one or more hydrogens, in particular from 1 to 4 hydrogens, more in particular from 1 to 3 hydrogens, preferably 1 or 2 hydrogens, more preferably 1 hydrogen, on the atom or radical indicated in the expression using 'substituted' are replaced with a selection from the indicated group, provided that the normal valency is not exceeded, and that the substitution results in a chemically stable compound, i.e. a compound that is sufficiently robust to survive isolation to a useful degree of purity from a reaction mixture.

Combinations of substituents and/or variables are permissible only if such combinations result in chemically stable compounds. 'Stable compound' is meant to indicate a compound that is sufficiently robust to survive isolation to a useful degree of purity from a reaction mixture.

The skilled person will understand that when an atom or radical is substituted with 'a substituent', it is meant that the atom or radical referred to is substituted with one substituent selected from the indicated group.

The skilled person will understand that the term 'optionally substituted' means that the atom or radical indicated in the expression using 'optionally substituted' may or may not be substituted (this means substituted or unsubstituted respectively).

When two or more substituents are present on a moiety they may, where possible and unless otherwise indicated or clear from the context, replace hydrogens on the same atom or they may replace hydrogen atoms on different atoms in the moiety.

It will be clear for the skilled person that, unless otherwise is indicated or is clear from the context, a substituent on a heterocyclyl group may replace any hydrogen atom on a ring carbon atom or on a ring heteroatom.

Within the context of this invention 'saturated' means 'fully saturated', if not otherwise specified.

A 'non-aromatic group' embraces unsaturated ring systems without aromatic character, partially saturated and fully saturated carbocyclic and heterocyclic ring systems. The term 'partially saturated' refers to rings wherein the ring structure(s) contain(s) at least one multiple bond e.g. a C=C, N=C bond. The term 'fully saturated' refers to rings where there are no multiple bonds between ring atoms. Thus, a 'non-aromatic heterocyclyl' is a non-aromatic monocyclic or bicyclic system, unless otherwise specified, having for example, 3 to 12 ring members, more usually 5 to 10 ring members. Examples of monocyclic groups are groups containing 4 to 7 ring members, more usually, 5 or 6 ring members. Examples of bicyclic groups are those containing 8 to 12, more usually 9 or 10 ring members.

Non-limiting examples of monocyclic heterocyclyl systems containing at least one heteroatom selected from nitrogen, oxygen or sulfur (N, O, S) include, but are not limited to 4- to 7-membered heterocyclyl systems such as azetidinyl, oxetanyl, pyrrolidinyl, tetrahydrofuranyl, piperidinyl, piperazinyl, pyranyl, dihydropyranyl, tetrahydropyranyl, morpholinyl, thiomorpholinyl, and tetrahydro-2H-thiopyranyl 1,1-dioxide, in particular azetidinyl, oxetanyl, pyrrolidinyl, tetrahydrofuranyl, piperidinyl, piperazinyl, pyranyl, dihydropyranyl, tetrahydropyranyl, morpholinyl, and thiomorpholiny. Non-limiting examples of bicyclic heterocyclyl systems containing at least one heteroatom selected from nitrogen, oxygen or sulfur (N, O, S) include, but are not limited to octahydro-1H-indolyl, indolinyl,

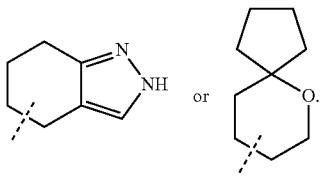

Unless otherwise specified, each can be bound to the remainder of the molecule of Formula (I) through any available ring carbon atom (C-linked) or nitrogen atom (N-linked), and may optionally be substituted, where possible, on carbon and/or nitrogen atoms according to the embodiments.

Examples of a C-linked 4- to 7-membered non-aromatic heterocyclyl containing at least one nitrogen atom include, but are not limited to, azetidinyl, pyrrolidinyl and piperidinyl, bound to the rest of the molecule through an available carbon atom.

The term 'C-linked 4- to 6-membered heterocyclyl containing an oxygen atom' as used herein alone or as part of another group, defines a saturated, cyclic hydrocarbon radical containing an oxygen atom having from 4 to 6 ring members, such as oxetanyl, tetrahydrofuranyl, and tetrahydropyranyl.

Whenever substituents are represented by chemical structure, '---' represents the bond of attachment to the remainder of the molecule of Formula (I).

Lines (such as '---') drawn into ring systems indicate that the bond may be attached to any of the suitable ring atoms.

Het$^1$ and Het$^2$ may be attached to the remainder of the molecule of Formula (I) through any available ring carbon or nitrogen atom as appropriate, if not otherwise specified.

It will be clear that a saturated cyclic moiety may, where possible, have substituents on both carbon and N-atoms, unless otherwise is indicated or is clear from the context.

It will be clear that when $L^2$ is >SO$_2$, this is equivalent to $L^2$ is —SO$_2$—. It will be clear that when $L^2$ is >CR$^{4a}$R$^{4b}$, this is equivalent to L is

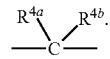

For example, in compound 1, $L^2$ is >CR$^{4a}$R$^{4b}$ wherein both R$^{4a}$ and R$^{4b}$ are hydrogen.

Similar, it will be clear that when $L^2$ is >CR$^{4c}$R$^{4d}$, this is equivalent to L is

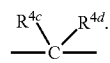

When any variable occurs more than one time in any constituent, each definition is independent.

When any variable occurs more than one time in any formula (e.g. Formula (I)), each definition is independent.

The term 'subject' as used herein, refers to an animal, preferably a mammal (e.g. cat, dog, primate or human), more preferably a human, who is or has been the object of treatment, observation or experiment.

The term 'therapeutically effective amount' as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term 'composition' is intended to encompass a product comprising the specified ingredients in the specified amounts, as well as any product which results, directly or indirectly, from combinations of the specified ingredients in the specified amounts.

The term 'treatment', as used herein, is intended to refer to all processes wherein there may be a slowing, interrupting, arresting or stopping of the progression of a disease, but does not necessarily indicate a total elimination of all symptoms.

The term 'compound(s) of the (present) invention' or 'compound(s) according to the (present) invention' as used herein, is meant to include the compounds of Formula (I) and the pharmaceutically acceptable salts, and the solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term 'compound(s) of Formula (I)' is meant to include the tautomers thereof and the stereoisomeric forms thereof.

The terms 'stereoisomers', 'stereoisomeric forms' or 'stereochemically isomeric forms' hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic saturated or partially saturated radicals may have either the cis- or trans-configuration; for example if a compound contains a disubstituted cycloalkyl group, the substituents may be in the cis or trans configuration.

Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above Formula (I) are intended to be included within the scope of the present invention. It follows that a single compound may exist in both stereoisomeric and tautomeric form.

Pharmaceutically acceptable salts include acid addition salts and base addition salts. Such salts may be formed by conventional means, for example by reaction of a free acid or a free base form with one or more equivalents of an appropriate base or acid, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable salts as mentioned hereinabove or hereinafter are meant to comprise the therapeutically active non-toxic acid and base salt forms which the compounds of Formula (I) and solvates thereof, are able to form.

Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine salt forms by treatment with appropriate organic and inorganic bases.

Appropriate base salt forms comprise, for example, the ammonium salts, the alkali and earth alkaline metal salts, e.g. the lithium, sodium, potassium, cesium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the solvent addition forms as well as the salts thereof, which the compounds of Formula (I) are able to form. Examples of such solvent addition forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and pharmaceutically acceptable salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature).

All isotopes and isotopic mixtures of any particular atom or element as specified herein are contemplated within the scope of the compounds of the invention, either naturally occurring or synthetically produced, either with natural abundance or in an isotopically enriched form. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{122}I$, $^{123}I$, $^{125}I$, $^{131}I$, $^{75}Br$, $^{76}Br$, $^{77}Br$ and $^{82}Br$.

Preferably, the radioactive isotope is selected from the group of $^{2}$H, $^{3}$H, $^{11}$C and $^{18}$F. More preferably, the radioactive isotope is $^{2}$H. In particular, deuterated compounds are intended to be included within the scope of the present invention.

Certain isotopically-labeled compounds of the present invention (e.g., those labeled with $^{3}$H and $^{14}$C) may be useful for example in substrate tissue distribution assays. Tritiated ($^{3}$H) and carbon-14 ($^{14}$C) isotopes are useful for their ease of preparation and detectability.

Further, substitution with heavier isotopes such as deuterium (i.e., $^{2}$H may afford certain therapeutic advantages resulting from greater metabolic stability (e.g., increased in vivo half-life or reduced dosage requirements) and hence may be preferred in some circumstances. Thus, in a particular embodiment of the present invention, R$^{2}$ is selected from hydrogen or deuterium, in particular deuterium. In another embodiment, L$^{2}$ can be >C($^{2}$H)$_{2}$. Positron emitting isotopes such as $^{15}$O, $^{13}$N, $^{11}$C and $^{18}$F are useful for positron emission tomography (PET) studies. PET imaging in cancer finds utility in helping locate and identify tumours, stage the disease and determine suitable treatment. Human cancer cells overexpress many receptors or proteins that are potential disease-specific molecular targets. Radiolabelled tracers that bind with high affinity and specificity to such receptors or proteins on tumour cells have great potential for diagnostic imaging and targeted radionuclide therapy (Charron, Carlie L. et al. Tetrahedron Lett. 2016, 57(37), 4119-4127). Additionally, target-specific PET radiotracers may be used as biomarkers to examine and evaluate pathology, by for example, measuring target expression and treatment response (Austin R. et al. Cancer Letters (2016), doi: 10.1016/j.canlet.2016.05.008).

The present invention relates in particular to compounds of Formula (I) and the pharmaceutically acceptable salts, and the solvates thereof, or any subgroup thereof as mentioned in any of the embodiments, wherein also the following compound and pharmaceutically acceptable addition salts, and solvates thereof, are excluded:

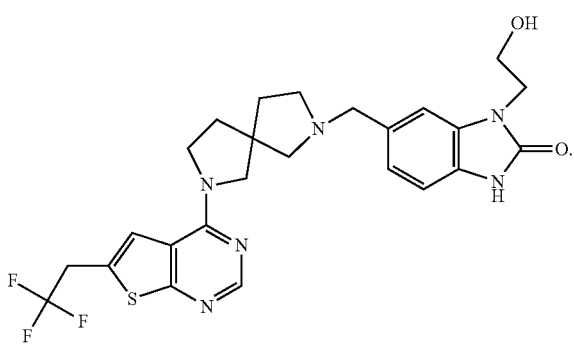 [SMILES: O=c1[nH]c2ccc(CN3CCC4(CCN(c5ncnc6sc(CC(F)(F)F)cc56)C4)C3)cc2n1CCO]

The present invention relates in particular to compounds of Formula (I) and the pharmaceutically acceptable salts, and the solvates thereof, or any subgroup thereof as mentioned in any of the embodiments, wherein the intermediates and compounds described in WO2017/112768, in as far as they are covered by the present invention, are excluded.

The present invention relates in particular to compounds of Formula (I) as defined herein, and the tautomers and the stereoisomeric forms thereof, wherein
R$^{1}$ is CF$_{3}$;
R$^{2}$ is selected from the group consisting of hydrogen and CH$_{3}$;

L$^{1}$ represents a 7- to 10-membered saturated spiroheterobicyclic system containing one or two N-atoms provided that it is N-linked to the thienopyrimidinyl heterocycle; and -L$^{2}$-R$^{3}$ is selected from (a), (b), (c), (d), (f) or (g), wherein (a) L$^{2}$ is selected from the group consisting of >CR$^{4a}$R$^{4b}$, and —CHR$^{4a}$CHR$^{5}$—; wherein L$^{2}$ is linked to a nitrogen atom of L$^{1}$; R$^{4a}$ is selected from the group consisting of hydrogen; —C(=O)NR$^{7a}$R$^{7b}$; C$_{1-4}$alkyl optionally substituted with a substituent selected from the group consisting of —OR$^{8}$, and —NR$^{9a}$R$^{9b}$; and C-linked 4- to 7-membered non-aromatic heterocyclyl containing at least one nitrogen atom;

R$^{5}$ is selected from the group consisting of hydrogen; —OR$^{6}$; and C$_{1-4}$alkyl;

R$^{4b}$ is selected from the group consisting of hydrogen and methyl; or

R$^{4a}$ and R$^{4b}$ together with the carbon atom to which they are attached form a C$_{3-5}$cycloalkyl or a C-linked 4- to 6-membered heterocyclyl containing an oxygen atom; wherein R$^{6}$, R$^{7a}$, R$^{7b}$, R$^{8}$, R$^{9a}$ and R$^{9b}$ are each independently selected from the group consisting of hydrogen; and C$_{2-4}$alkyl substituted with a substituent selected from the group consisting of —OR$^{11}$ and —NR$^{10a}$R$^{10b}$; wherein R$^{10a}$, R$^{10b}$ and R$^{11}$ are each independently selected from the group consisting of hydrogen; and C$_{1-4}$alkyl; and R$^{3}$ is selected from the group consisting of Ar, Het$^{1}$, Het$^{2}$, and a 7- to 10-membered saturated spirocarbobicyclic system; or (b) L$^{2}$ is >CR$^{4c}$R$^{4d}$, wherein R$^{4c}$ and R$^{4d}$ are hydrogen; and R$^{3}$ is

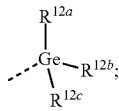

wherein R$^{12a}$, R$^{12b}$, and R$^{12c}$ are C$_{1-6}$alkyl 1; or (c) -L$^{2}$-R$^{3}$ is C$_{1-6}$alkyl optionally substituted with one, two or three fluoro substituents; or (d) L$^{2}$ is O and R$^{3}$ is —CH$_{2}$—Ar; or (f) -L$^{2}$-R$^{3}$ is

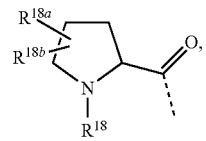

wherein
R$^{18}$ is selected from the group consisting of hydrogen; and C$_{1-4}$alkyl;
R$^{18a}$ is selected from the group consisting of hydrogen, and fluoro;
R$^{18b}$ is selected from the group consisting of fluoro, —OC$_{1-4}$alkyl, and C$_{1-4}$alkyl optionally substituted with 1, 2 or 3 fluoro substituents; or
R$^{18a}$ and R$^{18b}$ are bound to the same carbon atom and together form a C$_{3-5}$cycloalkyl; or (g) -$L^2$-$R^3$ is

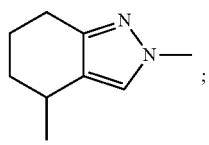

and wherein

Ar is phenyl which may be optionally substituted with one, two, or three substituents each independently selected from the group consisting of halo, —$OR^{24}$, and $C_{1-4}$alkyl optionally substituted with —$OR^{26}$;

$Het^1$ is a monocyclic heteroaryl selected from the group consisting of pyridyl, 4-, 5- or 6-pyrimidinyl, pyrazinyl, pyridazinyl, pyrrolyl, pyrazolyl, imidazolyl, 4- or 5-thiazolyl, isothiazolyl, and isoxazolyl; or a bicyclic heteroaryl selected from the group consisting of indolyl, imidazopyridinyl; each of which may be optionally substituted with one, two, or three substituents each independently selected from the group consisting of halo, —CN, —$OR^{24}$, and $C_{1-4}$alkyl optionally substituted with a substituent selected from the group consisting of —CN, —$OR^{26}$, and —$NR^{27a}R^{27b}$; and $Het^2$ is a non-aromatic heterocyclyl optionally substituted with one, two, or three substituents each independently selected from the group consisting of halo, —CN, and $C_{1-4}$alkyl optionally substituted with —$OR^{26}$;
wherein
$R^{24}$, $R^{26}$, $R^{27a}$, and $R^{27b}$ are each independently selected from the group consisting of hydrogen; $C_{1-4}$alkyl; and $C_{2-4}$alkyl substituted with —$NR^{28a}R^{28b}$; wherein $R^{28a}$ and $R^{28b}$ are hydrogen;
and the pharmaceutically acceptable salts and the solvates thereof.

The present invention relates in particular to compounds of Formula (I) as defined herein, and the tautomers and the stereoisomeric forms thereof, wherein
(a) $L^2$ is selected from the group consisting of >$SO_2$, >$CR^{4a}R^{4b}$, and —$CHR^{4a}CHR^5$—; wherein
 (i) when $L^2$ is linked to a carbon atom of $L^1$, then $R^{4a}$ and $R^5$ are each independently selected from the group consisting of hydrogen; —$OR^6$; —$NR^{7a}R^{7b}$; —C(=O)$NR^{7a}R^{7b}$; $C_{1-4}$alkyl optionally substituted with a substituent selected from the group consisting of fluoro, —CN, —$OR^8$, and —$NR^{9a}R^{9b}$; and C-linked 4- to 7-membered non-aromatic heterocyclyl containing at least one nitrogen, oxygen or sulfur atom;
 (ii) when $L^2$ is linked to a nitrogen atom of $L^1$, then $R^{4a}$ is selected from the group consisting of hydrogen; —C(=O)$NR^{7a}R^{7b}$; $C_{1-4}$alkyl optionally substituted with a substituent selected from the group consisting of fluoro, —CN, —$OR^8$, and —$NR^{9a}R^{9b}$; and C-linked 4- to 7-membered non-aromatic heterocyclyl containing at least one nitrogen, oxygen or sulfur atom;
$R^5$ is selected from the group consisting of hydrogen; —$OR^6$; —$NR^{7a}R^{7b}$; —C(=O)$NR^{7a}R^{7b}$; $C_{1-4}$alkyl optionally substituted with a substituent selected from the group consisting of fluoro, —CN, —$OR^8$, and —$NR^{9a}R^{9b}$; and C-linked 4- to 7-membered non-aromatic heterocyclyl containing at least one nitrogen, oxygen or sulfur atom;
$R^{4b}$ is selected from the group consisting of hydrogen and methyl; or >$CR^{4a}R^{4b}$ form a >$C_{3-5}$cycloalkanediyl or a >C-linked 4- to 6-membered heterocyclediyl containing an oxygen atom; wherein
$R^6$, $R^{7a}$, $R^{7b}$, $R^8$, $R^{9a}$ and $R^{9b}$ are each independently selected from the group consisting of hydrogen; $C_{1-4}$alkyl optionally substituted with a substituent selected from the group consisting of fluoro, —CN, and —C(=O)$NR^{10a}R^{10b}$; and $C_{2-4}$alkyl substituted with a substituent selected from the group consisting of —$OR^{11}$ and —$NR^{10a}R^{10b}$; wherein
$R^{10a}$, $R^{10b}$ and $R^{11}$ are each independently selected from the group consisting of hydrogen; and $C_{1-4}$alkyl; and
$R^3$ is selected from the group consisting of Ar, $Het^1$, $Het^2$, and a 7- to 10-membered saturated spirocarbobicyclic system; or
(b) $L^2$ is selected from the group consisting of >$CR^{4c}R^{4d}$ and —$CHR^{4c}CHR^{5a}$—, wherein $R^{4c}$, $R^{4d}$, and $R^{5a}$ are each independently selected from the group consisting of hydrogen and $C_{1-4}$alkyl; and
$R^3$ is selected from the group consisting of

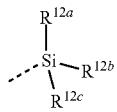

and

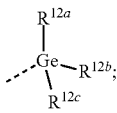

wherein $R^{12a}$, $R^{12b}$, and $R^{12c}$ are each independently selected from the group consisting of $C_{1-6}$alkyl optionally substituted with a —OH or a —$NH_2$ substituent; or
(c) -$L^2$-$R^3$ is $C_{1-6}$alkyl optionally substituted with one, two or three fluoro substituents; or
(d) $L^2$ is O and $R^3$ is selected from the group consisting of Ar, $Het^1$; —$CH_2$—Ar, —$CH_2$-$Het^1$, and —$CH_2$-(a 7- to 10-membered saturated spirocarbobicyclic system); when $L^2$ is linked to a carbon atom of $L^1$; or
(e) -$L^2$-$R^3$ is selected from the group consisting of

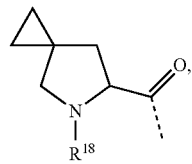

wherein
$R^{18}$ is hydrogen; or
(f) -$L^2$-$R^3$ is

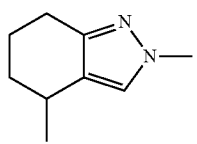

or

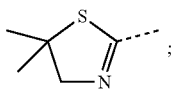

and wherein
Ar is phenyl optionally substituted with one, two, or three substituents each independently selected from the group consisting of halo, —CN, and $C_{1-4}$alkyl optionally substituted with a substituent selected from the group consisting of fluoro, —CN, —OR$^{26}$, —NR$^{27a}$R$^{27b}$, and —C(=O)NR$^{27a}$R$^{27b}$;

Het$^1$ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, thiadiazolyl, and isoxazolyl; or a bicyclic heteroaryl selected from imidazopyridinyl, in particular imidazo[1,2-a]pyridinyl; each of which may be optionally substituted with one, two, or three substituents each independently selected from the group consisting of halo, —CN, and $C_{1-4}$alkyl optionally substituted with a substituent selected from the group consisting of fluoro, —CN, —OR$^{26}$, —NR$^{27a}$R$^{27b}$, and —C(=O)NR$^{27a}$R$^{27b}$; and Het$^2$ is a non-aromatic heterocyclyl selected from azetidinyl, pyrrolidinyl and piperidinyl;
wherein
R$^{26}$, R$^{27a}$, and R$^{27b}$ are each independently selected from the group consisting of hydrogen and $C_{1-4}$alkyl;
and the pharmaceutically acceptable salts and the solvates thereof.

The present invention relates in particular to compounds of Formula (I) as defined herein, and the tautomers and the stereoisomeric forms thereof, wherein
R$^1$ is selected from the group consisting of CH$_3$, CH$_2$F, CHF$_2$, and CF$_3$;
R$^2$ is selected from the group consisting of hydrogen and CH$_3$;
L$^1$ represents a 7- to 10-membered saturated spiroheterobicyclic system containing one or two N-atoms provided that it is N-linked to the thienopyrimidinyl heterocycle; and
-L$^2$-R$^3$ is selected from (a), (b), (d), (e), or (f), wherein
(a) L$^2$ is selected from the group consisting of >SO$_2$, >CR$^{4a}$R$^{4b}$, and —CHR$^{4a}$CHR$^5$—; wherein
  (i) when L$^2$ is linked to a carbon atom of L$^1$, then R$^{4a}$ and R$^5$ are each independently selected from the group consisting of hydrogen; —OR$^6$; —NR$^{7a}$R$^{7b}$; —C(=O)NR$^{7a}$R$^{7b}$; $C_{1-4}$alkyl optionally substituted with a substituent selected from the group consisting of fluoro, —CN, —OR$^8$, and —NR$^{9a}$R$^{9b}$; and C-linked 4- to 7-membered non-aromatic heterocyclyl containing at least one nitrogen, oxygen or sulfur atom;
  (ii) when L$^2$ is linked to a nitrogen atom of L$^1$, then R$^{4a}$ is selected from the group consisting of —C(=O)NR$^{7a}$R$^{7b}$; $C_{1-4}$alkyl optionally substituted with a substituent selected from the group consisting of fluoro, —CN, —OR$^8$, and —NR$^{9a}$R$^{9b}$; and C-linked 4- to 7-membered non-aromatic heterocyclyl containing at least one nitrogen, oxygen or sulfur atom;
  R$^5$ is selected from the group consisting of hydrogen; —OR$^6$; —NR$^{7a}$R$^{7b}$; —C(=O)NR$^{7a}$R$^{7b}$; $C_{1-4}$alkyl optionally substituted with a substituent selected from the group consisting of fluoro, —CN, —OR$^8$, and —NR$^{9a}$R$^{9b}$; and C-linked 4- to 7-membered non-aromatic heterocyclyl containing at least one nitrogen, oxygen or sulfur atom;

R$^{4b}$ is selected from the group consisting of hydrogen and methyl; or R$^{4a}$ and R$^{4b}$ together with the carbon atom to which they are attached form a $C_{3-5}$cycloalkyl or a C-linked 4- to 6-membered heterocyclyl containing an oxygen atom; wherein
R$^6$, R$^{7a}$, R$^{7b}$, R$^8$, R$^{9a}$ and R$^{9b}$ are each independently selected from the group consisting of hydrogen; $C_{1-4}$alkyl optionally substituted with a substituent selected from the group consisting of fluoro, —CN, and —C(=O)NR$^{10a}$R$^{10b}$; and $C_{2-4}$alkyl substituted with a substituent selected from the group consisting of —OR$^{11}$ and —NR$^{10a}$R$^{10b}$; wherein
R$^{10a}$, R$^{10b}$ and R$^{11}$ are each independently selected from the group consisting of hydrogen; $C_{1-4}$alkyl; and C-linked 4- to 7-membered non-aromatic heterocyclyl containing at least one nitrogen, oxygen or sulfur atom; and
R$^3$ is selected from the group consisting of Ar, Het$^1$, Het$^2$, and a 7- to 10-membered saturated spirocarbobicyclic system; or
(b) L$^2$ is selected from the group consisting of >CR$^{4c}$R$^{4d}$ and —CHR$^{4c}$CHR$^{5a}$—, wherein R$^{4c}$, R$^{4d}$, and R$^{5a}$ are each independently selected from the group consisting of hydrogen and $C_{1-4}$alkyl; and
R$^3$ is selected from the group consisting of

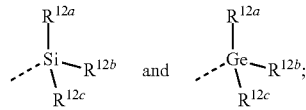

wherein R$^{12a}$, R$^{12b}$, and R$^{12c}$ are each independently selected from the group consisting of $C_{1-6}$alkyl optionally substituted with a —OH or a —NH$_2$ substituent; and —OC$_{1-6}$alkyl; or
(d) L$^2$ is O and R$^3$ is selected from the group consisting of $C_{3-6}$alkyl optionally substituted with one, two or three fluoro substituents; Ar; Het$^1$; Het$^2$; a 7- to 10-membered saturated spirocarbobicyclic system; —CH$_2$—Ar; —CH$_2$-Het; —CH$_2$-Het$^2$; and —CH$_2$-(a 7- to 10-membered saturated spirocarbobicyclic system); when L$^2$ is linked to a carbon atom of L$^1$; or
(e) -L$^2$-R$^3$ is —O—CHR$^5$—R$^3$ when L$^2$ is linked to a carbon atom of L$^1$, wherein
R$^5$ is selected from the group consisting of —C(=O)NR$^{13a}$R$^{13b}$; $C_{1-4}$alkyl optionally substituted with a substituent selected from the group consisting of fluoro, —OR$^{14}$, and —NR$^{15a}$R$^{15b}$; and C-linked 4- to 7-membered non-aromatic heterocyclyl containing at least one nitrogen, oxygen or sulfur atom; wherein
R$^{13a}$R$^{13b}$, R$^{14}$, R$^{15a}$ and R$^{15b}$ are each independently selected from the group consisting of hydrogen; $C_{1-4}$alkyl optionally substituted with a substituent selected from the group consisting of fluoro and —C(=O)NR$^{16a}$R$^{16b}$; and $C_{2-4}$alkyl substituted with a substituent selected from the group consisting of —OR$^{17}$ and —NR$^{16a}$R$^{16b}$; wherein
R$^{16a}$, R$^{16b}$ and R$^{17}$ are each independently selected from the group consisting of hydrogen; $C_{1-4}$alkyl; and C-linked 4- to 7-membered non-aromatic heterocyclyl containing at least one nitrogen, oxygen or sulfur atom; and
R$^3$ is selected from the group consisting of hydrogen; $C_{1-4}$alkyl optionally substituted with one, two, or three fluoro substituents; —CN; Ar, Het¹; Het²; and a 7- to 10-membered saturated spirocarbobicyclic system; or (f) -L²-R³ is

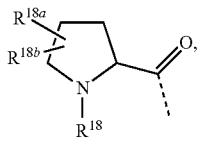

wherein
R¹⁸ is selected from the group consisting of hydrogen; $C_{1-4}$alkyl optionally substituted with a fluoro or a —CN substituent; and $C_{2-4}$alkyl substituted with a substituent selected from the group consisting of —OR¹⁹ and —NR²⁰ᵃR²⁰ᵇ; wherein R¹⁹, R²⁰ᵃ and R²⁰ᵇ are each independently selected from the group consisting of hydrogen; $C_{1-4}$alkyl optionally substituted with a substituent selected from the group consisting of fluoro, —CN, and —C(=O)NR²¹ᵃR²¹ᵇ; $C_{2-4}$alkyl substituted with a substituent selected from the group consisting of —OR²² and —NR²¹ᵃR²¹ᵇ; and C-linked 4- to 7-membered non-aromatic heterocyclyl containing at least one nitrogen, oxygen or sulfur atom; wherein R²¹ᵃ, R²¹ᵇ and R²² are each independently selected from the group consisting of hydrogen and $C_{1-4}$alkyl; and R¹⁸ᵃ is selected from the group consisting of hydrogen, fluoro and $C_{1-4}$alkyl;

R¹⁸ᵇ is selected from the group consisting of fluoro, —O$C_{1-4}$alkyl, and $C_{1-4}$alkyl optionally substituted with 1, 2 or 3 fluoro substituents; or R¹⁸ᵃ and R¹⁸ᵇ are bound to the same carbon atom and together form a $C_{3-5}$cycloalkyl or a C-linked 4- to 6-membered heterocyclyl containing an oxygen atom; and wherein Ar is phenyl or naphthyl, each of which may be optionally substituted with one, two, or three substituents each independently selected from the group consisting of halo, —CN, —OR²⁴, —NR²⁵ᵃR²⁵ᵇ, and $C_{1-4}$alkyl optionally substituted with a substituent selected from the group consisting of fluoro, —CN, —OR²⁶, —NR²⁷ᵃR²⁷ᵇ, and —C(=O)NR²⁷ᵃR²⁷ᵇ;

Het¹ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, thiadiazolyl, and isoxazolyl; or a bicyclic heteroaryl selected from the group consisting of imidazothiazolyl, imidazoimidazolyl, benzofuranyl, benzothiophenyl, benzimidazolyl, benzoxazolyl, isobenzoxazolyl, benzisoxazolyl, benzothiazolyl, benzisothiazolyl, isobenzofuranyl, indolyl, isoindolyl, indolizinyl, indolinyl, isoindolinyl, indazolyl, pyrazolopyridinyl, pyrazolopyrimidinyl, imidazopyridinyl, imidazopyrazinyl, imidazopyridazinyl; each of which may be optionally substituted with one, two, or three substituents each independently selected from the group consisting of halo, —CN, —OR²⁴, —NR²⁵ᵃR²⁵ᵇ, and $C_{1-4}$alkyl optionally substituted with a substituent selected from the group consisting of fluoro, —CN, —OR²⁶, —NR²⁷ᵃR²⁷ᵇ, and —C(=O)NR²⁷ᵃR²⁷ᵇ; and Het² is a non-aromatic heterocyclyl optionally substituted with one, two, or three substituents each independently selected from the group consisting of halo, —CN, —OR²⁴, —NR²⁵ᵃR²⁵ᵇ, and $C_{1-4}$alkyl optionally substituted with a substituent selected from the group consisting of fluoro, —CN, —OR²⁶, —NR²⁷ᵃR²⁷ᵇ, and —C(=O)NR²⁷ᵃR²⁷ᵇ;

wherein
R²⁴, R²⁵ᵃ, R²⁵ᵇ, R²⁶, R²⁷ᵃ, and R²⁷ᵇ are each independently selected from the group consisting of hydrogen; $C_{1-4}$alkyl optionally substituted with a substituent selected from the group consisting of fluoro and —C(=O)NR²⁸ᵃR²⁸ᵇ; and $C_{2-4}$alkyl substituted with a substituent selected from the group consisting of —OR²⁹ and —NR²⁸ᵃR²⁸ᵇ; wherein R²⁸ᵃ, R²⁸ᵇ and R²⁹ are each independently selected from the group consisting of hydrogen; $C_{1-4}$alkyl; and C-linked 4- to 7-membered non-aromatic heterocyclyl containing at least one nitrogen, oxygen or sulfur atom;

and the pharmaceutically acceptable salts and the solvates thereof.

The present invention relates in particular to compounds of Formula (I) as defined herein, and the tautomers and the stereoisomeric forms thereof, wherein R¹ is CF₃;

(a) L² is >CR⁴ᵃR⁴ᵇ; wherein
R⁴ᵃ is selected from the group consisting of hydrogen; —C(=O)NR⁷ᵃR⁷ᵇ; $C_{1-4}$alkyl; and C-linked 4- to 7-membered non-aromatic heterocyclyl containing at least one nitrogen, oxygen or sulfur atom; and R⁴ᵇ is selected from the group consisting of hydrogen and methyl; wherein R⁷ᵃ and R⁷ᵇ are each independently selected from the group consisting of hydrogen; $C_{1-4}$alkyl; and $C_{2-4}$alkyl substituted with a substituent selected from the group consisting of —OR¹¹ and —NR¹⁰ᵃR¹⁰ᵇ; wherein R¹⁰ᵃ, R¹⁰ᵇ and R¹¹ are each independently selected from the group consisting of hydrogen and $C_{1-4}$alkyl; and R³ is selected from the group consisting of Ar, Het¹, Het², and a 7- to 10-membered saturated spirocarbobicyclic system; or (b) L² is >CR⁴ᶜR⁴ᵈ, wherein R⁴ᶜ and R⁴ᵈ are each independently selected from the group consisting of hydrogen and $C_{1-4}$alkyl; and R³ is selected from the group consisting of

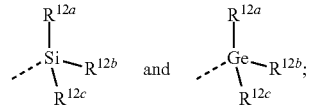

wherein R¹²ᵃ, R¹²ᵇ, and R¹²ᶜ are each independently selected from the group consisting of $C_{1-6}$alkyl optionally substituted with a —NH₂ substituent; or (c) -L²-R³ is $C_{1-6}$alkyl optionally substituted with one, two or three fluoro substituents; or (d) L² is O and R³ is selected from the group consisting of Ar, Het¹, —CH₂—Ar, —CH₂-Het¹, and —CH₂-(a 7- to 10-membered saturated spirocarbobicyclic system); when L² is linked to a carbon atom of L¹; or (e) -L²-R³ is selected from the group consisting of

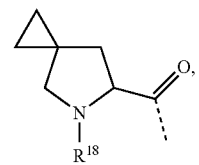

wherein

R$^{18}$ is hydrogen; or (f) -L$^2$-R$^3$ is

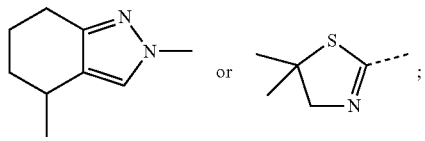

or and wherein

Ar is phenyl optionally substituted with a halo substituent;

Het$^1$ is a monocyclic heteroaryl selected from the group consisting of pyridyl, 4-, 5- or 6-pyrimidinyl, pyrazinyl, pyridazinyl, pyrrolyl, pyrazolyl, imidazolyl, and 4- or 5-thiazolyl; or a bicyclic heteroaryl selected from imidazopyridinyl, in particular imidazo[1,2-a]pyridinyl; each of which may be optionally substituted with one, two, or three substituents each independently selected from the group consisting of halo and C$_{1-4}$alkyl optionally substituted with a substituent selected from the group consisting of fluoro, —CN, —OR$^{26}$, —NR$^{27a}$R$^{27b}$, and —C(=O)NR$^{27a}$R$^{27b}$; and Het$^2$ is a non-aromatic heterocyclyl selected from azetidinyl, pyrrolidinyl and piperidinyl;

wherein

R$^{26}$, R$^{27a}$, and R$^{27b}$ are each independently selected from the group consisting of hydrogen and C$_{1-4}$alkyl;

and the pharmaceutically acceptable salts and the solvates thereof.

The present invention relates in particular to compounds of Formula (I) as defined herein, and the tautomers and the stereoisomeric forms thereof, wherein R$^1$ is CF$_3$;

L$^1$ represents a N-linked 7- to 10-membered saturated spiro-heterobicyclic system containing one or two N-atoms selected from the group consisting of (a), (b), (c), (d), (e), (f) and (g)

(a)

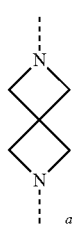

(b)

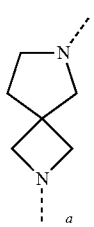

(c)

(d)

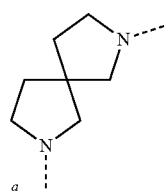

(e)

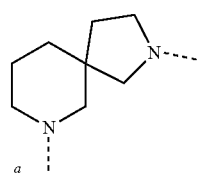

(f)

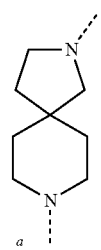

(g)

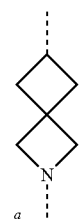

wherein a represents the position of linkage to the thieno-pyrimidinyl heterocycle;

(a) L$^2$ is >CH$_2$; and R$^3$ is selected from the group consisting of Ar, Het$^1$, and a 7- to 10-membered saturated spirocarbobicyclic system; or (b) -L$^2$-R$^3$ is C$_{1-6}$alkyl optionally substituted with one, two or three fluoro substituents; and wherein Ar is phenyl optionally substituted with a halo substituent; and Het$^1$ is a monocyclic heteroaryl selected from the group consisting of 4-, 5- or 6-pyrimidinyl, pyrazinyl, pyridazinyl, pyrrolyl, pyrazolyl, imidazolyl, and 4- or 5-thiazolyl; or a bicyclic heteroaryl selected from imidazopyridinyl, in particular imidazo[1,2-a]pyridinyl; each of which may be optionally substituted with one or two substituents each independently selected from the group consisting of halo and C$_{1-4}$alkyl;

and the pharmaceutically acceptable salts and the solvates thereof.

The present invention relates in particular to compounds of Formula (I) as defined herein, and the tautomers and the stereoisomeric forms thereof, wherein $R^1$ is $CF_3$;

$R^2$ is hydrogen;

$L^1$ represents a N-linked 7- to 10-membered saturated spiro-heterobicyclic system containing one or two N-atoms selected from the group consisting of (a), (b), (c), (d), (e), (f) and (g)

(a) 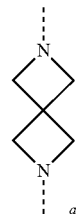

(b) 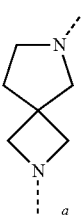

(c) 

(d) 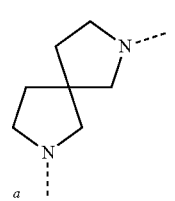

(e) 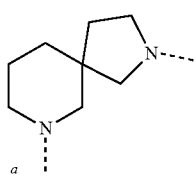

(f) 

(g) 

wherein a represents the position of linkage to the thienopyrimidinyl heterocycle;

(a) $L^2$ is >$CH_2$; and $R^3$ is selected from the group consisting of Ar, $Het^1$, and a 7- to 10-membered saturated spirocarbobicyclic system; or (b) -$L^2$-$R^3$ is $C_{1-6}$alkyl optionally substituted with one, two or three fluoro substituents; and wherein Ar is phenyl optionally substituted with a halo substituent; and $Het^1$ is a monocyclic heteroaryl selected from the group consisting of 4-, 5- or 6-pyrimidinyl, pyrazinyl, pyridazinyl, pyrrolyl, pyrazolyl, and imidazolyl; or a bicyclic heteroaryl selected from imidazopyridinyl, in particular imidazo[1,2-a]pyridinyl; each of which may be optionally substituted with one or two substituents each independently selected from the group consisting of halo and $C_{1-4}$alkyl;

and the pharmaceutically acceptable salts and the solvates thereof.

Another embodiment of the present invention relates to those compounds of Formula (I) and the pharmaceutically acceptable salts, and the solvates thereof, or any subgroup thereof as mentioned in any of the other embodiments wherein one or more of the following restrictions apply:

(a) $R^1$ is $CF_3$;

(b) $R^2$ is hydrogen;

(c) $L^1$ is a N-linked 7- to 10-membered saturated spiroheterobicyclic system containing one or two N-atoms selected from the group consisting of (a), (b), (c), (d), (e), (f) and (g) as defined herein;

(d) $L^1$ is a N-linked 7- to 10-membered saturated spiroheterobicyclic system containing one or two N-atoms selected from the group consisting of (a), (b), (c), (d), (e), and (f) as defined herein;

(e) $L^1$ is a N-linked 7- to 10-membered saturated spiroheterobicyclic system containing one or two N-atoms selected from the group consisting of (c) and (e);

(f) $L^2$ is >$CH_2$;

(g) $L^2$ is >$CH_2$; and $R^3$ is selected from the group consisting of Ar, $Het^1$, and a 7- to 10-membered saturated spirocarbobicyclic system;

(h) -$L^2$-$R^3$ is selected from the group consisting of

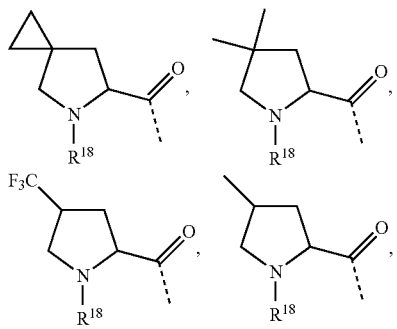

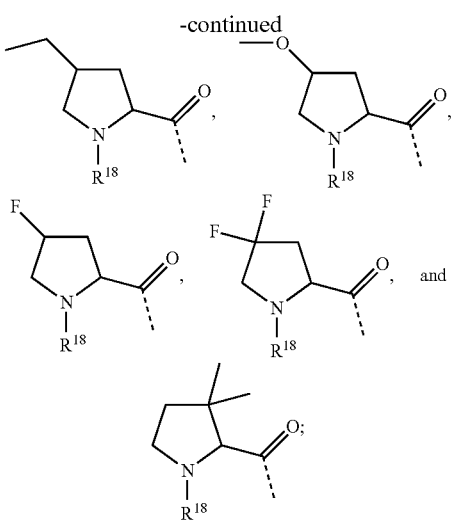

wherein
- R¹⁸ is selected from the group consisting of hydrogen; $C_{1-4}$alkyl optionally substituted with a fluoro or —CN substituent; and $C_{2-4}$alkyl substituted with a substituent selected from the group consisting of —OR¹⁹ and —NR²⁰ᵃR²⁰ᵇ; wherein
  R¹⁹, R²⁰ᵃ and R²⁰ᵇ are each independently selected from the group consisting of hydrogen; $C_{1-4}$alkyl optionally substituted with a substituent selected from the group consisting of fluoro, —CN, and —C(=O)NR²¹ᵃR²¹ᵇ; $C_{2-4}$alkyl substituted with a substituent selected from the group consisting of —OR²² and —NR²¹ᵃR²¹ᵇ; and C-linked 4- to 7-membered non-aromatic heterocyclyl containing at least one nitrogen, oxygen or sulfur atom; wherein
    R²¹ᵃ, R²¹ᵇ and R²² are each independently selected from the group consisting of hydrogen and $C_{1-4}$alkyl;
- (i) Ar is phenyl optionally substituted with one or two independently selected halo substituents;
- (j) Ar is phenyl optionally substituted with one halo substituent;
- (k) Ar is phenyl;
- (l) Het¹ is a monocyclic heteroaryl selected from the group consisting of pyrazolyl, imidazolyl, pyrrolyl, 4- or 5-thiazolyl, pyridyl, pyridazinyl, 4-, 5- or 6-pyrimidinyl, and pyrazinyl; or is a bicyclic heteroaryl selected from imidazopyridinyl, in particular imidazo[1,2-a]pyridinyl; each of which may be optionally substituted with one or two substituents each independently selected from the group consisting of halo and $C_{1-4}$alkyl optionally substituted with a substituent selected from the group consisting of fluoro, —CN, —OR²⁵, —NR²⁶ᵃR²⁶ᵇ, and —C(=O)NR²⁶ᵃR²⁶ᵇ; wherein R²⁵, R²⁶ᵃ, and R²⁶ᵇ are each independently selected from the group consisting of hydrogen and $C_{1-4}$alkyl;
- (m) Het¹ is a monocyclic heteroaryl selected from the group consisting of pyrazolyl, imidazolyl, pyrrolyl, 4- or 5-thiazolyl, pyridyl, pyridazinyl, 4-, 5- or 6-pyrimidinyl, and pyrazinyl; or is a bicyclic heteroaryl selected from imidazopyridinyl, in particular imidazo[1,2-a]pyridinyl; each of which may be optionally substituted with one or two substituents each independently selected from the group consisting of halo and $C_{1-4}$alkyl optionally substituted with a substituent selected from the group consisting of —CN, —OR²⁵, —NR²⁶ᵃR²⁶ᵇ, and —C(=O)NR²⁶ᵃR²⁶ᵇ; wherein R²⁵, R²⁶ᵃ, and R²⁶ᵇ are each independently selected from the group consisting of hydrogen and $C_{1-4}$alkyl;
- (n) Het¹ is a monocyclic heteroaryl selected from the group consisting of pyrazolyl, imidazolyl, pyrrolyl, pyridazinyl, 4-, 5- or 6-pyrimidinyl, and pyrazinyl; or is a bicyclic heteroaryl selected from imidazopyridinyl, in particular imidazo[1,2-a]pyridinyl; each of which may be optionally substituted with one or two substituents each independently selected from the group consisting of halo and $C_{1-4}$alkyl;
- (o) Het¹ is a monocyclic heteroaryl selected from the group consisting of pyridazinyl, 4-, 5- or 6-pyrimidinyl, and pyrazinyl, each of which may be optionally substituted with a halo substituent;
- (p) Het¹ is a bicyclic heteroaryl selected from imidazopyridinyl, in particular imidazo[1,2-a]pyridinyl-6-yl or imidazo[1,2-a]pyridinyl-2-yl;
- (q) 7- to 10-membered saturated spirocarbobicyclic system is in particular

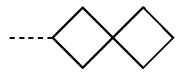

In an embodiment, the present invention relates to those compounds of Formula (I) and the pharmaceutically acceptable salts, and the solvates thereof, or any subgroup thereof as mentioned in any of the other embodiments, wherein R¹ is CF₃.

In an embodiment, the present invention relates to those compounds of Formula (I) and the pharmaceutically acceptable salts, and the solvates thereof, or any subgroup thereof as mentioned in any of the other embodiments, wherein R¹ is CF₃, and wherein R² is hydrogen.

In an embodiment, the present invention relates to those compounds of Formula (I) and the pharmaceutically acceptable salts, and the solvates thereof, or any subgroup thereof as mentioned in any of the other embodiments, wherein Ar is phenyl optionally substituted according to any of the other embodiments.

In an embodiment, the present invention relates to those compounds of Formula (I) and the pharmaceutically acceptable salts, and the solvates thereof, or any subgroup thereof as mentioned in any of the other embodiments, wherein L² is linked to a carbon atom of L¹.

In an embodiment, the present invention relates to those compounds of Formula (I) and the pharmaceutically acceptable salts, and the solvates thereof, or any subgroup thereof as mentioned in any of the other embodiments, wherein -L²-R³ is (a).

In an embodiment, the present invention relates to those compounds of Formula (I) and the pharmaceutically acceptable salts, and the solvates thereof, or any subgroup thereof as mentioned in any of the other embodiments, wherein -L²-R³ is (b).

In an embodiment, the present invention relates to those compounds of Formula (I) and the pharmaceutically acceptable salts, and the solvates thereof, or any subgroup thereof as mentioned in any of the other embodiments, wherein -L²-R³ is (C).

In an embodiment, the present invention relates to those compounds of Formula (I) and the pharmaceutically acceptable salts, and the solvates thereof, or any subgroup thereof as mentioned in any of the other embodiments, wherein -L²-R³ is (d).

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (e).

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (f).

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (g).

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (a); (b), (d), (e) or (f); and R$^{4a}$ is other than hydrogen. In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (a) or (f); and R$^{4a}$ is other than hydrogen.

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (a); and R$^{4a}$ is other than hydrogen.

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (a); and when L$^2$ is linked to a nitrogen atom of L$^1$ then R$^{4a}$ is other than hydrogen.

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (a) or (f); and when L$^2$ is linked to a nitrogen atom of L$^1$ then R$^{4a}$ is other than hydrogen.

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (a), (b), (d), (e) or (f); and when L$^2$ is linked to a nitrogen atom of L$^1$ then R$^{4a}$ is other than hydrogen.

In an embodiment, the present invention relates to those compounds of Formula (I) and the pharmaceutically acceptable salts, and the solvates thereof, or any subgroup thereof as mentioned in any of the other embodiments, wherein L represents

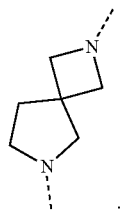

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (a); R$^3$ is Het$^1$ or Het$^2$.

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (a); R$^3$ is Het$^1$.

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (a); R$^3$ is Het$^1$; and Het$^1$ is azetidinyl optionally substituted as defined in any of the other embodiments.

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (a); R$^3$ is Het$^1$ or Het$^2$; Het$^1$ is a monocyclic heteroaryl selected from the group consisting of pyridyl, 4-, 5- or 6-pyrimidinyl, pyrazinyl, pyridazinyl, pyrrolyl, pyrazolyl, and imidazolyl; each of which may be optionally substituted with one, two, or three substituents each independently selected from the group consisting of halo, —CN, —OR$^{24}$, —NR$^{25a}$R$^{25b}$, and C$_{1-4}$alkyl optionally substituted with a substituent selected from the group consisting of fluoro, —CN, —OR$^{26}$, —NR$^{27a}$R$^{27b}$, and —C(=O)NR$^{27a}$R$^{27b}$; and Het$^2$ is a non-aromatic heterocyclyl selected from the group consisting of azetidinyl, pyrrolidinyl, and piperidinyl; each of which may be optionally substituted with one, two, or three substituents each independently selected from the group consisting of halo, —CN, —OR$^{24}$, —NR$^{25a}$R$^{25b}$, and C$_{1-4}$alkyl optionally substituted with a substituent selected from the group consisting of fluoro, —CN, —OR$^{26}$, —NR$^{27a}$R$^{27b}$, and —C(=O)NR$^{27a}$R$^{27b}$.

In an embodiment, the present invention relates to those compounds of Formula (I) and the pharmaceutically acceptable salts, and the solvates thereof, or any subgroup thereof as mentioned in any of the other embodiments, wherein Ar is phenyl which may be optionally substituted with one, two, or three substituents each independently selected from the group consisting of halo, —CN, —OR$^{24}$, —NR$^{25a}$R$^{25b}$, and C$_{1-4}$alkyl optionally substituted with a substituent selected from the group consisting of fluoro, —CN, —OR$^{26}$, —NR$^{27a}$R$^{27b}$, and —C(=O)NR$^{27a}$R$^{27b}$;

Het$^1$ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, thiadiazolyl, and isoxazolyl; each of which may be optionally substituted with one, two, or three substituents each independently selected from the group consisting of halo, —CN, —OR$^{24}$, —NR$^{25a}$R$^{25b}$, and C$_{1-4}$alkyl optionally substituted with a substituent selected from the group consisting of fluoro, —CN, —OR$^{26}$, —NR$^{27a}$R$^{27b}$, and —C(=O)NR$^{27a}$R$^{27b}$; and Het$^2$ is a monocyclic non-aromatic heterocyclyl optionally substituted with one, two, or three substituents each independently selected from the group consisting of halo, —CN, —OR$^{24}$, —NR$^{25a}$R$^{25b}$, and C$_{1-4}$alkyl optionally substituted with a substituent selected from the group consisting of fluoro, —CN, —OR$^{26}$, —NR$^{27a}$R$^{27b}$, and —C(=O)NR$^{27a}$R$^{27b}$.

In an embodiment, the present invention relates to those compounds of Formula (I) and the pharmaceutically acceptable salts, and the solvates thereof, or any subgroup thereof as mentioned in any of the other embodiments, wherein -$L^2$-$R^3$ is (a), wherein
$L^2$ is selected from the group consisting of >$CR^{4a}R^{4b}$, and —$CHR^{4a}CHR^5$—; wherein
$L^2$ is linked to a nitrogen atom of $L^1$;
$R^{4a}$ is selected from the group consisting of —C(=O)$NR^{7a}R^{7b}$; and C-linked 4- to 7-membered non-aromatic heterocyclyl containing at least one nitrogen, oxygen or sulfur atom;
$R^5$ is selected from the group consisting of hydrogen; —$OR^6$; —$NR^{7a}R^{7b}$; —C(=O)$NR^{7a}R^{7b}$; $C_{1-4}$alkyl optionally substituted with a substituent selected from the group consisting of fluoro, —CN, —$OR^8$, and —$NR^{9a}R^{9b}$;
$R^{4b}$ is selected from the group consisting of hydrogen and methyl; and
$R^3$ is selected from the group consisting of Ar, $Het^1$, $Het^2$, and a 7- to 10-membered saturated spirocarbobicyclic system.

In an embodiment, the present invention relates to those compounds of Formula (I) and the pharmaceutically acceptable salts, and the solvates thereof, or any subgroup thereof as mentioned in any of the other embodiments, wherein
-$L^2$-$R^3$ is (a), wherein
$L^2$ is >$CR^{4a}R^{4b}$; wherein
$L^2$ is linked to a nitrogen atom of $L^1$;
$R^{4a}$ is selected from the group consisting of —C(=O)$NR^{7a}R^{7b}$; and C-linked 4- to 7-membered non-aromatic heterocyclyl containing at least one nitrogen, oxygen or sulfur atom;
$R^{4b}$ is hydrogen; and
$R^3$ is selected from the group consisting of Ar, $Het^1$, $Het^2$, and a 7- to 10-membered saturated spirocarbobicyclic system.

In an embodiment, the present invention relates to those compounds of Formula (I) and the pharmaceutically acceptable salts, and the solvates thereof, or any subgroup thereof as mentioned in any of the other embodiments, wherein
-$L^2$-$R^3$ is (a), wherein
$L^2$ is >$CR^{4a}R^{4b}$; wherein
$L^2$ is linked to a nitrogen atom of $L^1$;
$R^{4a}$ is selected from the group consisting of —C(=O)$NR^{7a}R^{7b}$; and C-linked 4- to 7-membered non-aromatic heterocyclyl containing at least one nitrogen, oxygen or sulfur atom;
$R^{4b}$ is hydrogen; and
$R^3$ is selected from the group consisting of Ar, and $Het^2$.

In an embodiment, the present invention relates to those compounds of Formula (I) and the pharmaceutically acceptable salts, and the solvates thereof, or any subgroup thereof as mentioned in any of the other embodiments, wherein
-$L^2$-$R^3$ is (a), wherein
$L^2$ is selected from the group consisting of >$CR^{4a}R^{4b}$, and —$CHR^{4a}CHR^5$—; wherein
$L^2$ is linked to a nitrogen atom of $L^1$;
$R^{4a}$ is —C(=O)$NR^{7a}R^{7b}$;
$R^5$ is selected from the group consisting of hydrogen; —$OR^6$; —$NR^{7a}R^{7b}$; —C(=O)$NR^{7a}R^{7b}$; $C_{1-4}$alkyl optionally substituted with a substituent selected from the group consisting of fluoro, —CN, —$OR^8$, and —$NR^{9a}R^{9b}$;
$R^{4b}$ is selected from the group consisting of hydrogen and methyl; and
$R^3$ is selected from the group consisting of Ar, $Het^1$, $Het^2$, and a 7- to 10-membered saturated spirocarbobicyclic system.

In an embodiment, the present invention relates to those compounds of Formula (I) and the pharmaceutically acceptable salts, and the solvates thereof, or any subgroup thereof as mentioned in any of the other embodiments, wherein
-$L^2$-$R^3$ is (a), wherein
$L^2$ is >$CR^{4a}R^{4b}$; wherein
$L^2$ is linked to a nitrogen atom of $L^1$;
$R^{4a}$ is —C(=O)$NR^{7a}R^{7b}$;
$R^{4b}$ is hydrogen; and
$R^3$ is selected from the group consisting of Ar, $Het^1$, $Het^2$, and a 7- to 10-membered saturated spirocarbobicyclic system.

In an embodiment, the present invention relates to those compounds of Formula (I) and the pharmaceutically acceptable salts, and the solvates thereof, or any subgroup thereof as mentioned in any of the other embodiments, wherein
-$L^2$-$R^3$ is (a), wherein
$L^2$ is >$CR^{4a}R^{4b}$; wherein
$L^2$ is linked to a nitrogen atom of $L^1$;
$R^{4a}$ is —C(=O)$NR^{7a}R^{7b}$;
$R^{4b}$ is hydrogen; and
$R^3$ is selected from the group consisting of Ar, and $Het^2$.

In an embodiment, the present invention relates to those compounds of Formula (I) and the pharmaceutically acceptable salts, and the solvates thereof, or any subgroup thereof as mentioned in any of the other embodiments, wherein
-$L^2$-$R^3$ is (a), wherein
$L^2$ is selected from the group consisting of >$CR^{4a}R^{4b}$, and —$CHR^{4a}CHR^5$—; wherein
$L^2$ is linked to a nitrogen atom of $L^1$;
$R^{4a}$ is C-linked 4- to 7-membered non-aromatic heterocyclyl containing at least one nitrogen, oxygen or sulfur atom;
$R^5$ is selected from the group consisting of hydrogen; —$OR^6$; —$NR^{7a}R^{7b}$; —C(=O)$NR^{7a}R^{7b}$; $C_{1-4}$alkyl optionally substituted with a substituent selected from the group consisting of fluoro, —CN, —$OR^8$, and —$NR^{9a}R^{9b}$;
$R^{4b}$ is selected from the group consisting of hydrogen and methyl; and
$R^3$ is selected from the group consisting of Ar, $Het^1$, $Het^2$, and a 7- to 10-membered saturated spirocarbobicyclic system.

In an embodiment, the present invention relates to those compounds of Formula (I) and the pharmaceutically acceptable salts, and the solvates thereof, or any subgroup thereof as mentioned in any of the other embodiments, wherein
-$L^2$-$R^3$ is (a), wherein
$L^2$ is >$CR^{4a}R^{4b}$; wherein
$L^2$ is linked to a nitrogen atom of $L^1$;
$R^{4a}$ is C-linked 4- to 7-membered non-aromatic heterocyclyl containing at least one nitrogen, oxygen or sulfur atom;
$R^{4b}$ is hydrogen; and
$R^3$ is selected from the group consisting of Ar, $Het^1$, $Het^2$, and a 7- to 10-membered saturated spirocarbobicyclic system.

In an embodiment, the present invention relates to those compounds of Formula (I) and the pharmaceutically acceptable salts, and the solvates thereof, or any subgroup thereof as mentioned in any of the other embodiments, wherein
-$L^2$-$R^3$ is (a), wherein
$L^2$ is >$CR^{4a}R^{4b}$; wherein
$L^2$ is linked to a nitrogen atom of $L^1$;
$R^{4a}$ is C-linked 4- to 7-membered non-aromatic heterocyclyl containing at least one nitrogen, oxygen or sulfur atom;
$R^{4b}$ is hydrogen; and
$R^3$ is selected from the group consisting of Ar, and $Het^2$.

In an embodiment, the present invention relates to those compounds of Formula (I) and the pharmaceutically acceptable salts, and the solvates thereof, or any subgroup thereof as mentioned in any of the other embodiments, wherein $L^2$ is linked to a nitrogen atom of $L^1$.

In an embodiment, the present invention relates to those compounds of Formula (I) and the pharmaceutically acceptable salts, and the solvates thereof, or any subgroup thereof as mentioned in any of the other embodiments, wherein -L²-R³ is selected from the group consisting of

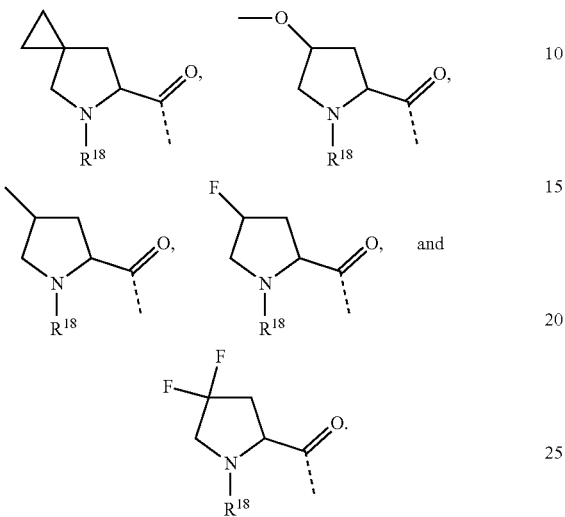

In an embodiment, the present invention relates to those compounds of Formula (I) and the pharmaceutically acceptable salts, and the solvates thereof, or any subgroup thereof as mentioned in any of the other embodiments, wherein -L²-R³ is selected from the group consisting of

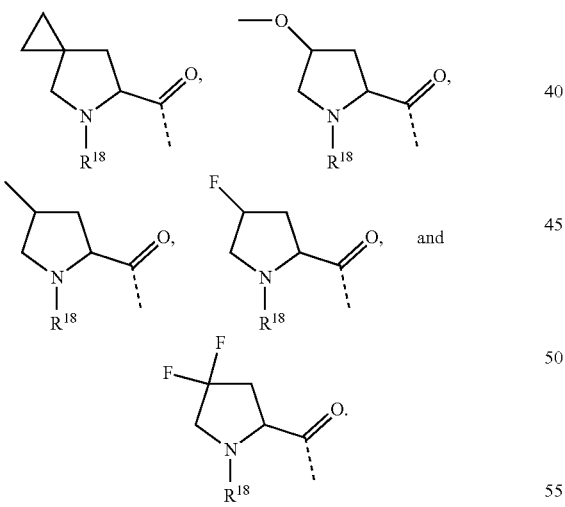

wherein R¹⁸ is hydrogen or methyl.

In an embodiment, the present invention relates to those compounds of Formula (I) and the pharmaceutically acceptable salts, and the solvates thereof, or any subgroup thereof as mentioned in any of the other embodiments, wherein L¹ represents a N-linked 7- to 10-membered saturated spiroheterobicyclic system containing one or two N-atoms selected from the group consisting of (a), (b), (c), (d), (e), (f), (g), (h), and (i)

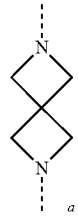 (a)

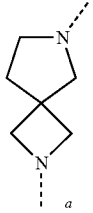 (b)

 (c)

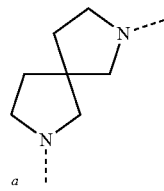 (d)

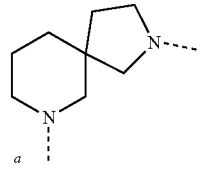 (e)

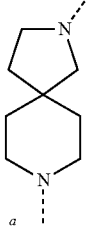 (f)

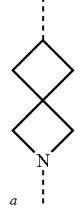 (g)

-continued (h)
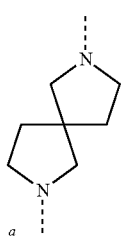
a (i)
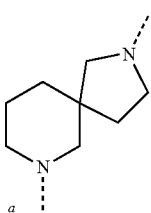
a wherein a represents the position of linkage to the thieno-pyrimidinyl heterocycle.

In an embodiment, the present invention relates to those compounds of Formula (I) and the pharmaceutically acceptable salts, and the solvates thereof, or any subgroup thereof as mentioned in any of the other embodiments, wherein Het$^2$ is monocyclic heterocyclyl optionally substituted with one, two, or three substituents as described in the other embodiments.

In an embodiment, the present invention relates to those compounds of Formula (I) and the pharmaceutically acceptable salts, and the solvates thereof, or any subgroup thereof as mentioned in any of the other embodiments, wherein Het$^2$ is a non-aromatic heterocyclyl selected from azetidinyl, oxetanyl, tetrahydrofuranyl, piperidinyl, tetrahydropyranyl, tetrahydro-2H-thiopyranyl 1,1-dioxide,

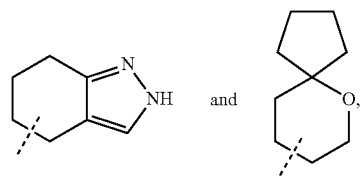
and each of which are optionally substituted with one, two, or three substituents as described in the other embodiments.

In an embodiment, the present invention relates to those compounds of Formula (I) and the pharmaceutically acceptable salts, and the solvates thereof, or any subgroup thereof as mentioned in any of the other embodiments, wherein Het$^2$ is a non-aromatic heterocyclyl selected from

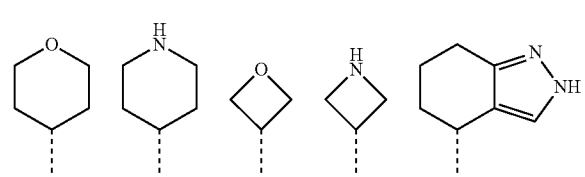

-continued

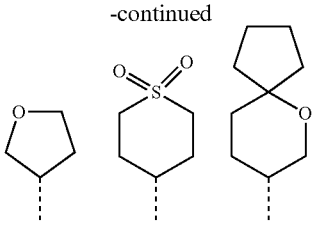

each of which are optionally substituted with one, two, or three substituents as described in the other embodiments.

Particular compounds of Formula (I) are compounds 82, 84, 273, and 274, including the stereoisomeric forms, the pharmaceutically acceptable salts thereof, in particular the hydrochloride salts thereof, and the solvates thereof.

Particular compounds of Formula (I) are compounds 82, 84, 273, and 274.

In an embodiment the compound of Formula (I) is selected from the group consisting of any of the exemplified compounds, and the free bases, the pharmaceutically acceptable addition salts, and the solvates thereof.

All possible combinations of the above-indicated embodiments are considered to be embraced within the scope of this invention.

Methods for the Preparation of Compounds of Formula (I)

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The skilled person will realize that in the reactions described in the Schemes, although this is not always explicitly shown, it may be necessary to protect reactive functional groups (for example hydroxy, amino, or carboxy groups) where these are desired in the final product, to avoid their unwanted participation in the reactions. For example in Scheme 1, the NH moiety on the L$^1$ N-linked 7- to 10-membered saturated spiroheterobicyclic system containing one or two N-atoms can be protected with a tert-butoxycarbonyl protecting group. In general, conventional protecting groups can be used in accordance with standard practice. The protecting groups may be removed at a convenient subsequent stage using methods known from the art. This is illustrated in the specific examples.

The skilled person will realize that in the reactions described in the Schemes, it may be advisable or necessary to perform the reaction under an inert atmosphere, such as for example under N$_2$-gas atmosphere.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of Formula (I).

The skilled person will realize that intermediates and final compounds shown in the Schemes below may be further functionalized according to methods well-known by the person skilled in the art. The intermediates and compounds described herein can be isolated in free form or as a salt.

Scheme 1

In general, compounds of Formula (I) wherein all variables are defined according to the scope of the present invention, can be prepared according to the following reaction Scheme 1. In Scheme 1,

represents $L^1$ as a 7- to 10-membered saturated spiroheterobicyclic system containing two N-atoms and which is N-linked to the thienopyrimidinyl heterocycle, $LG^1$ and $LG^2$ each represent a suitable leaving group, such as for example halo or methanesulfonyl; $PG^1$ represents a suitable protecting group, such as for example tert-butyloxycarbonyl; $R^{3a}$—$PG^2$ represents an $R^3$ as defined in Formula (I) with an appropriate protecting group, such as for example tert-butyloxycarbonyl, when the $R^3$ substituent bears an amino group. The X in formula (XI) represents CH or N (in formula (XI) $L^2$ can be linked to a carbon or a N-atom). All other variables in Scheme 1 are defined according to the scope of the present invention.

In Scheme 1, the following reaction conditions apply:

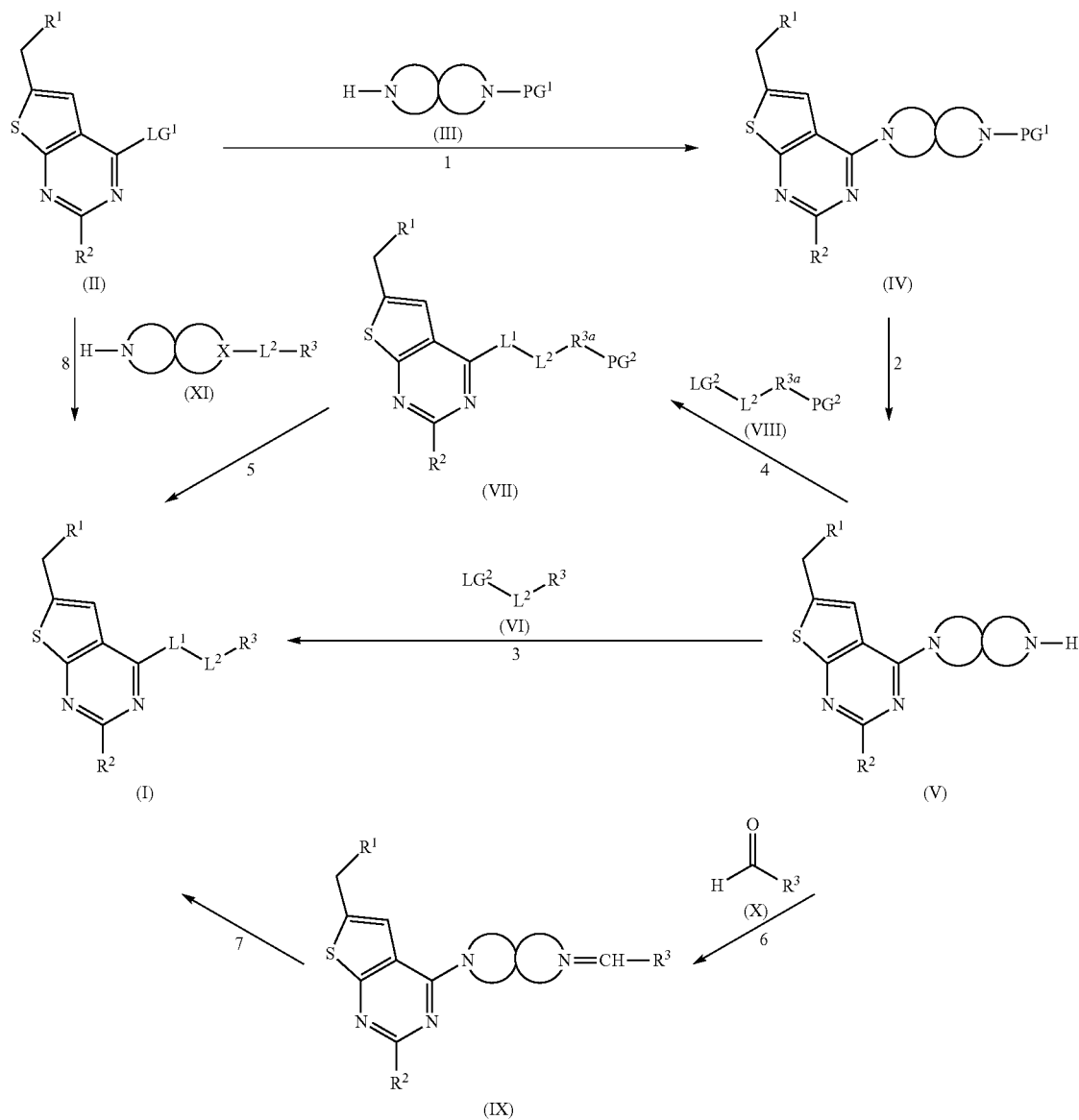

1: at a suitable temperature such as ranged from rt to 90° C., in the presence of a suitable base such as for example diisopropylethylamine, in a suitable solvent such as for example acetonitrile or isopropanol or ethanol;
2: at a suitable temperature range such as for example from 0° C. to room temperature, in the presence of suitable cleavage conditions, such as for example an acid such as HCl or trifluoroacetic acid in a suitable solvent such as acetonitrile or dichloromethane when $PG^1$ is tert-butyloxycarbonyl;
Alternatively, at a suitable temperature such as for example room temperature in a suitable solvent such as acetic acid
3: at a suitable temperature such as for example room temperature or reflux, in the presence of a suitable base such as for example potassium carbonate or 1,8-Diazabicyclo[5.4.0]undec-7-ene, in a suitable solvent such as for example acetonitrile or DMSO;
4: at a suitable temperature such as for example room temperature or 90° C., in the presence of a suitable base such as for example potassium carbonate or 1,8-Diazabicyclo[5.4.0]undec-7-ene, in a suitable solvent such as for example acetonitrile or DMSO;
5: at a suitable reaction temperature range such as for example from 0° C. to room temperature, in the presence of suitable cleavage conditions, such as for example an acid such as HCl or trifluoroactic acid in a suitable solvent such as acetonitrile or dichloromethane when $PG^2$ is tert-butyloxycarbonyl.
6: at a suitable temperature such as for example at room temperature, eventually in the presence of a suitable base such as for example trimethylamine or a suitable acid such as for example acetic acid, in a suitable solvent such as for example anhydrous dichloromethane, dichloroethane or tetrahydropyrane;
7: at a suitable temperature, for example room temperature, in the presence of a suitable reducing agent, such as for example $NaBH(OAc)_3$, in a suitable solvent such as dichloromethane, dichloroethane or tetrahydropyran; yielding a compound of Formula (I) wherein $L^1$ is a N-linked 7- to 10-membered saturated spiroheterobicyclic system containing two N-atoms and $L^2$ is $CH_2$.
Steps 6 and 7 can conveniently be performed as a one-pot procedure.
Alternatively, step 6 and 7 can be performed in the presence of a suitable acid such as for example acetic acid, a suitable catalyst such as platinum oxide, in a suitable solvent such as for example ethanol at a suitable temperature such as for example 60° C.;
8: at a suitable temperature such as for example at 90° C., in the presence of a suitable base such as for example diisopropylethylamine, in a suitable solvent such as for example acetonitrile or isopropanol. In step 8, reagent of Formula (XI), X represents CH or N, and $L^2$ and $R^3$ are as defined according to the scope of the invention. Reagents of Formula (XI) are either commercially available or can be prepared by methods known to the skilled person from commercially available starting materials, e.g. by appropriate protection/deprotection steps and functional group interconversion, from starting materials, such as 2-azaspiro[3.3]heptan-6-ol (CAS[1256352-97-2]).

Scheme 2

Intermediates of Formula (II), wherein $R^2$ is methyl, can be prepared according to the following reaction Scheme 2, wherein $LG^1$ represents a suitable leaving group, such as for example halo or methanesulfonyl. All other variables in Scheme 2 are defined according to the scope of the present invention.

In Scheme 2, the following reaction conditions apply:

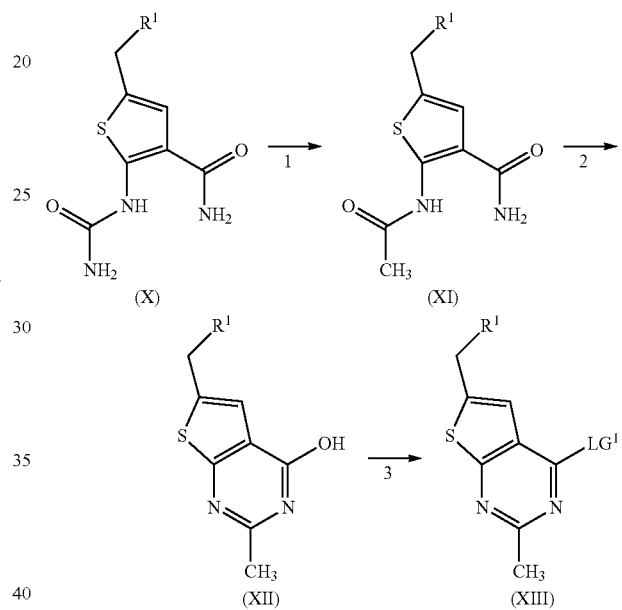

1: at a suitable temperature such as for example at reflux temperature, in the presence of acetic anhydride and a suitable base such as for example trimethylamine, in a suitable solvent such as for example toluene;
2: at a suitable temperature such as for example at reflux temperature, in the presence of a suitable base such as for example potassium hydroxide, in a suitable solvent such as for example ethanol;
3: under suitable reaction conditions to form a leaving group, such as for example, chloro, for example by reaction with phosphoryl trichloride at a suitable temperature such as 110° C.

Scheme 3

In general, compounds of Formula (I-a) wherein the variables are defined according to the scope of the present invention, but wherein $L^2$ is limited to $L^{2a}$ (the options that can be obtained by this Scheme), can be prepared according to the following reaction Scheme 3. All other variables in Scheme 3 are defined according to the scope of the present invention or as defined before.

In Scheme 3, the following reaction conditions apply:

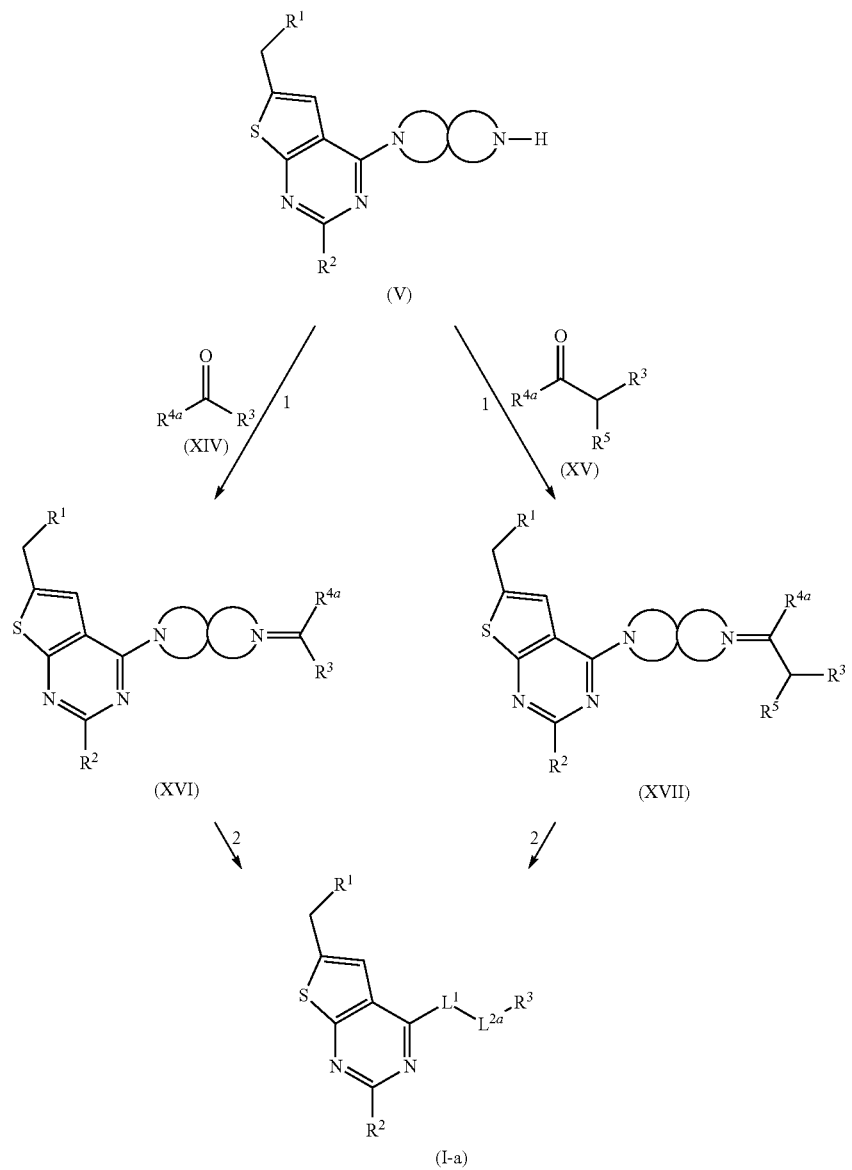

1: at a suitable temperature such as for example room temperature or 45° C., in the presence of titanium (IV) ethoxide or titanium (IV) isopropoxide, in a suitable solvent such as for example tetrahydropyrane, dichloroethane or a mixture of dichloroethane and methanol;

Alternatively, at a suitable temperature such as for example room temperature, with or without a suitable acid such as for example trifluoroacetic acid, in a suitable solvent such as for example tetrahydropyrane;

2: at a suitable temperature such as for example room temperature, in the presence of a suitable reducing agent such as for example sodium borohydride, sodium triacetoxyborohydride or sodium cyanoborohydride, in a suitable solvent such as for example tetrahydropyrane, dichloroethane or a mixture of dichloroethane and methanol; Steps 1 and 2 can be performed as a one-pot procedure.

Scheme 4

In general, compounds of Formula (I-b) wherein $R^{4a}$ is restricted to $R^{4a1}$ being $C_{1-4}$alkyl or a C-linked 4- to 7-membered non-aromatic heterocyclyl containing at least one nitrogen, oxygen or sulfur atom can be prepared according to the following reaction Scheme 4. In Scheme 4, halo means chloro, bromo or iodo. All other variables in Scheme 4 are defined according to the scope of the present invention or as defined before.

In Scheme 4, the following reaction conditions apply:

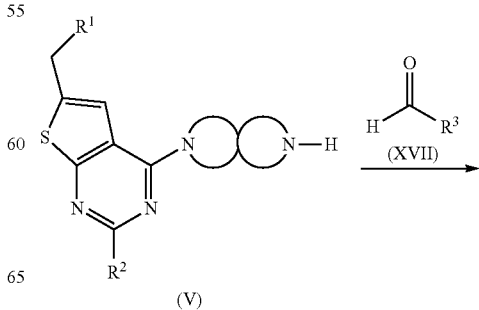

-continued

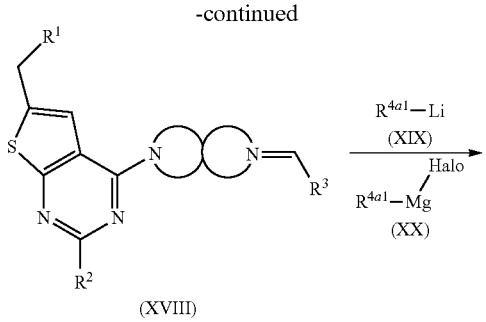

(XVIII)

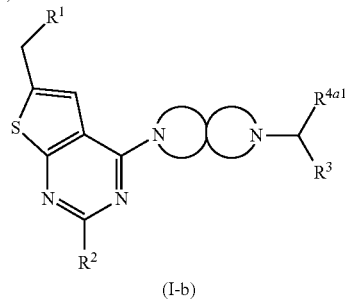

(I-b)

1: at a suitable temperature such as for example room temperature or 45° C., in the presence of titanium (IV) ethoxide or titanium (IV) isopropoxide, in a suitable solvent such as for example tetrahydropyran;
2: at a suitable temperature ranged from 0° C. to room temperature, in a suitable solvent such as for example tetrahydrofurane.

Steps 1 and 2 can be performed as a one-pot procedure.
Scheme 5

In general, compounds of Formula (Ic) wherein $R^3$ is restricted to $R^{3c}$ being

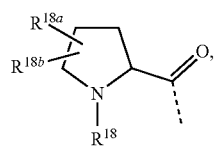

can be prepared according to the following reaction Scheme 5. All other variables in Scheme 5 are defined according to the scope of the present invention or as defined before. In Scheme 5, $L^2$ is linked to a N-atom of $L^1$.

In Scheme 5, the following reaction conditions apply:

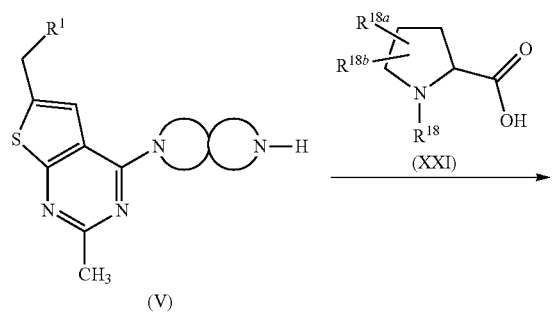

-continued

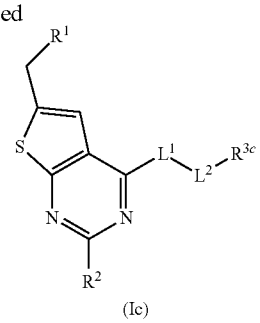

(Ic)

1: at a suitable temperature, such as for example room temperature, in the presence of a suitable acid coupling agent, such as for example 1-[bis(dimethylamino)methylene]-1H-benzotriazoliumhexafluorophosphate(1-)$_3$-oxide (HBTU) or 1-[Bis(dimethylamino)methylene]-1H-1,2,3-triazolo[4,5-b]pyridinium 3-oxide hexafluorophosphate (HATU), in the presence of a suitable base such as for example N-ethyl-N-(1-methylethyl)-2-propanamine (DIPEA), in a suitable solvent such as N,N-dimethylformamide (DMF);

Scheme 6

In general, compounds of Formula (Id) wherein $L^2$ is restricted to $SO_2$, can be prepared according to the following reaction Scheme 6. All other variables in Scheme 6 are defined according to the scope of the present invention or as defined before. In Scheme 6, $L^2$ (>$SO_2$ in Scheme 6) is linked to a N-atom of $L^1$.

In Scheme 6, the following reaction conditions apply:

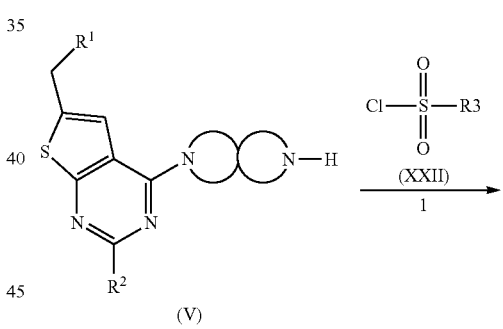

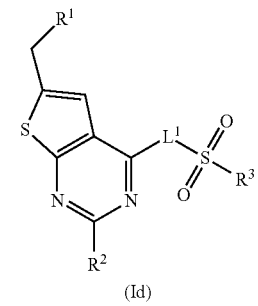

(Id)

1: at a suitable temperature, for example room temperature, in the presence of a suitable base such as for example potassium carbonate, in a suitable solvent such as for example acetonitrile.

Scheme 7

In general, compounds of Formula (Ie) and (If) can be prepared according to the following reaction Scheme 7. Both in (Ie) and (If) the $L^2$ part of the molecule is linked to a nitrogen atom of L[1]. All other variables are defined according to the scope of the present invention or as defined before.

In Scheme 7, the following reaction conditions apply:

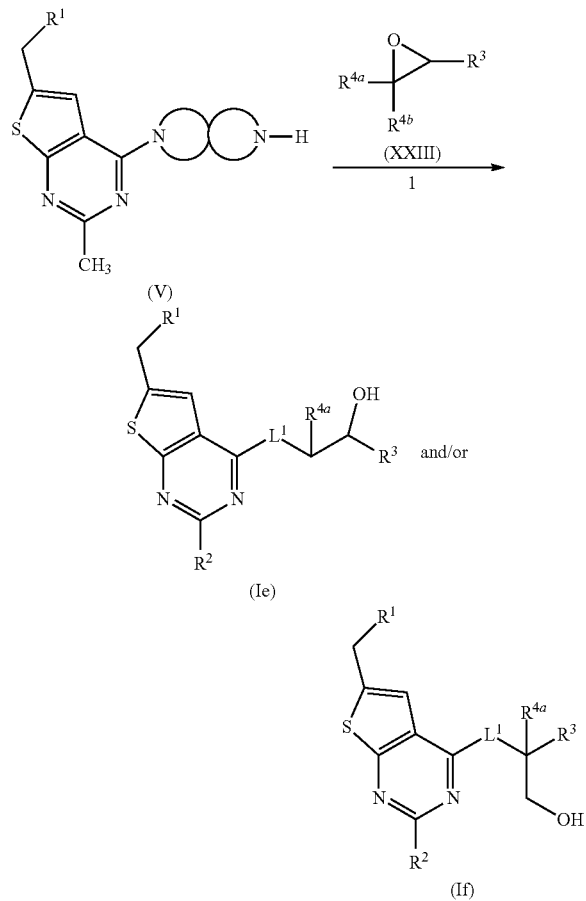

1: at a suitable temperature such as for example 60° C., in a suitable solvent such as for example ethanol.

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

The compounds of Formula (I) may be synthesized in the form of racemic mixtures of enantiomers which can be separated from one another following art-known resolution procedures. The racemic compounds of Formula (I) containing a basic nitrogen atom may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (Boc), benzyloxy-carbonyl (CBz) and 9-fluorenylmethyleneoxycarbonyl (Fmoc). The need for such protection is readily determined by one skilled in the art. For a general description of protecting groups and their use, see T. W. Greene and P. G. M. Wuts, Protective Groups in Organic Synthesis, 4th ed., Wiley, Hoboken, N.J., 2007.

Pharmacology

It has been found that the compounds of the present invention block the interaction of menin with MLL proteins and oncogenic MLL fusion proteins. Therefore the compounds according to the present invention and the pharmaceutical compositions comprising such compounds may be useful for the treatment or prevention, in particular treatment, of diseases such as cancer, myelodysplastic syndrome (MDS) and diabetes.

In particular, the compounds according to the present invention and the pharmaceutical compositions thereof may be useful in the treatment or prevention of cancer. According to one embodiment, cancers that may benefit from a treatment with menin/MLL inhibitors of the invention comprise leukemias, myeloma or a solid tumor cancer (e.g. prostate cancer, lung cancer, breast cancer, pancreatic cancer, colon cancer, liver cancer, melanoma and glioblastoma, etc.). In some embodiments, the leukemias include acute leukemias, chronic leukemias, myeloid leukemias, myelogeneous leukemias, lymphoblastic leukemias, lymphocytic leukemias, Acute myelogeneous leukemias (AML), Chronic myelogenous leukemias (CML), Acute lymphoblastic leukemias (ALL), Chronic lymphocytic leukemias (CLL), T cell prolymphocytic leukemias (T-PLL), Large granular lymphocytic leukemia, Hairy cell leukemia (HCL), MLL-rearranged leukemias, MLL-PTD leukemias, MLL amplified leukemias, MLL-positive leukemias, leukemias exhibiting HOX/MEIS1 gene expression signatures etc.

Hence, the invention relates to compounds of Formula (I), the tautomers and the stereoisomeric forms thereof, and the pharmaceutically acceptable salts, and the solvates thereof, for use as a medicament.

The invention also relates to the use of a compound of Formula (I), a tautomer or a stereoisomeric form thereof, or a pharmaceutically acceptable salt, or a solvate thereof, or a pharmaceutical composition according to the invention, for the manufacture of a medicament.

The present invention also relates to a compound of Formula (I), a tautomer or a stereoisomeric form thereof, or a pharmaceutically acceptable salt, or a solvate thereof, or a pharmaceutical composition according to the invention, for use in the treatment, prevention, amelioration, control or reduction of the risk of disorders associated with the interaction of menin with MLL proteins and oncogenic MLL fusion proteins in a mammal, including a human, the treatment or prevention of which is affected or facilitated by blocking the interaction of menin with MLL proteins and oncogenic MLL fusion proteins.

Also, the present invention relates to the use of a compound of Formula (I), a tautomer or a stereoisomeric form thereof, or a pharmaceutically acceptable salt, or a solvate thereof, or a pharmaceutical composition according to the invention, for the manufacture of a medicament for treating, preventing, ameliorating, controlling or reducing the risk of disorders associated with the interaction of menin with MLL proteins and oncogenic MLL fusion proteins in a mammal, including a human, the treatment or prevention of which is affected or facilitated by blocking the interaction of menin with MLL proteins and oncogenic MLL fusion proteins.

The invention also relates to a compound of Formula (I), a tautomer or a stereoisomeric form thereof, or a pharmaceutically acceptable salt, or a solvate thereof, for use in the treatment or prevention of any one of the diseases mentioned hereinbefore.

The invention also relates to a compound of Formula (I), a tautomer or a stereoisomeric form thereof, or a pharmaceutically acceptable salt, or a solvate thereof, for use in treating or preventing any one of the diseases mentioned hereinbefore.

The invention also relates to the use of a compound of Formula (I), a tautomer or a stereoisomeric form thereof, or a pharmaceutically acceptable salt, or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), the tautomers and the stereoisomeric forms thereof, and the pharmaceutically acceptable salts, and the solvates thereof, there is provided a method of treating warm-blooded animals, including humans, suffering from any one of the diseases mentioned hereinbefore.

Said method comprises the administration, i.e. the systemic or topical administration, preferably oral administration, of a therapeutically effective amount of a compound of Formula (I), a tautomer or a stereoisomeric form thereof, or a pharmaceutically acceptable salt, or a solvate thereof, to warm-blooded animals, including humans.

Therefore, the invention also relates to a method for the treatment or prevention of any one of the diseases mentioned hereinbefore comprising administering a therapeutically effective amount of compound according to the invention to a patient in need thereof.

One skilled in the art will recognize that a therapeutically effective amount of the compounds of the present invention is the amount sufficient to have therapeutic activity and that this amount varies inter alias, depending on the type of disease, the concentration of the compound in the therapeutic formulation, and the condition of the patient. Generally, the amount of a compound of the present invention to be administered as a therapeutic agent for treating the disorders referred to herein will be determined on a case by case by an attending physician.

Those of skill in the treatment of such diseases could determine the effective therapeutic daily amount from the test results presented hereinafter. An effective therapeutic daily amount would be from about 0.005 mg/kg to 100 mg/kg, in particular 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. A particular effective therapeutic daily amount might be 1 mg/kg body weight, 2 mg/kg body weight, 4 mg/kg body weight, or 8 mg/kg body weight. The amount of a compound according to the present invention, also referred to herein as the active ingredient, which is required to achieve a therapeutically effect may vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The present invention also provides compositions for preventing or treating the disorders referred to herein. Said compositions comprising a therapeutically effective amount of a compound of Formula (I), a tautomer or a stereoisomeric form thereof, or a pharmaceutically acceptable salt, or a solvate thereof, and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences ($18^{th}$ ed., Mack Publishing Company, 1990, see especially Part 8: Pharmaceutical preparations and their Manufacture). A therapeutically effective amount of the particular compound, in base form or salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound of Formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds of the present invention may be administered alone or in combination with one or more additional therapeutic agents. Combination therapy includes administration of a single pharmaceutical dosage formulation which contains a compound according to the present invention and one or more additional therapeutic agents, as well as administration of the compound according to the present invention and each additional therapeutic agent in its own separate pharmaceutical dosage formulation. For example, a compound according to the present invention and a therapeutic agent may be administered to the patient together in a single oral dosage composition such as a tablet or capsule, or each agent may be administered in separate oral dosage formulations.

Therefore, an embodiment of the present invention relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular condition, in particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The following examples further illustrate the present invention.

EXAMPLES

Several methods for preparing the compounds of this invention are illustrated in the following examples. Unless otherwise noted, all starting materials were obtained from commercial suppliers and used without further purification.

Hereinafter, the terms: 'ACN or 'MeCN' means acetonitrile, 'DCM' means dichloromethane, 'DIPEA' means N,N-diisopropylethylamine, 'DIPE or 'DiPE'' means diisopropyl ether, 'h' means hours(s), 'min' means minute(s), 'DMF' means dimethylformamide, 'DSC' means differential scanning calorimetry, 'TEA or 'Et$_3$N' means triethyl amine, 'Et$_2$O' means diethyl ether, 'EtOAc' or 'EA' means ethyl acetate, 'EtOH' means ethanol, 'HPLC' means High-performance Liquid Chromatography, 'iPrOH' means isopropyl alcohol, 'LC/MS' means Liquid Chromatography/Mass Spectrometry, 'MeOH' means methanol, 'NMR' means Nuclear Magnetic Resonance, 'rt or 'RT' means room temperature, 'SFC' means supercritical fluid chromatography, 'OR' means optical rotation, 'sat. aq.' means saturated aqueous. 'AcCl' means acetyl chloride, 'AcOH' or 'HOAc' means acetic acid, 'BOC' or 'Boc' means tert-butyloxycarbonyl, 'Celite®' means diatomaceous earth, 'CH$_3$COONH$_4$' means ammonium acetate, 'COMUx' means (1-Cyano-2-ethoxy-2-oxoethylidenaminooxy)dimethylamino-morpholino-carbenium hexafluorophosphate, 'CO$_2$' means carbon dioxide, 'DCE' means dichloroethane, 'DMAP' means dimethylarninopyridine, 'DMSO' means dimethyl sulfoxyde, 'DBU' means 1,8-diazabicyclo[5.4.0]undecene-7, 'EDCl.HCl' means 1-(3-Dimethylaminopropyl)-3-ethyl-carbodiimide hydrochloride, 'ee' means enantiomeric excess, 'eq.' or 'equiv.' means equivalent(s), 'EtMgBr' means ethyl magnesium bromide, 'Et$_2$O' means diethyl ether, 'EtOAc' means ethyl acetate, 'Et$_3$N' or 'TEA' means triethylamine, 'EtOH' means ethanol, 'h' means hours(s), 'HATU' means O-(7-Azabenzotriazol-1-yl)-N,N,N,N-tetramethyluronium hexafluorophosphate, '—HCl' means hydrochloric acid, 'HOBT' means N-Hydroxybenzotrizole monohydrate, 'H₂O' means water, 'iPrMgCl' means isopropyl magnesium chloride, 'iPrNH₂' means isopropylamine, 'K₂CO₃' means potassium carbonate, 'Me-THF' means 2-methyl-tetrahydrofuran, 'MeMgBr' or 'CH₃MgBr' means methyl magnesium bromide, 'MeOH' means methanol, 'MgSO₄' means magnesium sulfate. 'min' means minute(s), 'NaBH(OAc)₃' means sodium triacetoxyborohydride, 'NaBH₃CN' means sodium cyanoborohydride, 'Na₂CO₃' means sodium carbonate, 'NaH' means sodium hydride, 'NaHCO₃' means sodium hydrogenocarbonate, 'NaOH' means potassium hydroxide, 'Na₂SO₄' means sodium sulfate, 'NH₄Cl' means ammonium chloride, 'NH₄HCO₃' means ammonium bicarbonate, 'NH₄OH' means ammonia solution 30% aqueous, 'Quant. or quant' means quantitative, 'R$_t$' means retention time, 'SFC' means supercritical fluid chromatography, 'T' means temperature, 'TBAF' means tetrabutylammonium fluoride, 'TBDMS' or 'SMDBT' means tert-butyldimethylsilyl, 'TFA' or 'CF₃COOH' means trifluoroacetic acid, 'THF' means tetrahydrofuran, 'Ti(OEt)₄' means titanium ethoxyde, 'Ti(OiPr)₄' means titanium isopropoxide, 'v.' means volume, 'F₃C' or 'CF₃' means trifluoromethyl, 'HBTU' means 1-[bis(dimethylamino)methylene]-1H-benzotriazoliumhexafluorophosphate(1-)₃-oxide.

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

The stereochemical configuration for centres in some compounds may be designated "R" or "S" when the mixture (s) was separated; for some compounds, the stereochemical configuration at indicated centres has been designated as "*R" (first eluted from the column in case the column conditions are described in the synthesis protocol and when only one stereocentre present) or "*S" (second eluted from the column in case the column conditions are described in the synthesis protocol and when only one stereocentre present) when the absolute stereochemistry is undetermined (even if the bonds are drawn stereospecifically) although the compound itself has been isolated as a single stereoisomer and is enantiomerically pure.

For example, it will be clear that compound 179

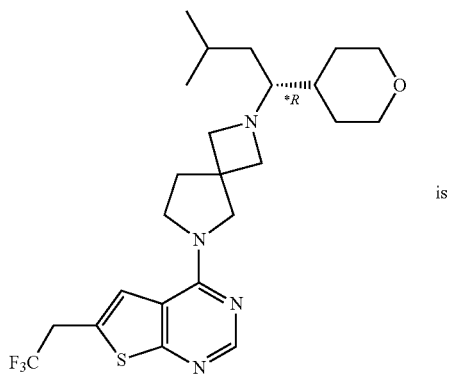

is

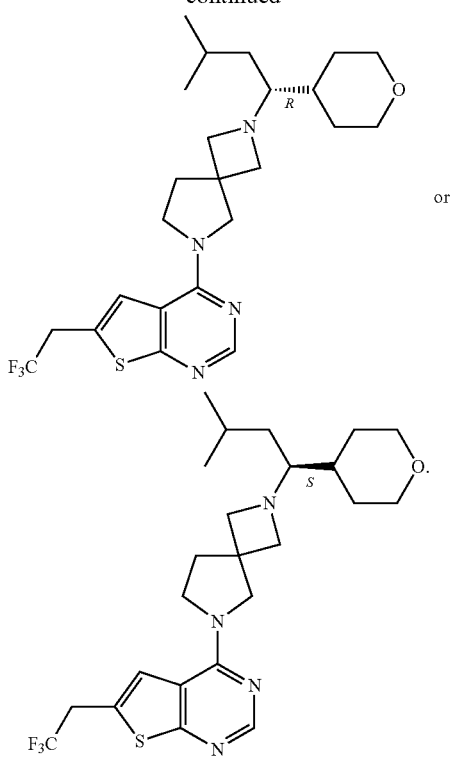

or

Compounds having two stereocentres of which only the stereochemical configuration of one stereocentre is indicated by * (e.g. *R or *S) (see for example compound 186 or 281), follow a similar rule as above. This means that the absolute stereoconfiguration of the stereocentre indicated by * is undetermined (even if the bonds are drawn stereospecifically) although the compound is enantiomerically pure at the indicated centre.

For compounds such as 188, 189, 190, 191, 235, 236, 237, and 238, wherein the stereochemical configuration of two stereocentres is indicated by * (e.g. *R or *S), the absolute stereochemistry of the stereocentres is undetermined (even if the bonds are drawn stereospecifically), although the compound itself has been isolated as a single stereoisomer and is enantiomerically pure. In this case, the configuration of the first stereocentre is independent of the configuration of the second stereocentre in the same compound.

For example, for Compound 188

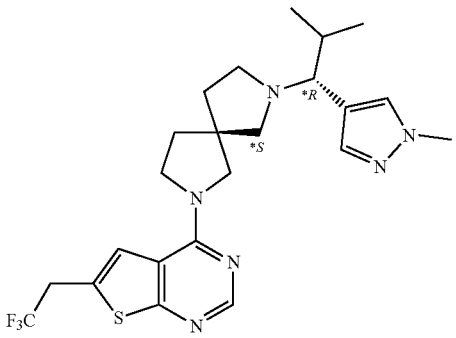

this means that the compound is

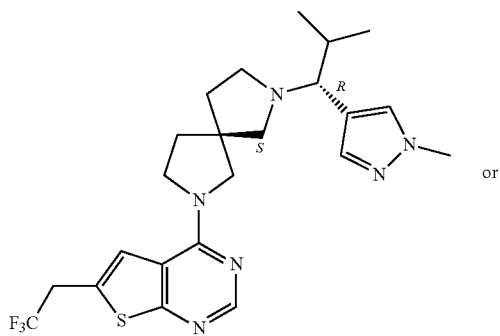

or

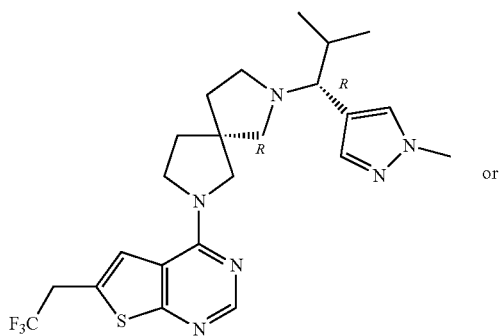

or

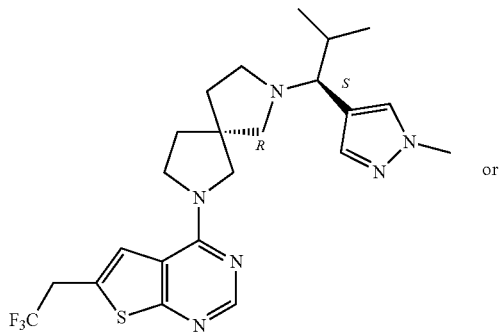

or

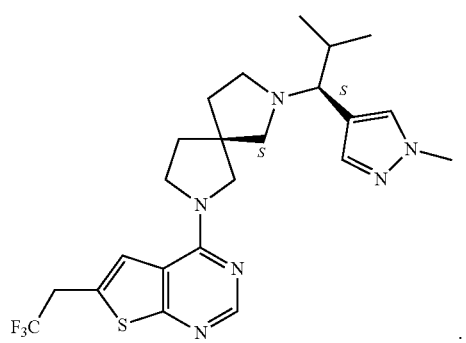

The paragraphs above about stereochemical configurations, also apply to intermediates.

The term "enantiomerically pure" as used herein means that the product contains at least 800% by weight of one enantiomer and 20% by weight or less of the other enantiomer. Preferably the product contains at least 90% by weight of one enantiomer and 10% by weight or less of the other enantiomer. In the most preferred embodiment the term "enantiomerically pure" means that the composition contains at least 99% by weight of one enantiomer and 1% or less of the other enantiomer.

When an intermediate or compound in the experimental part below is indicated as 'HCl salt', 'HCOOH salt' or 'TFA salt' without indication of the number of equivalents of HCl or TFA, this means that the number of equivalents of HCl or TFA was not determined.

A skilled person will realize that, even where not mentioned explicitly in the experimental protocols below, typically after a column chromatography purification, the desired fractions were collected and the solvent was evaporated.

In case no stereochemistry is indicated in the spirocycle represented by $L^1$, this means it is a mixture of stereoisomers, unless otherwise is indicated or is clear from the context.

When a stereocentre is indicated with 'RS' this means that a racemic mixture was obtained at the indicated centre, unless otherwise indicated.

A. Preparation of the Intermediates

Preparation of Intermediate 1:

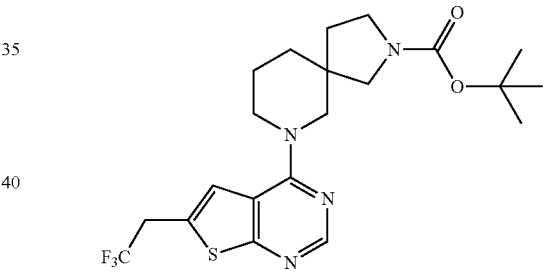

A mixture of 4-chloro-6-(2,2,2-trifluoroethyl)thieno[2,3-d]pyrimidine (525 mg, 2.08 mmol) prepared as described in Journal of Medicinal Chemistry (2016), 59(3), 892-913, tert-butyl 2,7-diazaspiro[4.5]decane-2-carboxylate (550 mg, 2.29 mmol) and DIPEA (1.43 mL, 8.3 mmol) in ACN (12 mL) was heated at 80° C. overnight. The solution was cooled and the mixture was poured into cooled water, the product was extracted with EtOAc, the organic layer was dried over MgSO$_4$, filtered and evaporated to dryness. The residue was purified by chromatography over silica gel (stationary phase: irregular 15-40 μm 50 g, mobile phase: DCM/MeOH: gradient from 100/0 to 99/1). The product containing fractions were collected and evaporated to dryness yielding 770 mg (yield 81%) of intermediate 1.

The compounds in the Table below were prepared by using an analogous method as described for the preparation of intermediate 1, starting from the respective starting materials

| Intermediate number | Structure | Quantity (mg) | Yield (%) |
| --- | --- | --- | --- |
| Intermediate 2 (from CAS[336191-17-4] and [1628317-85-0]) | 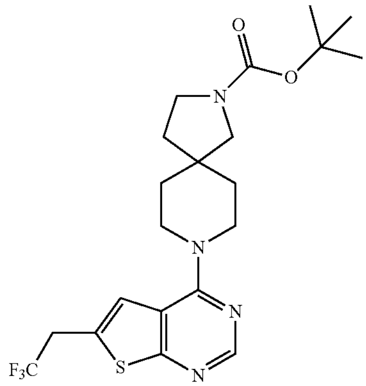 [SMILES: CC(C)(C)OC(=O)N1CCC2(CCN(c3ncnc4sc(CC(F)(F)F)cc34)CC2)C1] | 350 | 100 |
| Intermediate 3 (from CAS[885270-84-8] and [1628317-85-0]) | 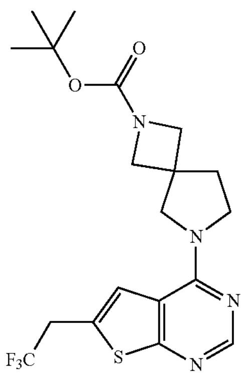 [SMILES: CC(C)(C)OC(=O)N1CC2(CCN(c3ncnc4sc(CC(F)(F)F)cc34)C2)C1] | 200 | 73 |
| Intermediate 4 (from CAS[885270-86-0] and [1628317-85-0]) | 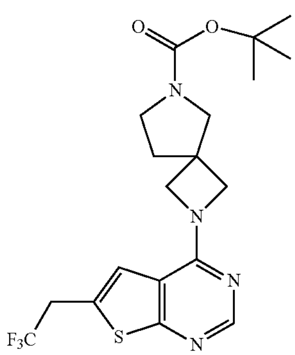 [SMILES: CC(C)(C)OC(=O)N1CCC2(C1)CN(c1ncnc3sc(CC(F)(F)F)cc13)C2] | 660 | 78 |
| Intermediate 5 (from CAS [885268-42-8] and intermediate 15) | 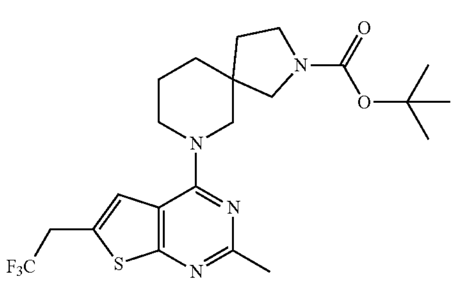 [SMILES: Cc1nc(N2CCCC3(CCN(C(=O)OC(C)(C)C)C3)C2)c2cc(CC(F)(F)F)sc2n1] | 355 | 57 |

Preparation of Intermediate 3:

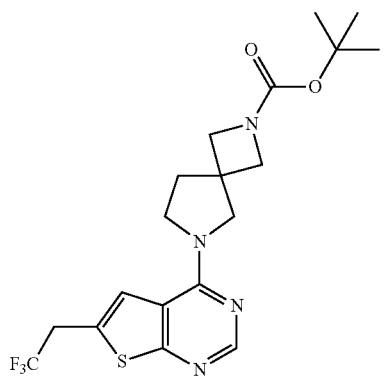 [SMILES: CC(C)(C)OC(=O)N1CC2(CCN(c3ncnc4sc(CC(F)(F)F)cc34)C2)C1]

A solution of 4-chloro-6-(2,2,2-trifluoroethyl)thieno[2,3-d]pyrimidine (11.4 g; 44.96 mmol), ter butyl 2,6 diazaspiro[3.4]octane-2-carboxylate (10.5 g; 49.46 mmol) and DIPEA (15.5 mL; 89.93 mmol) in iPrOH (183 mL) was heated at 90° C. overnight. The solution was cooled to rt and the solution was poured into water then extracted with EtOAc (3×). The organic layer was washed with brine, dried over MgSO$_4$ and filtered off.

A precipitate (in aqueous layer) was filtered off, washed with few DCM and combined with a previous filtrate. The solvent was evaporated to give 19.9 g of brown solid. The residue was taken up with diethylether, the precipitate was filtered and dried to give 18.5 g of pale brown solid of intermediate 3 (96%).

Alternative Preparation of Intermediate 3:

To a mixture of 4-chloro-6-(2,2,2-trifluoroethyl)thieno[2,3-d]pyrimidine (3.00 g, 11.9 mmol) and tert-butyl 2,6-diazaspiro[3.4] octane-2-carboxylate (2.5 g, 11.8 mmol) in EtOH (50 mL) was added DIPEA (2 g, 15.5 mmol) in one portion. The mixture was stirred at room temperature for 18 h. The mixture was evaporated and the residue was diluted in EA (200 mL). The solution was washed with water (100 mL*2), dried over Na$_2$SO$_4$, filtered and evaporated to give intermediate 3 (5.10 g, 11.9 mmol, 100% yield) as brown oil.

Preparation of Intermediate 6:

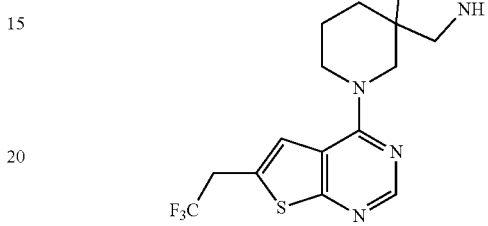

A mixture of intermediate 1 (770 mg, 1.69 mmol), and a solution of 4N HCl in dioxane (4.22 mL, 16.9 mmol) in ACN (45 mL) was stirred at rt overnight. The mixture was poured out into iced water, basified with 3N NaOH, the product was extracted with DCM, the organic layer was dried over MgSO$_4$, evaporated to dryness providing 670 mg of intermediate 6 which was used without further purification for the next step.

The compounds in the Table below were prepared by using an analogous method as described for the preparation of intermediate 6, starting from the respective starting materials.

| Intermediate number | Structure | Quantity (mg) | Yield (%) |
| --- | --- | --- | --- |
| Intermediate 7 (from intermediate 2) | HCl salt | 320 | |
| Intermediate 8 (from intermediate 4) | HCl salt | 582 | |

Preparation of Intermediate 9:

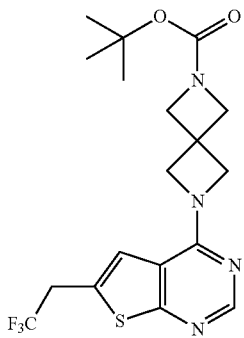 [SMILES: CC(C)(C)OC(=O)N1CC2(C1)CN(c1ncnc3sc(CC(F)(F)F)cc13)C2]

In a sealed tube, 4-chloro-6-(2,2,2-trifluoroethyl)thieno[2,3-d]pyrimidine (0.6 g, 2.37 mmol) prepared as described in Journal of Medicinal Chemistry (2016), 59(3), 892-913, tert-butyl 2,6-diazaspiro[3.3]heptane-2-carboxylate (0.57 g, 2.85 mmol), DIPEA (0.82 mL, 4.75 mmol) in iPrOH (15 mL) were heated at 90° C. for 2 h. The solution was cooled to rt and the reaction mixture was poured into water then extracted with EtOAc. The organic layer was washed with water, dried over MgSO$_4$, filtered and evaporated to dryness. The crude product was crystallized from Et$_2$O providing 0.6 g (yield 61%) of intermediate 9.

Preparation of Intermediate 10:

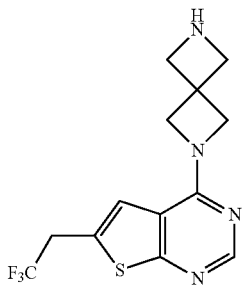 [SMILES: FC(F)(F)Cc1cc2c(N3CC4(CNC4)C3)ncnc2s1]

A mixture of intermediate 9 (4.43 g; 10.69 mmol) in formic acid (24 mL) was stirred at RT overnight. The reaction mixture was evaporated. The residue was taken up twice with Et$_2$O and evaporated to dryness. The residue was purified by chromatography over silica gel (irregular SiOH; 80 g; mobile phase: 90% DCM, 10% MeOH, 1% NH$_4$OH). The pure fractions were collected and evaporated to dryness yielding 3.34 g (99%) of intermediate 10.

Preparation of Intermediate 10b:

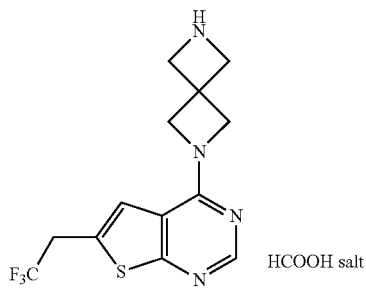 [SMILES: FC(F)(F)Cc1cc2c(N3CC4(CNC4)C3)ncnc2s1]

A mixture of intermediate 9 (0.55 g, 1.33 mmol) in formic acid (3 mL) was stirred at RT for 20 h. The mixture was evaporated in vacuo to give a residue that was taken-up twice with Et$_2$O and evaporated to dryness giving 0.4 g (yield 96%) of intermediate 10b (formic acid salt). The crude product was used without any further purification in the next step.

The compounds in the Table below were prepared by using an analogous method as described for the preparation of intermediate 10b, starting from the respective starting materials.

| Intermediate number | Structure |
|---|---|
| Intermediate 12 (from intermediate 5) | 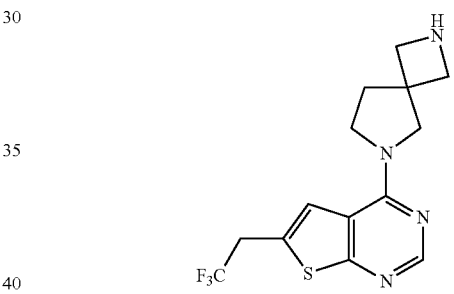<br>HCOOH salt |

Preparation of Intermediate 11:

A mixture of intermediate 3 (8.57 g; 20 mmol) in formic acid (51 mL) was stirred at rt for 20 h. The reaction mixture was stirred at rt for the week-end. The mixture was evaporated and the residue was cooled to 5° C., taken-up with DCM and neutralized with aqueous solution of NaOH 3N. The organic layer was washed with water, dried over MgSO$_4$, filtered and the solvent was evaporated. The residue (7.63 g of orange oil) was purified by chromatography over silica gel (irregular bare silica 120 g, mobile phase: 1% NH$_4$OH, 85% DCM, 15% MeOH). The pure fractions were collected and the solvent was evaporated to give 3.65 g of yellow oil intermediate 11 (56%).

Alternative Preparation of Intermediate 11:

TFA (17.9 mL; 233.38 mmol) was added to a solution of intermediate 3 (5 g; 11.67 mmol) in DCM (130 mL) at 5° C. and the reaction mixture was stirred at rt for 4 h. The reaction mixture was diluted with heptane and evaporated to dryness (3×) to give 10.7 g of brown oil. The residue was purified by chromatography over silica gel (irregular SiOH 40 μm; 220 g, mobile phase: 1% NH$_4$OH, 90% DCM, 10% MeOH). The pure fractions were collected and the solvent was evaporated. The residue (4 g) was solubilized with DCM and the product was crystallized. The mixture was evaporated and taken up several times with ACN and the solvent was evaporated to give 4 g of pale yellow solid intermediate 11.

Preparation of Intermediate 11b:

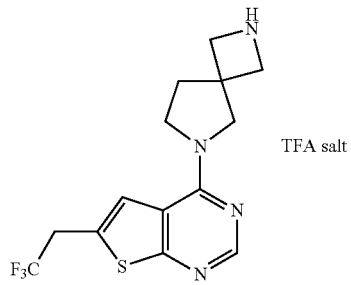 [SMILES: FC(F)(F)Cc1cc2c(N3CCC4(CNC4)C3)ncnc2s1]

TFA salt

TFA (2.2 mL; 28 mmol) was added to a solution of intermediate 3 (600 mg; 1.4 mmol) in DCM (13 mL) at 0° C. then the reaction mixture was stirred at rt overnight. The reaction mixture was evaporated till dryness to give 1.26 g of intermediate 11b as TFA salt. The product was used it directly without purification.

Preparation of Intermediate 11c:

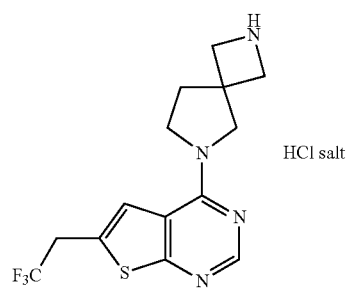 [SMILES: FC(F)(F)Cc1cc2c(N3CCC4(CNC4)C3)ncnc2s1]

HCl salt

A solution of HCl 4M in dioxane (150 mL) was added to intermediate 3 (6.5 g; 15.17 mmol) at rt. The reaction mixture was stirred at rt for 1 h. The mixture was evaporated in vacuum to give 5.7 g of yellow solid intermediate 11c as HCl salt. The product was used without purification for the next step.

Preparation of Intermediate 13:

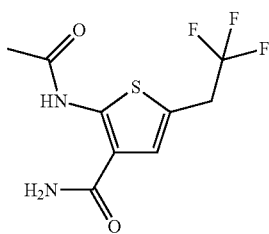 [SMILES: CC(=O)Nc1sc(CC(F)(F)F)cc1C(N)=O]

Acetic anhydride (1 mL, 10.7 mmol) was added dropwise at rt, to a solution of 2-amino-5-(2,2,2-trifluoroethyl)thiophene-3-carboxamide (2 g, 8.92 mmol) in toluene (50 mL) and trimethylamine (6.2 mL, 44.6 mmol). The solution was heated at reflux for 5 h, poured into water, extracted with EtOAc, and washed with brine (×2). The organic layer was dried over MgSO$_4$, filtered and evaporated to dryness, the crude product was taken-up with Et$_2$O and the precipitate was filtered to provide 1.5 g of intermediate 13 (yield 63%/brown solid).

Preparation of Intermediate 14:

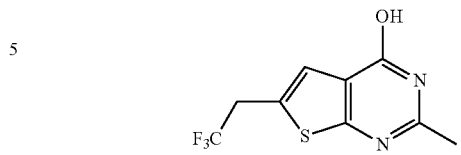

To a solution of intermediate 13 (1.5 g, 5.63 mmol) in EtOH (70 mL) at rt, was added dropwise a 1M solution of KOH. The reaction mixture was stirred at rt for 30 min, then the mixture was heated at reflux for 3 h. The reaction mixture was cooled to rt then poured into ice water, acidified with 3N HCl, extracted with DCM and decanted. The combined organic layers were washed with brine and dried over MgSO$_4$, filtered and evaporated to dryness. The residue was crystallized from Et$_2$O to give 0.7 g of intermediate 14 (yield 50%) that was used without further purification in the next step.

Preparation of Intermediate 15:

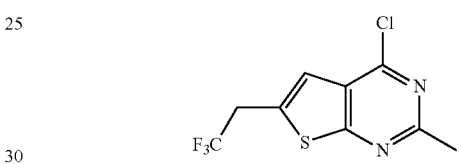

Intermediate 14 (0.7 g, 2.82 mmol) and phosphoryl trichloride (5 mL) were heated at 110° C. for 2 h. The reaction mixture was cooled to rt, then evaporated to dryness. The residue was taken-up carefully with ice and DCM, basified with an aqueous solution of K$_2$CO$_3$ (10%) and the organic layer was washed with water, dried over MgSO$_4$, filtered and evaporated to dryness to give 0.75 g (yield 99%) of intermediate 15, that was used without further purification in the next step.

Preparation of Intermediate 16:

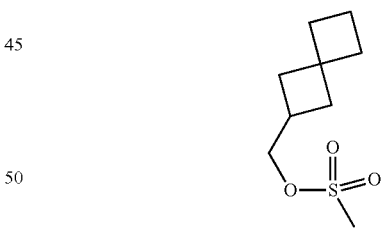

Spiro[3.3]heptan-2-ylmethyl methanesulfonate

To a solution of spiro[3.3]heptan-2-ylmethanol (153 mg, 1.08 mmol) in 4 mL of DCM was added TEA (0.464 mL, 3.2 mmol) and the reaction mixture was cooled to 0° C. Methylsulfonylchloride (0.184 g, 1.605 mmol) was then added dropwise, the mixture was allowed to warm to rt and stirred for 2 h. An aqueous solution of saturated NaHCO$_3$ (30 mL) and DCM (30 mL) were added. The mixture was separated, the organic layer was collected, washed with brine (10 mL), dried over Na$_2$SO$_4$, and evaporated to give 300 mg of intermediate 16 as a yellow oil which was used without further purification in the next step.

Preparation of Intermediate 17:

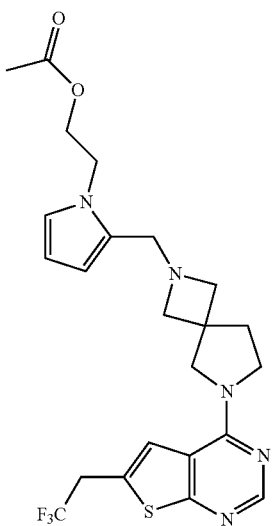 [SMILES: CC(=O)OCCn1cccc1CN1CC2(CCN(c3ncnc4sc(CC(F)(F)F)cc34)C2)C1]

To a solution of intermediate 11c (400 mg) and TEA (0.38 mL, 2.76 mmol) under a $N_2$ flow in DCM (20 mL) was added 1-[2-(acetyloxy)ethyl]-1H-pyrrole-2-carboxaldehyde (200 mg, 1.11 mmol). The mixture was stirred at rt for 4 h. $NaBH(OAc)_3$ (390 mg, 1.84 mmol) was added and the mixture was stirred at rt for 48 h. Then, it was poured into ice water and the mixture was separated and the aqueous layer was extracted with DCM. The organic layers were combined, washed with brine then dried over $MgSO_4$ and evaporated to dryness. The residue was purified by chromatography over silica gel (stationary phase: irregular SiOH 15-40 µm 24 g, mobile phase: DCM/MeOH: 97/3). The pure fractions were collected and the solvent was evaporated under vacuum yielding 180 mg of intermediate 17.

Preparation of Intermediate 35

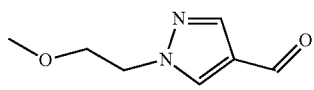

1H-pyrazole-4-carbaldehyde (0.5 g; 5.2 mmol) and cesium carbonate (3.39 g; 10.4 mmol) were diluted in ACN (10 mL). Then, 2-bromoethyl methyl ether (0.636 mL; 6.77 mmol) was added and the reaction mixture was refluxed for 2 hours. The reaction mixture was partitioned between a saturated solution of $NaHCO_3$ and EtOAc. The organic layer was separated, dried over $MgSO_4$, filtered and concentrated.

The residue was purified by silica gel chromatography (irregular $SiO_2$, 120 g, DCM/MeOH: 100/0 to 95/5). The fractions containing the product were mixed and concentrated to afford 439 mg (55%) of intermediate 35.

Preparation of Intermediate 20:

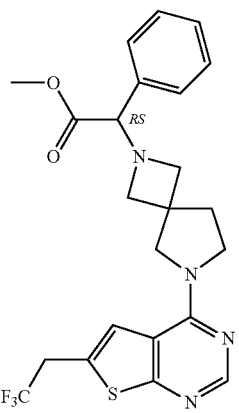 [SMILES: COC(=O)C(c1ccccc1)N1CC2(CCN(c3ncnc4sc(CC(F)(F)F)cc34)C2)C1]

Intermediate 11 (150 mg, 0.46 mmol), (+/−)-methyl alpha-bromophenylacetate (0.08 mL, 0.50 mmol) and $K_2CO_3$ (127 mg; 0.92 mmol) in DMF (10 mL) were stirred at rt for 5 h. The reaction mixture was poured into ice water and EtOAc was added. The organic layer was separated, washed with brine, dried over $MgSO_4$, filtered and evaporated till dryness. The residue was purified by chromatography over silica gel (stationary phase: irregular SiOH 15-40 µm 24 g, mobile phase: DCM/MeOH (+10% $NH_4OH$): gradient from 97/3 to 95/5). The pure fractions were collected and evaporated to dryness yielding 162 mg (yield 74%) of intermediate 20.

Preparation of Intermediate 32

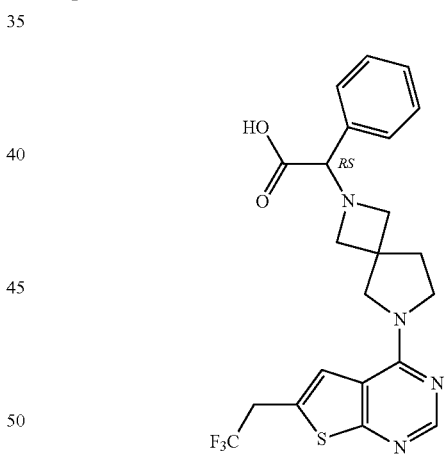

Lithium hydroxide monohydrate (71 mg; 1.7 mmol) was added, at rt, to a solution of intermediate 20 (162 mg; 0.34 mmol) in THF (3 mL) and water (3 mL). The mixture was stirred at rt overnight, then concentrated and acidified with an aqueous solution of HCl 3N (pH=2-4). The precipitate was filtered and dry to give 33 mg (21%) of intermediate 32 (90% of purity based on LC/MS). The mother layer was evaporated till dryness to give 243 mg of an impure fraction of intermediate 32.

Preparation of Intermediate 54

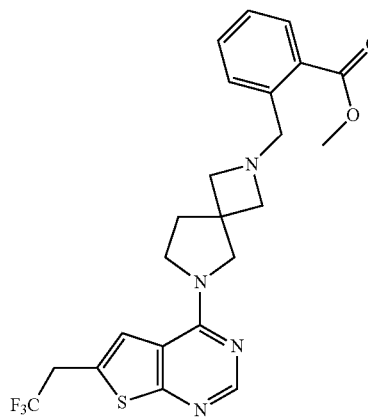

Intermediate 11c (333 mg), methyl 2-formylbenzoate (148.5 mg; 0.905 mmol), NaBH(OAc)$_3$ (872 mg; 4.11 mmol) and trimethylamine (250 mg; 2.47 mmol) were mixed in dichloroethane (16 mL) and the reaction was stirred at RT overnight. Then, an aqueous solution of NaHCO$_3$ (1 mL) was added and the mixture was extracted with DCM (4*15 mL). The organic layers were separated, mixed, dried over MgSO$_4$, filtered and concentrated to afford 450 mg of intermediate 54 as white solid.

The intermediates in the Table below were prepared by using an analogous method as described for the preparation of intermediate 54, starting from the respective starting materials.

Preparation of Intermediate 47

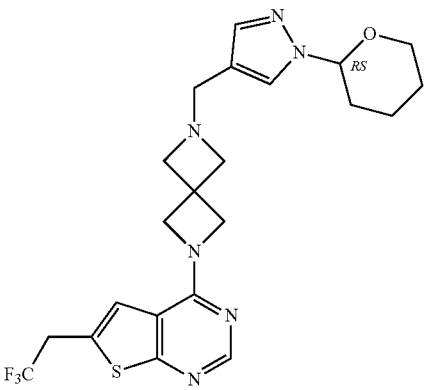

A mixture of intermediate 10b (150 mg), 1-(tetrahydro-2H-pyran-2-yl)-1H-pyrazole-4-carboxaldehyde (225 mg; 1.249 mmol) and AcOH (24 μL; 0.416 mmol) in dichloroethane (4.5 mL) was stirred at 50° C. for 2 hours. The reaction mixture was cooled to room temperature and NaBH(OAc)$_3$ (265 mg; 1.249 mmol) was added. The reaction mixture was stirred at room temperature overnight, poured onto a 10% aqueous solution of K$_2$CO$_3$ and extracted with DCM. The organic layer was decanted, dried over MgSO$_4$, filtered and evaporated to dryness. The residue was purified by chromatography over silica gel (irregular SiOH, 24 g; mobile phase: gradient from 0% MeOH, 100% DCM to 10% MeOH, 90% DCM). The pure fractions were collected and evaporated to dryness yielding 150 mg of intermediate 47.

The intermediates in the Table below were prepared by using an analogous method as described for the preparation of intermediate 47, starting from the respective starting materials.

| Intermediate number | Structure | Quantity (mg) | Yield (%) |
| --- | --- | --- | --- |
| Intermediate 44 (from intermediate 11c and intermediate 52) | 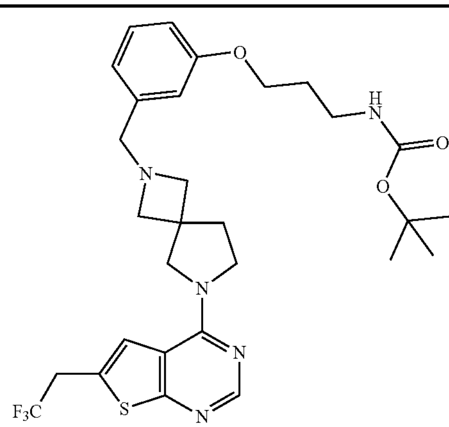 | 340 | |

| Intermediate number | Structure | Quantity (mg) | Yield (%) |
|---|---|---|---|
| Intermediate 48 (from intermediate 10b and 1-(oxan-2-yl)pyrazole-3-carbaldehyde) | 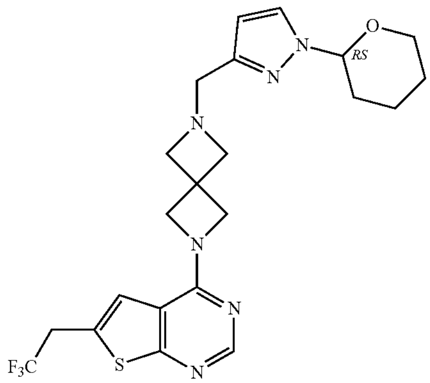 [SMILES: FC(F)(F)Cc1cc2c(N3CC4(CN(Cc5ccn(C6CCCCO6)n5)C4)C3)ncnc2s1] | 158 | |

Preparation of Intermediate 25:

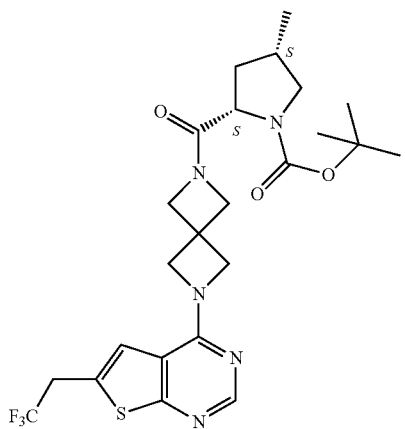

A mixture of (4S)-1-Boc-4-methyl-L-proline (174 mg, 0.761 mmol), HBTU (288 mg, 0.761 mmol) and DIPEA (0.65 mL, 3.804 mmol) in DMF (7.5 mL) was stirred for 1 h. Then, a solution of intermediate 10 (250 mg, 0.761 mmol) in DMF (5 mL) was added. The reaction mixture was stirred at rt overnight. The reaction mixture was poured into iced water, basified with a 10% aqueous solution of $K_2CO_3$ and extracted with EtOAc. The organic layer was washed with water, then brine, dried over $MgSO_4$, filtered and evaporated to dryness. The residue (490 mg) was purified by chromatography over silica gel (irregular SiOH, 40 g; mobile phase: $NH_4OH$/DCM/MeOH: 0.5/95/5). The pure fractions were collected and evaporated to dryness yielding 330 mg (yield 82%) of intermediate 25.

The intermediates in the Table below were prepared by using an analogous method as described for the preparation of intermediate 25, starting from the respective starting materials.

| Intermediate number | Structure | Quantity (mg) | Yield (%) |
|---|---|---|---|
| Intermediate 26 (from intermediate 10b and N-Boc-(2S,4S)-4-fluoropyrrolidine-2-carboxylic acid) | 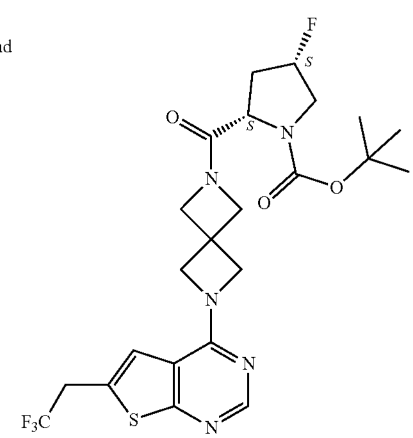 | 200 | |

| Intermediate number | Structure | Quantity (mg) | Yield (%) |
|---|---|---|---|
| Intermediate 27 (from intermediate 11 and (R)-5-Boc azaspiro[2.4] heptane-6 carboxylic acid) | 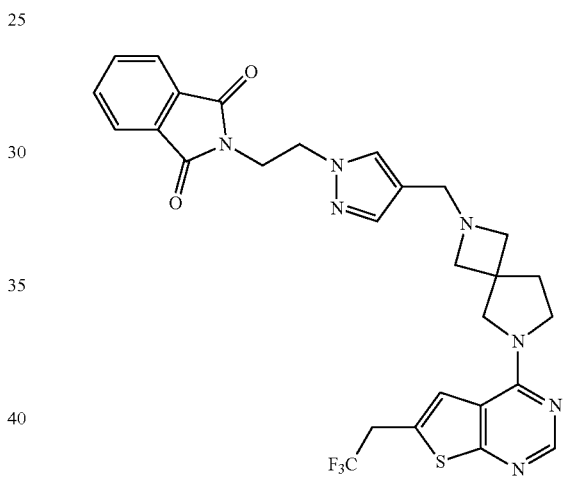 | 250 | 100 |

Preparation of Intermediate 104

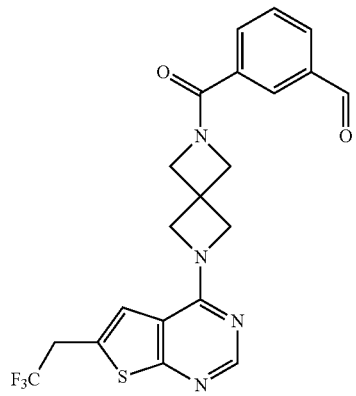 [SMILES: O=Cc1cccc(C(=O)N2CC3(C2)CN(c2ncnc4sc(CC(F)(F)F)cc24)C3)c1]

Preparation of Intermediate 41:

DIPEA (0.48 mL; 2.775 mmol) was added to a solution of intermediate 10b (200 mg), 3-carboxybenzaldehyde (100 mg; 0.666 mmol) and HATU (317 mg; 0.833 mmol) in DMF (10 mL) and the reaction mixture was stirred at room temperature for 4 hours. The reaction mixture was poured onto water and extracted with EtOAc. The organic layer was decanted, washed with water, then brine, dried over MgSO$_4$, filtered and evaporated to dryness. The residue was purified by chromatography over silica gel (irregular SiOH, 24 g; mobile phase: gradient from 0% MeOH, 100% DCM to 10% MeOH, 90% DCM). The pure fractions were collected and evaporated to dryness yielding 62 mg of intermediate 104.

Under a N$_2$ flow, at rt, to a solution of intermediate 11 (250 mg, 0.76 mmol) in DCM (12 mL) was added intermediate 42 (246 mg, 0.91 mmol). The mixture was stirred at room temperature for 3 h. The mixture was cooled to 5° C., NaBH(OAc)$_3$ (323 mg, 1.52 mmol) was added and the mixture was stirred at rt overnight. Then, it was poured into ice water and the layers were separated. The aqueous layer was extracted with DCM. The organic layers were combined, washed with brine then dried over MgSO$_4$, evaporated. The residue was crystallized from Et$_2$O and pentane. The white precipitate was filtered off and dried under vacuum yielding 55 mg (yield 100%) of intermediate 41.

Preparation of Intermediate 43:

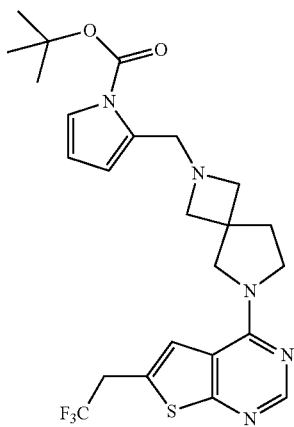 [SMILES: CC(C)(C)OC(=O)n1cccc1CN1CC2(CCN(c3ncnc4sc(CC(F)(F)F)cc34)C2)C1]

Intermediate 11 (500 mg, 1.52 mmol), 2-(chloromethyl)-1,1-dimethylethyl ester-1H-pyrrole-1-carboxylic acid) (493 mg, 2.28 mmol) and $K_2CO_3$ (1.05 g, 7.61 mmol) in ACN (12 mL) were stirred at room temperature for 24 h. The reaction mixture was poured into ice water and EtOAc was added. The organic layer was separated, washed with brine, dried over $MgSO_4$, filtered and evaporated till dryness. The residue was purified by chromatography over silica gel (stationary phase: irregular SiOH 15-40 μm 24 g, mobile phase: $NH_4OH/DCM/MeOH$: gradient from 0.1/97/3 to 0.1/95/5). The pure fractions were mixed and evaporated yielding 100 mg (yield 14%) of intermediate 43.

The intermediates in the Table below were prepared by using an analogous method as described for the preparation of intermediate 43, starting from the respective starting materials.

Preparation of Intermediate 50:

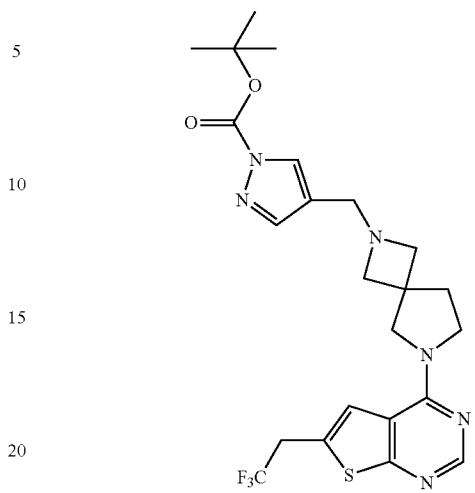

Under a $N_2$ flow, to a solution of intermediate 11 (202 mg, 0.62 mmol) in DCM (10 mL) was added tert-butyl 4-formyl-1H-pyrazole-1-carboxylate (133 mg, 0.68 mmol) and AcOH (35 μL, 0.62 mmol). The mixture was stirred at room temperature for 2 h. $NaBH(OAc)_3$ (521 mg, 2.46 mmol) was added and the mixture was stirred at rt overnight, poured into ice water and the layers were separated. The aqueous layer was extracted with DCM. The organic layers were combined, washed with brine then dried over $MgSO_4$, evaporated. The residue was purified by chromatography over silica gel (stationary phase: irregular SiOH 15-40 μm 24 g, mobile phase: DCM/MeOH(+10% $NH_4OH$): 97/3). The pure fractions were mixed and evaporated yielding 145 mg (yield 46%) of intermediate 50.

| Intermediate number | Structure | Quantity (mg) | Yield (%) |
|---|---|---|---|
| Intermediate 51 (from 1H-pyrrole-4-carboxaldehyde and 3-bromopropionitrile) | 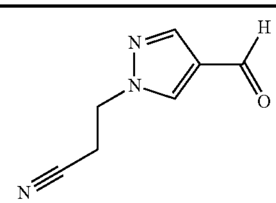 | 157 | 66 With 60° C. as reaction temperature |
| Intermediate 42 (from 1H-pyrrole-4-carboxaldehyde and N-(2-bromoethyl)phthalimide) | 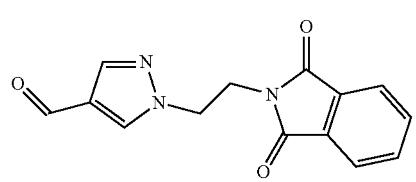 [SMILES: O=Cc1cnn(CCN2C(=O)c3ccccc3C2=O)c1] | 1000 | 71 With reflux as reaction temperature |
| Intermediate 52 (from 3-hydroxybenzaldehyde and 3-(Boc-amino)propyl bromide) | 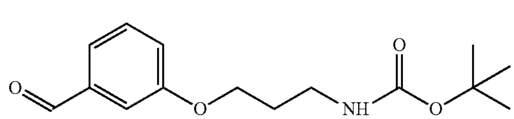 [SMILES: CC(C)(C)OC(=O)NCCCOc1cccc(C=O)c1] | 340 | 99 With 75° C. as reaction temperature |
| Intermediate 53 (from 1H-pyrazole-4-carbaldehyde and 2-bromoethoxy-t-butyl dimethylsilane) | 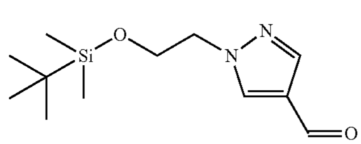 [SMILES: CC(C)(C)[Si](C)(C)OCCn1cc(C=O)cn1] | 1563 | 65 With reflux as reaction temperature |

Preparation of Intermediate 55:

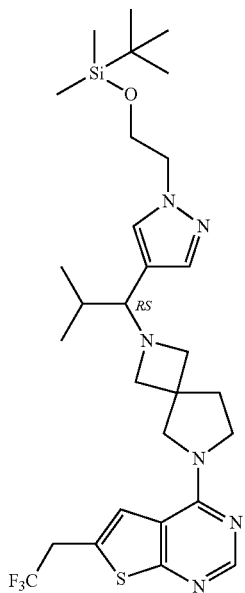 [SMILES: CC(C)C(c1cnn(CCO[Si](C)(C)C(C)(C)C)c1)N1CC2(CCN(c3ncnc4sc(CC(F)(F)F)cc34)C2)C1]

In a sealed tube, under a N$_2$ flow, intermediate 53 (349 mg, 1.37 mmol) and Ti(OiPr)$_4$ (436 µL, 1.83 mmol) were added to a solution of intermediate 11 (300 mg, 0.914 mmol) in THF (6 mL). The solution was stirred at 50° C. for 5 hours then, at rt overnight. The reaction mixture was cooled to 5° C. and 2N iPrMgCl in THF (2.28 mL, 4.57 mmol) was added dropwise. The reaction mixture was allowed to rise slowly to rt and stirred overnight. The reaction mixture was diluted with EtOAc and poured onto a 10% aqueous solution of K$_2$CO$_3$. The insoluble material was removed by filtration over Celite®. The organic layer was decanted, washed with brine, dried over MgSO$_4$, filtered and evaporated to dryness. The residue was purified by chromatography over silica gel (irregular SiOH, 40 g; mobile phase: MeOH/DCM: gradient from 0/100 to 10/90). The pure fractions were collected and evaporated to dryness yielding: 0.3 g (yield 54%) of intermediate 55.

Preparation of Intermediate 63

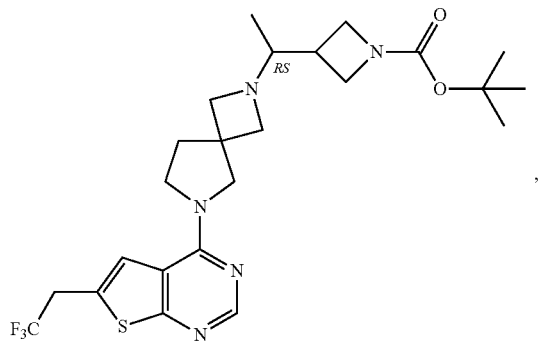 [SMILES: CC(C1CN(C(=O)OC(C)(C)C)C1)N1CC2(CCN(c3ncnc4sc(CC(F)(F)F)cc34)C2)C1]

Intermediate 63a

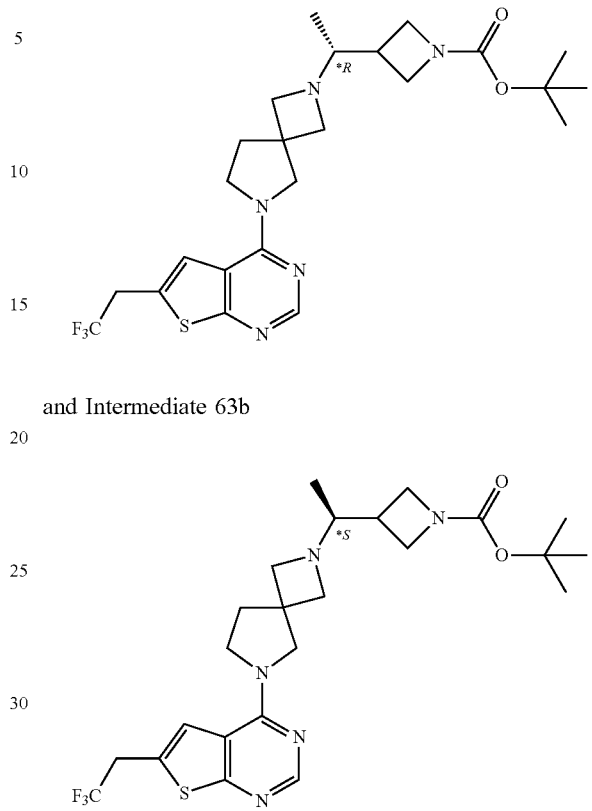

and Intermediate 63b

A solution of tert-butyl 3-acetylazetidine-1-carboxylate (364 mg; 1.83 mmol), intermediate 11 (400 mg; 1.22 mmol), titanium(IV)isopropoxide (725 µL; 2.44 mmol) in ethanol (2 mL) was stirred at 45° C. for 30 min (solution become dark yellow). Ethanol (12 mL) and NaBH$_4$ (138 mg; 3.66 mmol) were added and the solution become yellow pale. The reaction mixture was stirred at room temperature overnight. Then, it was poured onto a 10% aqueous solution of K$_2$CO$_3$ and DCM. The insoluble was filtered through a pad of Celite®. The organic layer was decanted, filtered through Chromabond® and the solvent was evaporated 624 mg of pale yellow oil which was purified by chromatography over silica gel (SiO$_2$; 25 g; mobile phase: gradient from 98% DCM, 2% MeOH to 96% DCM, 4% MeOH). The fractions containing the product were collected and the solvent was evaporated to give 223 mg (36%) of intermediate 63 as a white foam. Intermediate 63 was purified by chiral SFC (Stationary phase: CHIRALCEL OJ-H 5 µm 250×20 mm, Mobile phase: 92% CO$_2$, 8% MeOH(0.3% iPrNH$_2$)). The pure fractions were collected and the solvent was evaporated to give 83 mg (13%) of intermediate 63a as a colourless oil and 90 mg (14%) of intermediate 63b.

The intermediate in the Table below were prepared by using an analogous method as described for the preparation of intermediate 63, starting from the respective starting materials.

| Intermediate number | Structure | Quantity | Yield |
|---|---|---|---|
| Intermediate 60 (from intermediate 11 and N-Boc-4-acetylpiperidine | *RS* isomer structure | 600 mg | 52% |
| Intermediate 60a and intermediate 60b From chiral SFC separation of intermediate 60: (Chiralpak AD-H 5 μm 250 * 30 mm; mobile phase: 75% $CO_2$, 25% iPrOH (0.3% $iPrNH_2$)). | intermediate 60a (*R) | 221 mg | 20% |
| | Intermediate 60b (*S) | 229 mg | 20% |
| Intermediate 109 (from intermediate 11 and intermediate 108) | *RS* isopropyl structure | 324 mg | 33% |

Preparation of Intermediate 68

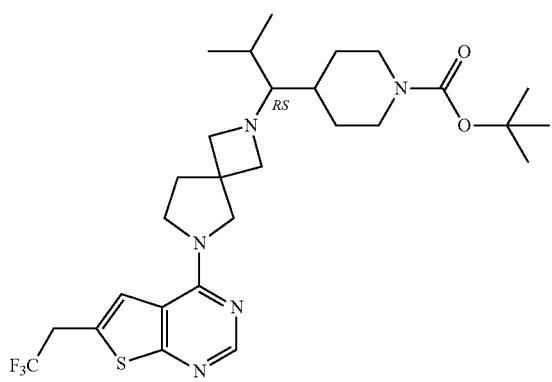 [SMILES: CC(C)C(C1CCN(C(=O)OC(C)(C)C)CC1)N1CC2(CCN(c3ncnc4sc(CC(F)(F)F)cc34)C2)C1]

Intermediate 68a

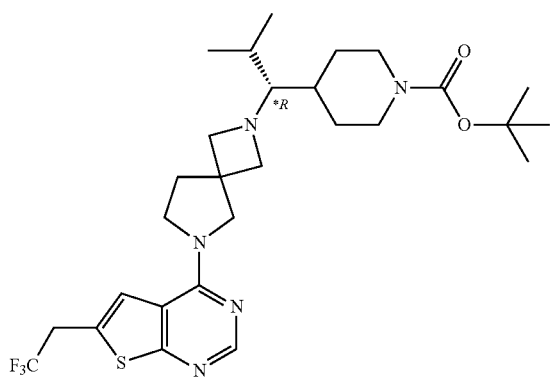 [SMILES: CC(C)[C@H](C1CCN(C(=O)OC(C)(C)C)CC1)N1CC2(CCN(c3ncnc4sc(CC(F)(F)F)cc34)C2)C1]

Intermediate 68b

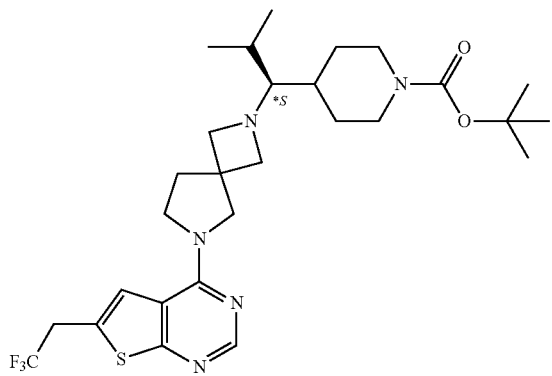 [SMILES: CC(C)[C@@H](C1CCN(C(=O)OC(C)(C)C)CC1)N1CC2(CCN(c3ncnc4sc(CC(F)(F)F)cc34)C2)C1]

and Compound 61:

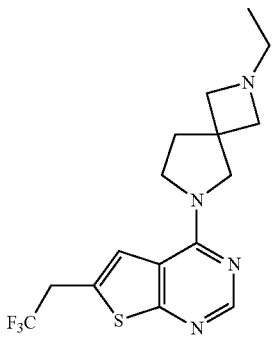 [SMILES: CCN1CC2(CCN(c3ncnc4sc(CC(F)(F)F)cc34)C2)C1]

A solution of intermediate 113 (1.67 g; 6.54 mmol) in THF (15 mL) was added to a solution of intermediate 11 (1.4 g; 4.36 mmol) and TFA (2 mL; 26.16 mmol) in THF (30 mL). The reaction mixture was stirred at rt overnight. Then NaBH(OAc)$_3$ (2.77 g; 13.08 mmol) was added portionwise. The reaction mixture was stirred at rt for 10 days. The solution was poured out into a 10% aqueous solution of K$_2$CO$_3$ and EtOAc was added. The mixture was extracted with EtOAc (3×). The organic layers were combined, washed with brine, dried over MgSO$_4$, filtered and the solvent was evaporated. The residue (2.9 g; yellow oil) was purified by chromatography over silica gel (SiO$_2$; 40 g; eluent: from 97% DCM, 3% MeOH, 0.3% NH$_4$OH to 90% DCM, 10% MeOH, 1% NH$_4$OH). The desired fractions were collected and the solvent was evaporated to give 266 mg of colourless oil intermediate 68, and 215 mg of colourless oil fraction 1.

Intermediate 68 was purified by chiral SFC (Lux-cellulose-2 5 μm 250*30 mm, mobile phase: 50% CO$_2$, 50% MeOH (0.3% iPrNH$_2$)). The pure fractions were collected and the solvent was evaporated to give 114 mg (5%) of colourless oil intermediate 68a and 109 mg (4%) of colourless oil intermediate 68b.

Fraction 1 was purified by reverse phase (YMC-actus Triart C18 10 μm 30*150 mm, mobile phase: gradient from 65% NH$_4$HCO$_3$ 0.2%, 35% ACN to 25% NH$_4$HCO$_3$ 0.2%, 75% ACN). The fractions containing the product were collected and the solvent was evaporated. The residue (160 mg; colourless oil) was freeze-dried with water-ACN to give 90 mg (6%) of white solid compound 61.

Preparation of Intermediate 69

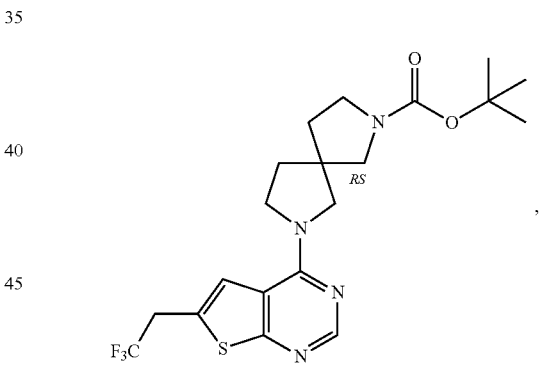

Intermediate 69a

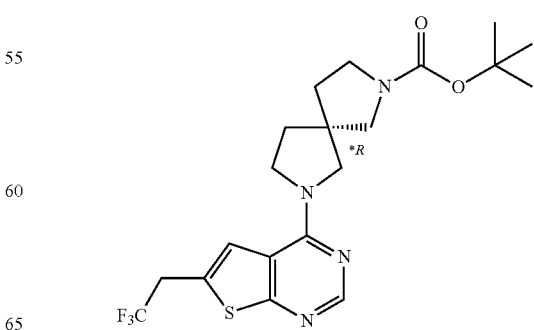

and Intermediate 69b

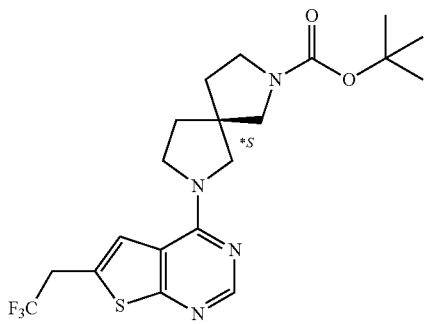 [SMILES: CC(C)(C)OC(=O)N1CC[C@]2(CCN(c3ncnc4sc(CC(F)(F)F)cc34)C2)C1]

A solution of 4-chloro-6-(2,2,2-trifluoroethyl)thieno[2,3-d]pyrimidine (5.07 g; 20.08 mmol), 2-BOC-2,7-diaza-spiro[4.4]nonane (5 g; 22.09 mmol) and DIPEA (6.9 mL; 40.17 mmol) in iPrOH (80 mL) was heated at 90° C. overnight. The solution was cooled to rt and the solution was poured into water then extracted with EtOAc (3×). The organic layer was washed with brine, dried over MgSO$_4$ and the solvent was evaporated to dryness. The residue (9 g, pale brown solid) was taken up with diethylether, the precipitate was filtered and dried to give 8.4 g of intermediate 69 (95%, off-white solid). Intermediate 69 was purified by chiral SFC (Chiralpak IG 5 µm 250*20 mm, mobile phase: 65% CO$_2$, 35% iPrOH (0.3% iPrNH$_2$)). The pure fractions were collected and the solvent was evaporated to give 4.07 g of intermediate 69a (46%, yellow foam) and 4.29 g of intermediate 69b (48%, yellow foam).

Preparation of Intermediate 70a:

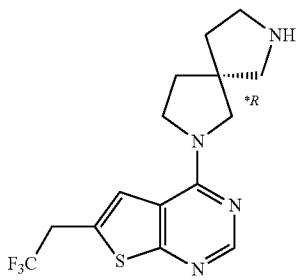 [SMILES: FC(F)(F)Cc1cc2c(N3CC[C@@]4(CCNC4)C3)ncnc2s1]

The intermediate 70a was prepared by using an analogous method as described for the alternative preparation of intermediate 11, starting from the respective starting material intermediate 69a.

The intermediate in the Table below were prepared by using an analogous method as described for the alternative preparation of intermediate 11, starting from the respective starting materials.

| Intermediate number | Structure | Quantity | Yield |
|---|---|---|---|
| Intermediate 70b (from intermediate 69b) | 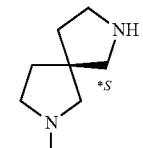 | 3.4 g | Quant. |

Preparation of Intermediate 71

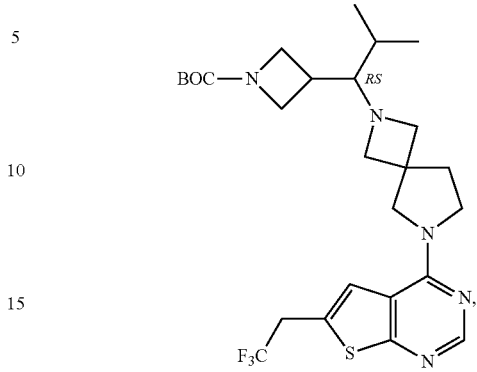

Intermediate 71a

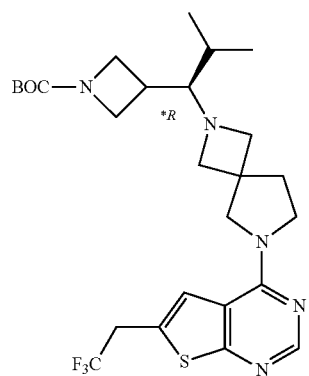 [SMILES: CC(C)[C@H](C1CN(C(=O)OC(C)(C)C)C1)N1CC2(CCN(c3ncnc4sc(CC(F)(F)F)cc34)C2)C1]

and Intermediate 71b

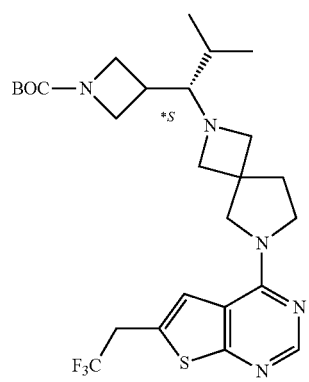 [SMILES: CC(C)[C@@H](C1CN(C(=O)OC(C)(C)C)C1)N1CC2(CCN(c3ncnc4sc(CC(F)(F)F)cc34)C2)C1]

Method A:

A mixture of intermediate 11b (4.2 g) and intermediate 72 (1.6 g; 7 mmol) in THF (50 mL) was stirred at RT overnight. Then, NaBH(OAc)$_3$ (3 g; 14 mmol) was added portion-wise. The reaction mixture was stirred at room temperature for 24 hours. The solution was poured onto cold water, basified with an aqueous solution of NaOH 3N and EtOAc was added. The organic layer was separated, dried over MgSO₄, filtered and evaporated to dryness. The residue was purified by chromatography over silica gel (irregular SiOH 80 g, mobile phase: gradient from 98% DCM, 2% MeOH (+10% NH₄OH) to 95% DCM, 5% MeOH (+10% NH₄OH)). The pure fractions were collected and evaporated to dryness yielding 852 mg of intermediate 71.

The enantiomers were separated by chiral SFC (CHIRALCEL OD-H 5 μm 250*30 mm; mobile phase: 70% CO₂, 30% EtOH). The pure fractions were collected and evaporated to dryness yielding 294 mg of intermediate 71a and 303 mg of intermediate 71b.

Method B:

The experiment was performed 6 times on the same quantity (640 mg; 1.95 mmol) Ti(OEt)₄ (0.8 mL; 3.9 mmol) was added at room temperature to a solution of intermediate 11 (640 mg; 1.95 mmol) and intermediate 72 (665 mg; 2.92 mmol) in DCE (20 mL) and MeOH (8 mL). The reaction mixture was stirred at RT for 24 h, cooled at 10° C. then NaBH₃CN (367 mg; 5.84 mmol) was added portion wise. The reaction mixture was stirred at room temperature for 8 days. The solutions were gathered for the work-up: poured out into cold water, basified with K₂CO₃ powder and extracted with DCM. The suspension was filtered through a pad of Celite®. The filtrate was decanted, dried over MgSO₄, filtered and evaporated to dryness.

The residue was purified by chromatography over silica gel (irregular SiOH, 40 g; mobile phase: gradient from 100% DCM, 0% MeOH to 97% DCM, 3% MeOH, 0.1% NH₄OH). The pure fractions were collected and evaporated to dryness yielding 1.7 g (28%) of intermediate 71.

The enantiomers were separated by chiral SFC (Chiralcel OD-H 5 μm 250*30 mm; mobile phase: 70% CO₂, 30% EtOH (0.3% iPrNH₂)). The pure fractions were collected and evaporated to dryness yielding 697 mg (11%) of intermediate 71a and 727 mg (12%) of intermediate 71b.

The intermediates in the table below were prepared following Method A as described for the preparation of intermediate 71, 71a and 71b starting from the respective starting materials.

| Intermediate number | Structure | Quantity | Yield |
|---|---|---|---|
| intermediate 88 | 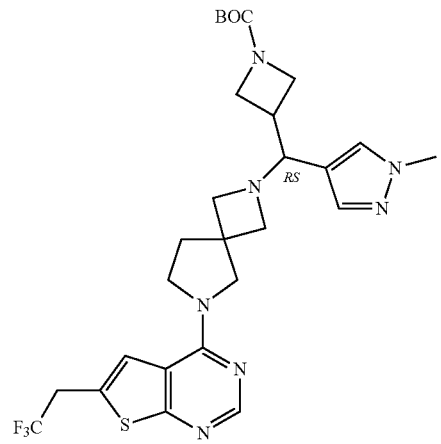 [SMILES: Cn1cc(C(C2CN(C(=O)OC(C)(C)C)C2)N2CC3(CCN(c4ncnc5sc(CC(F)(F)F)cc45)C3)C2)cn1]<br>From intermediate 11b and intermediate 89 | 130 mg | |
| intermediate 82 | 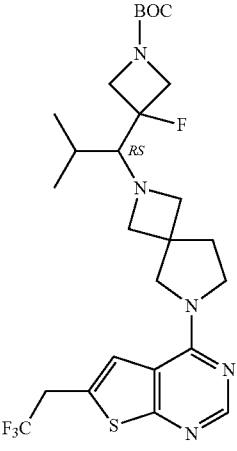 [SMILES: CC(C)C(N1CC2(CCN(c3ncnc4sc(CC(F)(F)F)cc34)C2)C1)C1(F)CN(C(=O)OC(C)(C)C)C1]<br>From intermediate 11b and intermediate 83 | 40 mg | |

| Intermediate number | Structure | Quantity | Yield |
|---|---|---|---|
| Intermediate 82a and intermediate 82b | 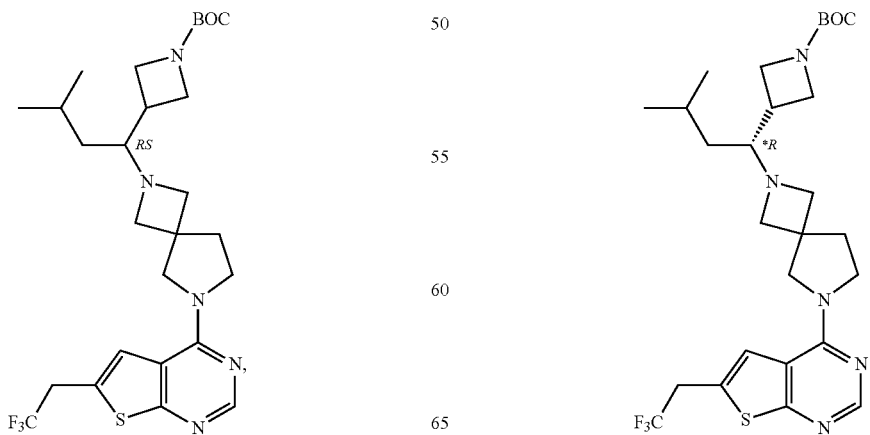 From chiral SFC separation of intermediate 82 (Stationary phase: CHIRALPAK AD-H 5 μm 250 * 30 mm, Mobile phase: 70% CO2, 30% iPOH (0.3% iPrNH₂)) | | |
Preparation of Intermediate 77
Intermediate 77a and Intermediate 77b

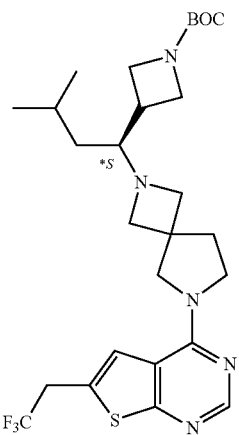 [SMILES: CC(C)C[C@@H](C1CN(C(=O)OC(C)(C)C)C1)N1CC2(CCN(c3ncnc4sc(CC(F)(F)F)cc34)C2)C1]

Reaction Mixture 1:

In a sealed tube, a solution of intermediate 78 (2 equivalents), intermediate 11 (100 mg; 0.305 mmol) and Ti(OiPr)$_4$ (6 equivalents) in EtOH (0.2 mL) was heated at 45° C. for 1 hour. The mixture was cooled down to room temperature, diluted with EtOH (3 mL) and NaBH$_4$ (2 equivalents) was added. The reaction mixture was stirred at room temperature for 4 hours indicating, according to LC/MS the formation of 60% of intermediate 77

Reaction Mixture 2 and 3:

The reaction was performed twice on the same quantity: In a sealed tube, a solution of intermediate 78 (2 equivalents), intermediate 11 (450 mg; 1.37 mmol) and Ti(OiPr)$_4$ (6 equivalents) in EtOH (0.9 mL) was heated at 45° C. for 1 hour. The mixture was cooled down to room temperature, diluted with EtOH (13 mL) and NaBH$_4$ (2 equivalents) was added. The reaction mixture was stirred at room temperature for 18 hours.

The three reaction mixtures were diluted with EtOAc and poured onto a mixture of 10% K$_2$CO$_3$ and brine. The suspension was sonicated for 30 min and filtered through a pad of Celite®. The organic layer was decanted, washed with 10% aqueous K$_2$CO$_3$, then brine, dried over MgSO$_4$, filtered and evaporated to dryness. The residue (2.6 g) was purified by chromatography over silica gel (irregular SiOH, 50 g; mobile phase: gradient from 0% NH$_4$OH, 0% MeOH, 100% DCM to 0.7% NH$_4$OH, 7% MeOH, 93% DCM). The pure fractions were collected and evaporated to dryness. The residue (1.5 g; 89%) was purified a second time by chromatography over silica gel (irregular SiOH, 40 g; mobile phase: 60% Heptane, 35% EtOAc, 5% MeOH (+10% NH$_4$OH)). The fractions containing the product were collected and evaporated to dryness yielding 980 mg (58%; 82% pure based on LC/MS) of intermediate 77.

The impure fraction of intermediate 77 was further purified by achiral SFC (DIETHYLAMINOPROPYL 5 μm 150×30 mm; mobile phase: 90% CO$_2$, 10% MeOH).

The pure fractions were collected and evaporated to dryness yielding 620 mg (37%) of intermediate 77.

The enantiomers were separated by chiral SFC (Lux Cellulose-2 5 μm 250*30 mm; mobile phase: 50% CO$_2$, 50% MeOH (0.3% iPrNH$_2$)). The fractions containing the products were collected and evaporated to dryness yielding 276 mg (16%) of intermediate 77a and 269 mg (16%) of intermediate 77b.

The intermediates in the table below were prepared using an analogous method as described for the preparation of intermediate 77, 77a and 77b starting from the respective starting materials.

| Intermediate number | Structure | Quantity | Yield |
|---|---|---|---|
| intermediate 80 | ![structure] From intermediate 11 and tert-butyl 3-propanoylazetidine-1-carboxylate | 240 mg | 57% |

Preparation of Intermediate 72

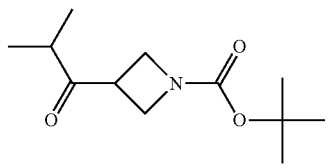 [SMILES: CC(C)C(=O)C1CN(C(=O)OC(C)(C)C)C1]

Under N$_2$ at 5° C., iPrMgCl 2M in THF (19 mL; 38.33 mmol) was added to a solution of intermediate 73 (4.6 g; 18.83 mmol) in THF (70 mL). The solution was stirred at 5° C. for 30 min, allowed to slowly rise RT, stirred for 1 h then, heated at 40° C. for 5 h. The reaction mixture was cooled to room temperature, poured out onto a mixture of iced water and a saturated aqueous NH$_4$Cl solution, and extracted with EtOAc. The organic layer was decanted, dried over MgSO$_4$, filtered and evaporated to dryness yielding 4.7 g of intermediate 72 (quantitative).

The intermediates in the table below were prepared using an analogous method as described for the preparation of intermediate 72 starting from the respective starting materials.

| intermediate number | Structure | Quantity | Yield |
|---|---|---|---|
| intermediate 75 | From intermediate 73 and cyclopropylmagnesium bromide 0.5 in THF | 25 g | Quant. |
| intermediate 78 | From intermediate 73 and Isobutylmagnesium bromide 0.4M | 19 g | 96% |
| intermediate 83 | From intermediate 84 and Isopropylmagnesium chloride 2M in THF | 137 mg | 49% |
| intermediate 105 | From N-Methoxy-N-methyltetrahydrofuran-3-carboxamide and Isopropylmagnesium chloride 2M in THF | 71 mg | 16% |
| Intermediate 108 | From N-Methyl-N-methoxy-1-(tert-butoxycarbonyl)piperidine-4-acetamide and Isopropylmagnesium chloride 2M in THF | 710 mg | 26% |
| Intermediate 111 | From intermediate 73 and chloro[(4-methylphenyl)methyl]magnesium | 770 mg | 40% |

| intermediate number | Structure | Quantity | Yield |
|---|---|---|---|
| Intermediate 113 | 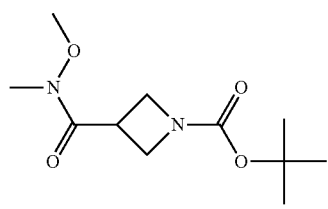 [SMILES: CON(C)C(=O)C1CN(C(=O)OC(C)(C)C)C1]<br>From 4-[(N-Methoxy-N-methylamino)carbonyl]-1-piperidinecarboxylic acid 1,1-dimethylethyl ester and Isopropylmagnesium chloride 2M in THF | 1230 mg | 33% |

Preparation of Intermediate 73

1-Boc-azetidine-3-carboxylic acid (5 g; 24.9 mmol) and N,O-dimethylhydroxylamine hydrochloride (3.64 g; 37.3 mmol) were placed in a round bottom flask under $N_2$. DCM (75 mL) was added, followed by EDCl.HCl (7.15 g; 37.3 mmol), DMAP (155 mg; 1.27 mmol) and DIPEA (6.5 mL, 37.4 mmol). The reaction mixture was stirred at RT for 16 h and diluted with DCM (100 mL). The organic layer was washed with aqueous 1M HCl (2×50 mL), sat. $NaHCO_3$ solution (50 mL), and brine (50 mL). The organic phase was decanted, dried over $MgSO_4$, filtered, and evaporated to dryness yielding 6.04 g (99%) of intermediate 73.

The intermediates in the table below were prepared using an analogous method as described for the preparation of intermediate 73 starting from the respective starting materials.

| intermediate number | Structure | Quantity | Yield |
|---|---|---|---|
| intermediate 84 | From 1-Boc-3-fluoroazetidine-3-carboxylic acid | 600 mg | 97% |

Preparation of Intermediate 85

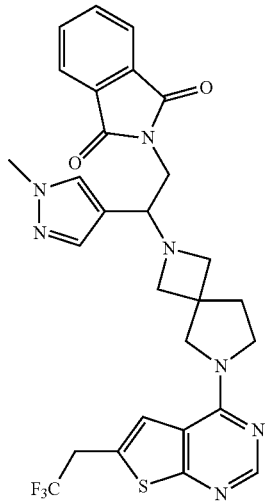 [SMILES: Cn1cc(C(CN2C(=O)c3ccccc3C2=O)N2CC3(CCN(c4ncnc5sc(CC(F)(F)F)cc45)C3)C2)cn1]

Under $N_2$, a solution of intermediate 11 (204 mg; 0.62 mmol), intermediate 86 (217 mg; 0.81 mmol) and $Ti(OEt)_4$ (0.26 mL; 1.24 mmol) in DCE (7 mL) was stirred at RT overnight. $NaBH_3CN$ (129 mg; 2 mmol) was added and the solution was stirred for 4 days. Water was added dropwise then the solution was filtered through a pad of Celite®. The filtrate was separated. The organic layer was washed with water, dried over $MgSO_4$, filtered and evaporated till dryness. The residue was purified by chromatography over silica gel (irregular SiOH, 24 g; mobile phase: gradient from 97% DCM, 3% MeOH (+10% $NH_4OH$) to 95% DCM, 5% MeOH (+10% $NH_4OH$)). The pure fractions were collected and evaporated to dryness yielding 209 mg (80%) of intermediate 85.

The intermediate in the table below was prepared using an analogous method as described for the preparation of intermediate 85 starting from the respective starting materials.

| intermediate number | Structure | Quantity | Yield |
|---|---|---|---|
| intermediate 87 | 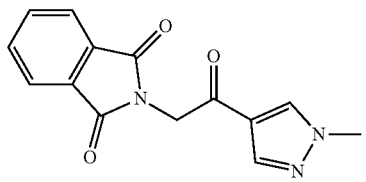 [SMILES: Cn1cc(C(=O)CN2C(=O)c3ccccc3C2=O)cn1]<br>From intermediate 11 and 4-[(1-methyl-1H-pyrazol-4-yl)carbonyl]-1-piperidinecarboxylic acid 1,1-dimethylethyl ester | 145 mg | 51% |

Preparation of Intermediate 86

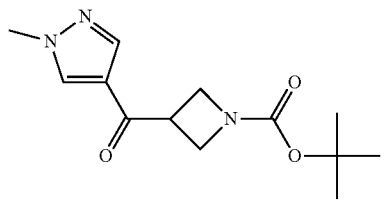 [SMILES: Cn1cc(C(=O)C2CN(C(=O)OC(C)(C)C)C2)cn1]

2-bromo-1-(1-methyl-1H-pyrazol-4-yl)-ethanone (0.5 g; 2.46 mmol) in DMF (10 mL) were added to potassium phthalimide (0.46 g; 2.46 mmol). The reaction mixture was stirred at RT for 5 h, poured into water-ice and EtOAc was added. The organic layer was separated, washed with water, brine, dried over MgSO₄, filtered and evaporated till dryness. The residue was purified by chromatography over silica gel (irregular SiOH 15-40 µm, 24 g; mobile phase: 97% DCM, 3% MeOH (+10% NH₄OH)). The pure fractions were collected and evaporated to dryness yielding 460 mg (69%) of intermediate 86.

Preparation of Intermediate 89

Under N₂, n-BuLi 1.6M in hexane (6.2 mL; 9.92 mmol) was added at −70° C. to a solution of 4-iodo-1-methyl-1H-pyrazole (1.7 g; 8.17 mmol) in THF (35 mL). The reaction mixture was stirred at −70° C. for 1 hour then, a solution of intermediate 73 (2 g; 8.19 mmol) in THF (10 mL) was added drop wise. The reaction mixture was stirred at −70° C. for 2 hours, allowed to warm up to room temperature and stirred overnight. The solution was poured out into a mixture of ice-water and a saturated NH₄Cl solution, then EtOAc was added. The organic layer was decanted, dried over MgSO₄, filtered and evaporated to dryness. The residue was purified by chromatography over silica gel (irregular SiOH, 50 g; mobile phase: gradient from 100% DCM, 0% MeOH to 98% DCM, 2% MeOH, 0.1% NH₄OH). The pure fractions were collected and evaporated to dryness yielding 320 mg (15%) of intermediate 89

Preparation of Intermediate 92

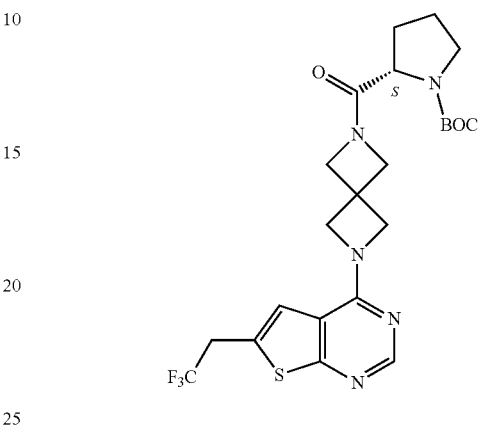

Under N₂, HBTU (210 mg; 0.555 mmol) was added to a solution of BOC-L-proline (119 mg; 0.555 mmol) and DIPEA (0.48 mL; 2.775 mmol) in DMF (10 mL). The solution was stirred for 30 min. Then, intermediate 10b (200 mg) was added and the solution was stirred at room temperature all over the weekend. Subsequently, the reaction mixture was poured into iced water, basified with a 10% aqueous solution of K₂CO₃ and extracted with EtOAc. The organic layer was washed by water, dried over MgSO₄, filtered and evaporated to dryness. The residue was purified by chromatography over silica gel (irregular SiOH, 24 g; mobile phase: gradient from 0.5% NH₄OH, 5% MeOH, 95% DCM to 1% NH₄OH, 10% MeOH, 90% DCM). The pure fractions were collected and evaporated to dryness yielding 168 mg of intermediate 92.

The intermediates in the table below were prepared using an analogous method as described for the preparation of intermediate 92 starting from the respective starting materials.

| intermediate number | Structure | Quantity | Yield |
|---|---|---|---|
| intermediate 93 | From intermediate 10b and (2S,4R)-N-boc-4-methylpyrrolidine-2-carboxylic acid | 510 mg | |

| intermediate number | Structure | Quantity | Yield |
|---|---|---|---|
| intermediate 101 | From intermediate 10b and (2S,4R)-1-(tert-butoxycarbonyl)-4-fluoropyrrolidine-2-carboxylic acid | 150 mg | |
| intermediate 96 | From intermediate 10 and cis-1-N-Boc-4-methoxy-L-proline | 283 mg | 94% |
| intermediate 102 | From intermediate 10b and (S)-5-Boc-5-Azaspiro[2.4]heptane-6-carboxylic acid | 200 mg | |
| intermediate 103 | From intermediate 11c and (S)-5-(tert-butoxycarbonyl)-5-azaspiro[2.4]heptane-6-carboxylic acid | 160 mg | |
| intermediate 98 | From intermediate 10b and (R)-5-(tert-butoxycarbonyl)-5-azaspiro[2.4]heptane-6-carboxylic acid | 348 mg | |
| Intermediate 99 | From intermediate 10 and (2S,4R)-1-(tert-butoxycarbonyl)-4-methoxypyrrolidine-2-carboxylic acid | 389 mg | 75% |

| intermediate number | Structure | Quantity | Yield |
|---|---|---|---|
| Intermediate 100 | 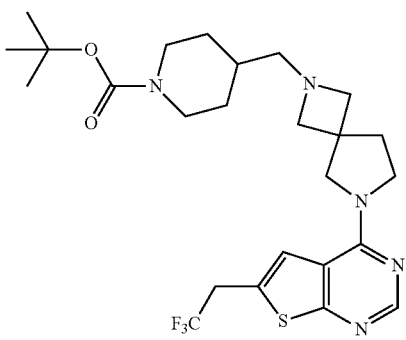 [SMILES: CC(C)(C)OC(=O)N1CCC(CN2CC3(CCN(c4ncnc5sc(CC(F)(F)F)cc45)C3)C2)CC1] From intermediate 10b and N-BOC-4,4-difluoro-L-proline | 100 mg | |

Preparation of Intermediate 107

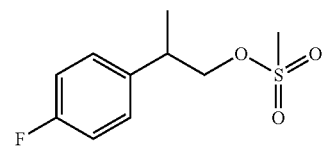

Under nitrogen, a solution of intermediate 11 (250 mg; 0.761 mmol), N-Boc-4-formylpiperidine (195 mg; 0.914 mmol) in THF (7 mL) was stirred at rt for 3 h. NaBH(OAc)$_3$ (323 mg; 1.52 mmol) was added and the mixture was stirred at rt overnight. A 10% aqueous solution of K$_2$CO$_3$ and DCM were added. The organic layer was separated, dried over MgSO$_4$, filtered and evaporated to dryness. The residue was purified by silica gel chromatography (irregular SiOH, 24 g; mobile phase: gradient from 100% DCM 0% MeOH (0% NH$_4$OH) to 90% DCM 10% MeOH (10% NH$_4$OH)). The fractions containing the product were mixed and evaporated to dryness yielding 383 mg (96%) of intermediate 107.
Preparation of Intermediate 110:

DIPEA (0.45 mL, 3.24 mmol) was added to an ice-cooled solution of 2-(4-fluorophenyl) propanol (CAS[59667-20-8]) (0.25 g, 1.62 mmol) in DCM (1.4 mL) followed by methane sulfonyl chloride (0.155 mL, 1.95 mmol). The mixture was stirred overnight at rt. The mixture was diluted with DCM (20 mL) and washed with a saturated sodium bicarbonate solution (15 mL). The solution was dried over MgSO$_4$, filtered and concentrated under reduced pressure yielding 0.377 g of intermediate 110. This product was used without further purification in the next step.
Preparation of Intermediate 112:

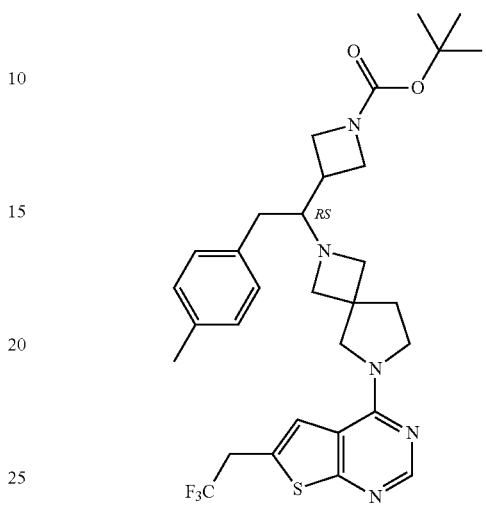

A solution of intermediate 111 (607 mg, 2.1 mmol) and titanium isopropoxyde (1.25 mL, 1.37 mmol) in EtOH (4.6 mL) was added dropwise at room temperature (over a period of 5 to 10 min) to a mixture of intermediate 11 (459 mg, 1.4 mmol) and NaBH$_3$CN (264 mg, 4.2 mmol) in EtOH (9.2 mL). The mixture was stirred for 1 h at rt. The reaction mixture was diluted with DCM and poured onto a 10% aqueous solution of K$_2$CO$_3$. The suspension was filtered over a pad of Celite®. The organic layer was decanted, washed with brine, dried over MgSO$_4$, filtered and evaporated to dryness. The residue was purified by chromatography over silica gel (irregular SiOH, 24 g; mobile phase: DCM/MeOH: gradient from 100/0 to 90/10). The pure fractions were collected and evaporated to dryness yielding 0.521 g (62%) of intermediate 112 (62%).

B. Preparation of the Compounds

Example B1

Preparation of Compound 1:

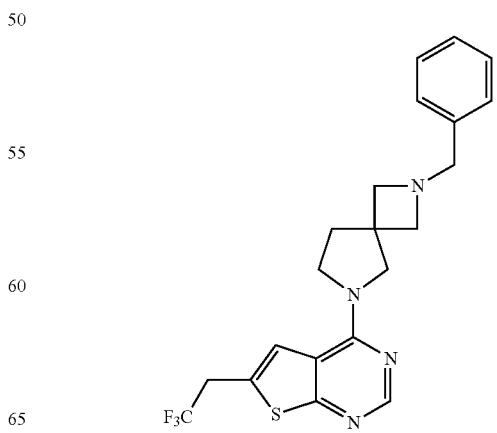

TEA (88.5 mg, 0.875 mmol) and benzaldehyde (46.4 mg, 0.44 mmol) were successively added to a solution of intermediate 11 (190 mg, 0.44 mmol) in anhydrous DCM (4 mL) and the mixture was stirred at rt for 30 min. NaBH(OAc)$_3$ was then added (185.4 mg, 0.875 mmol) and the mixture was stirred at rt overnight. Sat. aq. NaHCO$_3$ (10 mL) and DCM (10 mL) were added and the mixture decanted. The aqueous layer was extracted twice with DCM (10 mL). The organic layers were combined, washed with brine (10 mL), dried over Na$_2$SO$_4$ and evaporated to give a yellow oil. The crude residue was purified by chromatography over silica gel (column Gemini 150*25 5 um, mobile phase: water (0.05% ammonia hydroxide v/v)/ACN: gradient from 55/45 to 25/75). The residue was then freeze-dried to give 65 mg of compound 1 (35% yield) as a yellow solid.

Example B2

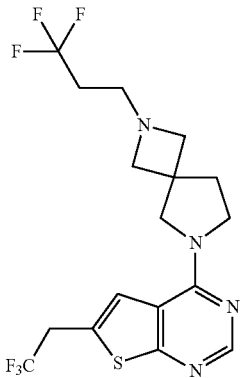 [SMILES: FC(F)(F)CCN1CC2(CCN(c3ncnc4sc(CC(F)(F)F)cc34)C2)C1]

Preparation of Compound 2:

Intermediate 11 (100 mg, 0.3 mmol), 3,3,3-trifluoropropanal (51 mg, 0.46 mmol) in dry DCM (3 mL) were stirred at rt for 1 h, then NaBH(OAc)$_3$ (129 mg, 0.61 mmol) was added and the mixture was stirred at rt overnight. The mixture was poured into water then extracted with DCM, the organic layer was dried over MgSO$_4$, filtered and evaporated to dryness. The residue was purified by chromatography over silica gel (stationary phase: irregular SiOH 15-40 μm 24 g, mobile phase: NH$_4$OH/DCM/MeOH: 0.1/97/3). The product containing fractions were collected and evaporated to dryness yielding 58 mg (45%) of compound 2, which was freeze-dried with ACN/water 20/80 to give 45 mg of compound 2.

Preparation of Compound 13

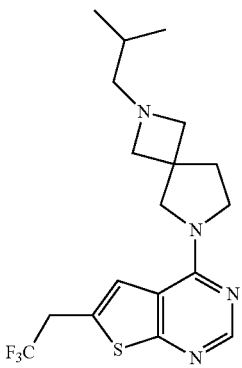 [SMILES: CC(C)CN1CC2(CCN(c3ncnc4sc(CC(F)(F)F)cc34)C2)C1]

A mixture of intermediate 11c (600 mg), isobutyraldehyde (160 mg; 2.221 mmol), NaBH(OAc)$_3$ (1.57 g; 7.405 mmol) and Et$_3$N (0.64 mL; 4.443 mmol) in DCE (12 mL) was stirred at room temperature overnight. A saturated aqueous solution of NaHCO$_3$ (20 mL) and DCM (20 mL) were added. The organic layer was decanted and the aqueous layer was extracted with DCM (20 mL*2). The combined organic layers were washed with brine (30 mL), dried over Na$_2$SO$_4$, filtered and evaporated to dryness. The residue was purified by chromatography over silica gel (mobile phase: gradient from petroleum ether/EtOAc from 100/0 to 0/100, then EtOAc/MeOH from 100/0 to 85/15). The pure fractions were collected, evaporated to dryness and freeze dried yielding 320 mg of compound 13.

The compounds in the Table below were prepared by using an analogous method as described for the preparation of compound 2, starting from the respective starting materials.

| Compound number | Structure | Quantity (mg) | Yield (%) |
|---|---|---|---|
| Compound 3 (from intermediate 7) | 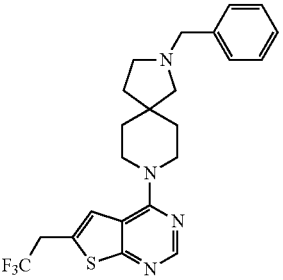 [SMILES: FC(F)(F)Cc1cc2c(N3CCC4(CCN(Cc5ccccc5)C4)CC3)ncnc2s1] as a hydrochloride salt | 80 | |
| Compound 4 (from intermediate 11) | 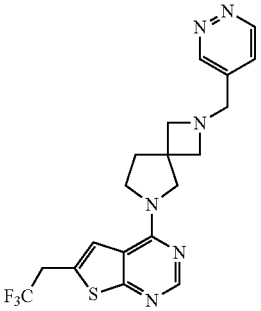 [SMILES: FC(F)(F)Cc1cc2c(N3CCC4(CN(Cc5ccnnc5)C4)C3)ncnc2s1] | 126 | 47 |
| Compound 5 (from intermediate 11) | 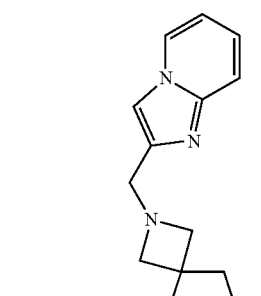 | 75 | 43 |

-continued

| Compound number | Structure | Quantity (mg) | Yield (%) |
|---|---|---|---|
| Compound 6 (from intermediate 11) | 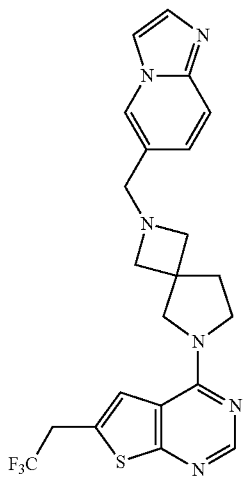 [SMILES: FC(F)(F)Cc1cc2c(N3CCC4(CN(Cc5ccc6nccn6c5)C4)C3)ncnc2s1] | 55 | 26 |
| Compound 7 (from intermediate 11) | 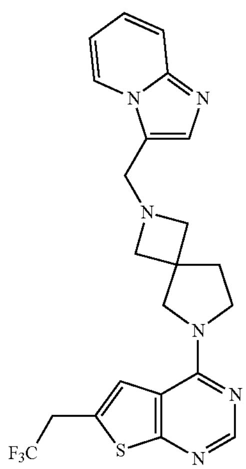 [SMILES: FC(F)(F)Cc1cc2c(N3CCC4(CN(Cc5cnc6ccccn56)C4)C3)ncnc2s1] | 55 | 31 |
| Compound 8 (from intermediate 11) | 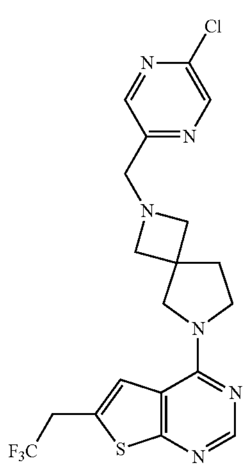 [SMILES: FC(F)(F)Cc1cc2c(N3CCC4(CN(Cc5cnc(Cl)cn5)C4)C3)ncnc2s1] | 75 | 43 |

-continued

| Compound number | Structure | Quantity (mg) | Yield (%) |
|---|---|---|---|
| Compound 9 (from intermediate 11) | | 75 | 39 |
| Compound 10 (from intermediate 11) | | 40 | 29 |
| Compound 11 (from intermediate 11) | | 65 | 37 |

-continued

| Compound number | Structure | Quantity (mg) | Yield (%) |
|---|---|---|---|
| Compound 12 (from intermediate 11) | 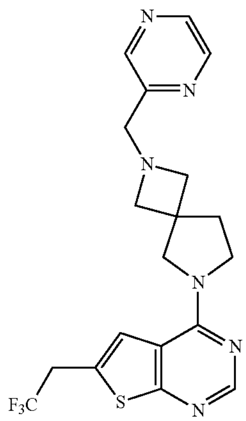 [SMILES: FC(F)(F)Cc1cc2c(N3CCC4(CN(Cc5cnccn5)C4)C3)ncnc2s1] | 80 | 41 |
| Compound 13 (from intermediate 11) | 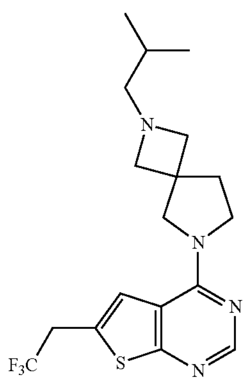 [SMILES: CC(C)CN1CC2(CCN(c3ncnc4sc(CC(F)(F)F)cc34)C2)C1] | 80 | 54 |
| Compound 23 (from intermediate 11 and 1-methyl-1H-imidazole-5-carboxaldehyde) | | 70 | 18 |

-continued

| Compound number | Structure | Quantity (mg) | Yield (%) |
|---|---|---|---|
| Compound 35 (from intermediate 11 and 1-methyl-1H-pyrazole-3-carbaldehyde) | | 155 | 40 |
| Compound 69 (from intermediate 11 and phenyl-acetaldehyde (CAS[122-78-1])) | | 60 | 22 |

Example B3

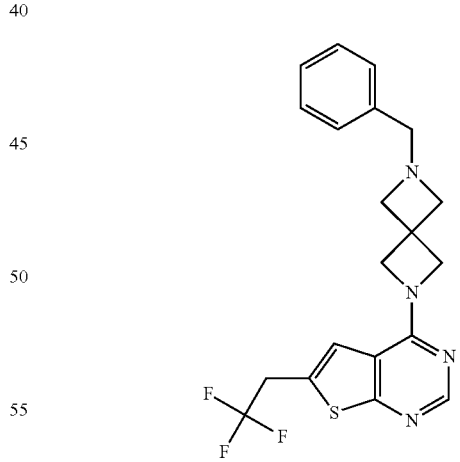

Preparation of Compound 14:

Intermediate 10b (0.42 g), benzyl bromide (0.19 mL, 1.6 mmol), and K₂CO₃ (0.55 g, 4.0 mmol) in ACN (20 mL) were stirred at rt overnight. The mixture was poured into water, extracted with EtOAc, the organic layer was washed with brine, then dried over MgSO₄, filtered and evaporated to dryness. The residue was purified by chromatography over silica gel (stationary phase: irregular SiOH 15-40 μm 40 g, mobile phase: NH₄OH/DCM/MeOH: 0.1/97/3). The product containing fractions were collected and evaporated to dryness yielding 170 mg (31%) of compound 14, which was crystallized from DIPE, filtered and dried to give 103 mg of compound 14.

The compounds and intermediates in the Table below were prepared by using an analogous method as described for the preparation of compound 14, starting from the respective starting materials.

| Compound number | Structure | Quantity (mg) | Yield (%) |
|---|---|---|---|
| Compound 15 (from intermediate 11) | 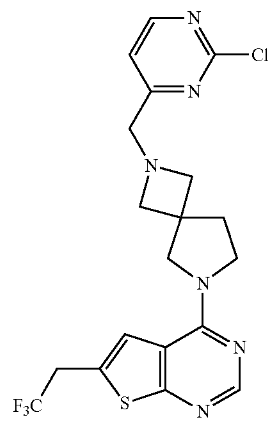 [SMILES: FC(F)(F)Cc1cc2c(N3CCC4(CN(Cc5ccnc(Cl)n5)C4)C3)ncnc2s1] | 65 | 37 |
| Compound 16 (from intermediate 8) | as a hydrochloride salt (1.7HCl•1.9H$_2$O) | 57 | |
| Compound 17 (from intermediate 11) (int. 11 was reacted with 1628318-10-4, followed by cleavage with TFA) | 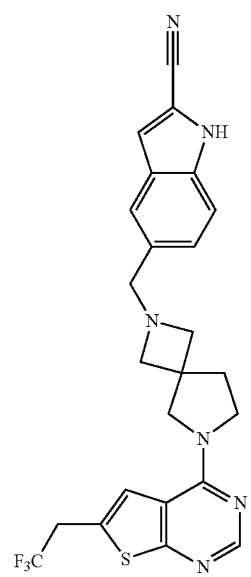 [SMILES: N#Cc1cc2cc(CN3CC4(CCN(c5ncnc6sc(CC(F)(F)F)cc56)C4)C3)ccc2[nH]1] | 60 | 32 |

-continued

| Compound number | Structure | Quantity (mg) | Yield (%) |
|---|---|---|---|
| Compound 18 (from intermediate 6) | 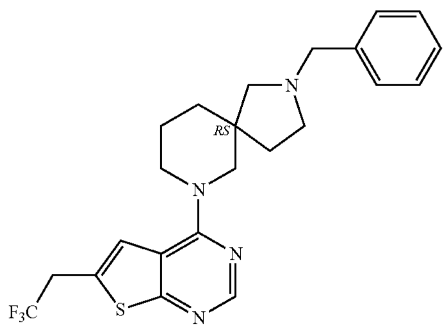 [SMILES: FC(F)(F)Cc1cc2c(N3CCCC4(CCN(Cc5ccccc5)C4)C3)ncnc2s1] | 130 | 49 |
| Compound 19 (from intermediate 12) | 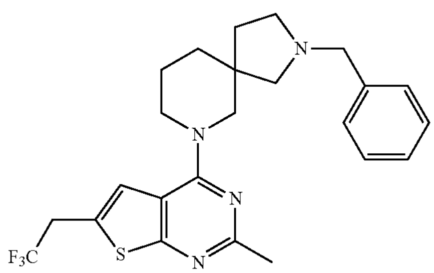 [SMILES: Cc1nc(N2CCCC3(CCN(Cc4ccccc4)C3)C2)c2cc(CC(F)(F)F)sc2n1] | 45 | 12 |
| Compound 30 (from intermediate 11 and chloromethyltrimethyl germane) | 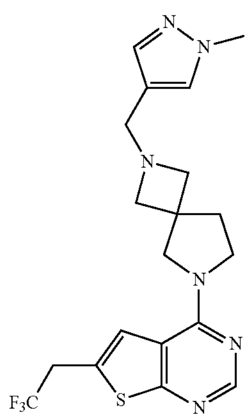 [SMILES: Cn1cc(CN2CC3(CCN(c4ncnc5sc(CC(F)(F)F)cc45)C3)C2)cn1] | 28 | 13 |
| Compound 31 (from intermediate 11 and chloromethyltrimethyl germane) | 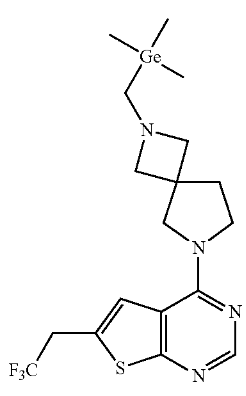 | 36 | 21 |

Example B4

Preparation of Compound 20:

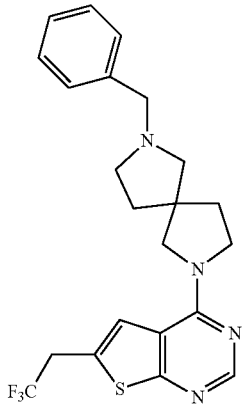 [SMILES: FC(F)(F)Cc1cc2c(N3CCC4(CCN(Cc5ccccc5)C4)C3)ncnc2s1]

A mixture of 4-chloro-6-(2,2,2-trifluoroethyl)thieno[2,3-d]pyrimidine (150 mg, 0.59 mmol) prepared as described in Journal of Medicinal Chemistry (2016), 59(3), 892-913, 2-benzyl 2,7-diaza-spiro-[4.4]nonane (CAS[885275-27-4]) (129 mg, 0.59 mmol) and DIPEA (0.31 mL, 1.78 mmol) in ACN (15 mL) were heated at 80° C. overnight. The mixture was cooled and poured into cooled water, the product was extracted with EtOAc, the organic layer was dried over MgSO$_4$, filtered and evaporated to dryness. The residue was purified by chromatography over silica gel (stationary phase: irregular bare silica 24 g, mobile phase: DCM/MeOH/NH$_4$OH: 97/3/0.1). The product containing fractions were collected and evaporated to dryness yielding 200 mg (yield 78%) of compound 20 (racemic mixture).

Preparation of Enantiomers

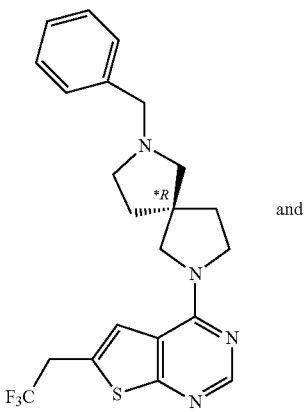

20a and

20b

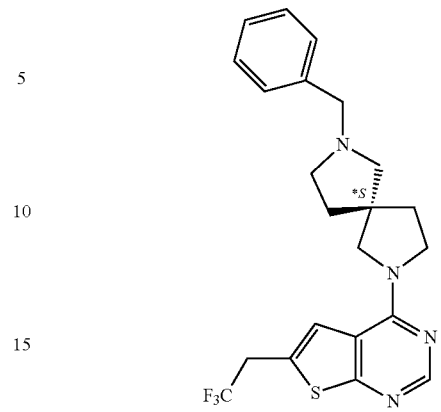

The enantiomers were separated via chiral SFC (stationary phase: Lux Cellulose-4 5 μm 250*21.2 mm, mobile phase: CO$_2$/MeOH (0.3% iPrNH$_2$): 70/30). The product containing fractions were collected and evaporated to dryness yielding 80 mg (yield 31%) of a first eluted fraction F1 and 81 mg (yield 31%) of a second eluted fraction F2.

F1 (80 mg; 0.185 mmol) was dissolved in acetone, at 10° C., and 4N HCl in dioxane (2 eq, 0.37 mmol, 93 μL) was added followed by Et$_2$O. The mixture was evaporated to dryness and taken up with Et$_2$O, a precipitate was filtered and dried giving 65 mg (yield 20%) of compound 20a as a hydrochloride salt (1.95HCl.1.25H$_2$O.0.19 Dioxane. 0.06 Et$_2$O)

F$_2$ (81 mg, 0.187 mmol) was dissolved in acetone, at 10° C., and 4N HCl in dioxane (2 eq, 0.37 mmol, 93 μL) was added followed by Et$_2$O. The mixture was evaporated to dryness, taken up with Et$_2$O, a precipitate was filtered and dried giving 49 mg (yield 15%) of compound 20b as a hydrochloride salt (2.0HCl.1.8H$_2$O).

Example B5

Preparation of Compound 18:

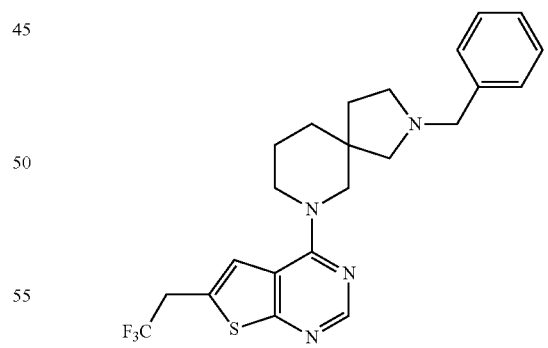

A mixture of intermediate 6 (222 mg, 0.63 mmol), benzyl bromide (82 μL, 0.685 mmol) and K$_2$CO$_3$ (430 mg, 3.11 mmol) in ACN (20 mL) was stirred at rt overnight. The solution was poured out into cooled water, the product was extracted with EtOAc, the organic layer was dried over MgSO$_4$, filtered and evaporated to dryness. The residue was purified by chromatography over silica gel (stationary phase: irregular 15-40 μm 30 g, mobile phase: DCM/MeOH/NH$_4$OH: gradient from 100/0/0 to 97/3/0.1). The product containing fractions were collected and evaporated to dryness yielding 170 mg (yield 61%) of compound 18 (racemic mixture).

Preparation of Enantiomers Compound 21a

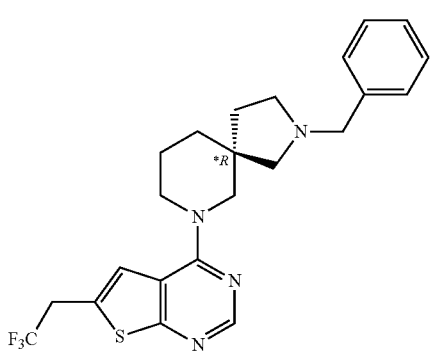

and Compound 21b

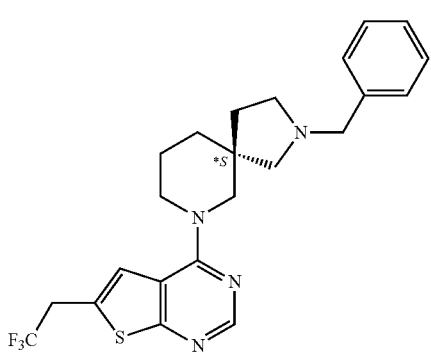 [SMILES: FC(F)(F)Cc1cc2c(N3CCCC4(CCN(Cc5ccccc5)C4)C3)ncnc2s1]

Compound 18 was separated into its enantiomers via chiral SFC (stationary phase: Lux Cellulose-2 5 μm 250*30 mm, mobile phase: $CO_2$/MeOH: 75/25). The product containing fractions were collected and evaporated to dryness yielding 72 mg (yield 26%) of a first eluted fraction F1 and 76 mg (yield 27%) of a second eluted fraction F2.

F1 was dissolved in acetone (3 mL), a solution of 4N HCl in dioxane (2 eq, 80 μL, 0.32 mmol) was added dropwise at 10° C., $Et_2O$ was added and after 30 min a precipitate was filtered and dried giving 54 mg (yield 16%) of compound 21a as a hydrochloride salt (1.8HCl.1.9$H_2O$).

F2 was dissolved in acetone (3 mL), a solution of 4N HCl in dioxane (2 eq, 85 μL, 0.34 mmol) was added dropwise at 10° C., $Et_2O$ was added and after 30 min a precipitate was filtered and dried giving 34 mg (yield 10%) of compound 21b as a hydrochloride salt (1.8HCl.2.1$H_2O$).

Example B6

Preparation of Compound 22:

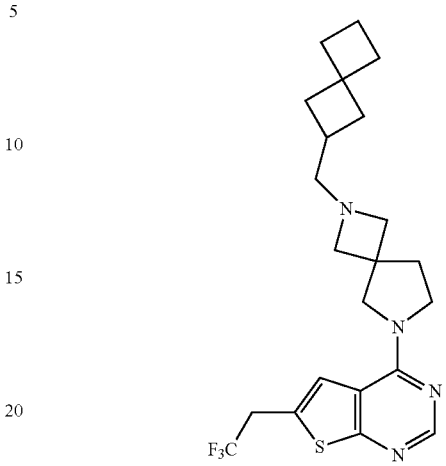

To a solution of intermediate 11 (200 mg, 0.51 mmol) in ACN (5 mL) was added intermediate 16 (220 mg, 1.08 mmol) and $K_2CO_3$ (221.4 mg, 1.53 mmol). The mixture was heated to 90° C. and stirred overnight. Water (10 mL) and DCM (10 mL) were added to the reaction mixture. The organic phase was separated, the aqueous layer was extracted with DCM (10 mL). The organic layers were combined, washed with brine (10 mL), evaporated to give a residue which was purified by chromatography over silica gel (Column: Gemini 150*25 5u; mobile phase: water (0.05% ammonia hydroxide v/v)/$CH_3CN$: gradient from 42/58 to 12/88, gradient Time (min): 10; 100% B Hold Time (min): 2; flow Rate (ml/min): 25).

The desired fractions were collected and dried in vacuum to give the residue. The residue was lyophilized to give 65 mg (yield 28%) of compound 22 as a light yellow solid.

Example B7

Preparation of Compound 24:

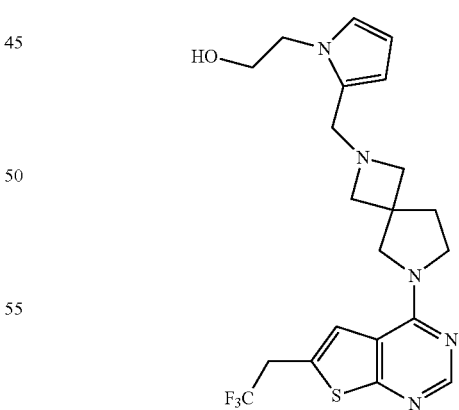

Intermediate 17 (180 mg, 0.36 mmol) and 3N NaOH (0.61 mL, 1.82 mmol) in MeOH (10 mL) were stirred at rt for 1 h. The mixture was cooled to rt, poured into water and extracted with EtOAc. The organic layer was dried over $MgSO_4$, filtered and evaporated to dryness. The residue was freeze-dried with acetonitrile/water 20/80 yielding 130 mg of compound 24 (79% yield).

Example B8

Preparation of Compound 25:

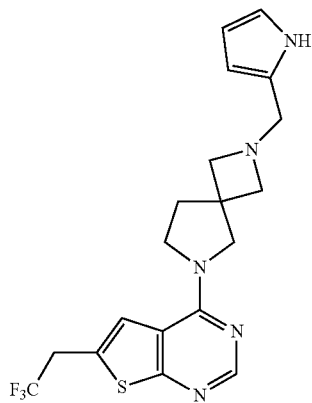 [SMILES: FC(F)(F)Cc1cc2c(N3CCC4(CN(Cc5ccc[nH]5)C4)C3)ncnc2s1]

At 5° C., to a solution of intermediate 43 (100 mg, 0.2 mmol) in DCM (10 mL), 4N HCl in dioxane (246 μL, 0.99 mmol) was added dropwise and the mixture was stirred at rt for 15 h. The reaction was evaporated to dryness. Then, the residue was taken-up with DCM, washed with NaHCO₃. The organic layer was dried over MgSO₄, filtered and evaporated to dryness. The residue was purified by chromatography over silica gel (stationary phase: irregular SiOH 15-40 μm 24 g, mobile phase: NH₄OH/DCM/MeOH gradient from 0.5/95/5 to 1/90/10). The pure fractions were collected and evaporated to dryness. The residue was freeze-dried with acetonitrile/water 20/80 yielding 25 mg of compound 25 (31% yield).

The compounds in the Table below were prepared by using an analogous method as described for the preparation of compound 25, starting from the respective starting materials.

Example B9

| Compound number | Structure | Quantity (mg) | Yield (%) |
|---|---|---|---|
| Compound 37 (from intermediate 44) | 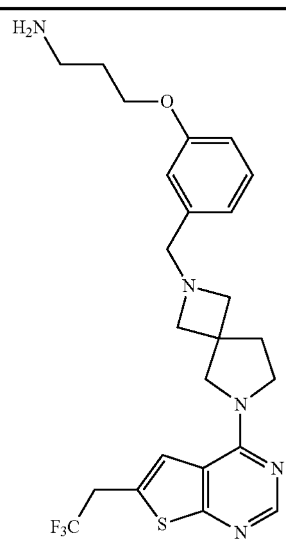 | 250 | 84 |

| Compound number | Structure | Quantity (mg) | Yield (%) |
|---|---|---|---|
| Compound 112 (from intermediate 27) | 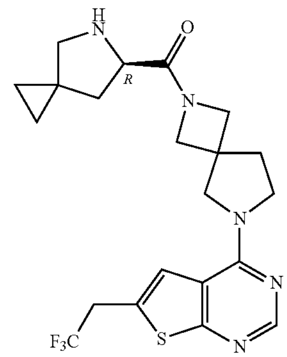 | 35 | 17 |

Preparation of Compound 26:

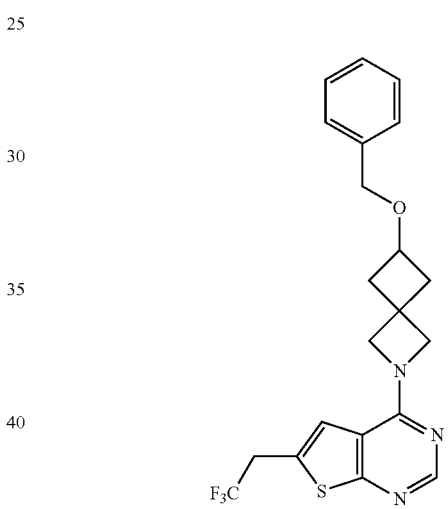

In a sealed tube, 4-chloro-6-(2,2,2-trifluoroethyl)thieno[2,3-d]pyrimidine (0.15 g, 0.594 mmol), 6-(phenylmethoxy)-2-azaspiro[3.3]heptane (0.145 g, 0.713 mmol) and DIPEA (0.205 mL, 1.19 mmol) in isopropanol (2 mL) were heated at 90° C. overnight. The solution was cooled to rt and poured into water then extracted with EtOAc. The organic layer was washed with water, dried over MgSO₄, filtered and evaporated to dryness. The crude product was crystallized from Et₂O and dried. The residue was purified by chromatography over silica gel (15-40 μm, 24 g, eluent: heptane/EtOAc: 80/20 to 20/80). The pure fractions were mixed and the solvent was evaporated. The residue was taken up by Et₂O, filtered and dried yielding 0.111 g of compound 26 (45% yield).

Example B10

Preparation of Compound 28:

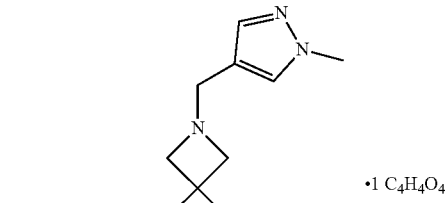

•1 C₄H₄O₄

A mixture of intermediate 10b (200 mg), 1-methyl-1H-pyrazole-4-carboxaldehyde (183 mg; 1.66 mmol) and AcOH (32 µL; 0.555 mmol) in DCE (6 mL) was stirred at 50° C. for 2 hours. The reaction mixture was cooled to room temperature and NaBH(OAc)₃ (353 mg; 1.665 mmol) was added. The reaction mixture was stirred at room temperature overnight, poured onto a 10% aqueous solution of K₂CO₃ and extracted with DCM. The organic layer was decanted, dried over MgSO₄, filtered and evaporated to dryness. The residue was purified by chromatography over silica gel (irregular SiOH, 24 g; mobile phase: gradient from 0% NH₄OH, 0% MeOH, 100% DCM to 1% NH₄OH, 10% MeOH, 90% DCM). The pure fractions were collected and evaporated to dryness yielding 165 mg of compound 28 as an oil (73%). Compound 28 was dissolved in ACN and HCl (4N in dioxane) (277 µL; 1.11 mmol) was added. The HCl salt was filtered but revealed to be too hydroscopic. The residue was then dissolved in DCM/MeOH and the organic layer was washed with a 10% aqueous solution of K₂CO₃, dried over MgSO₄, filtered and evaporated to dryness. The resulting residue was dissolved in ACN and fumaric acid (47 mg; 0.404 mmol; 1 eq) was added and the solution was allowed to stand until crystallization (overnight). The precipitate was filtered, washed with ACN then Et₂O and dried yielding 188 mg of compound 28 as the fumarate salt (1 equivalent based on 1H NMR).

The compounds in the Table below were prepared by using an analogous method as described for the preparation of compound 28, starting from the respective starting materials.

Example B11

| Compound number | Structure | Quantity (mg) | Yield (%) |
|---|---|---|---|
| Compound 34 (from intermediate 10b and 1-methyl-1H-pyrazole-3-carboxaldehyde) | 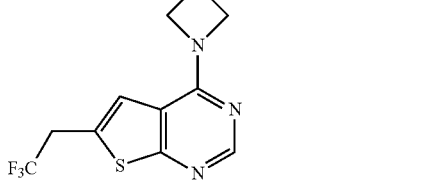 | 147 | |
| Compound 44 (from intermediate 10b and isobutyraldehyde) | 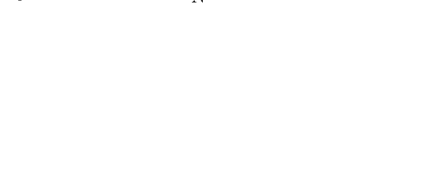 | 80 | |

Preparation of Compound 29:

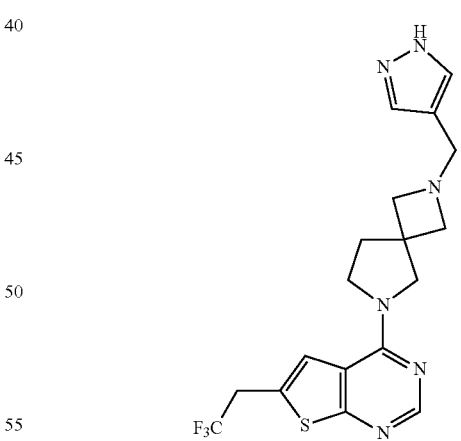

At 10° C., 4N HCl in dioxane (0.7 mL; 2.85 mmol) was added to a solution of intermediate 50 (145 mg; 0.28 mmol) in ACN (7 mL). The solution was stirred at rt overnight. The solution was evaporated to dryness. The residue was taken in ice water, basified with NH₄OH and DCM was added. The organic layer was separated, dried over MgSO₄, filtered and evaporated till dryness. The residue was purified by chromatography over silica gel (stationary phase: irregular SiOH 15-40 µm 12 g, mobile phase: DCM/MeOH/NH₄OH 90/10/10). The pure fractions were collected and evaporated to dryness. The residue was freeze-dried with acetonitrile/water 20/80 yielding 0.050 g (43% yield) of compound 29.

The compounds in the Table below were prepared by using an analogous method as described for the preparation of compound 29, starting from the respective starting materials.

| Compound number | Structure | Quantity (mg) | Yield (%) |
|---|---|---|---|
| Compound 40 (from intermediate 47) | | 102 | 61 |
| | 2.68HCl 2.1H$_2$O | | |
| Compound 41 (from intermediate 48) | | 72 | 55 |
| Compound 88 (from intermediate 26) | | 70 | 43 |

Example B12

Preparation of Compound 36

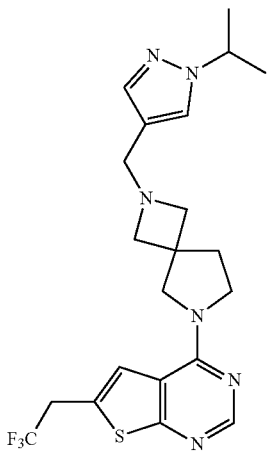 [SMILES: CC(C)n1cc(CN2CC3(CCN(c4ncnc5sc(CC(F)(F)F)cc45)C3)C2)cn1]

Under a N$_2$ flow, to a solution of intermediate 11 (287 mg, 0.87 mmol) in DCM (14 mL) was added 1-isopropyl-1H-pyrazole-4-carbaldehyde (133 mg, 0.68 mmol) and AcOH (51 µL, 0.87 mmol). The mixture was stirred at rt for 2 h. NaBH(OAc)$_3$ (742 mg, 3.5 mmol) was added and the mixture was stirred at rt overnight. The mixture was poured into ice water and was separated. The aqueous layer was extracted with DCM. The organic layer was washed with brine then, dried over MgSO$_4$, filtered and evaporated. The residue was purified by chromatography over silica gel (stationary phase: irregular SiOH 15-40 µm 24 g, mobile phase: DCM/MeOH (+10% NH$_4$OH): gradient from 97/3 to 90/10. The pure fractions were collected and evaporated to dryness. The residue was freeze-dried with acetonitrile/water: 20/80 yielding 0.057 g (15% yield) of compound 36.

The compounds in the Table below were prepared by using an analogous method as described for the preparation of compound 36, starting from the respective starting materials.

| Compound number | Structure | Quantity (mg) | Yield (%) |
|---|---|---|---|
| Compound 76 (from intermediate 11 and intermediate 51) | 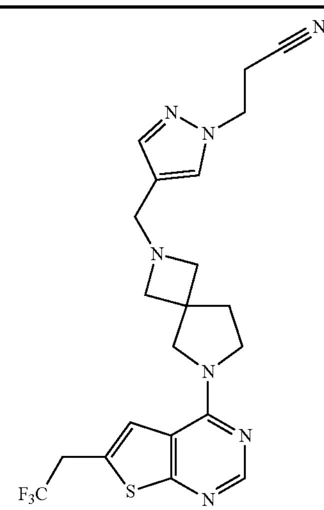 | 73 | 33 |

Example B13

Preparation of Compound 45

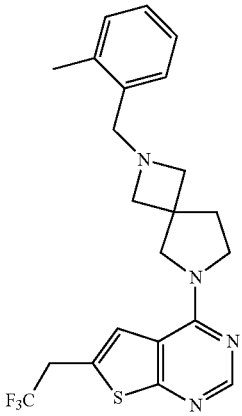 [SMILES: Cc1ccccc1CN1CC2(CCN(c3ncnc4sc(CC(F)(F)F)cc34)C2)C1]

To a solution of intermediate 11c (200 mg) in dichloroethane (10 mL) was added 2-methylbenzaldehyde (59 mg; 0.494 mmol), NaBH(OAc)$_3$ (523 mg; 2.47 mmol) and triethylamine (150 mg; 1.48 mmol). The mixture was stirred at room temperature overnight and then, a saturated aqueous solution of NaHCO$_3$ (10 mL) and DCM (10 mL) were added. The mixture was separated and the aqueous layer was extracted with DCM (10 mL*2).

The organic layers were combined, washed with water (10 mL), dried over Na$_2$SO$_4$, evaporated to give 300 mg of a yellow oil which was purified by preparative high-performance liquid chromatography (Column: Kromasil 150*25 mm*10 um; Conditions: A: water (0.05% ammonia hydroxide v/v), B: MeCN, at the beginning: A (52%) and B (48%), at the end: A: (22%) and B (78%), Gradient Time (min) 8; Flow Rate (ml/min) 30.

The fractions containing the product were collected and the solvent was evaporated under vacuum. The aqueous layer was lyophilized to dryness to give 150 mg (70%) of compound 45 as white solid.

The compounds in the Table below were prepared by using an analogous method as described for the preparation of compound 45, starting from the respective starting materials.

| Compound number | Structure | Quantity (mg) | Yield (%) |
|---|---|---|---|
| Compound 46 (from intermediate 11c and m-tolualdehyde) | HCl salt | 190 | |
| Compound 47 (from intermediate 11c and 2-methoxy-5-methyl-benzaldehyde) | 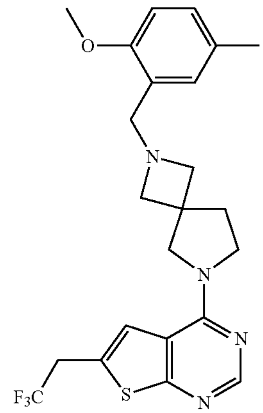 [SMILES: COc1ccc(C)cc1CN1CC2(CCN(c3ncnc4sc(CC(F)(F)F)cc34)C2)C1] | 120 | |
| Compound 48 (from intermediate 11c and 2,4-difluoro-benzaldehyde) | 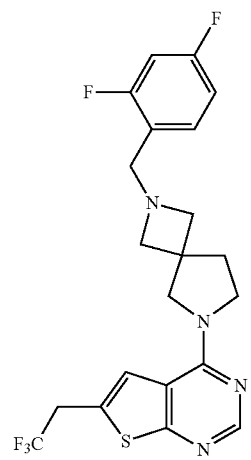 [SMILES: Fc1ccc(CN2CC3(CCN(c4ncnc5sc(CC(F)(F)F)cc45)C3)C2)c(F)c1] | 150 | |
| Compound 49 (from intermediate 11c and p-tolualdehyde) | 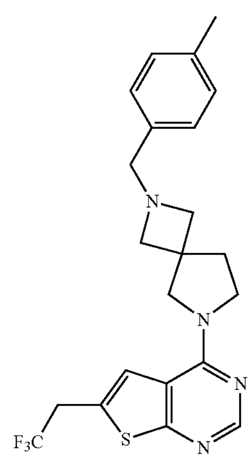 [SMILES: Cc1ccc(CN2CC3(CCN(c4ncnc5sc(CC(F)(F)F)cc45)C3)C2)cc1] | 160 | |

135
-continued

| Compound number | Structure | Quantity (mg) | Yield (%) |
|---|---|---|---|
| Compound 50 (from intermediate 11c and 2,4-dimethylbenzaldehyde) | | 155 | |
| Compound 54 (from intermediate 11c and 2-fluorobenzaldehyde) | 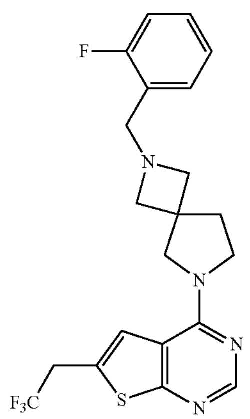 | 166 | |
| Compound 56 (from intermediate 11c and 3-fluorobenzaldehyde) | 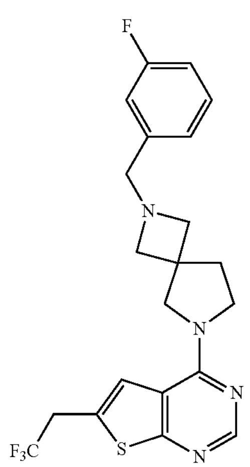 | 150 | |

136

Example B14

Preparation of Compound 108

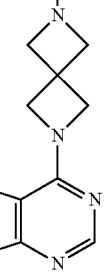

A mixture of S)-5-methyl-5-azaspiro[2.4]heptane-6-carboxylic acid (94 mg; 0.61 mmol), HBTU (231 mg; 0.61 mmol) and DIPEA (0.52 mL; 3.04 mmol) in DMF (5 mL) was stirred for 1 hour. Then, a solution of intermediate 10b (200 mg) in DMF (5 mL) was added and the reaction mixture was stirred at room temperature overnight. The reaction mixture was poured into iced water, basified with a 10% aqueous solution of $K_2CO_3$ and extracted with EtOAc. The organic layer was washed by $H_2O$, then brine, dried over $MgSO_4$, filtered and evaporated to dryness. The residue was purified by chromatography over silica gel (irregular SiOH, 10 g; mobile phase: gradient from 3% MeOH, 97% DCM to 10% MeOH, 90% DCM). The fractions containing the product were collected and evaporated to dryness yielding 144 mg of an impure fraction 1. A second purification was performed (irregular SiOH, 40 g; mobile phase: 0.5% $NH_4OH$, 95% DCM, 5% MeOH). The fractions containing the product were collected and evaporated to dryness yielding 43 mg of an impure fraction 2.

Fraction 2 was purified again by chromatography over silica gel (irregular SiOH, 10 g; mobile phase: gradient from 3% MeOH, 97% DCM to 10% MeOH, 90% DCM). The fractions containing the product were collected and evaporated to dryness. The resulting residue was taken up with diisopropyl ether. The solid was filtered and dried yielding 17 mg of compound 108.

The compounds in the Table below were prepared by using an analogous method as described for the preparation of compound 108, starting from the respective starting materials

| Compound number | Structure | Quantity (mg) | Yield (%) |
|---|---|---|---|
| Compound 74 (from intermediate 32 and N-isopropyl-ethylenediamine) | 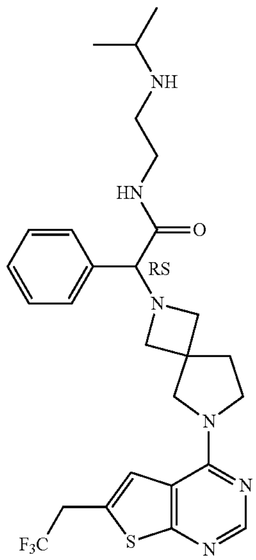 [SMILES: CC(C)NCCNC(=O)C(c1ccccc1)N1CC2(CCN(c3ncnc4sc(CC(F)(F)F)cc34)C2)C1] | 10 | 7 |
| Compound 75 (from intermediate 32 and 2-aminoethanol) | 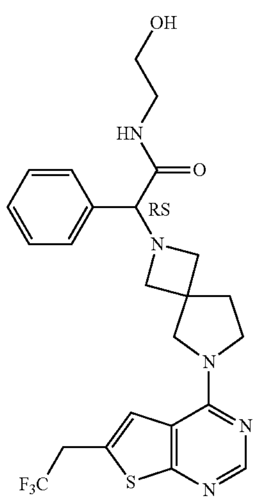 [SMILES: O=C(NCCO)C(c1ccccc1)N1CC2(CCN(c3ncnc4sc(CC(F)(F)F)cc34)C2)C1] | 22 | 13 |

Example B18

Preparation of Compound 57:

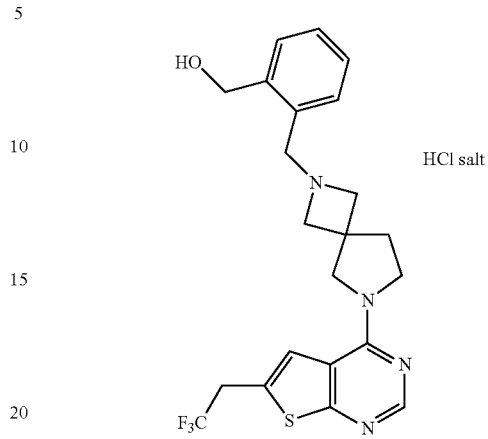

LiAlH$_4$ (66 mg, 1.73 mmol) was added to intermediate 54 (450 mg, 0.693 mmol) in THF (12 mL). The reaction was stirred at rt for 1.5 h. The reaction was quenched with a saturated aqueous solution of NH$_4$Cl, extracted with DCM and concentrated to afford a white solid. This solid was purified by preparative high-performance liquid chromatography (column: Xtimate C18 150*25 mm*10 um, condition: water (0.05% ammonia hydroxide, v/v)/ACN: gradient from 52/48 to 42/58). To the aqueous layer was added 0.1 mL 1N HCl. The solution was freeze-dried yielding 30 mg of compound 57 as a yellow solid (HCl salt).

Example B19

Preparation of Compound 58:

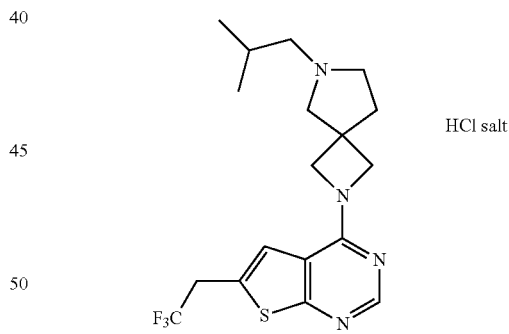

To a solution of intermediate 8 (200 mg, 0.5 mmol) in THF (10 mL) was added isobutyraldehyde (70 μL, 0.77 mmol) and TEA (0.37 mL, 2.63 mmol). The mixture was stirred at rt for 3 h. NaBH(OAc)$_3$ (317 mg, 1.5 mmol) was added and the solution was stirred at rt overnight. The solution was poured out into cooled water and was basified with K$_2$CO$_3$ powder. The product was extracted with EtOAc. The organic layer was dried over MgSO$_4$, filtered and evaporated to dryness. The residue was purified by chromatography over silica gel (stationary phase: irregular bare silica 40 g, mobile phase: NH$_4$OH/DCM/MeOH: 0.2/98/2). The residue was dissolved in 5 mL of ACN, 2 eq of 4N HCl in dioxane (117 μL; 0.47 mmol) was added dropwise at 10° C. Et$_2$O was added and after 30 mn, the solution was evaporated to dryness, Et$_2$O was added and a precipitate was filtered and dried yielding 38 mg of compound 58 (HCl salt).

The compounds in the Table below were prepared by using an analogous method as described for the preparation of compound 58, starting from the respective starting materials.

| Compound number | Structure | Quantity (mg) | Yield (%) |
|---|---|---|---|
| Compound 59 (from intermediate 8 and 1-methyl-1H-pyrazole-4-carbaldehyde) | 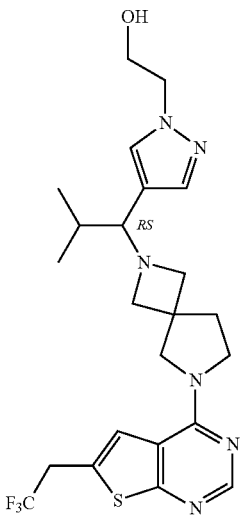 [SMILES: CC(C)C(c1cnn(CCO)c1)N1CC2(CCN(c3ncnc4sc(CC(F)(F)F)cc34)C2)C1] HCl salt | 73 | |

Example B21

Preparation of Compound 62:

1M TBAF in THF (0.815 mL, 0.815 mmol) was added dropwise to a solution of intermediate 55 (0.248 g, 0.407 mmol) in Me-THF (8 mL) and the reaction mixture was stirred at rt overnight. The reaction mixture was poured onto a 10% aqueous solution of K$_2$CO$_3$ and extracted with EtOAc. The organic layer was washed with 10% aqueous K$_2$CO$_3$ (30 mL), water (30 mL) and brine (30 mL), dried over MgSO$_4$, filtered and evaporated to dryness. The residue was purified by chromatography over silica gel (80 g, 15-40 μm, eluent: DCM/MeOH: 97/3 to 88/12). The pure fractions were mixed and the solvent was evaporated yielding 0.043 g of compound 62 (21% yield).

Example B22

Preparation of Compound 63:

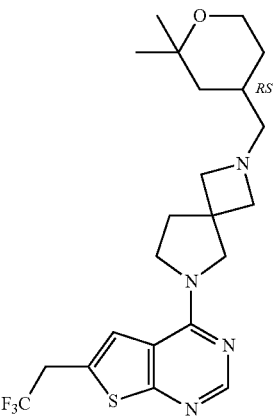 [SMILES: CC1(C)CC(CN2CC3(CCN(c4ncnc5sc(CC(F)(F)F)cc45)C3)C2)CCO1]

2,2-Dimethyl-tetrahydropyran-4-carbaldehyde (87 mg; 0.609 mmol) and NaBH(OAc)$_3$ (645 mg; 3.045 mmol) were added at rt to a solution of intermediate 11 (200 mg; 0.609 mmol) in DCE (4 mL) and the reaction mixture was stirred overnight. The reaction mixture was diluted with DCM and poured onto a 10% aqueous solution of K$_2$CO$_3$. The organic layer was decanted, dried over MgSO$_4$, filtered and evaporated to dryness. The residue was purified by chromatography over silica gel (irregular SiOH, 24 g; mobile phase: NH$_4$OH/MeOH/DCM: gradient from 0/0/100 to 0.7/7/93). The pure fractions were collected and evaporated to dryness. The residue was freeze-dried from water/ACN (80/20; 10 mL) yielding 155 mg of compound 63 (56% yield).

The compounds in the Table below were prepared by using an analogous method as described for the preparation of compound 63, starting from the respective starting materials.

Example B23

| Compound number | Structure | Quantity (mg) | Yield (%) |
|---|---|---|---|
| Compound 65 (from intermediate 11 and 3-methyloxetane-3-carbaldehyde) | 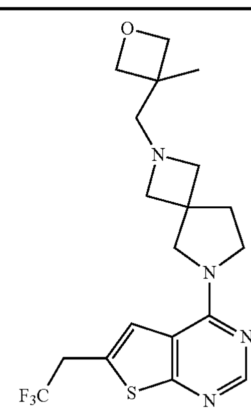 | 71 | 60 |

141

Preparation of Compound 64:

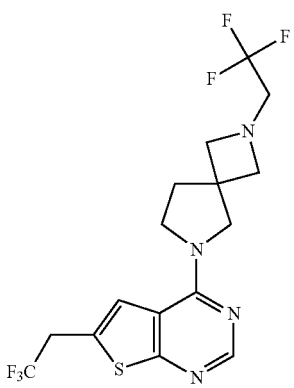 [SMILES: FC(F)(F)Cc1cc2c(N3CCC4(CN(CC(F)(F)F)C4)C3)ncnc2s1]

A mixture of intermediate 11 (150 mg, 0.457 mmol), 2,2,2-trifluoroethyl trifluoromethanesulfonate (69 µL, 0.502 mmol) and DBU (CAS[6674-22-2]) (136 µL, 0.914 mmol) in DMSO (3 mL) was stirred at rt for 18 h. The reaction mixture was poured onto water and extracted with EtOAc. The organic layer was washed several times with water, then brine, dried over $MgSO_4$, filtered and evaporated to dryness. The residue was purified by chromatography over silica gel (irregular SiOH, 24 g; mobile phase: $NH_4OH/MeOH/DCM$ gradient from 0/0/100 to 0.7/7/93). The pure fractions were collected and evaporated to dryness. The residue was purified a second time by chromatography over silica gel (irregular SiOH, 10 g; mobile phase: EtOAc/heptane: gradient from 60/40 to 80/20). The pure fractions were collected and evaporated to dryness. The residue was crystallized from DIPE yielding, after drying under vacuum at 50° C., 100 mg of compound 64 (53% yield).

Example B24

Preparation of Compound 67:

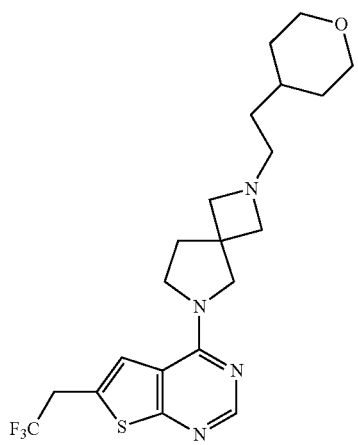 [SMILES: FC(F)(F)Cc1cc2c(N3CCC4(CN(CCC5CCOCC5)C4)C3)ncnc2s1]

Under $N_2$, to a solution of intermediate 11 (100 mg; 0.31 mmol), 2-(tetrahydro-2H-pyran-4-yl))acetaldehyde (48 µL; 0.37 mmol) in THF (3 mL) were stirred at rt for 3 h. $NaBH(OAc)_3$ (129 mg; 0.61 mmol) was added and the mixture was stirred at rt overnight. A 10% aqueous solution of $K_2CO_3$ and EtOAc were added. The mixture was extracted with EtOAc (×3). The organic layers were combined, washed with brine then dried over $MgSO_4$, filtered and the solvent was evaporated.

The residue (136 mg) was purified by chromatography over silica gel ($SiO_2$, 4 g; gradient: from 95% DCM, 5% MeOH, 0.5% $NH_4OH$ to 90% DCM, 10% MeOH, 1% $NH_4OH$). The fractions containing the product were collected and the solvent was evaporated to give 90 mg of colourless oil which was recrystallized with diisopropylether. The precipitate was filtered and dried to give 45 mg (34%) of compound 67 as a white solid.

Example B25

Preparation of Compound 71

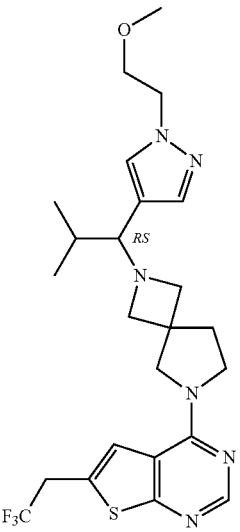 [SMILES: COCCn1cc(C(C(C)C)N2CC3(CCN(c4ncnc5sc(CC(F)(F)F)cc45)C3)C2)cn1]

In a sealed tube, under $N_2$, intermediate 35 (211 mg; 1.37 mmol) and $Ti(OiPr)_4$ (436 µL; 1.83 mmol) were added to a solution of intermediate 11 (300 mg; 0.914 mmol) in THF (6 mL). The solution was stirred at 50° C. for 5 hours then at rt overnight. The reaction mixture was cooled to 5° C. and isopropyl magnesium chloride 2M in THF (2.28 mL; 4.57 mmol) was added dropwise. The reaction mixture was allowed to rise slowly to rt and stirred overnight. The reaction mixture was diluted with EtOAc and poured onto a 10% aqueous solution of $K_2CO_3$. The precipitate was removed by filtration over Celite®. The organic layer was decanted, washed with brine, dried over $MgSO_4$, filtered and evaporated to dryness. The residue was purified by chromatography over silica gel (irregular SiOH, 40 g; mobile phase: gradient from 0% MeOH, 100% DCM to 10% MeOH, 90% DCM). The fractions containing the product were collected and evaporated to dryness to give 0.337 g of an intermediate residue which was purified again by chromatography via reverse phase (stationary phase: YMC-actus Triart C18 10 µm 30*150 mm, mobile phase: gradient from 55% $NH_4HCO_3$ 0.2%, 45% ACN to 0% $NH_4HCO_3$ 0.2%, 100% ACN). The pure fractions were collected and evaporated to dryness. The residue was freeze-dried with acetonitrile/water 20/80 to afford 120 mg (26%) of compound 71.

Example B26

Preparation of Compound 77:

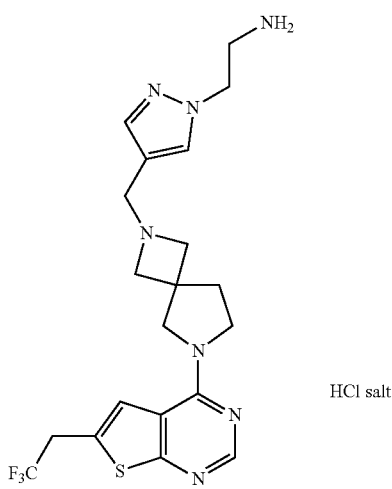 [SMILES: NCCn1cc(CN2CC3(CCN(c4ncnc5sc(CC(F)(F)F)cc45)C3)C2)cn1]

HCl salt

Hydrazine (36 μL, 0.92 mmol) was added to a solution of intermediate 41 (110 mg, 0.18 mmol) in ethanol (5 mL). The solution was heated at 70° C. for 1 h 30. The reaction was cooled to rt, then poured into water and extracted with DCM. The organic layer was washed with brine, then dried over MgSO$_4$, filtered and evaporated to dryness. The residue was purified by chromatography over silica gel (stationary phase: irregular bare silica 40 g, mobile phase: NH$_4$OH/DCM/MeOH: 1/85/15). The pure fractions were collected and evaporated to dryness. The residue was dissolved in 2 mL of ACN, 3 eq of 6N HCl in iPrOH were added dropwise at 10° C. Et$_2$O was added and after 30 mn, the precipitate was filtered and dried yielding 83 mg of compound 77 (37% yield).

Example B28

Preparation of Compound 82:

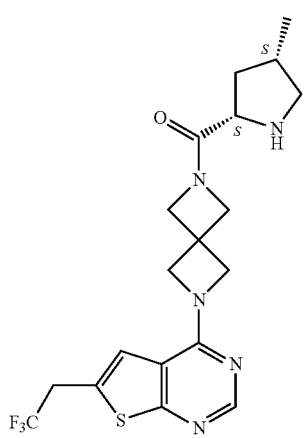

TFA (1.5 mL) was added to a solution of intermediate 25 (300 mg, 0.571 mmol) in DCM (15 mL) and the reaction mixture was stirred for 18 h. The reaction mixture was poured onto a 10% aqueous solution of K$_2$CO$_3$ and extracted with DCM. The organic layer was decanted, filtered over Chromabond® and evaporated to dryness. The residue was purified by chromatography over silica gel (irregular SiOH, 10 g; mobile phase: NH$_4$OH/MeOH/DCM: gradient from 0.3/3/97 to 1.5/15/85). The pure fractions were collected and evaporated to dryness. The residue was crystallized from DIPE and dried yielding 118 mg of compound 82 (48% yield).

The compounds in the Table below were prepared by using an analogous method as described for the preparation of compound 82, starting from the respective starting materials.

| Compound number | Structure | Quantity (mg) | Yield (%) |
|---|---|---|---|
| Compound 315 (from intermediate 109) | 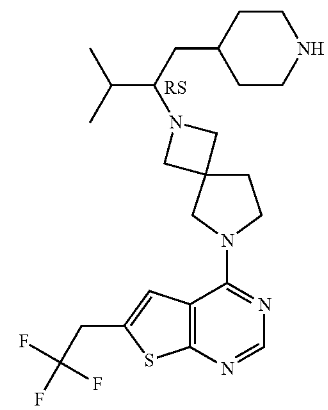 [SMILES: CC(C)C(CC1CCNCC1)N1CC2(CCN(c3ncnc4sc(CC(F)(F)F)cc34)C2)C1] | 140 | 52 |
| Compound 318 (from intermediate 112 and T = 0° C.) | TFA salt | 200 | |

145
Example B29

Preparation of Compound 84:

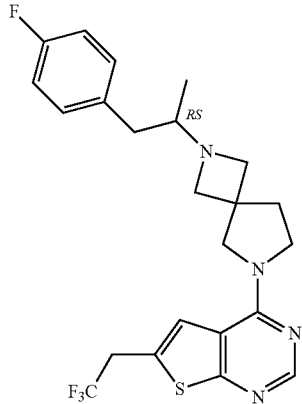 [SMILES: CC(Cc1ccc(F)cc1)N1CC2(CCN(c3ncnc4sc(CC(F)(F)F)cc34)C2)C1]

Intermediate 11b (198 mg) and 4-fluorophenylacetone (68 µL, 0.51 mmol) in THF (5 mL) were stirred at rt overnight. Then NaBH(OAc)$_3$ (161 mg, 0.76 mmol) was added portionwise. The mixture was stirred at rt for 24 h. The solution was poured out into cooled water and basified with a solution of 3N NaOH, EtOAc was added. The organic layer was separated, dried over MgSO$_4$, filtered and evaporated to dryness. The residue was purified by chromatography over silica gel (stationary phase: irregular bare silica 40 g, mobile phase: NH$_4$OH/DCM/MeOH: 0.1/97/3). The pure fractions were collected and the solvent was evaporated under vacuum. The residue was freeze-dried with acetonitrile/water 20/80 yielding 30 mg of compound 84.

The compounds in the Table below were prepared by using an analogous method as described for the preparation of compound 84, starting from the respective starting materials.

| Compound number | Structure | Quantity (mg) | Yield (%) |
|---|---|---|---|
| Compound 307 (from intermediate 11b and 1-(4-fluorophenyl)-3-metylbutan-2-one) | 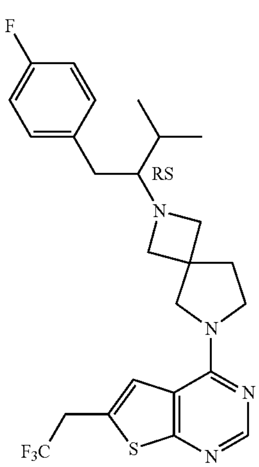 [SMILES: CC(C)C(Cc1ccc(F)cc1)N1CC2(CCN(c3ncnc4sc(CC(F)(F)F)cc34)C2)C1] | 46 | |

146
Example B32

Preparation of Compound 133

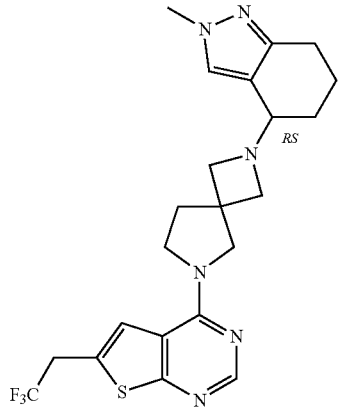 [SMILES: Cn1cc2c(n1)CCCC2N1CC2(CCN(c3ncnc4sc(CC(F)(F)F)cc34)C2)C1]

Compound 137

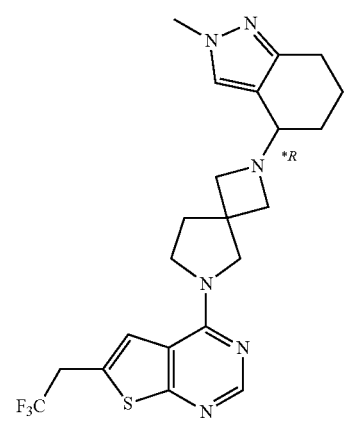 [SMILES: Cn1cc2c(n1)CCCC2N1CC2(CCN(c3ncnc4sc(CC(F)(F)F)cc34)C2)C1]

and Compound 138

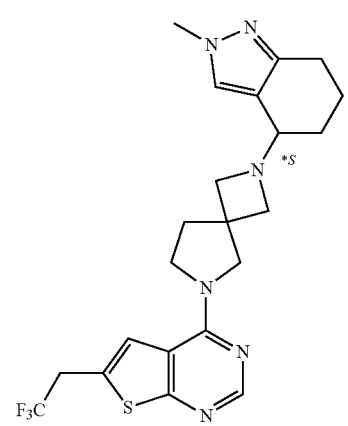

Ti(OEt)$_4$ (251 μL; 1.2 mmol) was added at room temperature to a solution of intermediate 11 (200 mg; 0.6 mmol) and 2,5,6,7-tetrahydro-2-methyl-4H-Indazol-4-one (120 mg; 0.8 mmol) in dichloroethane (5 mL) and MeOH (1.5 mL). The mixture was stirred at rt for 2 hours then NaBH$_3$CN (127 mg; 2 mmol) was added portionwise. The mixture was stirred at room temperature for 2 days. The solution was poured out into cooled water and DCM was added. The mixture was basified with K$_2$CO$_3$ powder, filtered through a pad of Celite®. The product was extracted with DCM. The organic layer was dried over MgSO$_4$, filtered and evaporated to dryness.

The residue (361 mg) was purified by silica gel chromatography (Stationary phase: irregular bare silica 40 g, Mobile phase: 0.5% NH$_4$OH, 95% DCM, 5% MeOH). The fraction containing the product were mixed and concentrated to afford 120 mg (43%) of compound 133.

Chiral separation of compound 133 was performed via chiral SFC (Stationary phase: Chiralpak AD-H 5 μm 250*30 mm, Mobile phase: 70% CO$_2$, 30% MeOH (0.3% iPrNH$_2$)). The fractions containing the products were mixed and concentrated to afford:
- 45 mg of fraction 1 which was freeze-dried with acetonitrile/water 20/80 to give 40 mg (43%) of compound 137 as a white powder.
- 46 mg of fraction 2 which was freeze-dried with acetonitrile/water 20/80 to give 42 mg (46%) of compound 138 as a white powder.

Example B33

Preparation of Compound 145

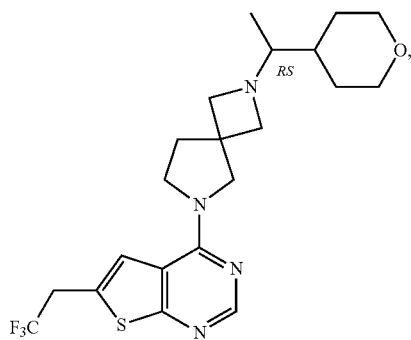 [SMILES: CC(C1CCOCC1)N1CC2(CCN(c3ncnc4sc(CC(F)(F)F)cc34)C2)C1]

Compound 154

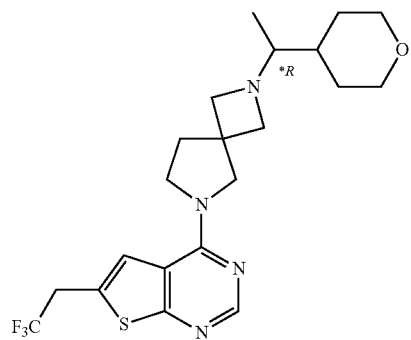 [SMILES: CC(C1CCOCC1)N1CC2(CCN(c3ncnc4sc(CC(F)(F)F)cc34)C2)C1]

and Compound 155

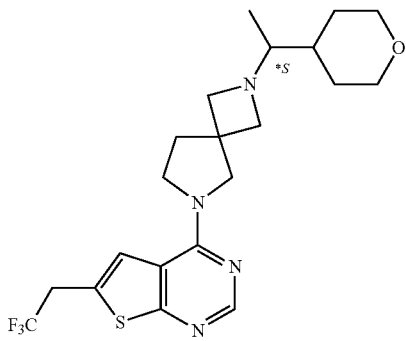 [SMILES: CC(C1CCOCC1)N1CC2(CCN(c3ncnc4sc(CC(F)(F)F)cc34)C2)C1]

A solution of 1-tetrahydro-2H-pyran-4-ylethanone (351 mg; 2.74 mmol), intermediate 11 (600 mg; 1.83 mmol), Ti(OiPr)$_4$ (870 μL; 2.92 mmol) in EtOH (3 mL) was stirred for 2 hours at 45° C. Additional EtOH (18 mL) and NaBH$_4$ (138 mg; 3.65 mmol) were added. The reaction mixture was stirred at room temperature for 5 hours. The reaction mixture was diluted with DCM and poured onto a 10% aqueous solution of K$_2$CO$_3$. The insoluble material was removed by filtration over Celite®. The organic layer was separated, washed with water, dried over MgSO$_4$, filtered and evaporated to dryness. The residue was purified by chromatography over silica gel (irregular SiOH, 24 g; mobile phase: gradient from 0% NH$_4$OH, 0% MeOH, 100% DCM to 1% NH$_4$OH, 10% MeOH, 90% DCM). The fractions containing the product were collected and evaporated to dryness yielding 487 mg (60%) of compound 145. The enantiomers of compound 145 were separated by chiral SFC (CHIRALPAK AD-H 5 μm 250*30 mm; mobile phase: 70% CO$_2$, 30% mixture of EtOH/iPrOH 50/50 v/v). The fractions containing the products were collected and evaporated to dryness. The residues were freeze dried from water/ACN (80/20; 10 mL) yielding 171 mg (21%) of compound 154 and 178 mg (22%) of compound 155.

The compounds in the Table below were prepared by using an analogous method as described for the preparation of compound 145, starting from the respective starting materials. The most relevant minor deviations are indicated in the column 'Compound number'.

| Compound number | Structure | Quantity | Yield |
|---|---|---|---|
| Compound 279 (from intermediate 11 and 1-(3-methyloxetan-3-yl)ethenone [1363381-04-7] With 6 eq. of Ti(iPrO)₄ and 2 eq. of NaBH₄ | 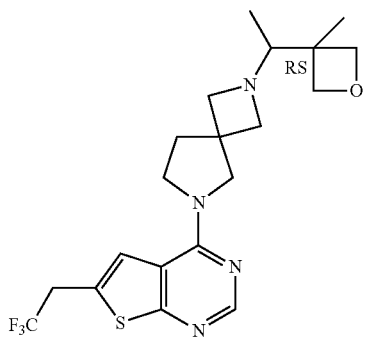 [SMILES: CC(N1CC2(CCN(c3ncnc4sc(CC(F)(F)F)cc34)C2)C1)C1(C)COC1] | 243 mg | 37% |
| Compound 158 and compound 159 From SFC purification of intermediate 158 CHIRACEL OJ-H 5 μm 250 * 30 mm, mobile phase: 80% CO₂, 20% EtOH(0.3% iPrNH₂)) | 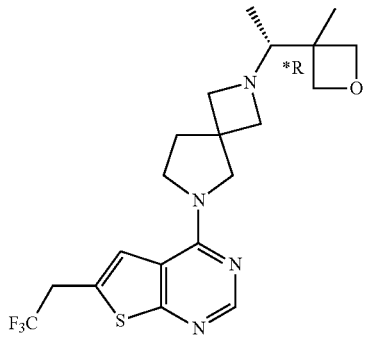<br>Compound 158 | 77 mg | 12% |
| | 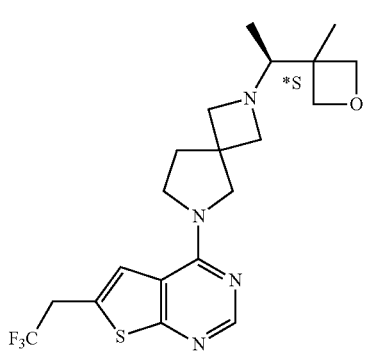<br>Compound 159 | 80 mg | 12% |
| Compound 192 (from intermediate 11 and 1-(tetrahydro-2,6-dimethyl-2H-pyran-4-yl)-1-Propanone With 1.6 eq. of Ti(iPrO)₄ and 2 eq. of NaBH₄ | 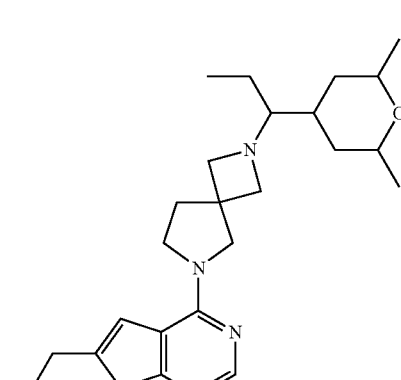 | 76 mg | 14% |

| Compound number | Structure | Quantity | Yield |
|---|---|---|---|
| Compound 280 (from intermediate 11b and 3-methyl-1-(tetrahydro-2H-pyran-4-yl)-1-Butanone With 6 eq. of Ti(iPrO)$_4$ and 2 eq. of NaBH$_4$ | 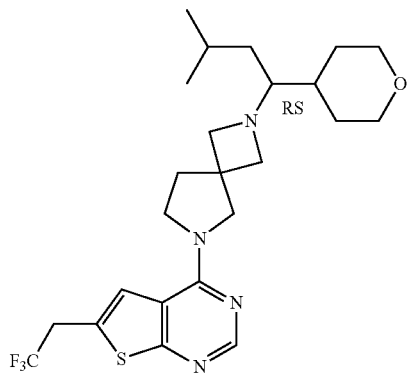 [SMILES: CC(C)CC(C1CCOCC1)N1CC2(CCN(c3ncnc4sc(CC(F)(F)F)cc34)C2)C1] | 195 mg | |
| Compound 179 and compound 180 From SFC purification of compound 280 CHIRALPAK AD-H 5 μm 250 * 30 mm; mobile phase: 75% CO$_2$, 25% MeOH(0.3% iPrNH$_2$)) | 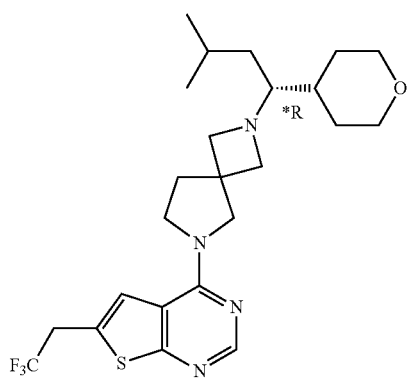
Compound 179 | 70 mg | 10% |
| | 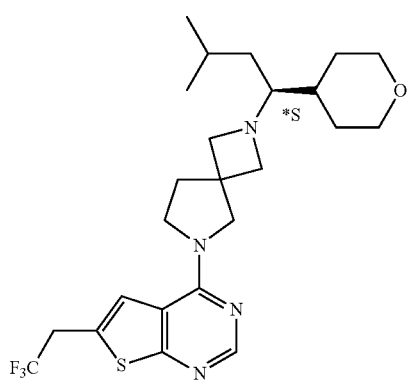
Compound 180 | 69 mg | 10% |

-continued
| Compound number | Structure | Quantity | Yield |
|---|---|---|---|
| Compound 250 With 6 eq. of Ti(iPrO)$_4$ and 2 eq. of NaBH$_4$ | 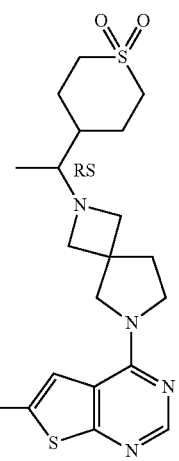 Compound 250 From intermediate 11 and 1-(1,1-dioxidotetrahydro-2H-thiopyran-4-yl)ethenone | 369 mg | 62% |
| compound 163 and | 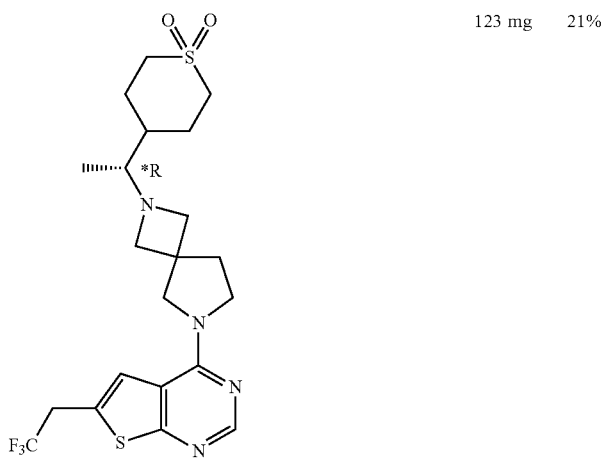 Compound 163 | 123 mg | 21% |

-continued
| Compound number | Structure | Quantity | Yield |
|---|---|---|---|
| compound 164 | 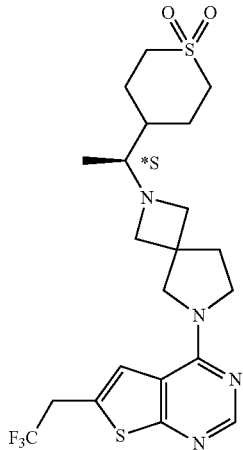 Compound 164 | 123 mg | 21% |
From compound 250 chiral
SFC: CHIRACEL OJ-H
5 μm 250 * 30 mm; mobile
phase: 70% CO$_2$, 30%
MeOH (0.3% iPrNH$_2$)
| Compound 314 (From intermediate 11 and 4-Cyanophenylacetone) | 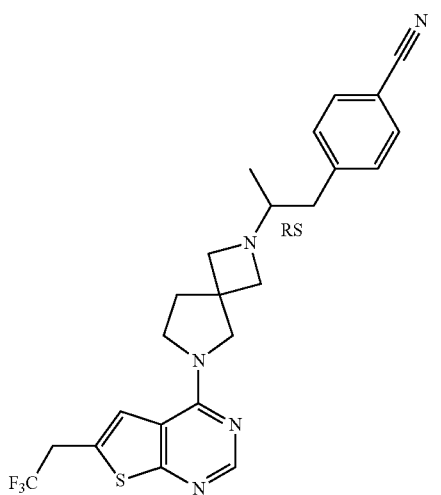 [SMILES: CC(Cc1ccc(C#N)cc1)N1CC2(CCN(c3ncnc4sc(CC(F)(F)F)cc34)C2)C1] | 105 mg | 15% |

157

Preparation of Compound 312 (Diastereoisomer a (Mixture of 2 Compounds (RR and SS) or (RS and SR)) and Compound 313 (Diastereoisomer B (Mixture of 2 Compounds (RS and SR) or (RR and SS)):

Co 312: Diastereoisomer A (RR and SS) or (RS and SR)
Co 313: Diastereoisomer B (RS and SR) or (RR and SS)

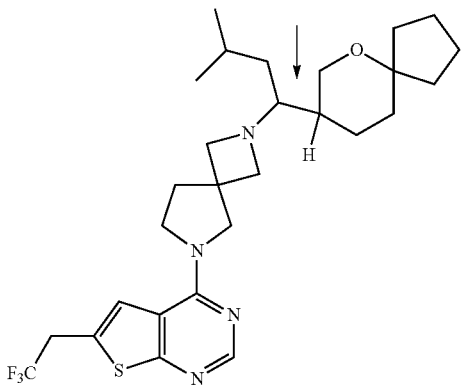 [SMILES: CC(C)CC(C1CCC2(CCCC2)OC1)N1CC2(CCN(c3ncnc4sc(CC(F)(F)F)cc34)C2)C1]

Reaction Mixture 1:

A solution of 3-methyl-1-(6-oxaspiro[4.5]dec-9-yl)-1-Butanone (1.5 eq.), intermediate 11 (100 mg; 0.285 mmol), Ti(OiPr)$_4$ (1.6 eq.) in ethanol (0.25 mL) was stirred for 2 hours at 45° C. Ethanol (3 mL) was added and NaBH$_4$ (2 eq.) was added. The reaction mixture was stirred at room temperature for 18 hours.

Reaction Mixture 2:

A solution of 3-methyl-1-(6-oxaspiro[4.5]dec-9-yl)-1-Butanone (546 mg; 2.436 mmol; 2 eq), intermediate 11 (400 mg; 1.22 mmol), Ti(OiPr)$_4$ (580 μL; 1.95 mmol) in ethanol (1 mL) was stirred for 2 hours at 45° C. Ethanol (12 mL) was added and NaBH$_4$ (92 mg; 2.436 mmol) was added. The reaction mixture was stirred at room temperature for 18 hours.

The two reaction mixtures were gathered and diluted with EtOAc, poured onto a 10% aqueous solution of K$_2$CO$_3$ and filtered through a pad of Celite®. The organic layer was decanted, washed with brine, dried over MgSO$_4$, filtered and evaporated to dryness. The residue was purified by chromatography over silica gel (irregular SiOH, 24 g; mobile phase: gradient from 0% NH$_4$OH, 0% MeOH, 100% DCM to 0.9% NH$_4$OH, 9% MeOH, 91% DCM). The desired fractions were collected and evaporated to dryness.

The residue (280 mg) was further separated by chromatography over silica gel (irregular SiOH, 24 g; mobile phase: 67% heptane, 33% EtOAc (+5% MeOH containing 10% NH$_4$OH)). The desired fractions were collected and evaporated to dryness yielding:

158

100 mg (12%) of compound 312 (eluted first; not pure enough) which was further purified by chromatography over silica gel (irregular SiOH, 24 g; mobile phase: gradient from 0% NH$_4$OH, 0% MeOH, 100% DCM to 0.5% NH$_4$OH, 5% MeOH, 95% DCM). The pure fractions were collected and evaporated to dryness. The pure fractions were freeze dried from water/ACN (80/20; 10 mL) yielding 80 mg (10%) of compound 312.

110 mg (13%) of compound 313 (eluted second; not pure enough) which was further purified by chromatography over silica gel (irregular SiOH, 24 g; mobile phase: gradient from 0% NH$_4$OH, 0% MeOH, 100% DCM to 0.5% NH$_4$OH, 5% MeOH, 95% DCM). The pure fractions were collected and evaporated to dryness. The pure fractions were freeze dried from water/ACN (80/20; 10 mL) yielding 70 mg (9%) of compound 313.

Example B34

Preparation of Compound 147:

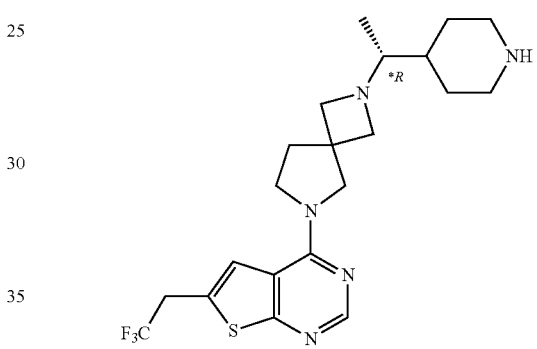

A mixture of intermediate 60a (216 mg; 0.4 mmol) and TFA (1 mL; 13.067 mmol) in DCM (10 mL) was stirred at rt for 4 h. The reaction mixture was diluted with DCM and basified with a 10% aqueous solution of K$_2$CO$_3$. The organic layer was decanted, washed with water, filtered through Chromabond® and evaporated to dryness. The residue (200 mg) was purified by chromatography over silica gel (irregular SiOH, 10 g; mobile phase: 85% DCM, 14% MeOH, 1% NH$_4$OH). The pure fractions were collected and evaporated to dryness. The residue was freeze-dried from water/ACN (80/20; 10 mL) yielding 136 mg of compound 147 (77%).

The compounds in the Table below were prepared by using an analogous method as described for the preparation of compound 147, starting from the respective starting materials.

| Compound number | Structure | Quantity | Yield |
|---|---|---|---|
| Compound 146 (from intermediate 60b) | 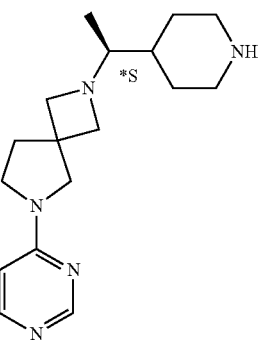 | 130 mg | 71% |
| Compound 150 (from intermediate 63a) | 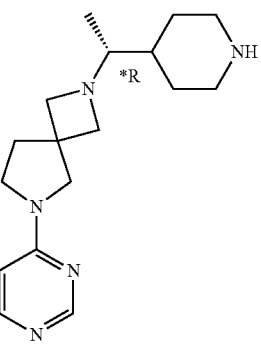 | 29 mg | 45% |
| Compound 148 (from intermediate 68) | 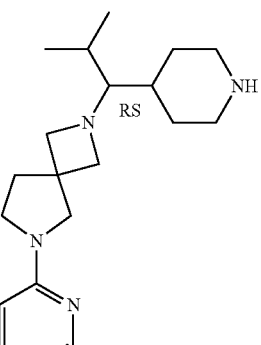<br>TFA salt | 50 mg | |
| Compound 168 (from intermediate 68a) | 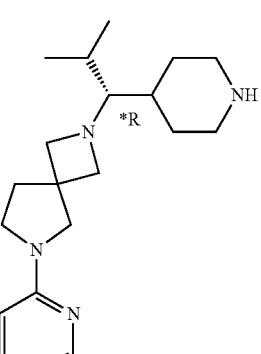 | 45 mg | 50% |

| Compound number | Structure | Quantity | Yield |
|---|---|---|---|
| Compound 169 (from intermediate 68b | 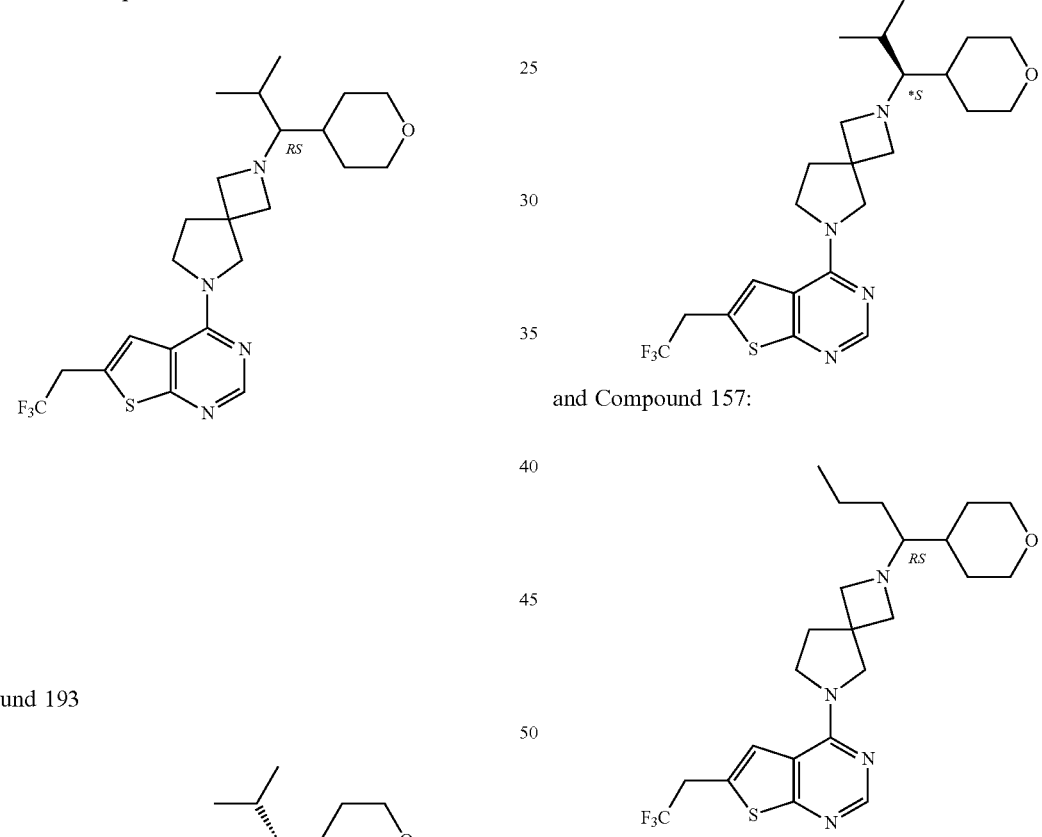 | 50 mg | 58% |

Example B35

Preparation of Compound 156

Compound 193

Compound 162 and Compound 157:

A solution of 2-methyl-1-(tetrahydro-2H-pyran-4-yl)-1-Propanone (1.66 g; 10.63 mmol) in THF (30 mL) was added to a solution of intermediate 11 (2.33 g; 7.08 mmol) and TFA (3.3 mL; 42.5 mmol) in THF (45 mL). The reaction mixture was stirred at rt overnight. Then NaBH(OAc)$_3$ (4.5 g; 21.25 mmol) was added portionwise. The reaction mixture was stirred at rt for 7 days. The reaction mixture was stirred at rt for 3 days. The solution was poured out into a 10% aqueous solution of K$_2$CO$_3$, EtOAc was added. The mixture was extracted with EtOAc (3×). The organics layers were combined, washed with brine, dried over MgSO$_4$, filtered and the solvent was evaporated. The residue (3.9 g; yellow oil) was purified by chromatography over silica gel (SiO$_2$; 40 g;

eluent: from 97% DCM, 3% MeOH, 0.3% NH₄OH to 90% DCM, 10% MeOH, 1% NH₄OH). The pure fractions were collected and the solvent was evaporated to give 666 mg of pale brown solid compound 156.

Compound 156 was purified by reverse phase (YMC-actus Triart C18 10 µm 30*150 mm, mobile phase: gradient from 50% NH₄HCO₃ 0.2%, 50% ACN to 0% NH₄HCO₃ 0.2%, 100% ACN). The pure fractions were collected and the solvent was evaporated to give 66 mg of compound 157 (colourless oil) and 264 mg of compound 156 (8%; colourless oil). 50 mg of compound 156 was freeze-dried with water-ACN to give 47 mg of compound 156 (white solid).

Compound 157 was freeze-dried with water-ACN to give 53 mg of compound 157 (2%, white solid).

Compound 156 (214 mg) was purified by chiral SFC (CHIRALPAK AD-H 5 µm 250*30 mm, mobile phase: 75% CO₂, 25% EtOH (0.3% iPrNH₂)). The pure fractions were collected and the solvent was evaporated to give 82 mg of compound 193 (colourless oil) and 82 mg of compound 162 (colourless oil).

Compound 193 was freeze-dried with water-ACN to give 72 mg of compound 193 (2%, white solid).

Compound 162 was freeze-dried with water-ACN to give 77 mg of compound 162 (2%, white solid).

The compounds in the Table below were prepared by using an analogous method as described for the preparation of compound 193, starting from the respective starting materials.

Compound 166:

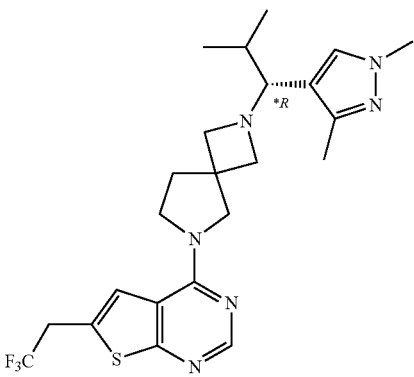

| Compound number | Structure | Quantity | Yield |
|---|---|---|---|
| Compound 309 as a mixture of 4 diasteoisomers (ratio: 65/35) (from intermediate 11 and 105) | 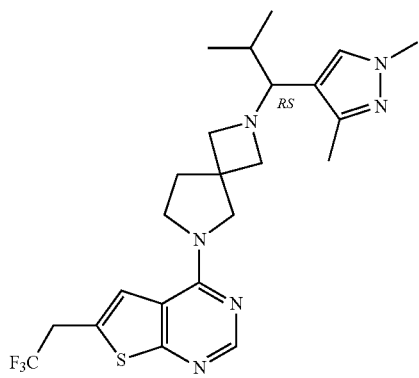 [SMILES: Cc1nn(C)cc1C(C(C)C)N1CC2(CCN(c3ncnc4sc(CC(F)(F)F)cc34)C2)C1] | 10 mg | 7% |

Preparation of Compound 161 and Compound 167: F

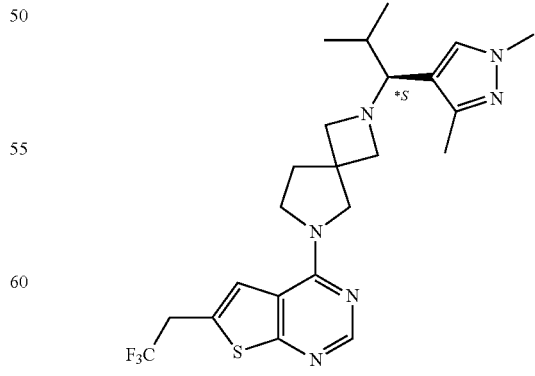

In a sealed tube, under N₂, 1,3-dimethyl-1H-pyrazole-4-carbaldehyde (284 mg; 2.28 mmol) and Ti(iPrO)₄ (727 µL; 3.05 mmol) were added to a solution of intermediate 11 (500 mg; 1.52 mmol) in THF (10 mL). The solution was stirred at 50° C. for 2 h. The reaction mixture was cooled to 5° C. and iPrMgCl (3.8 mL; 7.61 mmol) was added dropwise. The reaction mixture was allowed to rise slowly to rt and stirred overnight. The reaction mixture was poured onto a 10% aqueous solution of $K_2CO_3$ and EtOAc. The insoluble was filtered through a pad of Celite® then, the organic layer was decanted, dried over $MgSO_4$, filtered and the solvent was evaporated. The residue (866 mg, brown oil) was purified by chromatography over silica gel ($SiO_2$; 40 g; eluent: from 96% DCM, 4% MeOH, 0.4% $NH_4OH$ to 93% DCM, 7% MeOH, 0.7% $NH_4OH$). The pure fractions were collected and the solvent was evaporated to dryness. The residue (496 mg, yellow oil) was recrystallized with diethylether. The precipitate was filtered and dried to give 324 mg of compound 161 ((45%, white solid).

270 mg of compound 161 (was purified by chiral SFC (CHIRALPAK AD-H 5 μm 250*30 mm, mobile phase: 70% $CO_2$, 30% iPOH (0.3% $iPrNH_2$)). The pure fractions were collected and the solvent was evaporated to give 128 mg of compound 166 (18%, colourless oil) and 131 mg of compound 167 (18%, colourless oil).

Compound 166 was freeze-dried with water-ACN to give 110 mg of compound 166 (15%, white solid).

Compound 167 was freeze-dried with water-ACN to give 115 mg of compound 167 (16%, white solid).

The compounds in the Table below were prepared by using an analogous method as described for the preparation of compound 161, starting from the respective starting materials. The most relevant minor deviations are indicated in the column Yield.

| Compound number | Structure | Quantity | Yield |
|---|---|---|---|
| Compound 172 (from intermediate 11 and 1,5-dimetyl-1H-pyrazole-4-carbaldehyde | 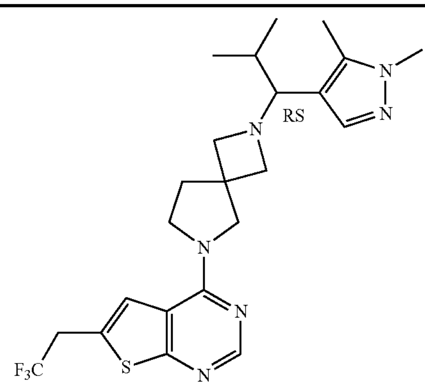 | 26 mg | 4% |
| Compound 173 and compound 174 From SFC purification of compound 172 CHIRALCEL OD-H 5 μm 250 * 30 mm, mobile phase: 80% $CO_2$, 20% EtOH (0.3% $iPrNH_2$)) | Compound 173 | 109 mg | 15% |
| | Compound 174 | 105 mg | 14% |

-continued

| Compound number | Structure | Quantity | Yield |
|---|---|---|---|
| Compound 186 (from intermediate 70b and 1-methyl-1H-Pyrazole-4-carboxaldehyde | 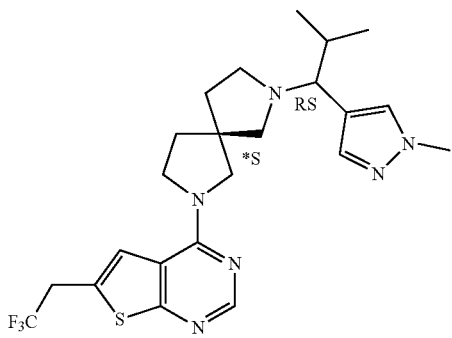 [SMILES: CC(C)C(c1cnn(C)c1)N1CC[C@]2(CCN(c3ncnc4sc(CC(F)(F)F)cc34)C2)C1] | 31 mg | 9% |
| Compound 188 and compound 189<br>From SFC purification of compound 186 (CHIRALPAK AD-H 5 μm 250 * 30 mm, mobile phase: 85% $CO_2$, 15% EtOH (0.3% $iPrNH_2$)) | 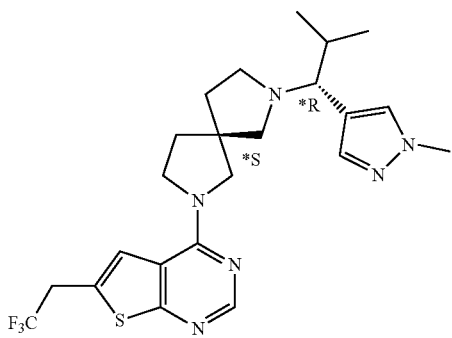<br>Compound 188 | 53 mg | 15% |
| | 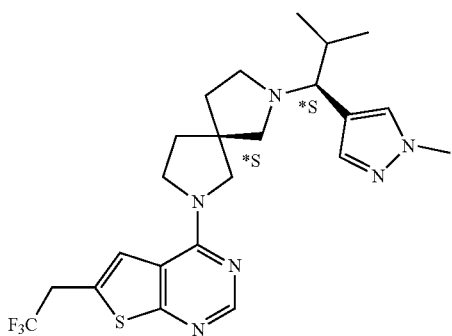<br>Compound 189 | 74 mg | 21% |
| Compound 281<br>From intermediate 70a and 1-methyl-1H-Pyrazole-4-carboxaldehyde. | 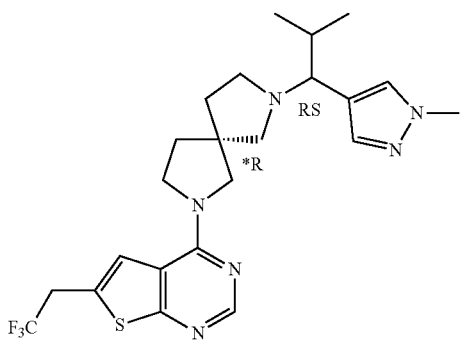 [SMILES: CC(C)C(c1cnn(C)c1)N1CC[C@@]2(CCN(c3ncnc4sc(CC(F)(F)F)cc34)C2)C1] | 250 | 71% $Ti(OEt)_4$ was used in the synthesis. |

| Compound number | Structure | Quantity | Yield |
|---|---|---|---|
| Compound 190 and compound 191 From SFC purification of compound 281 (CHIRALPAK AD-H 5 µm 250 * 30 mm, mobile phase: 85% CO₂, 15% EtOH (0.3% iPrNH₂)) | Compound 190 | 77 mg | 22% |
| | Compound 191 | 61 mg | 17% |

Example B38

Preparation of Compound 170:

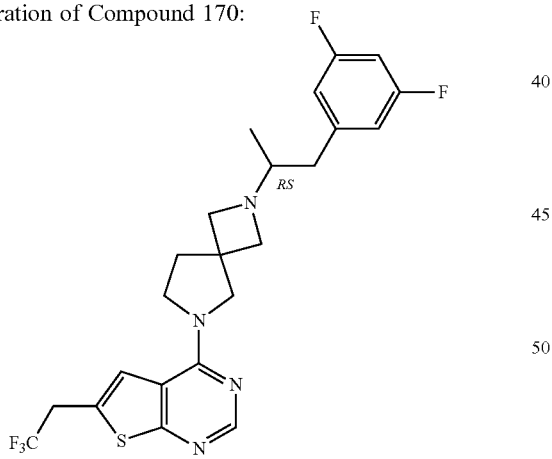

Intermediate 11b (198 mg) and 1-(3,5-difluorophenyl) propan-2-one) (86 mg; 0.51 mmol) in THF (5 mL). The mixture was stirred at rt overnight. Then NaBH(OAc)₃ (161 mg; 0.76 mmol) was added portionwise. The mixture was stirred at rt for 24 h. The solution was poured out into cooled water, basified with a solution of NaOH 3N, EtOAc was added. The organic layer was separated, dried over MgSO₄, filtered and evaporated to dryness. The residue (141 mg) was purified by chromatography over silica gel (irregular bare silica 40 g, mobile phase: 0.1% NH₄OH, 97% DCM, 3% MeOH). The pure fractions were collected and the solvent was evaporated. The residue (50 mg) was freeze-dried with ACN/water 20/80 to give 16 mg of compound 170.

The compounds in the Table below were prepared by using an analogous method as described for the preparation of compound 170, starting from the respective starting materials.

| Compound number | Structure | Quantity | Yield |
|---|---|---|---|
| Compound 171 (from intermediate 11b and 2-methoxyphenylacetone) | | 35 mg | |
| Compound 183 (from intermediate 11b (and 3-fluorophenylacetone) | HCl salt | 38 mg | |
| Compound 182 (from intermediate 11b and 3-methyl-1-phenyl2-butanone) | | 55 mg | |

| Compound number | Structure | Quantity | Yield |
|---|---|---|---|
| Compound 185 (from intermediate 70a and Tetrahydropyran-4-carbaldehyde [50675-18-8]) | | 143 mg | 56% |
| Compound 187 (from intermediate 70b and Tetrahydropyran-4-carbaldehyde [50675-18-8]) | | 124 mg | 48% |

Example B39

Preparation of Compound 184:

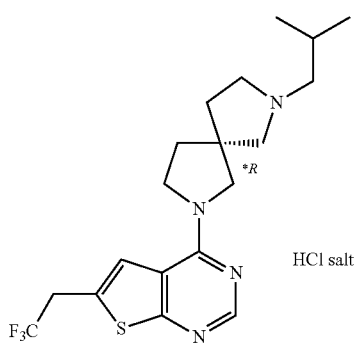 [SMILES: CC(C)CN1CC[C@@]2(CCN(c3ncnc4sc(CC(F)(F)F)cc34)C2)C1]

A mixture of intermediate 70a (250 mg; 0.73 mmol), isobutyraldehyde (200 µL; 2.19 mmol) and AcOH (42 µL; 0.73 mmol) in DCE (8 mL) was stirred at 50° C. for 3 h. The reaction mixture was cooled to rt and NaBH(OAc)$_3$ (464 mg; 2.19 mmol) was added. The reaction mixture was stirred at rt overnight, poured onto a 10% aqueous solution of K$_2$CO$_3$ and extracted with DCM. The organic layer was decanted, dried over MgSO$_4$, filtered and evaporated to dryness. The residue was purified by chromatography over silica gel (irregular SiOH, 24 g; mobile phase: gradient from 100% DCM to 10% MeOH (+100/NH$_4$OH), 90% DCM). The pure fractions were collected and evaporated to dryness. The hydrochloride salt was prepared: The residue (110 mg, 38%) was dissolved in ACN and HCl 4N in 1,4-dioxane (2 eq.) was added. The solution was evaporated to dryness and taken up several times with ACN. The residue was crystallized from Et$_2$O yielding 120 mg of compound 184 (HCl salt).

The compound in the Table below were prepared by using an analogous method as described for the preparation of compound 184, starting from the respective starting materials.

| Compound number | Structure | Quantity | Yield |
|---|---|---|---|
| Compound 288 (from intermediate 70b and isobutyraldehyde) | | 35 mg | 15% |

Preparation of Compound 289

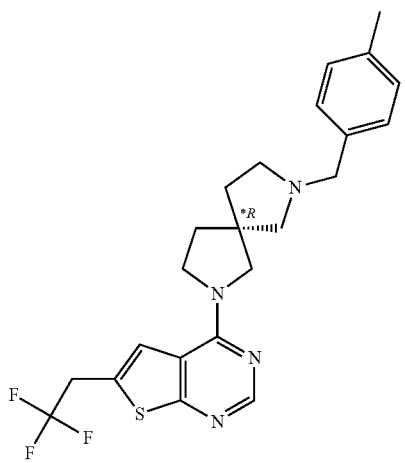 [SMILES: Cc1ccc(CN2CC[C@@]3(CCN(c4ncnc5sc(CC(F)(F)F)cc45)C3)C2)cc1]

A solution of intermediate 70a (100 mg; 0.29 mmol), p-tolualdehyde (50 µL; 0.35 mmol) in dichloroethane (3 mL) was stirred at rt for 3 h. NaBH(OAc)₃ (124 mg; 0.58 mmol) was added and the mixture was stirred at rt overnight. A 10% aqueous solution of K₂CO₃ and DCM were added. The organic layer was decanted, filtered through Chromabond® and evaporated to dryness. The residue was purified by chromatography over silica gel (irregular SiOH, 10 g; mobile phase: gradient from 0% NH₄OH, 0% MeOH, 100% DCM to 0.5% NH₄OH, 5% MeOH, 95% DCM). The pure fractions were collected and evaporated to dryness. The residue was freeze dried from water/ACN (80/20; 10 mL) yielding 73 mg (56%) of compound 289.

The compounds in the Table below were prepared by using an analogous method as described for the preparation of compound 289, starting from the respective starting materials. The most relevant minor deviations are indicated in the column Yield.

| Compound number | Structure | Quantity | Yield |
|---|---|---|---|
| Compound 290 (from intermediate 70b and p-tolualdehyde) | 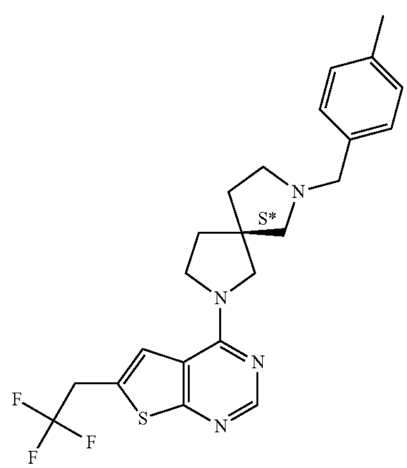 [SMILES: Cc1ccc(CN2CC[C@]3(CCN(c4ncnc5sc(CC(F)(F)F)cc45)C3)C2)cc1] | 85 mg | 65 |

-continued

| Compound number | Structure | Quantity | Yield |
|---|---|---|---|
| Compound 291 (from intermediate 70b and 4-fluorobenzaldehyde) | 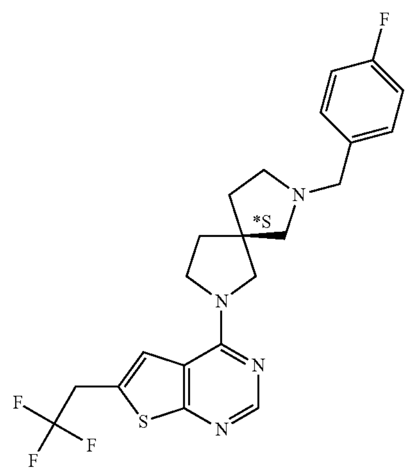 [SMILES: Fc1ccc(CN2CC[C@]3(CCN(c4ncnc5sc(CC(F)(F)F)cc45)C3)C2)cc1] | 89 mg | 68% THF as solvent |
| Compound 292 (from intermediate 70a and 4-fluorobenzaldehyde) | 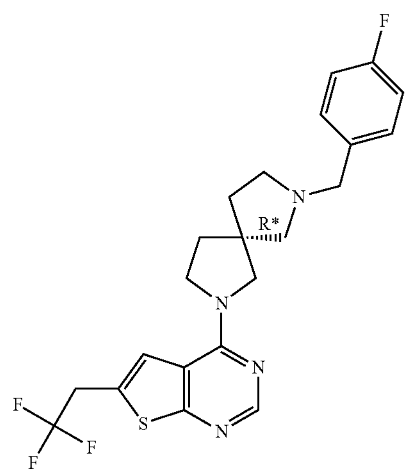 [SMILES: Fc1ccc(CN2CC[C@@]3(CCN(c4ncnc5sc(CC(F)(F)F)cc45)C3)C2)cc1] | 86 mg | 65% THF as solvent |
| Compound 293 (from intermediate 70a and 3-methylbutyraldehyde) | 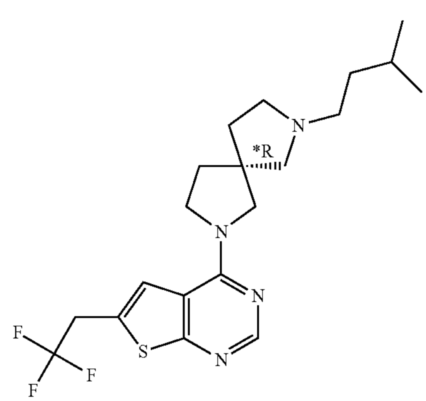 [SMILES: CC(C)CCN1CC[C@@]2(CCN(c3ncnc4sc(CC(F)(F)F)cc34)C2)C1] | 68 mg | 56% THF as solvent |

-continued

| Compound number | Structure | Quantity | Yield |
|---|---|---|---|
| Compound 294 (from intermediate 70b and 3-methylbutyraldehyde) | 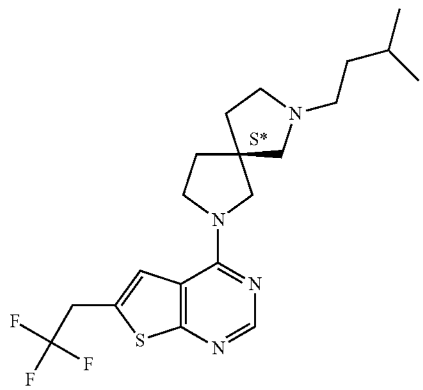 [SMILES: CC(C)CCN1CC[C@]2(CCN(c3ncnc4sc(CC(F)(F)F)cc34)C2)C1] | 72 mg | 60% THF as solvent |
| Compound 295 (from intermediate 70a and 1-methyl-1H-pyrazole-4-carbaldehyde) | 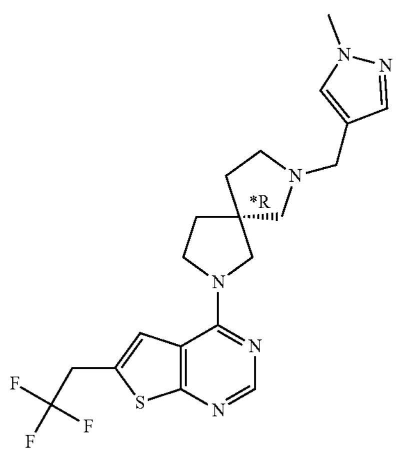 [SMILES: Cn1cc(CN2CC[C@@]3(CCN(c4ncnc5sc(CC(F)(F)F)cc45)C3)C2)cn1] | 50 mg | 39% THF as solvent |
| Compound 296 (from intermediate 70a and phenylacetaldehyde) | 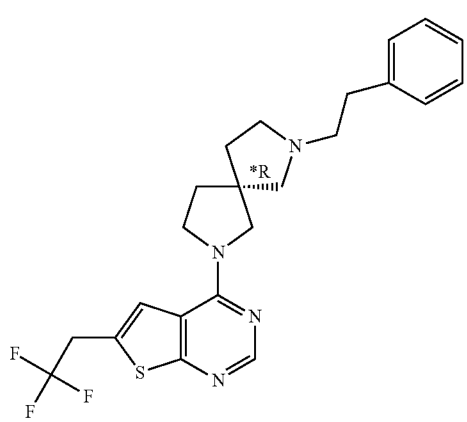 [SMILES: FC(F)(F)Cc1cc2c(N3CC[C@@]4(CCN(CCc5ccccc5)C4)C3)ncnc2s1] | 50 mg | 38% THF as solvent |

-continued

| Compound number | Structure | Quantity | Yield |
|---|---|---|---|
| Compound 297 (from intermediate 70b and phenylacetaldehyde) | 1.8 HCO₂H | 18 mg | 11% THF as solvent |
| Compound 298 (from intermediate 70a and 2-(4-fluorophenyl)acetaldehyde) | 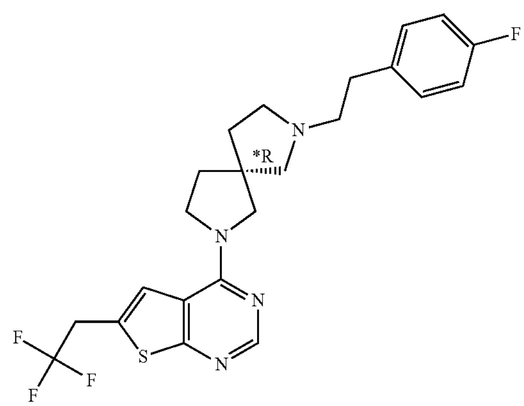 [SMILES: Fc1ccc(CCN2CC[C@@]3(CCN(c4ncnc5sc(CC(F)(F)F)cc45)C3)C2)cc1] | 20 mg | 14% |
| Compound 299 ((from intermediate 70b and 1-methyl-1H-pyrazole-4-carbaldehyde) | 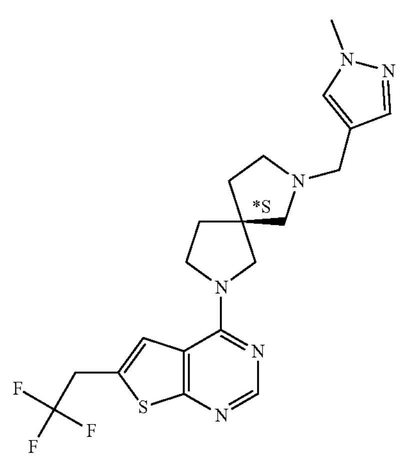 [SMILES: Cn1cc(CN2CC[C@]3(CCN(c4ncnc5sc(CC(F)(F)F)cc45)C3)C2)cn1] | 74 mg | 58% THF as solvent |

Example B41

Preparation of Compound 273

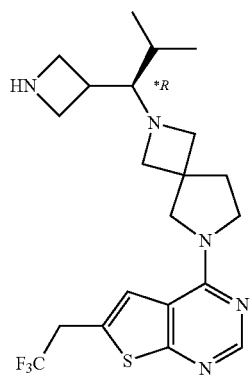 [SMILES: CC(C)[C@H](C1CNC1)N1CC2(CCN(c3ncnc4sc(CC(F)(F)F)cc34)C2)C1]

Compound 200

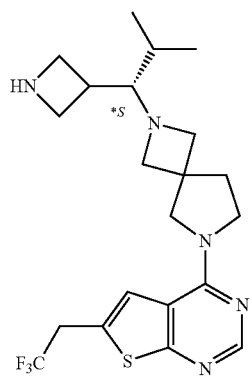 [SMILES: CC(C)[C@@H](C1CNC1)N1CC2(CCN(c3ncnc4sc(CC(F)(F)F)cc34)C2)C1]

and Compound 222

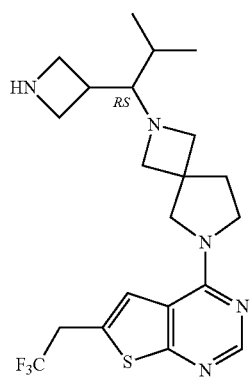 [SMILES: CC(C)C(C1CNC1)N1CC2(CCN(c3ncnc4sc(CC(F)(F)F)cc34)C2)C1]

A mixture of intermediate 71 (546 mg; 1.01 mmol) and TFA (1.5 mL; 19.6 mmol) in DCM (15 mL) was stirred at RT for 4 hours. The mixture was evaporated to dryness. The residue was taken up with DCM and $H_2O$ then, basified with aqueous NaOH 3N. The organic layer was decanted, dried over $MgSO_4$, filtered and evaporated to dryness yielding 400 mg (90%) of compound 222.

The enantiomers were separated by chiral SFC (Chiralpak AD-H 5 μm 250*30 mm; mobile phase: 50% $CO_2$, 50% EtOH (0.3% $iPrNH_2$)). The pure fractions were collected and evaporated to dryness yielding 106 mg (24%) of compound 273 and 130 mg (29%) of compound 200.

Compound 273 can also be prepared from intermediate 71a using the same procedure. Compound 200 can also be prepared from intermediate 71b using the same procedure. The compounds in the table below were prepared using an analogous method as described for the preparation of compound 273 starting from the respective starting materials.

| compound number | Structure | Quantity | Yield |
|---|---|---|---|
| compound 211 | From intermediate 77a | 125 mg | 56% |
| compound 213 | From intermediate 77b | 123 mg | 55% |
| compound 259 | From intermediate 80 | 96 mg | 49% |

-continued

| compound number | Structure | Quantity | Yield |
|---|---|---|---|
| compound 269 | From intermediate 82 | 18 mg | 55% |
| compound 269a | From intermediate 82a | 170 mg | 99% |
| compound 269b | From intermediate 82b | 193 mg | Quant. |

Example B42

Preparation of Compound 274

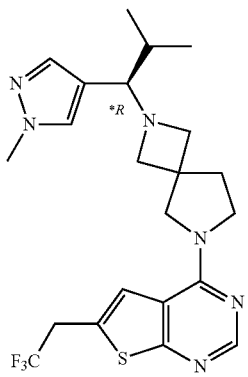 [SMILES: CC(C)[C@H](c1cnn(C)c1)N1CC2(CCN(c3ncnc4sc(CC(F)(F)F)cc34)C2)C1]

and Compound 203

Under $N_2$ at RT, 1-methyl-1H-pyrazole-4-carbaldehyde (100 mg; 0.913 mmol) and Ti(OEt)$_4$ (0.25 mL; 1.233 mmol) were added to a solution of intermediate 11 (200 mg; 0.609 mmol) in THF (3 mL). The solution was stirred at room temperature for 20 hours. The reaction mixture was cooled to 5° C. and iPrMgCl 2M in THF (1.5 mL; 3.045 mmol) was added dropwise. The reaction mixture was stirred for 30 min at 5° C., allowed to rise slowly RT over 6 hours and poured onto a cold aqueous solution of $K_2CO_3$. DCM was added and the reaction mixture was filtered through a pad of Celite®. The insoluble material was washed several times with DCM. The organic layer was decanted, filtered over Chromabond® and evaporated to dryness. The residue was purified by chromatography over silica gel (irregular SiOH, 24 g; mobile phase: gradient from 0% NH$_4$OH, 0% MeOH, 100% DCM to 0.8% NH$_4$OH, 8% MeOH, 92% DCM). The pure fractions were collected and evaporated to dryness yielding 195 mg (69%) of racemic compound. The enantiomers were separated by chiral SFC (Lux Cellulose-2 5 μm 250*30 mm; mobile phase: 55% CO$_2$, 45% MeOH (0.3% iPrNH$_2$)). The two fractions were freeze dried from water/ACN (80/20; 12 mL) yielding 80 mg (28%) of compound 274 and 82 mg (29%) of compound 203.

Example B43

Preparation of Compound 19

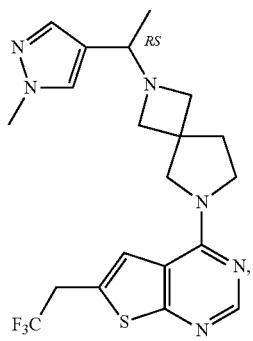 [SMILES: CC(c1cnn(C)c1)N1CC2(CCN(c3ncnc4sc(CC(F)(F)F)cc34)C2)C1]

Compound 198

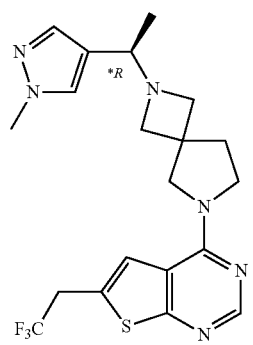 [SMILES: C[C@H](c1cnn(C)c1)N1CC2(CCN(c3ncnc4sc(CC(F)(F)F)cc34)C2)C1]

and Compound 199

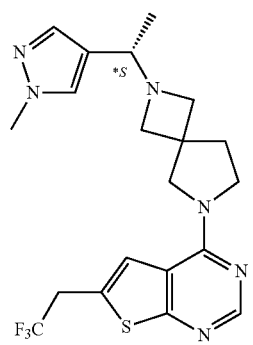 [SMILES: C[C@@H](c1cnn(C)c1)N1CC2(CCN(c3ncnc4sc(CC(F)(F)F)cc34)C2)C1]

Under N$_2$ at RT, 1-methyl-1H-pyrazole-4-carbaldehyde (99 mg; 0.9 mmol) and Ti(OEt)$_4$ (0.25 mL; 1.2 mmol) were added to a solution of intermediate 11 (197 mg; 0.6 mmol) in THF (3 mL), the solution was stirred at RT for 20 hours. The reaction mixture was cooled to 0° C. and CH$_3$MgBr (3M in Et$_2$O; 1 mL; 3 mmol) was added dropwise. The solution was stirred for 30 min at 0° C. and allowed to slowly rise RT for 6 hours. The solution was poured onto a mixture of cold water and aqueous saturated NH$_4$Cl then EtOAc was added. The mixture was filtered through a pad of Celite® and extracted with EtOAc. The organic layer was dried over MgSO$_4$, filtered and evaporated to dryness. The residue was purified by chromatography over silica gel (irregular SiOH, 24 g; mobile phase: gradient from 0% NH$_4$OH, 0% MeOH, 100% DCM to 0.5% NH$_4$OH, 5% MeOH, 95% DCM). The pure fractions were collected and evaporated to dryness yielding 130 mg (50%) of compound 197. The enantiomers were separated by chiral SFC (Lux Cellulose-4 5 μm 250*21.2 mm; mobile phase: 60% CO$_2$, 40% MeOH (+0.3% iPrNH$_2$)). The pure fractions were collected, evaporated and freeze dried from water/ACN (80/20) yielding 46 mg (17%) of compound 198 and 45 mg (17%) of compound 199.

The compounds in the table below were prepared using an analogous method as described for the preparation of compound 274 starting from the respective starting materials.

| Compound number | Structure | Quantity | Yield |
| --- | --- | --- | --- |
| compound 214 | From intermediate 11, 1-Isopropyl-1H-pyrazole-4-carbaldehyde and iPrMgCl 2M in THF | 19 mg | 13% |
| compound 283 | compound 283<br>From intermediate 11, 1-methyl-1H-pyrazole-4-carbaldehyde and EtMgBr 1M in THF | 143 mg | 52% |
| compound 220 | compound 220 | 58 mg | 21% |

| Compound number | Structure | Quantity | Yield |
|---|---|---|---|
| and | | | |
| compound 221 | compound 221 — From purification of compound 283 by Chiral SFC: CHIRALPAK IC 5 μm 250*21.2 mm; mobile phase: 60% CO₂, 40% EtOH (0.3% iPrNH₂) | 61 mg | 22% |
| compound 223 | From intermediate 11, tert-butyl 4-formyl-1H-pyrazole-1-carboxylate and MeMgBr 3M in Et₂O | 28 mg | 20% |
| compound 228 | From intermediate 11, isothiazole-4-carbaldehyde and MeMgBr 3M in Et₂O | 77 mg | 57% |
| compound 230 | Compound 230 — From intermediate 11, 1-methyl-1H-pyrazole-4-carbaldehyde and isobutylmagnesium bromide 2M in Et₂O | 343 mg | 78% |
| compound 247 | Compound 247 | 118 mg | 27% |
| and | | | |
| compound 248 | Compound 248 — From purification of compound 230 by chiral SFC: Lux Cellulose-2 5 μm 250*30 mm; mobile phase: 55% CO₂, 45% MeOH (0.3% iPrNH₂). | 114 mg | 26% |

-continued

| Compound number | Structure | Quantity | Yield |
|---|---|---|---|
| compound 231 | From intermediate 11, isoxazole-4-carbaldehyde and MeMgBr 3M in Et₂O | 25 mg | 19% |
| compound 233 | From intermediate 11, pyridine-3-carboxaldehyde and MeMgBr 3M in Et₂O | 26 mg | 19% |
| compound 235 | Compound 235 | 23 mg | 8% |

-continued

| Compound number | Structure | Quantity | Yield |
|---|---|---|---|
| and compound 236 | Compound 236 | 17 mg | 6% |
| and compound 237 | Compound 237 | 27 mg | 9% |
| and compound 238 | Compound 238 | 29 mg | 10% |

From intermediate 11, 1-methyl-1H-pyrazole-4-carbaldehyde and sec-butyl magnesium chloride 25% wt in THF chiral SFC purification: CHIRALPAK AD-H 5 μm 250*30 mm; mobile phase: 80% CO₂, 20% iPrOH (0.6% iPrNH₂).
Compounds 237 and 238 were obtained after an additional chiral SFC:

| Compound number | Structure | Quantity | Yield |
|---|---|---|---|
| | CHIRALPAK AD-H 5 μm 250*30 mm; mobile phase: 80% CO₂, 20% iPrOH (0.6% iPrNH₂) then chiral SFC: Chiralcel OD-H 5 μm 250 × 21.2 mm; mobile phase: 82% CO₂, 18% iPrOH (0.3% iPrNH₂). | | |
| compound 284 | Compound 284 From intermediate 11, 1-methyl-1H-pyrazole-4-carbaldehyde and n-butyl magnesium chloride 2M in THF | 174 mg | 50% |
| compound 243 | Compound 243 | 58 mg | 20% |
| and compound 244 | Compound 244 From chiral SFC separation of compound 384: CHIRALPAK IC 5 μm 250*30 mm; mobile phase: 60% CO₂, 40% EtOH (0.3% iPrNH₂). | 64 mg | 22% |
| compound 285 | Compound 285 From intermediate 11, tert-butyl 4-formyl-1H-pyrazole-1-carboxylate and iPrMgCl 2M in THF | 75 mg | 22% |
| compound 245 | compound 245 | 25 mg | 7% |
| and compound 246 | compound 246 From Chiral SFC separation of compound 285: CHIRALPAK AD-H 5 μm 250*30 mm; mobile phase: 70% CO₂, 30% EtOH (0.3% iPrNH₂) | 24 mg | 7% |

| Compound number | Structure | Quantity | Yield |
|---|---|---|---|
| compound 249 | From intermediate 11, thiazole-5-carbaldehyde and MeMgBr 3M in Et₂O | 25 mg | 19% |
| compound 286 | Compound 286<br>From intermediate 11, 1-methyl-1H-imidazole-5-carbaldehyde [CAS39021-62-0] and MeMgBr 3M in Et₂O | 94 mg | 71% |
| compound 253 | compound 253 | 22 mg | 16% |
| and compound 254 | compound 254<br>From Chiral SFC separation of compound 286: Chiralcel OD-H 5 µm 250 × 21.2 mm; mobile phase: 70% CO₂, 30% MeOH (0.3% iPrNH₂)) | 22 mg | 15% |

Example B44

Preparation of Compound 195

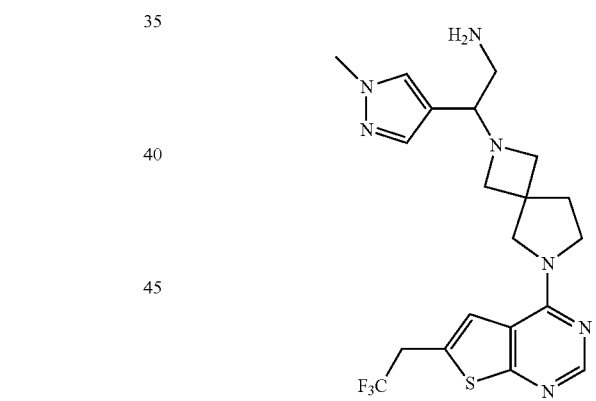

Hydrazine monohydrate (34 µL; 0.86 mmol) was added to a solution of intermediate 85 (100 mg; 0.17 mmol) in EtOH (4 mL). The solution was heated at 50° C. for 2 h 30. The reaction mixture was poured into ice water and extracted with DCM. The organic layer was separated, dried over MgSO₄, filtered and evaporated till dryness. The residue was purified by chromatography over silica gel (irregular SiOH, 12 g; mobile phase: 90% DCM, 10% MeOH (+10% NH₄OH)). The pure fractions were collected and evaporated to dryness. The residue was taken up with Et₂O and evaporated to dryness yielding 35 mg (45%) of compound 195.

Example B45

Preparation of compound 287

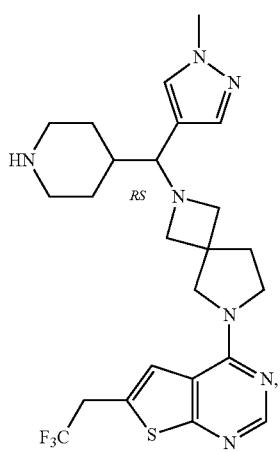 [SMILES: Cn1cc(C(C2CCNCC2)N2CC3(CCN(c4ncnc5sc(CC(F)(F)F)cc45)C3)C2)cn1]

Compound 201

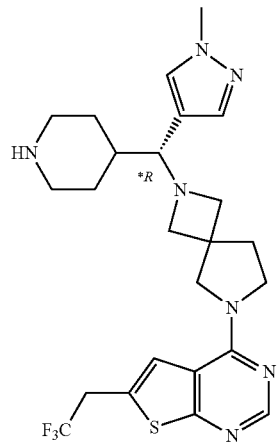 [SMILES: Cn1cc([C@@H](C2CCNCC2)N2CC3(CCN(c4ncnc5sc(CC(F)(F)F)cc45)C3)C2)cn1]

and Compound 202

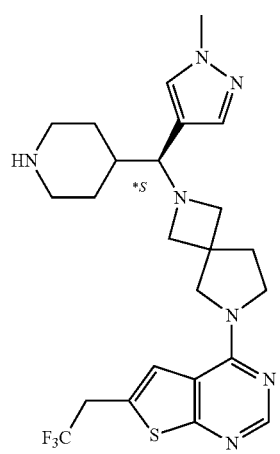 [SMILES: Cn1cc([C@H](C2CCNCC2)N2CC3(CCN(c4ncnc5sc(CC(F)(F)F)cc45)C3)C2)cn1]

A mixture of intermediate 87 (145 mg; 0.24 mmol) and TFA (0.7 mL; 9.15 mmol) in DCM (7 mL) was stirred at RT overnight. The reaction mixture was evaporated to dryness. The residue was diluted with DCM and $H_2O$ then, basified with aqueous NaOH 3N. The organic layer was decanted, dried over $MgSO_4$, filtered and evaporated to dryness yielding 100 mg (83%) of compound 287.

The enantiomers were separated by chiral SFC (CHIRAL-PAK IC 5 μm 250×20 mm; mobile phase: 50% $CO_2$, 50% MeOH (+2% $iPrNH_2$)). The fractions containing each enantiomer were collected, evaporated to dryness and purified by reverse phase chromatography (YMC-actus Triart-C18 10 μm 30*150 mm; mobile phase: gradient from 75% $NH_4HCO_3$ 0.2%, 25% ACN to 35% $NH_4HCO_3$ 0.2%, 65% ACN). The pure fractions were collected, evaporated to dryness and freeze dried from ACN/water (20/80) yielding 21 mg (17%) of compound 201 and 23 mg (19%) of compound 202.

Example B46

Preparation of Compound 224

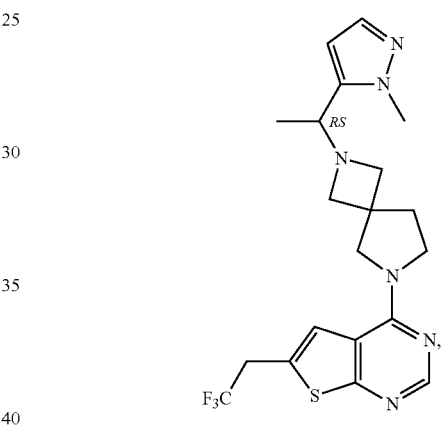

Compound 251

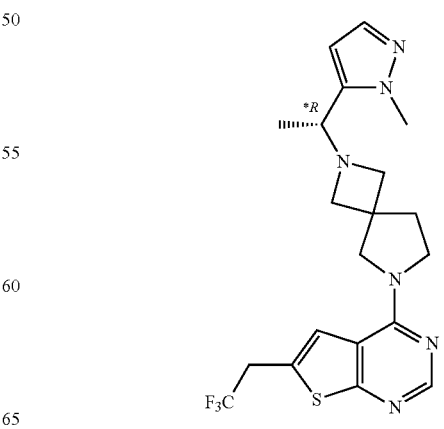

and Compound 252

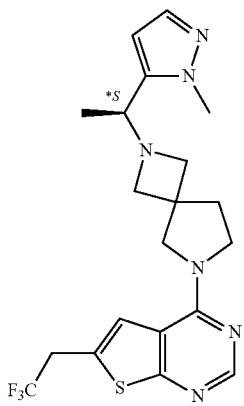 [SMILES: C[C@@H](c1ccnn1C)N1CC2(CCN(c3ncnc4sc(CC(F)(F)F)cc34)C2)C1]

Under N$_2$, a mixture of intermediate 11b (1 g) and 5-acetyl-1-methylpyrazole (168 mg 1.35 mmol) in THF (15 mL) was stirred at rt overnight. Then, NaBH(OAc)$_3$ (718 mg; 3.4 mmol) was added portion wise. The reaction mixture was stirred at room temperature for 72 h, poured into cold water, basified with K$_2$CO$_3$ powder and extracted with EtOAc. The organic layer was dried over MgSO$_4$, filtered and evaporated to dryness. The residue was purified by chromatography over silica gel (irregular SiOH, 12 g; mobile phase: gradient from 100% DCM, 0% MeOH to 95% DCM, 5% MeOH, 0.3% NH$_4$OH). The fractions were collected and evaporated to dryness. The residue (300 mg) was purified a second time by reverse phase chromatography (YMC-actus Triart C18 10 μm 30*150 mm; mobile phase: gradient from 65% NH$_4$HCO$_3$ 0.2% aq, 35% ACN to 25% NH$_4$HCO$_3$ 0.2% aq, 75% ACN). The pure fractions were collected, evaporated to dryness yielding 104 mg of compound 224.

Compound 224 was submitted to chiral SFC separation ((Stationary phase: Chiralcel OD-H 5 μm 250×21.2 mm, Mobile phase: 70% CO$_2$, 30% EtOH (0.3% iPrNH$_2$)).

The fractions containing the product were mixed, concentrated and freeze-dried (ACN/water: 80/20) to afford 48 mg of compound 251 and 46 mg of compound 252.

The compounds in the table below were prepared using an analogous method as described for the preparation of compound 224 starting from the respective starting materials.

| compound number | Structure | Quantity Yield |
|---|---|---|
| compound 232 | From intermediate 11b and 4-acetylpyridine | 63 mg |
| compound 258 | From intermediate 11b and 5-acetylpyrimidine | 45 mg |

Example B47

Preparation of Compound 234

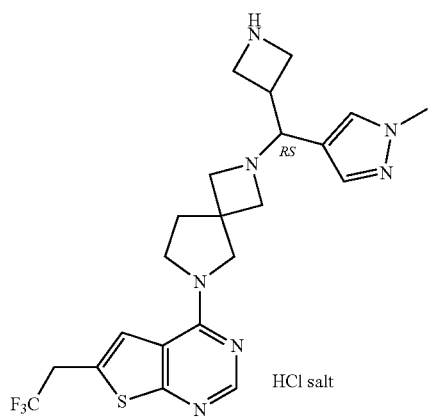 [SMILES: Cn1cc(C(C2CNC2)N2CC3(CCN(c4ncnc5sc(CC(F)(F)F)cc45)C3)C2)cn1]

A mixture of intermediate 88 (130 mg; 0.225 mmol) and HCl 4M in 1,4-dioxane (0.7 mL; 2.8 mmol) in MeOH (7 mL) was stirred at rt for 24 hours. The solution was cooled at 5° C. and Et$_2$O was added. The precipitate was filtered and dried yielding 111 mg of compound 234 (HCl salt).

Example B48

Preparation of Compound 270

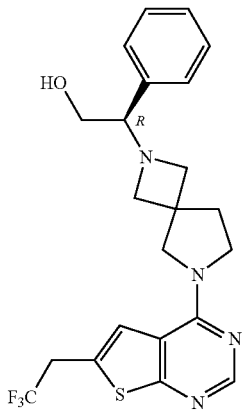

and Compound 271

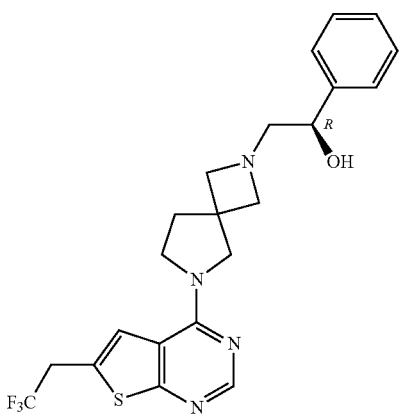

A mixture of intermediate 11 (300 mg; 0.854 mmol) and (R)-Styrene oxide (293 µL; 2.563 mmol) in EtOH (6 mL) was stirred at 60° C. for 4 hours. The reaction mixture was evaporated to dryness and the residue was purified by chromatography over silica gel (irregular SiOH, 12 g; mobile phase: gradient from 0% NH$_4$OH, 0% MeOH, 100% DCM to 1% NH$_4$OH, 10% MeOH, 90% DCM). The fractions containing the products were collected and evaporated to dryness yielding 157 mg of an intermediate residue which was purified by reverse phase chromatography (YMC-actus Triart C18 10 µm 30*150 mm; mobile phase: gradient from 60% NH$_4$HCO$_3$ 0.2% aq, 40% ACN to 40% NH$_4$HCO$_3$ 0.2% aq, 60% ACN). The fractions containing the products were collected, evaporated to dryness and freeze dried from water/ACN (80/20; 10 mL) yielding 58 mg (15%) of compound 270 and 62 mg (16%) of compound 271.

Example B50

Preparation of Compound 105

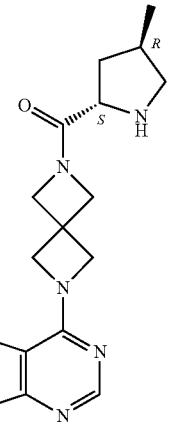

TFA (2.5 mL) was added to a solution of intermediate 93 (500 mg; 0.95 mmol) in DCM (25 mL) and the reaction mixture was stirred for 18 hours. The reaction mixture was poured onto a 10% aqueous solution of K$_2$CO$_3$ and extracted with DCM. The organic layer was separated, filtered over Chromabond® and evaporated to dryness. The residue was purified by chromatography over silica gel (irregular SiOH, 10 g; mobile phase: 0.7% NH$_4$OH, 7% MeOH, 93% DCM). The pure fractions were collected and evaporated to dryness. The residue was crystallized from diisopropyl ethyl ether and dried yielding 120 mg (29%) of compound 105.

The compounds in the table below were prepared using an analogous method as described for the preparation of compound 105 starting from the respective starting materials.

| compound or number | Structure | Quantity | Yield |
|---|---|---|---|
| compound 110 | 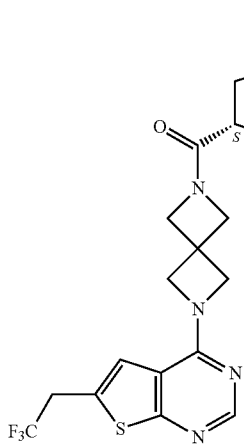 From intermediate 96 | 78 mg | 34% |

203

-continued

| compound or number | Structure | Quantity | Yield |
|---|---|---|---|
| compound 109 | From intermediate 98 | 117 mg | 41% |
| compound 111 | From intermediate 99 | 47 mg | 15% |
| compound 90 | From intermediate 100 | 58 mg | 71% |

204

Example B51

Preparation of Compound 89

HCl 4N in 1,4-dioxane (0.708 mL; 2.833 mmol) was added to a solution of intermediate 101 (150 mg; 0.283 mmol) in ACN (7.5 mL) and the reaction mixture was stirred at room temperature overnight. The reaction mixture was poured onto a 10% aqueous solution of $K_2CO_3$ and extracted with DCM. The organic layer was decanted, filtered over Chromabond® and evaporated to dryness. The residue was purified by chromatography over silica gel (irregular SiOH, 12 g; mobile phase: gradient from 0% MeOH, 100% DCM to 15% MeOH, 85% DCM). The pure fractions were collected and evaporated to dryness. The residue was taken up several times with $Et_2O$ yielding 30 mg (25%) of compound 89.

The compounds in the table below were prepared using an analogous method as described for the preparation of compound 89 starting from the respective starting materials.

| compound number | Structure | Quantity | Yield |
|---|---|---|---|
| compound 87 | From intermediate 102 | 47 mg | 29% |

| compound number | Structure | Quantity | Yield |
|---|---|---|---|
| compound 86 | From intermediate 102 | 55 mg | 42% |
| Compound 311 | From intermediate 107 | 181 mg | 58% |

Example B56

Preparation of Compound 317

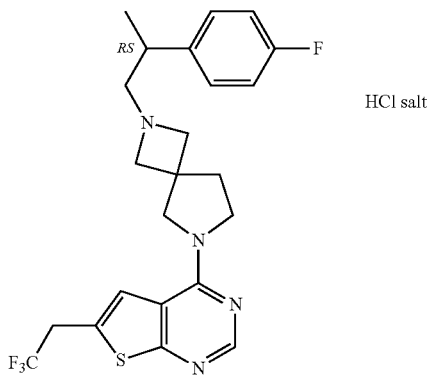 [SMILES: CC(CN1CC2(CCN(c3ncnc4sc(CC(F)(F)F)cc34)C2)C1)c1ccc(F)cc1]

HCl salt

Intermediate 11 (266 mg, 0.812 mmol), intermediate 110 (377 mg, 1.62 mmol) and $K_2CO_3$ in ACN (8 mL) were stirred overnight at 90° C. The mixture was poured into water then extracted with EtOAc. The organic layer was dried over $MgSO_4$, filtered and evaporated to dryness. The residue was purified by chromatography over silica gel (Stationary phase: irregular SiOH 15-40 μm 40 g, mobile phase: DCM/MeOH: gradient from 100/0 to 92/8). The residue was purified by chromatography over silica gel by reverse phase (stationary phase: YMC-actus Triart-C18 10 μm 30*150 mm, mobile phase: 0.2% $NH_4HCO_3$/ACN: gradient from 60/40 to 0/100). The fractions containing the product were collected and evaporated to dryness. The resulting residue was solubilized in ACN and 2 equivalents of a 4N solution of HCl in dioxane was added. The mixture was concentrated and, then freeze-dried with acetonitrile/water 20/80 yielding 0.091 g of compound 317 (HCl salt).

Example B57

Preparation of Compound 320

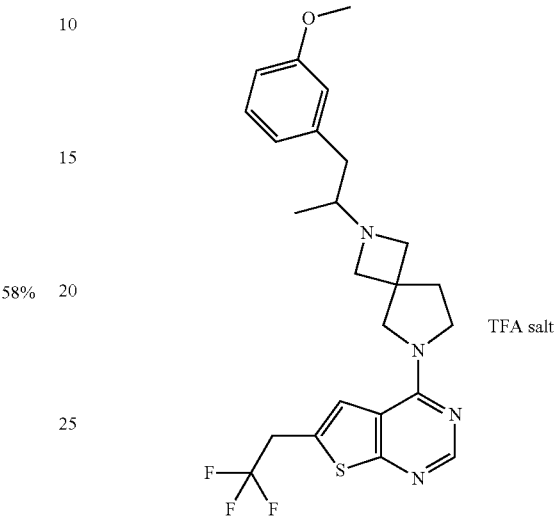

TFA salt

To a solution of intermediate 11b (200 mg) in ethanol (5 mL) was added 1-(3-methoxyphenyl)propan-2-one (200 mg, 1.218 mmol), $PtO_2$ (20 mg) and AcOH (2 drops). After stirring at 60° C. overnight under $H_2$, the reaction mixture was concentrated to give a residue which was purified by prep-HPLC (Column: SunFire 19*250 mm 10 um, Mobile Phase A: 0.1% TFA/$H_2O$, B: ACN) to give 35 mg (12%) of compound 320 as yellow solid.

The compounds in the table below were prepared using an analogous method as described for the preparation of compound 320 starting from the respective starting materials.

| compound number | Structure | Quantity | Yield |
|---|---|---|---|
| compound 321 | TFA salt<br>From intermediate 11b and 1-(4-methoxyphenyl)propan-2-one | 44 mg | |

| compound number | Structure | Quantity | Yield |
|---|---|---|---|
| Compound 322 | 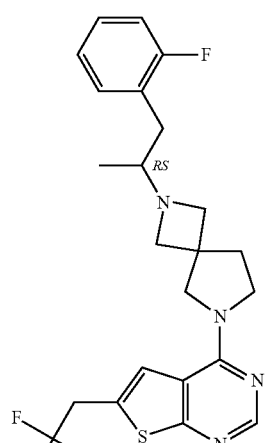 TFA salt From intermediate 11b and 2-Fluorophenylacetone | 54 mg | |
| Compound 323 | HO— <br> TFA salt From intermediate 11b and 4-hydroxyphenylacetone | 36 mg | |

| compound number | Structure | Quantity | Yield |
|---|---|---|---|
| Compound 324 | 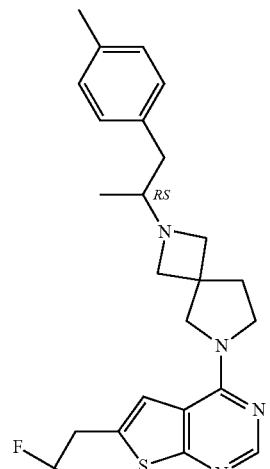 TFA salt From intermediate 11b and 1-(p-tolyl)propan-2-one | 40 mg | |

Example B57

Compound 61 was synthesized together with intermediate 68, 68a and 68b. See synthesis protocol for intermediate 68, 68a and 68b.

Conversion

Conversion C1

Preparation of Compound 196 s

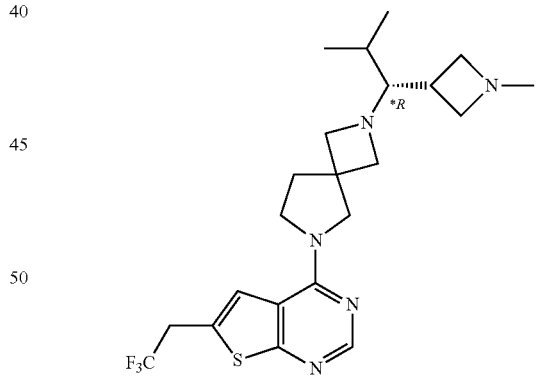

A solution of compound 273 (106 mg; 0.24 mmol), aqueous formaldehyde 37% w/w (110 μL; 1.48 mmol) and MgSO$_4$ (580 mg; 4.83 mmol) in DCM (5 mL) was stirred at RT for 1 hour. NaBH(OAc)$_3$ (614 mg; 2.9 mmol) was added and the reaction mixture was stirred at RT for 15 hours. The solution was poured into iced water, basified with K$_2$CO$_3$ and extracted with DCM (×2). The organic layer was washed with brine, dried over MgSO$_4$, filtered and evaporated to dryness. The residue was purified by chromatography over silica gel (irregular SiOH, 10 g, mobile phase: gradient from 100% DCM, 0% MeOH, 0% NH$_4$OH to 90% DCM, 10% MeOH, 0.5% NH$_4$OH). The pure fractions were collected, evaporated to dryness and the residue was freeze dried from ACN/water (20/80) yielding 70 mg (64%) of compound 196.

The compounds in the table below were prepared using an analogous method as described for the preparation of compound 196 starting from the respective starting materials.

| compound number | Structure | Quantity | Yield |
|---|---|---|---|
| compound 304a | From compound 269a | 50 mg | 28% |
| Compound 304b | From compound 269b | 52 mg | 30% |

Conversion C2
Preparation of Compound 216

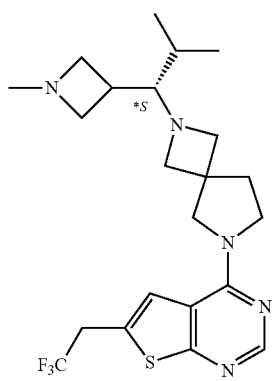 [SMILES: CC(C)[C@@H](C1CN(C)C1)N1CC2(CCN(c3ncnc4sc(CC(F)(F)F)cc34)C2)C1]

A solution of compound 200 (110 mg; 0.25 mmol) and aqueous formaldehyde 37% w/w (19 µL; 0.25 mmol) in MeOH (5 mL) was stirred at RT for 3 hours. NaBH$_4$ (19 mg; 0.5 mmol) was added and the reaction mixture was stirred at RT for 15 hours, poured into ice water, basified with K$_2$CO$_3$ and extracted with DCM (×2). The organic layer was washed with brine then dried over MgSO$_4$, filtered and evaporated to dryness. The residue was purified by chromatography over silica gel (irregular SiOH 300 g; mobile phase: gradient from 0.1% NH$_4$OH, 5% MeOH, 95% DCM to 1% NH$_4$OH, 10% MeOH, 90% DCM). The pure fractions were collected, evaporated to dryness and freeze-dried from ACN/water 20/80 yielding 15 mg (13%) of compound 216.

Conversion C3
Preparation of Compound 303

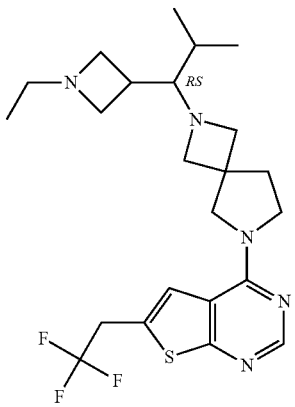 [SMILES: CCN1CC(C(C(C)C)N2CC3(CCN(c4ncnc5sc(CC(F)(F)F)cc45)C3)C2)C1]

Under N$_2$ at 10° C., ethyl bromide (45 µL; 0.6 mmol) was added to a solution of compound 222 (150 mg; 0.34 mmol) and DIPEA (207 µL; 1.2 mmol) in THF (3 mL). The solution was stirred at rt overnight, then, poured onto cooled water. The product was extracted with EtOAc. The organic layer was dried over MgSO$_4$, filtered and evaporated to dryness. The residue (164 mg) was purified by silica gel chromatography (Stationary phase: irregular bare silica 12 g, Mobile phase: Gradient from 100% DCM, 0% MeOH (+10% NH$_4$OH) to 90% DCM, 10% MeOH (+10% NH$_4$OH)). The fractions containing the product were mixed and concentrated to afford 77 mg of an intermediate fraction which was further purified by via reverse phase (Stationary phase: YMC-actus Triart C18 10 µm 30*150 mm, Mobile phase: Gradient from 65% NH$_4$HCO$_3$ 0.2%, 35% ACN to 25% NH$_4$HCO$_3$ 0.2%, 75% ACN). The fractions containing the product were mixed and concentrated to afford 40 mg of a residue which was freeze-dried with acetonitrile/water 20/80 to give 34 mg (21%) of compound 303 as a white powder.

Conversion C4
Preparation of Compound 316

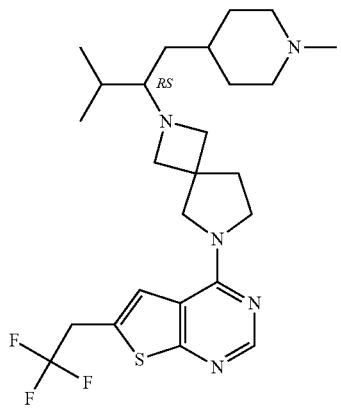 [SMILES: CC(C)C(CC1CCN(C)CC1)N1CC2(CCN(c3ncnc4sc(CC(F)(F)F)cc34)C2)C1]

A solution of compound 315 (114 mg; 0.237 mmol), formaldehyde, 37% in water (106 µL; 1.42 mmol) and MgSO$_4$ (568 mg) in DCM (5 mL) was stirred at rt for 1 hour. Then, NaBH(OAc)$_3$ (602 mg; 2.84 mmol) was added and the mixture was stirred at rt overnight.

The reaction mixture was diluted with DCM and basified with a 10% aqueous solution of K$_2$CO$_3$. The organic layer was decanted, dried over $MgSO_4$, filtered and evaporated to dryness. The residue was purified by chromatography over silica gel (irregular SiOH, 12 g; mobile phase: gradient from 0% $NH_4OH$, 0% MeOH, 100% DCM to 1% $NH_4OH$, 10% MeOH, 90% DCM). The fractions containing the product were collected, evaporated to dryness and freeze dried from water/ACN (80/20; 10 mL) yielding 110 mg (94%) of compound 316.

Analytical Part
LCMS (Liquid Chromatography/Mass Spectrometry)
General Procedure The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]+$, $[M+HCOO]^-$, etc. . . . ). For molecules with multiple isotopic patterns (Br, Cl . . . ), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector. All other abbreviations used are as defined before.

TABLE 1a

LCMS Method codes (Flow expressed in mL/min; column temperature (T) in ° C.; Run time in minutes).

| Method code | Instrument | Column | Mobile phase | Gradient | Flow Column T | Run time |
|---|---|---|---|---|---|---|
| 1 | Agilent: 1200-DAD and MSD6110 | Phenomenex: Luna-C18 (5 μm, 2 × 50 mm) | A: $CF_3COOH$ 0.1% in water, B: $CF_3COOH$ 0.05% in $CH_3CN$ | 90% A for 0.8 min, to 20% A in 3.7 min, held for 3 min, back to 90% A in 2 min. | 0.8 50 | 10 |
| 2 | Agilent: 1200-DAD and MSD6110 | Phenomenex: Luna-C18 (5 μm, 2 × 50 mm) | A: $CF_3COOH$ 0.1% in water, B: $CF_3COOH$ 0.05% in $CH_3CN$ | 100% A for 1 min, to 40% A in 4 min, to 15% A in 2.5 min, back to 100% A in 2 min. | 0.8 50 | 10 |
| 3 | Waters: Acquity UPLC ®-DAD and Quattro Micro ™ | Waters: BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 40 | 6.2 |
| 4 | Waters: Acquity ® H-Class-DAD and SQD2 ™ | Waters: BEH C18 (1.7 μm, 2.1 × 100 mm) | A: 95% $CH_3COONH_4$ 7 mM/5% $CH_3CN$, B: $CH_3CN$ | 84.2% A to 10.5% A in 2.18 min, held for 1.96 min, back to 84.2% A in 0.73 min, held for 0.73 min. | 0.343 40 | 6.1 |
| 5 | Shimadzu: LC-MS2020-SPD-M20A and Alltech 3300ELSD | SunFire C18 5 μm 50 * 4.6 mm | A: HCOOH 0.1% in water, B: HCOOH 0.1% in $CH_3CN$ | 70% A for 0.4 min, to 5% A in 1.2 min, to 1% A in 1.0 min. | 2.0 40 | 2.6 |
| 6 | Waters UPLC-QDa-PDA Detector | ACQUITY UPLC BEH C18 1.7 μm 2.1 * 50 mm | A: HCOOH 0.1% in water, B: HCOOH 0.1% in $CH_3CN$ | 90% A for 0.1 min, to 5% A in 1.1 min, hold 5% A in 0.8 min. | 0.6 50 | 2.0 |
| 7 | Waters UPLC-QDa-PDA Detector | ACQUITY UPLC BEH C18 1.7 μm 2.1 * 100 mm | A: HCOOH 0.1% in water, B: HCOOH 0.1% in $CH_3CN$ | 80% A for 1.0 min, to 5% A in 7.0 min, hold 5% A in 1.0 min. | 0.4 50 | 9.0 |

TABLE 1b

LCMS data. Co. No. means compound number; $R_t$ means retention time in min.

| Co. No. | Rt (min) | [M + H]⁺ | Adduct/[M − H]⁻ | LCMS Method |
|---|---|---|---|---|
| 1 | 2.725 | 419.2 | — | 1 |
| 2 | 2.88 | 425.1 | 483.4 [M + CH₃COO]⁻ | 3 |
| 3 | 2.9 | 447.2 | — | 1 |
| 4 | 2.26 | 421.1 | 479.4 [M + CH₃COO]⁻ | 3 |
| 5 | 3.314 | 459 | — | 2 |
| 6 | 3.176 | 459 | — | 2 |
| 7 | 3.129 | 459 | — | 2 |
| 8 | 3.71 | 454.9 | — | 2 |
| 9 | 3.333 | 421 | — | 2 |
| 10 | 3.269 | 421 | — | 2 |
| 11 | 3.652 | 454.9 | — | 2 |
| 12 | 3.409 | 421 | — | 2 |
| 13 | 2.498 | 385 | — | 1 |
| 14 | 2.76 | 405 | 463.4 [M + CH₃COO]⁻ | 3 |
| 15 | 3.516 | 455 | — | 2 |
| 16 | 2.88 | 419.5 | 463.3 [M + CH₃COO]⁻ | 4 |
| 17 | 3.074 | 482.9 | — | 1 |
| 18 | 2.94 | 447 | — | 1 |
| 19 | 3.92 | 461.2 | 519.7 [M + CH₃COO]⁻ | 3 |
| 20a | 3.15 | 433.1 | 491.4 [M + CH₃COO]⁻ | 3 |
| 20b | 3.15 | 433.1 | 491.4 [M + CH₃COO]⁻ | 3 |
| 21a | 3.66 | 447.4 | 445.4 | 3 |
| 21b | 3.65 | 447.3 | 445.3 | 3 |
| 22 | 3.104 | 437 | — | 1 |
| 23 | 2.11 | 423.5 | 481.3 [M + CH₃COO]⁻ | 4 |
| 24 | 2.46 | 452.5 | 510.3 [M + CH₃COO]⁻ | 4 |
| 25 | 2.43 | — | 466.3 [M + CH₃COO]⁻ | 3 |
| 26 | 3.28 | 420.1 | — | 3 |
| 28 | 2.08 | 409.1 | — | 3 |
| 29 | 2.09 | 409.1 | — | 3 |
| 30 | 2.17 | 423.2 | 481.4 [M + CH₃COO]⁻ | 3 |
| 31 | 2.67 | 461 | 519.3 [M + CH₃COO]⁻ | 3 |
| 34 | 2.16 | 409.1 | 467.4 [M + CH₃COO]⁻ | 3 |
| 35 | 2.26 | 423.2 | 481.4 [M + CH₃sCOO]⁻ | 3 |
| 36 | 2.39 | 451.2 | 509.5 [M + CH₃COO]⁻ | 3 |
| 37 | 2.375 | 492 | — | 1 |
| 40 | 1.98 | 395.1 | — | 3 |
| 41 | 1.95 | 395.4 | — | 4 |
| 44 | 2.31 | 371.5 | 429.2 [M + CH₃COO]⁻ | 4 |
| 45 | 2.936 | 433 | — | 1 |
| 46 | 2.871 | 433 | — | 1 |
| 47 | 3.05 | 463 | — | 1 |
| 48 | 2.79 | 545.9 | — | 1 |
| 49 | 2.901 | 433 | — | 1 |
| 50 | 3.019 | 447 | — | 1 |
| 54 | 2.66 | 436.9 | — | 1 |
| 56 | 2.731 | 436.9 | — | 1 |
| 57 | 3.604 | 449 | — | 2 |
| 58 | 2.67 | 385 | 443.2 [M + CH₃COO]⁻ | 3 |
| 59 | 2.2 | 423 | 481.2 [M + CH₃COO]⁻ | 3 |
| 61 | 2.11 | 357 | 415.1 [M + CH₃COO]⁻ | 3 |
| 62 | 2.45 | 495.2 | — | 3 |
| 63 | 2.55 | 455.2 | 513.4 [M + CH₃COO]⁻ | 3 |
| 64 | 2.92 | 411 | 469.1 [M + CH₃COO]⁻ | 3 |
| 65 | 2.46 | 413.1 | 471.2 [M + CH₃COO]⁻ | 3 |
| 66 | 2.31 | 427.1 | 485.2 [M + CH₃COO]⁻ | 3 |
| 67 | 2.25 | 441.5 | 499.4 [M + CH₃COO]⁻ | 4 |
| 69 | 2.89 | 433.1 | 491.3 [M + CH₃COO]⁻ | 3 |
| 71 | 2.75 | 509.2 | — | 3 |
| 74 | 2.54 | 547.4 | 605.7 [M + CH₃COO]⁻ | 3 |
| 75 | 2.56 | 506.3 | 564.5 [M + CH₃COO]⁻ | 3 |
| 76 | 2.23 | 462.2 | 520.4 [M + CH₃COO]⁻ | 3 |
| 77 | 2.01 | 452.1 | 520.5 [M + CH₃COO]⁻ | 3 |
| 82 | 1.95 | 426.4 | 484.2 [M + CH₃COO]⁻ | 4 |
| 84 | 3.05 | 465.1 | 523.3 [M + CH₃COO]⁻ | 3 |
| 88 | 2.13 | 488.4 | 546.3 [M + CH₃COO]⁻ | 3 |
| 112 | 2.24 | 452.1 | 510.4 [M + CH₃COO]⁻ | 3 |
| 86 | 2.20 | 452.2 | 510.5 [M + CH₃COO]⁻ | 3 |
| 87 | 2.13 | 438.2 | 496.6 [M + CH₃COO]⁻ | 3 |
| 89 | 2.14 | 430.1 | 488.3 [M + CH₃COO]⁻ | 3 |
| 90 | 2.32 | 448.1 | 506.4 [M + CH₃COO]⁻ | 3 |
| 105 | 1.96 | 426.4 | 484.3 [M + CH₃COO]⁻ | 4 |
| 108 | 2.34 | 452.2 | 510.4 [M + CH₃COO]⁻ | 3 |
| 109 | 2.13 | 438.1 | 496.4 [M + CH₃COO]⁻ | 3 |
| 110 | 1.93 | 442.5 | 500.2 [M + CH₃COO]⁻ | 4 |
| 111 | 1.90 | 442.5 | 500.3 [M + CH₃COO]⁻ | 4 |
| 163 | 2.42 | 489.1 | 547.4 [M + CH₃COO]⁻ | 3 |
| 164 | 2.43 | 489.2 | 547.4 [M + CH₃COO]⁻ | 3 |
| 195 | 1.90 | 452.5 | 510.3 [M + CH₃COO]⁻ | 4 |
| 196 | 2.35 | 454.2 | 512.4 [M + CH₃COO]⁻ | 3 |
| 197 | 2.29 | 437.2 | 495.5 [M + CH₃COO]⁻ | 3 |
| 198 | 2.25 | 437.2 | 495.4 [M + CH₃COO]⁻ | 3 |
| 199 | 2.25 | 437.2 | 495.5 [M + CH₃COO]⁻ | 3 |
| 200 | 2.28 | 440.1 | 498.3 [M + CH₃COO]⁻ | 3 |
| 201 | 1.92 | 506.5 | 564.4 [M + CH₃COO]⁻ | 4 |
| 202 | 1.89 | 506.5 | 564.5 [M + CH₃COO]⁻ | 4 |
| 203 | 2.70 | 465.2 | 523.4 [M + CH₃COO]⁻ | 3 |
| 211 | 2.40 | 454.1 | 512.3 [M + CH₃COO]⁻ | 3 |
| 214 | 2.98 | 493.3 | 551.5 [M + CH₃COO]⁻ | 3 |
| 220 | 2.43 | 451.1 | 509.3 [M + CH₃COO]⁻ | 3 |
| 221 | 2.44 | 451.1 | 509.3 [M + CH₃COO]⁻ | 3 |
| 222 | 2.31 | 440.1 | 498.3 [M + CH₃COO]⁻ | 3 |
| 223 | 2.20 | 423.0 | 421.1 | 3 |
| 224 | 2.51 | 437.1 | 495.3 [M + CH₃COO]⁻ | 3 |
| 228 | 2.68 | 440.0 | 498.2 [M + CH₃COO]⁻ | 3 |
| 230 | 2.70 | 479.2 | 537.4 [M + CH₃COO]⁻ | 3 |
| 231 | 2.59 | 424.1 | 482.3 [M + CH₃COO]⁻ | 3 |
| 232 | 2.58 | 434.1 | 492.3 [M + CH₃COO]⁻ | 3 |
| 233 | 2.56 | 434.1 | 492.3 [M + CH₃COO]⁻ | 3 |
| 234 | 2.03 | 478.2 | 536.4 [M + CH₃COO]⁻ | 3 |
| 235 | 2.91 | 479.2 | 537.4 [M + CH₃COO]⁻ | 3 |
| 236 | 2.91 | 479.2 | 537.4 [M + CH₃COO]⁻ | 3 |
| 237 | 2.89 | 479.3 | 537.5 [M + CH₃COO]⁻ | 3 |
| 238 | 2.89 | 479.2 | 537.5 [M + CH₃COO]⁻ | 3 |
| 243 | 2.75 | 479.2 | 537.4 [M + CH₃COO]⁻ | 3 |
| 244 | 2.75 | 479.2 | 537.4 [M + CH₃COO]⁻ | 3 |
| 245 | 2.54 | 451.1 | 449.2 | 3 |
| 246 | 2.53 | 451.1 | 449.2 | 3 |
| 247 | 2.69 | 479.2 | 537.4 [M + CH₃COO]⁻ | 3 |
| 248 | 2.69 | 479.2 | 537.4 [M + CH₃COO]⁻ | 3 |
| 249 | 2.59 | 440.0 | 498.2 [M + CH₃COO]⁻ | 3 |
| 250 | 2.42 | 489.1 | 547.3 [M + CH₃COO]⁻ | 3 |
| 251 | 2.50 | 437.1 | 495.3 [M + CH₃COO]⁻ | 3 |
| 252 | 2.50 | 437.1 | 495.3 [M + CH₃COO]⁻ | 3 |
| 253 | 2.34 | 437.1 | 495.4 [M + CH₃COO]⁻ | 3 |
| 254 | 2.34 | 437.1 | 495.3 [M + CH₃COO]⁻ | 3 |
| 258 | 2.42 | 435.1 | 493.2 [M + CH₃COO]⁻ | 3 |
| 259 | 2.16 | 426.1 | 484.3 [M + CH₃COO]⁻ | 3 |
| 269 | 2.34 | 458.4 | 516.4 [M + CH₃COO]⁻ | 4 |
| 270 | 2.52 | 449.4 | 507.4 [M + CH₃COO]⁻ | 4 |
| 271 | 2.48 | 449.4 | 507.4 [M + CH₃COO]⁻ | 4 |
| 273 | 2.29 | 440.2 | 498.5 [M + CH₃COO]⁻ | 3 |
| 274 | 2.71 | 465.2 | 523.4 [M + CH₃COO]⁻ | 3 |
| 133 | 2.36 | 463.2 | 521.5 [M + CH₃COO]⁻ | 3 |
| 137 | 2.26 | 463.5 | 521.4 [M + CH₃COO]⁻ | 4 |
| 138 | 2.27 | 463.5 | 521.4 [M + CH₃COO]⁻ | 4 |
| 145 | 2.42 | 441.1 | 499.4 [M + CH₃COO]⁻ | 3 |
| 147 | 2.11 | 440.1 | 498.2 [M + CH₃COO]⁻ | 3 |
| 146 | 2.10 | 440.1 | 498.2 [M + CH₃COO]⁻ | 3 |
| 148 | 2.35 | 468.2 | 466.4 | 3 |
| 154 | 2.46 | 441.1 | 499.4 [M + CH₃COO]⁻ | 3 |
| 155 | 2.44 | 441.1 | 499.3 [M + CH₃COO]⁻ | 3 |
| 150 | 2.05 | 412.0 | 470.2 [M + CH₃COO]⁻; 410.0 | 3 |
| 193 | 2.96 | 469.2 | 527.5 [M + CH₃COO]⁻; 467.8 | 3 |
| 162 | 2.96 | 469.2 | 527.5 [M + CH₃COO]⁻; 467.8 | 3 |
| 156 | 2.96 | 469.2 | 527.4 [M + CH₃COO]⁻; 467.2 | 3 |
| 157 | 2.81 | 469.2 | 527.4 [M + CH₃COO]⁻; 467.2 | 3 |
| 158 | 2.60 | 427.1 | 485.3 [M + CH₃COO]⁻ | 3 |
| 159 | 2.60 | 427.1 | 485.3 [M + CH₃COO]⁻ | 3 |
| 161 | 2.76 | 479.2 | 537.4 [M + CH₃COO]⁻; 477.2 | 3 |

TABLE 1b-continued

LCMS data. Co. No. means compound number; $R_t$ means retention time in min.

| Co. No. | Rt (min) | [M + H]⁺ | Adduct/[M − H]⁻ | LCMS Method |
|---|---|---|---|---|
| 166 | 2.76 | 479.2 | 537.3 [M + CH₃COO]⁻; 477.2 | 3 |
| 167 | 2.75 | 479.2 | 537.3 [M + CH₃COO]⁻; 477.1 | 3 |
| 172 | 2.75 | 479.2 | 537.4 [M + CH₃COO]⁻; 477.4 | 3 |
| 173 | 2.76 | 479.2 | 537.4 [M + CH₃COO]⁻; 477.3 | 3 |
| 174 | 2.75 | 479.2 | 537.4 [M + CH₃COO]⁻; 477.2 | 3 |
| 168 | 2.40 | 468.2 | 526.4 [M + CH₃COO]⁻; 466.3 | 3 |
| 169 | 2.39 | 468.2 | 526.4 [M + CH₃COO]⁻; 466.3 | 3 |
| 170 | 3.20 | 483.1 | 541.3 [M + CH₃COO]⁻ | 3 |
| 171 | 2.93 | 477.2 | 535.4 [M + CH₃COO]⁻ | 3 |
| 183 | 3.09 | 465.1 | 523.4 [M + CH₃COO]⁻ | 3 |
| 182 | 3.48 | 475.2 | 533.4 [M + CH₃COO]⁻ | 3 |
| 192 | 2.90 | 483.5 | 541.4 [M + CH₃COO]⁻ | 4 |
| 179 | 3.03 | 483.2 | 541.5 [M + CH₃COO]⁻ | 3 |
| 180 | 3.04 | 483.3 | 541.5 [M + CH₃COO]⁻ | 3 |
| 184 | 2.73 | 399.4 | 457.3 [M + CH₃COO]⁻ | 4 |
| 288 | 2.74 | 399.1 | 457.2 [M + CH₃COO]⁻; 397.1 | 3 |
| 185 | 2.48 | 441.5 | 499.4 [M + CH₃COO]⁻ | 4 |
| 187 | 2.42 | 441.1 | 499.3 [M + CH₃COO]⁻; 439.4 | 3 |
| 186 | 2.87 | 479.2 | 537.5 [M + CH₃COO]⁻; 477.2 | 3 |
| 188 | 2.80 | 479.5 | 537.4 [M + CH₃COO]⁻; 523.4 [M + HCOO]⁻ | 4 |
| 189 | 2.78 | 479.5 | 537.4 [M + CH₃COO]⁻; 523.2 [M + HCOO]⁻ | 4 |
| 190 | 2.80 | 479.5 | 537.4 [M + CH₃COO]⁻ | 4 |
| 191 | 2.79 | 479.5 | 537.4 [M + CH₃COO]⁻ | 4 |
| 289 | 3.32 | 447 | 505 [M + CH₃COO]⁻ | 3 |
| 290 | 3.33 | 447 | 505 [M + CH₃COO]⁻ | 3 |
| 291 | 3.25 | 451 | 509 [M + CH₃COO]⁻ | 3 |
| 292 | 3.25 | 451 | 509 [M + CH₃COO]⁻ | 3 |
| 293 | 2.78 | 413 | 471 [M + CH₃COO]⁻ | 3 |
| 294 | 2.77 | 413 | 471 [M + CH₃COO]⁻ | 3 |
| 295 | 2.24 | 437 | 495 [M + CH₃COO]⁻ | 3 |
| 296 | 3.07 | 447 | 505 [M + CH₃COO]⁻ | 3 |
| 297 | 3.07 | 447 | 505 [M + CH₃COO]⁻ | 3 |
| 298 | 3.11 | 465 | 523 [M + CH₃COO]⁻ | 3 |
| 299 | 2.25 | 437 | 495 [M + CH₃COO]⁻ | 3 |
| 303 | 2.42 | 468 | 526 [M + CH₃COO]⁻ | 3 |
| 304a | 2.69 | 472 | 530 [M + CH₃COO]⁻ | 3 |
| 304b | 2.70 | 472 | 530 [M + CH₃COO]⁻ | 3 |
| 307 | 3.51 | 493 | 551 [M + CH₃COO]⁻ | 3 |
| 309 | 2.92 & 3.02 | 455 | 513 [M + CH₃COO]⁻ | 3 |
| 311 | 1.99 | 426 | 484 [M + CH₃COO]⁻ | 3 |
| 312 | 3.76 | 537 | 595 [M + CH₃COO]⁻ | 3 |
| 313 | 3.76 | 537 | 595 [M + CH₃COO]⁻ | 3 |
| 314 | 2.90 | 472 | 530 [M + CH₃COO]⁻ | 3 |
| 315 | 2.22 | 482 | 540 [M + CH₃COO]⁻ | 3 |
| 316 | 2.30 | 496 | 554 [M + CH₃COO]⁻ | 3 |
| 317 | 3.14 | 465 | — | 3 |
| 318 | 2.57 | 502 | — | 3 |
| 320 | 0.893 | 477.2 | — | 5 |
| 321 | 1.300 | 477.4 | — | 6 |
| 322 | 6.213 | 465.3 | — | 7 |
| 323 | 1.203 | 463.3 | — | 6 |
| 324 | 0.692 | 461.2 | — | 5 |

SFCMS-Methods

General Procedure for SFC-MS Methods

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

TABLE 2a

Analytical SFC-MS Methods (Flow expressed in mL/min; column temperature (T) in ° C.; Run time in minutes; Backpressure (BPR) in bars; all other abbreviations used in the table below are as defined before)

| Method code | column | mobile phase | gradient | Flow Col T | Run time BPR |
|---|---|---|---|---|---|
| 1 | Phenomenex Luxcellulose-4 column (3 μm, 100 × 4.6 mm) | A: $CO_2$ B: MeOH (0.3% iPrNH₂) | 30% B hold 3 min, | 3.5 35 | 3 103 |
| 2 | Phenomenex Luxcellulose-2 column (3 μm, 100 × 4.6 mm) | A: $CO_2$ B: MeOH (0.3% iPrNH₂) | 25% B hold 3 min, | 3.5 35 | 3 103 |
| 3 | Daicel Chiralpak ® AD-3 (3 μm, 100 × 4.6 mm) | A: $CO_2$ B: EtOH/iPrOH 50/50 (0.3% iPrNH₂) | 30% B hold 3 min, | 3.5 35 | 3 103 |
| 4 | Daicel Chiralpak ® AD-3 (3 μm, 100 × 4.6 mm) | A: $CO_2$ B: EtOH (0.3% iPrNH₂) | 25% B hold 3 min, | 3.5 35 | 3 103 |
| 5 | Daicel Chiralpak ® AD-3 (3 μm, 100 × 4.6 mm) | A: $CO_2$ B: EtOH (0.3% iPrNH₂) | 30% B hold 3 min, | 3.5 35 | 3 103 |
| 7 | Daicel Chiralpak ® AD-3 (3 μm, 100 × 4.6 mm) | A: $CO_2$ B: EtOH (0.3% iPrNH₂) | 50% B hold 4 min, | 3.5 35 | 4 103 |

TABLE 2a-continued

Analytical SFC-MS Methods (Flow expressed in mL/min; column temperature (T) in °C.; Run time in minutes; Backpressure (BPR) in bars; all other abbreviations used in the table below are as defined before)

| Method code | column | mobile phase | gradient | Flow Col T | Run time BPR |
|---|---|---|---|---|---|
| 8 | Daicel Chiralpak® AD-3 (3 μm, 100 × 4.6 mm) | A: $CO_2$ B: iPrOH (0.3% $iPrNH_2$) | 20% B hold 6 min, | 3.5 35 | 6 103 |
| 9 | Daicel Chiralpak® AD-3 (3 μm, 100 × 4.6 mm) | A: $CO_2$ B: iPrOH (0.3% $iPrNH_2$) | 30% B hold 3 min, | 3.5 35 | 3 103 |
| 10 | Daicel Chiralpak® AD-3 (3 μm, 100 × 4.6 mm) | A: $CO_2$ B: iPrOH (0.3% $iPrNH_2$) | 40% B hold 3 min, | 3.5 35 | 3 103 |
| 11 | Daicel Chiralpak® AD-3 (3 μm, 100 × 4.6 mm) | A: $CO_2$ B: MeOH (0.3% $iPrNH_2$) | 25% B, hold 3 min, | 3.5 35 | 3 103 |
| 12 | Daicel Chiralpak® AD-3 (3 μm, 100 × 4.6 mm) | A: $CO_2$ B: MeOH (+0.3% $iPrNH_2$) | 30% B, hold 3 min, | 3.5 35 | 3 103 |
| 16 | Phenomenex Lux cellulose 2 (3 μm, 100 × 4.6 mm) | A: $CO_2$ B: MeOH (0.3% $iPrNH_2$) | 40% B hold 6 min, | 3.5 35 | 6 103 |
| 17 | Phenomenex Lux cellulose 2 (3 μm, 100 × 4.6 mm) | A: $CO_2$ B: MeOH (0.3% $iPrNH_2$) | 50% B hold 10 min, | 3.5 35 | 10 103 |
| 18 | Daicel Chiralpak® IC-3 (3 μm, 100 × 4.5 mm) | A: $CO_2$ B: EtOH (0.3% $iPrNH_2$) | 40% B hold 3 min, | 3.5 35 | 3 103 |
| 20 | Daicel Chiralcel® OD-3 (3 μm, 100 × 4.6 mm) | A: $CO_2$ B: EtOH (0.3% $iPrNH_2$) | 20% B hold 3 min, | 3.5 35 | 3 103 |
| 21 | Daicel Chiralcel® OD-3 (3 μm, 100 × 4.6 mm) | A: $CO_2$ B: EtOH (0.3% $iPrNH_2$) | 30% B hold 3 min, | 3.5 35 | 3 103 |
| 22 | Daicel Chiralcel® OD-3 (3 μm, 100 × 4.6 mm) | A: $CO_2$ B: iPrOH (0.3% $iPrNH_2$) | 20% B hold 3 min, | 3.5 35 | 3 103 |
| 23 | Daicel Chiralcel® OD-3 (3 μm, 100 × 4.6 mm) | A: $CO_2$ B: MeOH (0.3% iPrNH2) | 30% B hold 3 min, | 3.5 35 | 3 103 |
| 24 | Daicel Chiralcel® OJ-3 (3 μm, 100 × 4.6 mm) | A: $CO_2$ B: EtOH (0.3% $iPrNH_2$) | 15% B hold 3 min, | 3.5 35 | 3 103 |
| 25 | Daicel Chiralcel® OJ-3 (3 μm, 100 × 4.6 mm | A: $CO_2$ B: MeOH (0.3% $iPrNH_2$) | 10% B hold 3 min, | 3.5 35 | 3 103 |
| 26 | Daicel Chiralcel® OJ-3 (3 μm, 100 × 4.6 mm | A: $CO_2$ B: MeOH (0.3% $iPrNH_2$) | 30% B hold 3 min, | 3.5 35 | 3 103 |
| 37 | Daicel Chiralpak® IC-3 (3 μm, 100 × 4.6 mm) | A: $CO_2$ B: iPrOH (0.3% $iPrNH_2$) | 40% B hold 3 min, | 3.5 35 | 3 103 |
| 38 | Daicel Chiralpak® IC-3 (3 μm, 100 × 4.6 mm) | A: $CO_2$ B: MeOH (0.3% $iPrNH_2$) | 20% B hold 6 min, | 3.5 35 | 6 103 |
| 39 | Daicel Chiralcel® OD-3 (3 μm, 100 × 4.6 mm | A: $CO_2$ B: MeOH (0.3% iPrNH2) | 15% B hold 3 min, | 3.5 35 | 3 103 |
| 40 | Phenomenex Lux cellulose 2 (3 μm, 100 × 4.6 mm) | A: $CO_2$ B: EtOH (0.3% $iPrNH_2$) | 40% B hold 3 min, | 3.5 35 | 3 103 |

TABLE 2b

SFC-MS data. (Isomer elution order 'A' elutes before 'B' under the described conditions)

| Co. No. | $R_t$ (min) | UV % Area | Isomer elution order | SFCMS Method |
|---|---|---|---|---|
| 20a | 2.62 | 100 | A | 1 |
| 20b | 3.00 | 99.71 | B | 1 |
| 21a | 2.66 | 98.09 | A | 2 |
| 21b | 3.01 | 96.93 | B | 2 |
| 82 | 1.49 | 99.72 | A | 5 |
| 105 | 1.65 | 97.6 | B | 5 |
| 110 | 1.32 | 97.6 | A | 12 |
| 111 | 2.27 | 100 | B | 12 |
| 163 | 0.94 | 100 | A | 26 |
| 164 | 1.44 | 100 | B | 26 |
| 198 | 1.54 | 100 | A | 1 |
| 199 | 2.29 | 100 | B | 1 |
| 273 | 0.75 | 99.6 | A | 7 |
| 200 | 1.19 | 99.6 | B | 7 |
| 274 | 1.29 | 100 | A | 2 |
| 203 | 2.04 | 100 | B | 2 |
| 211 | 1.58 | 100 | A | 12 |
| 213 | 2.22 | 99.05 | B | 12 |
| 220 | 1.29 | 100 | A | 18 |
| 221 | 1.90 | 100 | B | 18 |
| 235* | 2.81 | 100 | A | 8 |
| 236* | 3.46 | 100 | B | 8 |
| 237* | 1.97 | 100 | A | 22 |
| 238* | 2.43 | 100 | B | 22 |
| 243 | 1.26 | 100 | A | 18 |
| 244 | 1.80 | 99.6 | B | 18 |
| 245 | 2.02 | 100 | A | 4 |
| 246 | 2.54 | 99.5 | B | 4 |
| 247 | 1.11 | 99.95 | A | 16 |
| 248 | 3.20 | 100 | B | 16 |
| 251 | 0.78 | 100 | A | 21 |
| 252 | 1.23 | 99.95 | B | 21 |
| 253 | 0.99 | 100 | A | 23 |
| 254 | 1.82 | 99.2 | B | 23 |
| 137 | 0.98 | 100 | A | 12 |
| 138 | 1.33 | 99.81 | B | 12 |
| 147 | 1.99 | 100 | B | 5 |
| 146 | 1.46 | 99.18 | A | 5 |
| 154 | 1.15 | 100 | A | 3 |
| 155 | 1.35 | 99.14 | B | 3 |
| 193 | 1.16 | 100 | A | 4 |
| 162 | 1.44 | 99.04 | B | 4 |
| 158 | 1.16 | 100 | A | 24 |
| 159 | 1.66 | 100 | B | 24 |
| 166 | 1.07 | 100 | A | 9 |
| 167 | 1.31 | 99.03 | B | 9 |
| 173 | 1.22 | 100 | A | 20 |
| 174 | 1.81 | 100 | B | 20 |
| 168 | 2.15 | 99.17 | B | 10 |
| 169 | 1.21 | 100 | A | 10 |
| 179 | 0.90 | 100 | A | 11 |
| 180 | 1.29 | 99.58 | B | 11 |
| 184 | 1.20 | 100 | A | 37 |
| 288 | 1.40 | 98.50 | B | 37 |
| 185 | 1.34 | 100 | A | 25 |
| 187 | 1.58 | 100 | B | 25 |
| 295 | 1.04 | 100 | A | 5 |
| 299 | 1.29 | 98.11 | B | 5 |
| 296 | 1.40 | 100 | A | 9 |
| 297 | 1.88 | 100 | B | 9 |
| 290 | 1.42 | 100 | A | 37 |
| 289 | 1.57 | 100 | B | 37 |
| 291 | 3.50 | 99.92 | A | 38 |
| 292 | 3.79 | 100 | B | 38 |
| 293 | 1.24 | 100 | A | 39 |
| 294 | 1.58 | 100 | B | 39 |
| 304a | 1.40 | 100 | A | 40 |
| 304b | 1.92 | 99.02 | B | 40 |
| 188 | 2.78 | 100 | B | 8 |
| 189 | 3.02 | 96.66 | C | 8 |
| 190 | 2.40 | 100 | A | 8 |
| 191 | 3.21 | 99.15 | D | 8 |

*Isomer elution order Co. No. 235 vs Co. No. 236; Co. No. 237 vs Co. No. 238.
SFC-MS was also measured for compounds 188, 189, 190 and 191 under the same SFCMS conditions. The results are shown in Table 2c. (Isomer elution order 'A' before 'B', 'B' before 'C', 'C' before 'D')

Optical Rotation (OR)

Optical Rotation is measured with a polarimeter 341 Perkin Elmer. The polarized light is passed through a sample with a path length of 1 decimeter and a sample concentration of 0.2 to 0.4 gram per 100 milliliters. 2 to 4 mg of the product in vial are weight, then dissolved with 1 to 1.2 ml of spectroscopy solvent (DMF for example). The cell is filled with the solution and put into the polarimeter at a temperature of 20° C. The OR is read with 0.004° of precision.

Calculation of the concentration: weight in gram× 100/volume in ml

Specific rotation (OR): $[\alpha]_d^{20}$: (read rotation×100)/ (1.000 dm×concentration).

$d$ is sodium D line (589 nanometer).

TABLE 3

OR data: wavelength: 589 nm (specicied if different); solvent: DMF (specicied if different); temperature: 20° C.; 'conc' means concentration (g/100 mL); 'OR' means optical rotation.

| Co. No. | OR (°) | Conc. | Wavelength (nm) | Solvent |
|---|---|---|---|---|
| 20a | −31.43 | 0.28 | 589 | DMF |
| 20b | +26.25 | 0.32 | 589 | DMF |
| 21a | −38.48 | 0.33 | 589 | DMF |
| 21b | +42.02 | 0.326 | 589 | DMF |
| 112 | +23.11 | 0.251 | 589 | DMF |
| 86 | −29.55 | 0.264 | 589 | DMF |
| 87 | −26.22 | 0.267 | 589 | DMF |
| 108 | −29.61 | 0.206 | 589 | DMF |
| 109 | +25.37 | 0.272 | 589 | DMF |
| 198 | −28.25 | 0.308 | 589 | DMF |
| 199 | +20.91 | 0.263 | 589 | DMF |
| 196 | +8.92 | 0.269 | 589 | DMF |
| 200 | −11.54 | 0.26 | 589 | DMF |
| 201 | +7.81 | 0.269 | 589 | DMF |
| 202 | −5.38 | 0.26 | 589 | DMF |
| 203 | −6.22 | 0.225 | 365 | DMF |
| 211 | +5.65 | 0.248 | 589 | DMF |
| 213 | −9.89 | 0.263 | 589 | DMF |
| 216 | −19.57 | 0.281 | 589 | DMF |
| 220 | −22.63 | 0.243 | 589 | DMF |
| 221 | +11.58 | 0.259 | 589 | DMF |
| 235 | −12.02 | 0.258 | 589 | DMF |
| 236 | +8.58 | 0.233 | 589 | DMF |
| 237 | +31.58 | 0.228 | 365 | DMF |
| 238 | −32.09 | 0.215 | 365 | DMF |
| 243 | −30.12 | 0.332 | 365 | DMF |
| 244 | +20.94 | 0.277 | 365 | DMF |
| 245 | −17.12 | 0.292 | 589 | DMF |
| 247 | −17.25 | 0.255 | 365 | DMF |
| 248 | +5.86 | 0.239 | 365 | DMF |
| 251 | −20.6 | 0.267 | 589 | DMF |
| 252 | +12 | 0.275 | 589 | DMF |
| 253 | −25.4 | 0.252 | 589 | DMF |
| 254 | +17.92 | 0.318 | 589 | DMF |

TABLE 3-continued

OR data: wavelength: 589 nm (specicied if different); solvent: DMF (specicied if different); temperature: 20° C.; 'conc' means concentration (g/100 mL); 'OR' means optical rotation.

| Co. No. | OR (°) | Conc. | Wavelength (nm) | Solvent |
|---|---|---|---|---|
| 273 | +10.38 | 0.26 | 589 | DMF |
| 274 | −5.41 | 0.222 | 589 | DMF |
| 137 | +29.32 | 0.249 | 589 | DMF |
| 138 | −24.9 | 0.261 | 589 | DMF |
| 147 | +8.06 | 0.273 | 589 | DMF |
| 146 | −12.65 | 0.245 | 589 | DMF |
| 154 | −8.59 | 0.256 | 589 | DMF |
| 155 | +6.64 | 0.241 | 589 | DMF |
| 150 | +14.1 | 0.234 | 365 | DMF |
| 193 | −8.62 | 0.232 | 365 | DMF |
| 162 | −5.45 | 0.275 | 589 | DMF |
| 158 | +16.54 | 0.26 | 365 | DMF |
| 159 | −22.31 | 0.251 | 365 | DMF |
| 166 | −12.6 | 0.254 | 589 | DMF |
| 167 | +7.97 | 0.276 | 589 | DMF |
| 173 | +17.92 | 0.279 | 365 | DMF |
| 174 | −21.99 | 0.282 | 365 | DMF |
| 168 | −4.59 | 0.283 | 365 | DMF |
| 179 | +20.19 | 0.208 | 365 | DMF |
| 180 | −93.02 | 0.215 | 365 | DMF |
| 184 | +17.31 | 0.219 | 589 | DMF |
| 288 | −26.63 | 0.338 | 589 | MeOH |
| 185 | +32.45 | 0.256 | 589 | DMF |
| 187 | −32.45 | 0.228 | 589 | DMF |
| 289 | +36.73 | 0.245 | 589 | DMF |
| 290 | −41.87 | 0.246 | 589 | DMF |
| 291 | −37.05 | 0.278 | 589 | DMF |
| 292 | +32.39 | 0.247 | 589 | DMF |
| 293 | +29.15 | 0.295 | 589 | DMF |
| 294 | −30.83 | 0.253 | 589 | DMF |
| 295 | +27.38 | 0.263 | 589 | DMF |
| 296 | +50.44 | 0.113 | 589 | DMF |
| 297 | −32.45 | 0.265 | 589 | DMF |
| 299 | −33.79 | 0.29 | 589 | DMF |
| 304a | +8.42 | 0.285 | 589 | DMF |
| 304b | −6.49 | 0.385 | 589 | DMF |

NMR

NMR experiments were carried out using a Bruker Avance 500 spectrometer equipped with a Bruker 5 mm BBFO probe head with z gradients and operating at 500 MHz for the proton and 125 MHz for carbon, or using a Bruker Avance DRX 400 spectrometer using internal deuterium lock and equipped with reverse double-resonance ($^1$H, $^{13}$C, SEI) probe head with z gradients and operating at 400 MHz for the proton and 100 MHz for carbon. Chemical shifts (δ) are reported in parts per million (ppm). J values are expressed in Hz. Alternatively, some NMR experiments were carried out using a Bruker Avance III 400 spectrometer at ambient temperature (298.6 K), using internal deuterium lock and equipped with 5 mm PABBO BB-probe head with z gradients and operating at 400 MHz for the proton and 100 MHz for carbon. Chemical shifts (δ) are reported in parts per million (ppm). J values are expressed in Hz.

Compound 13:
1H NMR (400 MHz, CHLOROFORM-d) δ ppm 8.42 (s, 1H), 7.38 (s, 1H), 3.95 (br s, 2H), 3.83 (br t, J=6.6 Hz, 2H), 3.63 (q, J=10.1 Hz, 2H), 3.27 (br s, 4H), 2.32 (d, J=6.8 Hz, 2H), 2.28-2.18 (m, 2H), 1.69-1.57 (m, 1H), 0.90 (d, J=6.6 Hz, 6H)

Compound 20b:
$^1$H NMR (500 MHz, DMSO-d$_6$) δ ppm 11.64 (br s, 1H) 8.49 (s, 1H) 7.77 (s, 1H) 7.67 (br d, J=3.8 Hz, 2H) 7.35-7.51 (m, 3H) 4.32-4.48 (m, 2H) 4.03-4.18 (m, 2H) 3.91 (br s, 4H) 3.17-3.61 (m, 4H) 2.00-2.32 (m, 4H)

Compound 82:
$^1$H NMR (500 MHz, DMSO-d$_6$) δ ppm 8.35 (s, 1H) 7.39 (s, 1H) 4.28-4.77 (m, 6H) 4.01-4.19 (m, 4H) 3.62 (br t, J=7.9 Hz, 1H) 2.88 (dd, J=9.9, 6.8 Hz, 1H) 2.45 (br dd, J=9.9, 7.7 Hz, 1H) 2.00-2.21 (m, 2H) 1.17-1.28 (m, 1H) 0.95 (d, J=6.3 Hz, 3H)

Compound 84:
$^1$H NMR (500 MHz, DMSO-d$_6$) δ ppm 8.33 (s, 1H) 7.72 (s, 1H) 7.22 (dd, J=8.4, 5.8 Hz, 2H) 7.09 (t, J=9.0 Hz, 2H) 4.08 (q, J=11.0 Hz, 2H) 3.66-3.96 (m, 4H) 3.17 (s, 4H) 2.65-2.73 (m, 1H) 2.38-2.45 (m, 1H) 2.27 (dd, J=12.9, 8.5 Hz, 1H) 2.14 (br s, 2H) 0.72 (d, J=6.3 Hz, 3H)

Compound 193:
$^1$H NMR (400 MHz, DMSO-d$_6$) δ ppm 8.32 (s, 1H) 7.70 (s, 1H) 4.07 (q, J=11.1 Hz, 2H) 3.65-3.91 (m, 6H) 3.07-3.30 (m, 6H) 2.14 (br s, 2H) 1.85 (br s, 1H) 1.70-1.82 (m, 1H) 1.63 (br s, 1H) 1.28-1.52 (m, 4H) 0.88 (dd, J=9.6, 7.1 Hz, 6H)

Compound 196:
$^1$H NMR (500 MHz, DMSO-d$_6$) δ ppm 8.32 (s, 1H) 7.70 (s, 1H) 4.07 (q, J=10.9 Hz, 2H) 3.52-3.97 (m, 4H) 3.34-3.43 (m, 2H) 3.02-3.22 (m, 4H) 2.72 (dd, J=8.5, 6.3 Hz, 1H) 2.58 (dd, J=8.8, 6.6 Hz, 1H) 2.51-2.53 (m, 1H) 2.28-2.35 (m, 1H) 2.19 (dd, J=9.5, 2.2 Hz, 1H) 2.12 (s, 4H) 1.58 (td, J=7.1, 2.2 Hz, 1H) 0.79 (dd, J=14.8, 6.9 Hz, 6H)

Compound 273:
$^1$H NMR (500 MHz, DMSO-d$_6$) δ ppm 8.32 (s, 1H) 7.67 (s, 1H) 4.03 (q, J=11.0 Hz, 2H) 3.87 (s, 2H) 3.79 (t, J=6.9 Hz, 2H) 3.61 (br t, J=7.6 Hz, 1H) 3.46 (br t, J=7.9 Hz, 1H) 3.12-3.34 (m, 7H) 2.66-2.77 (m, 1H) 2.28 (dd, J=9.1, 2.2 Hz, 1H) 2.15 (t, J=6.9 Hz, 2H) 1.62 (td, J=6.9, 2.2 Hz, 1H) 0.82 (dd, J=14.2, 6.9 Hz, 6H)

Compound 274:
$^1$H NMR (500 MHz, DMSO-d$_6$) δ ppm 8.31 (s, 1H) 7.69 (s, 1H) 7.45 (s, 1H) 7.20 (s, 1H) 4.07 (q, J=10.9 Hz, 2H) 3.58-3.93 (m, 7H) 2.97-3.08 (m, 4H) 2.52-2.55 (m, 1H) 2.12 (br s, 2H) 1.7 (td, J=6.6, 4.4 Hz, 1H) 0.70 (dd, J=12.6, 6.6 Hz, 6H)

Compound 320:
1HNMR (400 MHz, CD$_3$OD) δ 8.37 (s, 1H), 7.63 (s, 1H), 7.28 (t, J=8.8 Hz, 1H), 6.87-6.86 (m, 3H), 4.30-4.18 (m, 5H), 4.08-3.93 (m, 3H), 3.91-3.88 (m, 2H), 3.88-3.85 (s, 3H), 3.72-3.70 (m, 1H), 3.06 (dd, J 5.2 Hz, J 13.6 Hz, 1H), 2.64 (dd, J 9.2 Hz, J 13.6 Hz, 1H), 2.47-2.385 (m, 2H), 1.19-1.18 (d, J 6.8 Hz 3H)

Compound 321:
$^1$H NMR (400 MHz, DMSO) (8.38 (d, J=5.2 Hz 1H), 7.65 (s, 1H), 7.21 (d, J=8.4 Hz, 2H), 6.92 (d, J=8.4 Hz, 2H), 3.75-4.33 (m, 11H), 3.74 (s, 3H), 3.61 (s, 1H), 2.93 (dd, J=3.6 Hz, 12.8 Hz, 1H), 2.27-2.36 (m, 2H), 1.03 (d, J=5.6 Hz, 3H).

Compound 322:
$^1$H NMR (400 MHz, CD$_3$OD) δ 8.40 (s, 1H), 7.66 (s, 1H), 7.38-7.34 (m, 2H), 7.22-1.13 (m, 2H), 4.37-4.26 (m, 5H), 4.13 (s, 1H), 4.01 (s, 2H), 3.91 (q, J=10.4 Hz, 2H), 3.74-3.69 (m, 1H), 2.98 (dd, J 3.6 Hz, 13.2 Hz 1H), 2.68 (dd, J 9.6 Hz, 13.2 Hz 1H), 2.47 (s, 2H), 1.20 (d, J 6.4 Hz 3H).

Compound 323:
$^1$HNMR (400 MHz, CD$_3$OD) δ 8.38 (s, 1H), 7.64 (s, 1H), 7.10 (d, J=8.4 Hz, 2H), 6.78 (d, J=8.4 Hz, 2H), 3.86-7.27 (m, 10H), 3.60-6.62 (m, 1H), 2.96 (dd, J=4.8 Hz, 14.0 Hz, 1H), 2.60 (dd, J 4.8 Hz, 14.0 Hz 1H), 2.37-2.46 (m, 2H), 1.18 (d, J 6.8 Hz, 3H).

Compound 324:
1H NMR (400 MHz, CD$_3$OD) δ 8.36 (s, 1H), 7.62 (s, 1H), 7.19-7.15 (m, 4H), 4.28-4.16 (m, 5H), 4.14-3.98 (m, 4H), 3.93-3.87 (m, 2H), 3.66-3.64 (m, 1H), 3.04 (dd, J 4.8 Hz, J 13.6 Hz, 1H), 2.63 (dd, J 9.2 Hz, J 13.6 Hz 1H), 2.46-2.32 (m, 5H), 1.18 (d, J 6.4 Hz, 3H).

Pharmacological Part

1) Menin/MLL Fluorescence Polarization Assay

To a non-surface binding, black 384-well microtiter plate was added 50 nL 160× test compound in DMSO and 4 µL 2× menin in assay buffer (40 mM Tris-HCl, pH 7.5, 50 mM NaCl, 1 mM DTT and 0.001% Tween 20). After incubation of test compound and menin for 10 min at ambient temperature, 4 µL 2×FITC-MBM1 peptide (FITC-(3-alanine-SARWRFPARPGT-NH$_2$) in assay buffer was added, the microtiter plate centrifuged at 1000 rpm for 1 min and the assay mixtures incubated for 15 min at ambient temperature. The relative amount of menin-FITC-MBM1 complex present in an assay mixture is determined by measuring the fluorescence polarization (FP) of the FITC label with a BMG Pherastar plate reader (ex. 485 nm/em. 520 nm) at ambient temperature. The final concentrations of reagents in the binding assay are 100 nM menin, 5 nM FITC-MBM1 peptide and 0.625% DMSO in assay buffer. Dose-response titrations of test compounds are conducted using an 11 point, three-fold serial dilution scheme, starting at 31 µM.

Compound potencies were determined by first calculating % inhibition at each compound concentration according to equation 1:

% inhibition=$((HC-LC)-(FP^{compound}-LC))/(HC-LC))*100$   (Eqn 1)

Where LC and HC are the FP values of the assay in the presence or absence of a saturating concentration of a compound that competes with FITC-MBM1 for binding to menin, and $FP^{compound}$ is the measured FP value in the presence of the test compound. HC and LC FP values represent an average of at least 16 replicates per plate. For each test compound, % inhibition values were plotted vs. the logarithm of the test compound concentration, and the IC$_{50}$ value derived from fitting these data to equation 2:

% inhibition=Bottom+(Top-Bottom)/(1+10^((log IC$_{50}$-log[cmpd])*h))   (Eqn 2)

Where Bottom and Top are the lower and upper asymptotes of the dose-response curve, respectively, IC$_{50}$ is the concentration of compound that yields 50% inhibition of signal and h is the Hill coefficient.

2) Proliferation Assay

The anti-proliferative effect of menin/MLL protein/protein interaction inhibitor test compounds was assessed in human leukemia cell lines. The cell lines MV-4-11 and MOLM14 harbor MLL translocations and express the MLL fusion proteins MLL-AF4 and MLL-AF9, respectively, as well as the wildtype protein from the second allele. Therefore, the MLL rearranged cell lines MV-4-11 and MOLM14 exhibit stem cell-like HOXA/MEIS1 gene expression signatures. K562 and KG1 were used as a control cell lines containing two MLL wildtype alleles in order to exclude compounds that display general cytotoxic effects.

MV-4-11 and MOLM14 were cultured in RPMI-1640 (Sigma Aldrich) supplemented with 10% fetal bovine serum (HyClone), 2 mM L-glutamine (Sigma Aldrich) and 50 µg/ml gentamycin (Gibco). K562 were propagated in RPMI-1640 (Sigma Aldrich) supplemented with 20% fetal bovine serum (HyClone), 2 mM L-glutamine (Sigma Aldrich) and 50 µg/ml gentamycin (Gibco). KG1 were cultured in Iscove's MDM (Gibco) supplemented with 20% fetal bovine serum (HyClone), 2 mM L-glutamine (Sigma Aldrich) and 50 µg/ml gentamycin (Gibco). Cells were kept at 0.3-2.5 million cells per ml during culturing and passage numbers did not exceed 25.

In order to assess the anti-proliferative effects, 1,500 MV-4-11, 300 MOLM14, 750 K562 or 1,300 KG1 cells were seeded in 200 µl media per well in 96-well round bottom, ultra-low attachment plates (Costar, catalogue number 7007). Cell seeding numbers were chosen based on growth curves to ensure linear growth throughout the experiment. Test compounds were added at different concentrations and the DMSO content was normalized to 0.3%. Cells were incubated for 8 d at 37° C. and 5% CO$_2$. Spheroid like growth was monitored in real-time by live-cell imaging (IncuCyteZOOM, Essenbio, 4× objective) acquiring one image every four hours for 8 d. Confluence (%) as a measure of spheroid size was determined using an integrated analysis tool.

In order to determine the cumulative effect of the test compounds over time, the area under the curve (AUC) in a plot of confluence against time was calculated. Confluence at the beginning of the experiment (t=0) was used as baseline for the AUC calculation.

Absolute IC$_{50}$ values were calculated according to the following procedure:

% Control=(AUC sample/AUC control)*100

AUC control=mean AUC of control values(cells without compound/DMSO as vehicle control)

A non-linear curve fit was applied using the least squares (ordinary) fit method to the plot of % control versus compound concentration. Based on this, the absolute IC$_{50}$ value (half maximal inhibitory concentration of the test compound causing an anti-proliferative effect of 50% relative to the vehicle control) was calculated.

3) Menin/MLL Homogenous Time-Resolved Fluorescence (HTRF) Assay

To an untreated, white 384-well microtiter plate was added 40 nL 200× test compound in DMSO and 4 µL 2× terbium chelate-labeled menin (vide infra for preparation) in assay buffer (40 mM Tris-HCl, pH 7.5, 50 mM NaCl, 1 mM DTT and 0.05% Pluronic F-127). After incubation of test compound and terbium chelate-labeled menin for 5 min at ambient temperature, 4 µL 2×FITC-MBM1 peptide (FITC-β-alanine-SARWRFPARPGT-NH$_2$) in assay buffer was added, the microtiter plate centrifuged at 1000 rpm for 1 min and the assay mixtures incubated for 15 min at ambient temperature. The relative amount of menin-FITC-MBM1 complex present in an assay mixture is determined by measuring the homogenous time-resolved fluorescence (HTRF) of the terbium/FITC donor/acceptor fluorphore pair using a BMG Pherastar plate reader (ex. 337 nm/terbium em. 490 nm/FITC em. 520 nm) at ambient temperature. The degree of fluorescence resonance energy transfer (the HTRF value) is expressed as the ratio of the fluorescence emission intensities of the FITC and terbium fluorophores ($F^{em}$ 520 nm/$PF^{em}$ 490 nm). The final concentrations of reagents in the binding assay are 100 pM terbium chelate-labeled menin, 75 nM FITC-MBM1 peptide and 0.5% DMSO in assay buffer. Dose-response titrations of test compounds are conducted using an 11 point, three-fold serial dilution scheme, starting at 31 µM.

Compound potencies were determined by first calculating % inhibition at each compound concentration according to equation 1:

% inhibition=$((HC-LC)-(FP^{compound}-LC))/(HC-LC))*100$   (Eqn 1)

Where LC and HC are the HTRF values of the assay in the presence or absence of a saturating concentration of a compound that competes with FITC-MBM1 for binding to menin, and $HTRF^{compound}$ is the measured HTRF value in the presence of the test compound. HC and LC HTRF values represent an average of at least 16 replicates per plate. For each test compound, % inhibition values were plotted vs. the logarithm of the test compound concentration, and the $IC_{50}$ value derived from fitting these data to equation 2:

% inhibition=Bottom+(Top−Bottom)/(1+10^((log $IC_{50}$−log[cmpd])*h))  (Eqn 2)

Where Bottom and Top are the lower and upper asymptotes of the dose-response curve, respectively, $IC_{50}$ is the concentration of compound that yields 50% inhibition of signal and h is the Hill coefficient.

Preparation of Terbium cryptate labeling of Menin: Menin (a.a. 1-610-6×his tag) was labeled with terbium cryptate as follows. 2 mg of Menin was buffer exchanged into 1× phosphate buffered saline. 16 uM Menin was incubated with 4-fold molar excess NHS-terbium cryptate (Cisbio Bioassays, Bedford, Mass.) for 2 hours at room temperature. The labeled protein was purified away from free label by running the reaction over a Superdex 200 Increase 10/300 GL column at 0.75 ml/min. Peak fractions were collected, aliquoted and frozen at −80° C.

MENIN Protein Sequence (SEQ ID NO: 1):

MGLKAAQKTLFPLRSIDDVVRLFAAELGREEPDLVLLSLVLGFVEHFLAV
NRVIPTNVPELTFQPSPAPDPPGGLTYFPVADLSIIAALYARFTAQIRGA
VDLSLYPREGGVSSRELVKKVSDVIWNSLSRSYFKDRAHIQSLFSFITGT
KLDSSGVAFAVVGACQALGLRDVHLALSEDHAWVVFGPNGEQTAEVTWHG
KGNEDRRGQTVNAGVAERSWLYLKGSYMRCDRKMEVAFMVCAINPSIDLH
TDSLELLQLQQKLLWLLYDLGHLERYPMALGNLADLEELEPTPGRPDPLT
LYHKGIASAKTYYRDEHIYPYMYLAGYHCRNRNVREALQAWADTATVIQD
YNYCREDEEIYKEFFEVANDVIPNLLKEAASLLEAGEERPGEQSQGTQSQ
GSALQDPECFAHLLRFYDGICKWEEGSPTPVLHVGWATFLVQSLGRFEGQ
VRQKVRIVSREAEAAEAEEPWGEEAREGRRRGPRRESKPEEPPPPKKPAL
DKGLGTGQGAVSGPPRKPPGTVAGTARGPEGGSTAQVPAPAASPPPEGPV
LTFQSEKMKGMKELLVATKINSSAIKLQLTAQSQVQMKKQKVSTPSDYTL
SFLKRQRKGLHHHHHH

TABLE 4

Biological data in the Menin fluorescence polarization (FP) assay (1), Menin/MLL homogenous time-resolved fluorescence (HTRF) assay (3) and proliferation assay (2). Co. No. means compound number. The values in table 4 are averaged values over all measurements.

| Co. No. | (1) Menin FP assay ($IC_{50}$ (μM)) | (3) Menin HTRF assay ($IC_{50}$ (nM)) | (2) Spheroid assay MV-4-11 ($IC_{50}$ (μM)) | (2) Spheroid assay MOLM14 ($IC_{50}$ (μM)) | (2) Spheroid assay K562 ($IC_{50}$ (μM)) | (2) Spheroid assay KG1 ($IC_{50}$ (μM)) |
|---|---|---|---|---|---|---|
| 18 | 0.14 | 227 | 3.9 | 7.7 | >15 | |
| 1 | 0.056 | 144 | 3.7 | 4.6 | >15 | |
| 3 | 0.10 | 216 | 3.8 | 5.6 | ~15 | |
| 14 | 0.11 | 178 | 2.2 | 4.9 | | |
| 20a | 0.076 | 13 | 0.96 | 5 | >15 | |
| 21a | 0.49 | 745 | 6.9 | 12.1 | >15 | |
| 21b | 0.13 | 389 | 4.2 | 4.6 | >15 | |
| 19 | 0.81 | 1960 | | | | |
| 5 | 0.67 | 600 | 6.4 | 30.6 | >15 | |
| 12 | 0.63 | 2247 | >15 | >15 | >15 | |
| 13 | 0.042 | 39 | 0.73 | 4.2 | >15 | |
| 11 | 0.76 | 2374 | | | | |
| 10 | 2.31 | | | | | |
| 9 | 0.84 | 1579 | | | | |
| 8 | 0.79 | 2525 | | | | |
| 6 | 0.24 | 339 | 2.4 | 10.1 | >15 | |
| 7 | 0.73 | 1216 | | | | |
| 4 | 0.73 | 3164 | | | | |
| 2 | 0.39 | 706 | 4.9 | 14.6 | >15 | |
| 15 | 0.57 | 471 | 14.0 | >15 | >15 | |
| 22 | 0.069 | 12 | 0.55 | 2.0 | >15 | |
| 23 | 0.95 | 1208 | | | | |
| 24 | 0.49 | 1486 | 9.1 | >15 | | |
| 25 | 0.31 | 1465 | 3.8 | 7.2 | | |
| 26 | 0.16 | 143 | 10.4 | >15 | | |
| 197 | 0.30 | 541 | 7.3 | >15 | | |
| 86 | 0.092 | 102 | 2.6 | 11.3 | >15 | |
| 133 | 0.12 | 385 | 2.1 | >15 | | |
| 30 | 0.53 | 839 | 9.2 | >15 | | |
| 88 | 0.32 | 486 | >15 | >15 | | |
| 89 | 0.045 | 31 | 1.3 | 10.5 | | |
| 90 | 0.11 | 288 | 11.1 | >15 | | |
| 74 | 0.12 | 211 | 2.0 | 6.1 | | |
| 75 | 2.36 | | | | | |
| 34 | 0.72 | 902 | | | | |
| 198 | 0.14 | 178 | 5.1 | 12.4 | | |
| 199 | 0.41 | 1196 | 12.9 | >15 | | |
| 35 | 0.99 | 2375 | | | | |

TABLE 4-continued

Biological data in the Menin fluorescence polarization (FP) assay (1),
Menin/MLL homogenous time-resolved fluorescence (HTRF) assay (3) and proliferation
assay (2). Co. No. means compound number. The values in table 4 are averaged values
over all measurements.

| Co. No. | (1) Menin FP assay (IC$_{50}$ (μM)) | (3) Menin HTRF assay (IC$_{50}$ (nM)) | (2) Spheroid assay MV-4-11 (IC$_{50}$ (μM)) | (2) Spheroid assay MOLM14 (IC$_{50}$ (μM)) | (2) Spheroid assay K562 (IC$_{50}$ (μM)) | (2) Spheroid assay KG1 (IC$_{50}$ (μM)) |
|---|---|---|---|---|---|---|
| 36 | 0.4 | 777 | | | | |
| 37 | 0.17 | 177 | 1.5 | 3.1 | | |
| 76 | 0.68 | 901 | | | | |
| 40 | 0.84 | 1465 | | | | |
| 195 | 1.07 | 1536 | | | | |
| 41 | 0.63 | 950 | | | | |
| 273 | 0.021 | 8 | 0.08 | 0.86 | 10.3 | 12 |
| 200 | 0.11 | 190 | 3.4 | 10.3 | | |
| 201 | | 1075 | 12.7 | >15 | | |
| 202 | | 490 | >15 | | | |
| 137 | | 1097 | 10.1 | >15 | | |
| 44 | | 344 | 4.1 | >15 | | |
| 82 | | 9 | 0.38 | 1.8 | >15 | >15 |
| 105 | | 15 | 0.67 | 3.4 | >15 | |
| 108 | | 753 | >15 | | | |
| 109 | | 571 | 8.1 | | | |
| 45 | | 330 | 3.4 | | | |
| 46 | | 448 | 4.1 | | | |
| 47 | | 669 | | | | |
| 48 | | 483 | 2.0 | | | |
| 49 | | 310 | 2.1 | | | |
| 50 | | 665 | | | | |
| 110 | | 236 | 4.0 | | | |
| 111 | | 394 | 9.3 | | | |
| 77 | | 191 | 12.1 | | | |
| 54 | | 342 | 3.7 | | | |
| 56 | | 304 | 4.9 | | | |
| 112 | | 1540 | | | | |
| 274 | | 7 | 0.36 | 2.3 | >15 | >15 |
| 203 | | 422 | 7.2 | | | |
| 145 | | 37 | 1.7 | 7.3 | | |
| 146 | | 46 | 2.4 | | | |
| 147 | | 341 | 8.2 | | | |
| 57 | | 179 | 4.2 | 8.6 | | |
| 148 | | 5 | 0.33 | | | |
| 211 | | 13 | 0.68 | 3.5 | | 12.5 |
| 213 | | 149 | 1.9 | | | |
| 214 | | 17 | 0.76 | 1.4 | | >15 |
| 150 | | 60 | 2.0 | | | |
| 220 | | 75 | 0.65 | 4.7 | >15 | >15 |
| 221 | | 1157 | | | | |
| 222 | | 4 | 0.2 | | | |
| 223 | | 496 | 6.1 | | | |
| 228 | | 238 | | | | |
| 58 | | 185 | 2.7 | | | |
| 59 | | 1245 | | | | |
| 230 | | 44 | | | | |
| 231 | | 107 | | | | |
| 232 | | 914 | | | | |
| 233 | | 782 | | | | |
| 234 | | 1045 | | | | |
| 235 | | 23 | 0.71 | | | |
| 236 | | 1041 | | | | |
| 237 | | 52 | 1.2 | | | |
| 238 | | 659 | | | | |
| 154 | | 328 | | | | |
| 155 | | 69 | 0.7 | 1.2 | | >15 |
| 243 | | 249 | | | | |
| 244 | | 848 | | | | |
| 245 | | 10 | 0.32 | 2 | | >15 |
| 246 | | 284 | | | | |
| 247 | | 19 | 0.45 | 2.1 | >15 | >15 |
| 248 | | 549 | | | | |
| 61 | | 513 | | | | |
| 249 | | 912 | | | | |
| 250 | | 190 | | | | |
| 251 | | 1660 | | | | |
| 252 | | 1007 | | | | |
| 253 | | 323 | | | | |

TABLE 4-continued

Biological data in the Menin fluorescence polarization (FP) assay (1), Menin/MLL homogenous time-resolved fluorescence (HTRF) assay (3) and proliferation assay (2). Co. No. means compound number. The values in table 4 are averaged values over all measurements.

| Co. No. | (1) Menin FP assay (IC$_{50}$ (μM)) | (3) Menin HTRF assay (IC$_{50}$ (nM)) | (2) Spheroid assay MV-4-11 (IC$_{50}$ (μM)) | (2) Spheroid assay MOLM14 (IC$_{50}$ (μM)) | (2) Spheroid assay K562 (IC$_{50}$ (μM)) | (2) Spheroid assay KG1 (IC$_{50}$ (μM)) |
|---|---|---|---|---|---|---|
| 254 | | 861 | | | | |
| 156 | | 21 | 0.79 | | | |
| 157 | | 101 | | | | |
| 158 | | 281 | | | | |
| 159 | | 1174 | | | | |
| 62 | | 28 | 0.64 | 4 | | >15 |
| 161 | | 187 | 4.2 | | | |
| 258 | | 3083 | | | | |
| 193 | | 25 | 0.65 | 1.7 | >15 | >15 |
| 162 | | 77 | 3.1 | | | |
| 63 | | 201 | | | | |
| 196 | | 4 | 0.3 | 1.1 | >15 | >15 |
| 163 | | 277 | | | | |
| 164 | | 1125 | | | | |
| 259 | | 20 | 1.3 | | | |
| 64 | | 1139 | | | | |
| 65 | | 65 | 3.2 | | | |
| 166 | | 79 | 2.4 | | | |
| 167 | | 1126 | | | | |
| 168 | | 3 | 0.19 | 0.86 | 11.9 | 15 |
| 169 | | 176 | 3.5 | | | |
| 170 | | 138 | 4.3 | | | |
| 84 | | 20 | 0.58 | 1.5 | | >15 |
| 171 | | 159 | 3.1 | | | |
| 66 | | 26 | 0.95 | 0.69 | | >15 |
| 172 | | 124 | 2.9 | | | |
| 173 | | 96 | 3.2 | | | |
| 174 | | 1386 | | | | |
| 67 | | 108 | 4.9 | | | |
| 179 | | 95 | 1.3 | | | |
| 180 | | 130 | 1.9 | | | |
| 69 | | 186 | 1.2 | | | |
| 182 | | 61 | 0.78 | 1.9 | | >15 |
| 183 | | 103 | 1.3 | | | |
| 71 | | 48 | 1.1 | | | |
| 184 | | 73 | 0.97 | | | >15 |
| 186 | | 91 | 1.3 | | | |
| 187 | | 72 | 1.4 | | | |
| 269 | | 8 | 0.67 | 4.6 | | >15 |
| 188 | | 115 | 1.5 | | | |
| 189 | | 108 | 0.92 | | | >15 |
| 270 | | 499 | | | | |
| 271 | | 623 | | | | |
| 190 | | 524 | | | | |
| 191 | | 1263 | | | | |
| 192 | | 619 | | | | |
| 312 | | 339 | | | | |
| 313 | | 159 | 3.6 | | | |
| 315 | | 21 | 0.32 | 1.5 | | >15 |
| 316 | | 20 | 0.4 | 0.96 | | >3.7 |
| 288 | | 68 | 1.4 | | | |
| 289 | | 6 | 0.21 | 1.3 | | |
| 290 | | 25 | 0.47 | 1.2 | | |
| 291 | | 13 | 0.66 | 1.2 | | >15 |
| 292 | | 12 | 0.29 | 1.5 | | >15 |
| 294 | | 82 | 1.83 | | | |
| 293 | | 81 | 1.67 | | | |
| 307 | | 11 | 0.28 | 1.5 | | 10.7 |
| 299 | | 57 | 3.18 | | | |
| 295 | | 34 | 1.16 | 6.7 | | |
| 303 | | 6 | 0.32 | 1.02 | | |
| 296 | | 200 | 4.89 | | | |
| 309 | | 16 | 0.74 | 1.6 | | |
| 297 | | 242 | | | | |
| 304b | | 440 | | | | |
| 304a | | 15 | 0.44 | 1.3 | | >15 |
| 317 | | 248 | 0.77 | | | >15 |
| 318 | | 72 | 1.09 | | | |
| 298 | | 122 | 4.23 | | | |

TABLE 4-continued

Biological data in the Menin fluorescence polarization (FP) assay (1), Menin/MLL homogenous time-resolved fluorescence (HTRF) assay (3) and proliferation assay (2). Co. No. means compound number. The values in table 4 are averaged values over all measurements.

| Co. No. | (1) Menin FP assay (IC$_{50}$ (μM)) | (3) Menin HTRF assay (IC$_{50}$ (nM)) | (2) Spheroid assay MV-4-11 (IC$_{50}$ (μM)) | (2) Spheroid assay MOLM14 (IC$_{50}$ (μM)) | (2) Spheroid assay K562 (IC$_{50}$ (μM)) | (2) Spheroid assay KG1 (IC$_{50}$ (μM)) |
|---|---|---|---|---|---|---|
| 314 |  | 25 | 0.73 |  |  |  |
| 320 |  | 259 | 1.37 |  |  |  |
| 321 |  | 210 | 1.1 |  |  |  |
| 322 |  | 200 | 1.7 |  |  |  |
| 323 |  | 47 | 0.75 |  |  |  |
| 324 |  | 143 | 1.9 |  |  |  |
| 31 | 0.087 | 116 | 1.3 | 9.8 |  |  |
| 224 |  | 2365 |  |  |  |  |
| 185 |  | 161 | 1.3 |  |  |  |
| 311 |  | 85 | 2.4 |  |  |  |

TABLE 5

Biological data in the Menin fluorescence polarization (FP) assay (1), Menin/MLL homogenous time-resolved fluorescence (HTRF) assay (3) and proliferation assay (2). Co. No. means compound number. The values in table 5 are values for individual measurements (not averaged): in case a value was determined more than 1 time, each value is reported individually in Table 5.

| Co. No. | (1) Menin FP assay (IC$_{50}$ (μM)) | (3) Menin HTRF assay (IC$_{50}$ (nM)) | (2) Spheroid assay MV-4-11 (IC$_{50}$ (μM)) | (2) Spheroid assay MOLM14 (IC$_{50}$ (μM)) | (2) Spheroid assay K562 (IC$_{50}$ (μM)) | (2) Spheroid assay KG1 (IC$_{50}$ (μM)) |
|---|---|---|---|---|---|---|
| 20b | 0.038 | 7 | 0.51 | >15 | >15 | >15 |
|  |  |  | 2.5 |  |  |  |
| 16 |  |  | 4.7 | 9.3 |  |  |
|  | 0.134 | 63 | >15 | 8.7 | >15 |  |
| 17 |  |  | 4.9 |  |  |  |
|  |  |  | 0.76 | 3.4 |  |  |
|  | 0.054 | 14 | 0.84 | 2.3 |  | 11 |
| 28 |  |  | 0.5 |  |  |  |
|  |  |  | 10.8 | 3.2 |  |  |
|  | 0.517 | 1262 | 10.9 | >15 |  |  |
| 29 |  |  | 1.8 |  |  |  |
|  |  |  | >15 | 10.8 |  |  |
|  | 0.346 | 1438 | 9.9 | >15 |  |  |
| 87 |  |  | 4.1 |  |  |  |
|  |  |  | 0.63 |  |  |  |
|  |  |  | 0.58 |  |  |  |
|  |  |  | 0.63 | 8.0 |  |  |
|  |  |  | 0.68 | 2.8 |  |  |
|  | 0.048 | 28 | 0.52 | 4.6 | >15 |  |
| 138 |  |  | ~15.4 |  |  |  |
|  |  |  | 1.0 |  |  |  |
|  |  | 62 | 1.4 | 7 |  |  |

The invention claimed is:

1. A compound of Formula (I)

(I)

or a tautomer or a stereoisomeric form thereof, wherein

R¹ is selected from the group consisting of CH₃, CH₂F, CHF₂, and CF₃;

R² is selected from the group consisting of hydrogen and CH₃;

L¹ is N-linked to the thienopyrimidinyl heterocycle and selected from

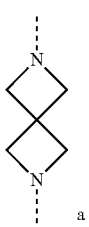

(a)

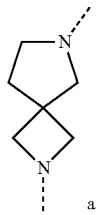

(b)

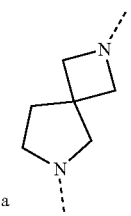

(c)

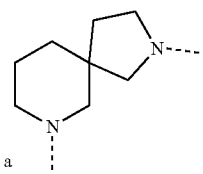

(e)

-continued (f)
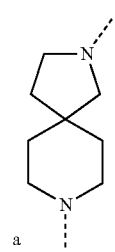
a (g)
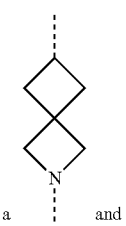
a and (i)
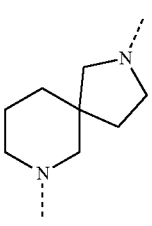
a ;

wherein a represents the position of linkage to the thienopyrimidinyl heterocycle; and
-L$^2$-R$^3$ is selected from (b) or (f), wherein
(b) L$^2$ is selected from the group consisting of >CR$^{4c}$R$^{4d}$ and —CHR$^{4c}$CHR$^{5a}$—, wherein R$^{4c}$, R$^{4d}$, and R$^{5a}$ are each independently selected from the group consisting of hydrogen and C$_{1-4}$alkyl; and
R$^3$ is selected from the group consisting of

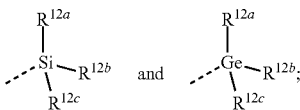

wherein R$^{12a}$, R$^{12b}$, and R$^{12c}$ are each independently selected from the group consisting of C$_{1-6}$alkyl optionally substituted with a OH or a NH$_2$ substituent; and —OC$_{1-6}$alkyl; or
(f) -L$^2$-R$^3$ is

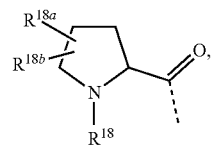

wherein
R$^{18}$ is selected from the group consisting of hydrogen; C$_{1-4}$alkyl optionally substituted with a fluoro or a —CN substituent; and C$_{2-4}$alkyl substituted with a substituent selected from the group consisting of —OR$^{19}$ and —NR$^{20a}$R$^{20b}$; wherein
R$^{19}$, R$^{20a}$ and R$^{20b}$ are each independently selected from the group consisting of hydrogen;

C$_{1-4}$alkyl optionally substituted with a substituent selected from the group consisting of fluoro, —CN, and —C(=O)NR$^{21a}$R$^{21b}$; C$_{2-4}$alkyl substituted with a substituent selected from the group consisting of —OR$^{22}$ and —NR$^{21a}$R$^{21b}$; and C-linked 4- to 7-membered non-aromatic heterocyclyl containing at least one nitrogen, oxygen or sulfur atom; wherein R$^{21a}$, R$^{21b}$ and R$^{22}$ are each independently selected from the group consisting of hydrogen and C$_{1-4}$alkyl; and
R$^{18a}$ is selected from the group consisting of hydrogen, fluoro and C$_{1-4}$alkyl;
R$^{18b}$ is selected from the group consisting of fluoro, —OC$_{1-4}$alkyl, and C$_{1-4}$alkyl optionally substituted with 1, 2 or 3 fluoro substituents; or
R$^{18a}$ and R$^{18b}$ are bound to the same carbon atom and together form a C$_{3-5}$cycloalkyl or a C-linked 4- to 6-membered heterocyclyl containing an oxygen atom;
or a pharmaceutically acceptable salt or a solvate thereof.

2. The compound according to claim 1, wherein
(b) L$^2$ is selected from the group consisting of >CR$^{4c}$R$^{4d}$ and —CHR$^{4c}$CHR$^{5a}$—, wherein R$^{4c}$, R$^{4d}$, and R$^{5a}$ are each independently selected from the group consisting of hydrogen and C$_{1-4}$alkyl; and
R$^3$ is selected from the group consisting of

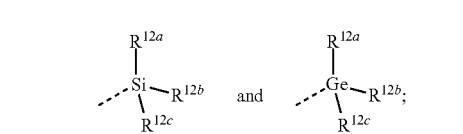

wherein R$^{12a}$, R$^{12b}$, and R$^{12c}$ are each independently selected from the group consisting of C$_{1-6}$alkyl optionally substituted with a —OH or a —NH$_2$ substituent; or
(f) -L$^2$-R$^3$ is selected from the group consisting of

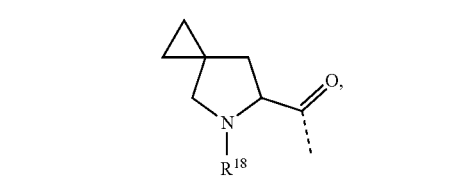

wherein
R$^{18}$ is hydrogen.

3. The compound according to claim 1, wherein
(b) L$^2$ is >CR$^{4c}$R$^{4d}$, wherein R$^{4c}$ and R$^{4d}$ are each independently selected from the group consisting of hydrogen and C$_{1-4}$alkyl; and
R$^3$ is selected from the group consisting of

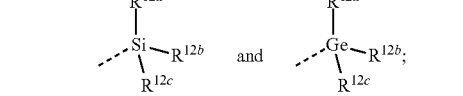

wherein R$^{12a}$, R$^{12b}$, and R$^{12c}$ are each independently selected from the group consisting of C$_{1-6}$alkyl optionally substituted with a —NH$_2$ substituent.

4. The compound according to claim 1, wherein
R$^1$ is CF$_3$; and
L$^1$ is selected from the group consisting of (a), (b), (c), (e), (f) and (g)

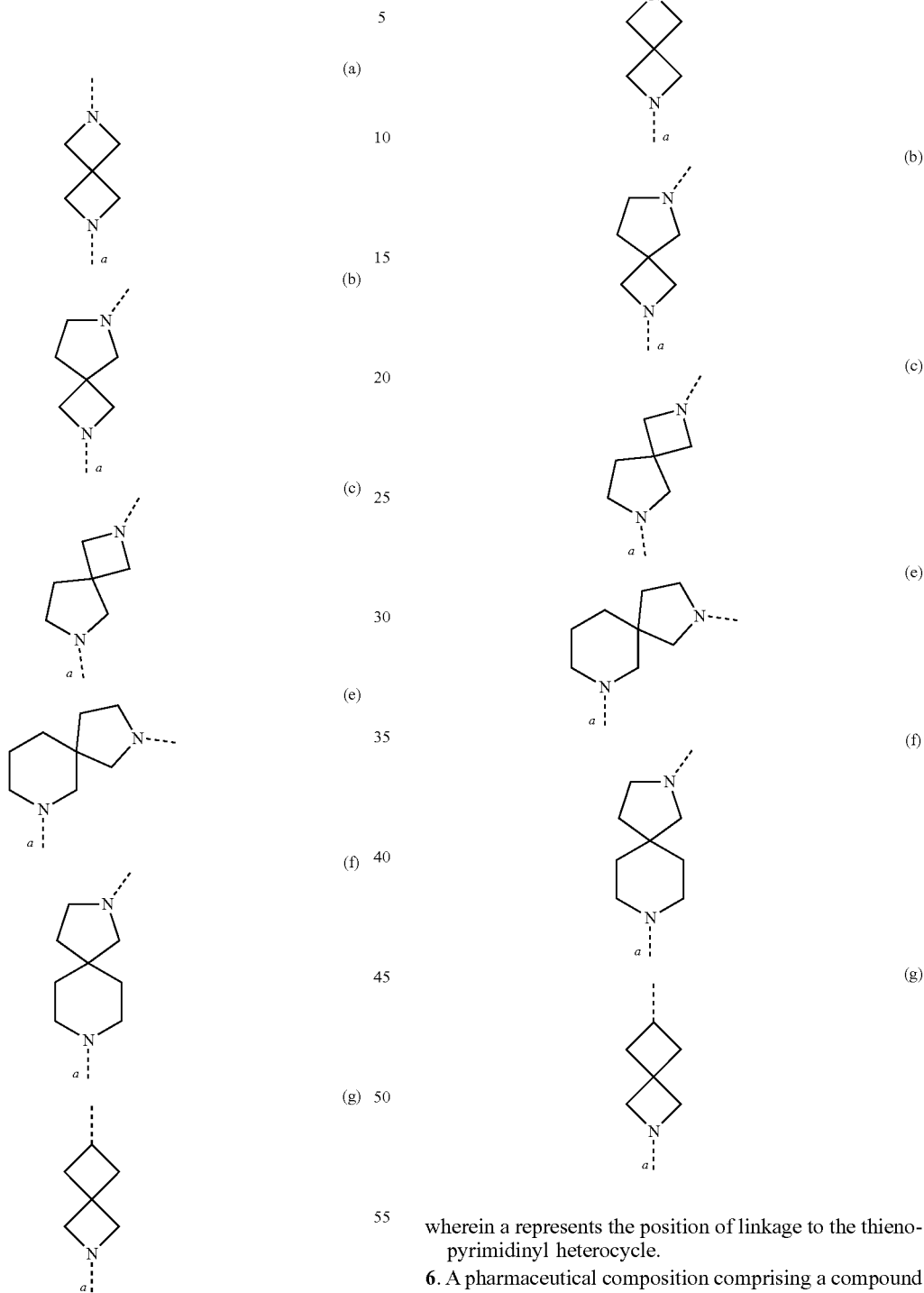

wherein a represents the position of linkage to the thieno-pyrimidinyl heterocycle.

5. The compound according to claim 1, wherein
R$^1$ is CF$_3$;
R$^2$ is hydrogen; and
L$^1$ is selected from the group consisting of (a), (b), (c), (e), (f) and (g)

wherein a represents the position of linkage to the thieno-pyrimidinyl heterocycle.

6. A pharmaceutical composition comprising a compound as claimed in claim 1 and a pharmaceutically acceptable carrier or diluent.

7. A process for preparing a pharmaceutical composition comprising mixing a pharmaceutically acceptable carrier or diluent with a therapeutically effective amount of a compound according to claim 1.

8. A method of inhibiting menin/MLL protein in a subject in need thereof comprising administering to the subject an effective amount of a compound as claimed in claim 1, wherein the subject is suffering from a disorder selected from cancer, myelodysplastic syndrome (MDS) and diabetes.

9. The method according to claim 8 wherein the disorder is cancer.

10. The method according to claim 9 wherein the cancer is selected from leukemias, myeloma, prostate cancer, lung cancer, breast cancer, pancreatic cancer, colon cancer, liver cancer, melanoma and glioblastoma.

11. The method according to claim 9 wherein the cancer is selected from acute leukemias, chronic leukemias, myeloid leukemias, myelogeneous leukemias, lymphoblastic leukemias, lymphocytic leukemias, Acute myelogeneous leukemias (AML), Chronic myelogenous leukemias (CIVIL), Acute lymphoblastic leukemias (ALL), Chronic lymphocytic leukemias (CLL), T cell prolymphocytic leukemias (T-PLL), Large granular lymphocytic leukemia, Hairy cell leukemia (HCL), MLL-rearranged leukemias, MLL-PTD leukemias, MLL amplified leukemias, MLL-positive leukemias, and leukemias exhibiting HOX/MEIS1 gene expression signatures.

12. A method of inhibiting menin/MLL protein in a subject comprising administering to the subject an effective amount of a compound as claimed in claim 1.

* * * * *